US009096951B2

(12) United States Patent
Freskgard et al.

(10) Patent No.: US 9,096,951 B2
(45) Date of Patent: *Aug. 4, 2015

(54) METHOD FOR PRODUCING SECOND-GENERATION LIBRARY

(75) Inventors: Per-Ola Freskgard, Norrkorping (SE); Alex Haahr Gouliaev, Veksoe Sjaelland (DK); Thomas Thisted, Frederikssund (DK); Eva Kampmann Olsen, Herlev (DK)

(73) Assignee: Nuevolution A/S, Copenhagen (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/179,283

(22) Filed: Jul. 8, 2011

(65) Prior Publication Data

US 2012/0028812 A1 Feb. 2, 2012

Related U.S. Application Data

(63) Continuation of application No. 10/546,538, filed as application No. PCT/DK2004/000117 on Feb. 23, 2004, now abandoned.

(60) Provisional application No. 60/448,480, filed on Feb. 21, 2003, provisional application No. 60/448,460, filed on Feb. 21, 2003, provisional application No. 60/504,748, filed on Sep. 22, 2003.

(30) Foreign Application Priority Data

Feb. 21, 2003 (DK) .................................. 2003 00268
Feb. 21, 2003 (DK) .................................. 2003 00269
Sep. 18, 2003 (DK) .................................. 2003 01356

(51) Int. Cl.
*C40B 50/06* (2006.01)
*C40B 40/08* (2006.01)
*B01J 19/00* (2006.01)
*C12N 15/10* (2006.01)
*C12Q 1/68* (2006.01)
*C40B 50/10* (2006.01)
*C40B 50/04* (2006.01)

(52) U.S. Cl.
CPC ............ *C40B 40/08* (2013.01); *B01J 19/0046* (2013.01); *C12N 15/1068* (2013.01); *C12Q 1/6811* (2013.01); *C40B 50/06* (2013.01); *B01J 2219/00592* (2013.01); *C40B 50/04* (2013.01); *C40B 50/10* (2013.01)

(58) Field of Classification Search
None
See application file for complete search history.

(56) References Cited

U.S. PATENT DOCUMENTS

| 4,822,731 A | 4/1989 | Watson et al. |
| 5,047,519 A | 9/1991 | Hobbs, Jr. et al. |
| 5,324,829 A | 6/1994 | Bahl et al. |
| 5,432,272 A | 7/1995 | Benner |
| 5,437,977 A | 8/1995 | Segev |
| 5,449,613 A | 9/1995 | Dordick et al. |
| 5,451,503 A | 9/1995 | Hogan et al. |
| 5,473,060 A | 12/1995 | Gryaznov et al. |
| 5,474,796 A | 12/1995 | Brennan |
| 5,476,930 A | 12/1995 | Letsinger et al. |
| 5,503,805 A | 4/1996 | Sugarman et al. |
| 5,571,677 A | 11/1996 | Gryaznov |
| 5,571,903 A | 11/1996 | Gryaznov |
| 5,573,905 A | 11/1996 | Lerner et al. |
| 5,604,097 A | 2/1997 | Brenner |
| 5,635,400 A | 6/1997 | Brenner |
| 5,639,603 A | 6/1997 | Dower et al. |
| 5,643,722 A | 7/1997 | Rothschild et al. |
| 5,654,413 A | 8/1997 | Brenner |
| 5,656,739 A | 8/1997 | Cubicciotti |
| 5,663,046 A | 9/1997 | Baldwin et al. |
| 5,665,975 A | 9/1997 | Kedar |
| 5,681,943 A | 10/1997 | Letsinger et al. |
| 5,684,169 A | 11/1997 | Hamada et al. |
| 5,686,243 A | 11/1997 | Royer et al. |
| 5,708,153 A | 1/1998 | Dower et al. |
| 5,723,320 A | 3/1998 | Dehlinger |
| 5,723,598 A | 3/1998 | Lerner et al. |
| 5,739,386 A | 4/1998 | Holmes |
| 5,741,643 A | 4/1998 | Gryaznov et al. |
| 5,763,175 A | 6/1998 | Brenner |

(Continued)

FOREIGN PATENT DOCUMENTS

DE 196 46 372 C1 6/1997
DE 196 42 751 A1 4/1998

(Continued)

OTHER PUBLICATIONS

Office Action in European application No. 07114663.3, dated Sep. 12, 2011.

(Continued)

*Primary Examiner* — Tracy Vivlemore
*Assistant Examiner* — Karen S Weiler
(74) *Attorney, Agent, or Firm* — Merchant & Gould P.C.

(57) ABSTRACT

The present invention relates to a method for generating a second-generation library. In a first step, a library of encoded molecules associated with an identifier nucleic acid comprising codons identifying chemical entities that have participated in the formation of the encoded molecule is provided. In a second step, the library is partitioned and encoded molecules having a certain property are selected. Codons of identifiers of selected encoded molecules are subsequently identified, and a second-generation library is prepared using at least some of the chemical entities coded for by the identified codons. The new focussed library may be used for another partition step to select encoded molecules with a certain property.

12 Claims, 23 Drawing Sheets

(56) References Cited

U.S. PATENT DOCUMENTS

| | | |
|---|---|---|
| 5,763,263 A | 6/1998 | Dehlinger |
| 5,770,358 A | 6/1998 | Dower et al. |
| 5,770,455 A | 6/1998 | Cargill et al. |
| 5,780,613 A | 7/1998 | Letsinger et al. |
| 5,789,162 A | 8/1998 | Dower et al. |
| 5,789,172 A | 8/1998 | Still et al. |
| 5,795,976 A | 8/1998 | Oefner et al. |
| 5,804,563 A | 9/1998 | Still et al. |
| 5,817,795 A | 10/1998 | Gryaznov et al. |
| 5,824,471 A | 10/1998 | Mashal et al. |
| 5,830,658 A | 11/1998 | Gryaznov |
| 5,840,485 A | 11/1998 | Lebl et al. |
| 5,843,650 A | 12/1998 | Segev |
| 5,843,701 A | 12/1998 | Gold et al. |
| 5,846,719 A | 12/1998 | Brenner et al. |
| 5,880,972 A | 3/1999 | Horlbeck |
| 5,942,609 A | 8/1999 | Hunkapiller et al. |
| 5,948,648 A | 9/1999 | Khan et al. |
| 6,001,579 A | 12/1999 | Still et al. |
| 6,056,926 A | 5/2000 | Sugarman et al. |
| 6,060,596 A | 5/2000 | Lerner et al. |
| 6,090,912 A | 7/2000 | Lebl et al. |
| 6,096,500 A | 8/2000 | Oprandy et al. |
| 6,096,875 A | 8/2000 | Khan et al. |
| 6,132,970 A | 10/2000 | Stemmer |
| 6,140,489 A | 10/2000 | Brenner |
| 6,140,493 A | 10/2000 | Dower et al. |
| 6,143,497 A | 11/2000 | Dower et al. |
| 6,143,503 A | 11/2000 | Baskerville et al. |
| 6,150,516 A | 11/2000 | Brenner et al. |
| 6,165,717 A | 12/2000 | Dower et al. |
| 6,165,778 A | 12/2000 | Kedar |
| 6,172,214 B1 | 1/2001 | Brenner |
| 6,194,550 B1 | 2/2001 | Gold et al. |
| 6,197,555 B1 | 3/2001 | Khan et al. |
| 6,207,446 B1 | 3/2001 | Szostak et al. |
| 6,210,900 B1 | 4/2001 | Yamashita et al. |
| 6,232,066 B1 | 5/2001 | Felder et al. |
| 6,235,475 B1 | 5/2001 | Brenner et al. |
| 6,235,889 B1 | 5/2001 | Ulanovsky |
| 6,248,568 B1 | 6/2001 | Khan et al. |
| 6,274,385 B1 | 8/2001 | Hochlowski et al. |
| 6,287,765 B1 | 9/2001 | Cubicciotti |
| 6,297,053 B1 | 10/2001 | Stemmer |
| 6,306,587 B1 | 10/2001 | Royer et al. |
| 6,352,828 B1 | 3/2002 | Brenner |
| 6,416,949 B1 | 7/2002 | Dower et al. |
| 6,429,300 B1 | 8/2002 | Kurz et al. |
| 6,434,490 B1 * | 8/2002 | Agrafiotis et al. ............... 702/27 |
| 6,479,264 B1 | 11/2002 | Louwrier |
| 6,503,759 B1 | 1/2003 | Still et al. |
| 6,514,736 B1 | 2/2003 | Erlich et al. |
| 6,537,776 B1 | 3/2003 | Short |
| 6,593,088 B1 | 7/2003 | Saito et al. |
| 6,613,508 B1 | 9/2003 | Ness et al. |
| 6,620,584 B1 | 9/2003 | Chee et al. |
| 6,620,587 B1 | 9/2003 | Taussig et al. |
| 6,780,981 B1 | 8/2004 | Southern et al. |
| 6,936,477 B2 | 8/2005 | Still et al. |
| 7,070,928 B2 | 7/2006 | Liu et al. |
| 7,223,545 B2 | 5/2007 | Liu et al. |
| 7,413,854 B2 | 8/2008 | Pedersen et al. |
| 7,442,160 B2 | 10/2008 | Liu et al. |
| 7,479,472 B1 | 1/2009 | Harbury et al. |
| 7,491,494 B2 | 2/2009 | Liu et al. |
| 7,557,068 B2 | 7/2009 | Liu et al. |
| 7,704,925 B2 | 4/2010 | Gouliaev et al. |
| 7,727,713 B2 | 6/2010 | Pedersen et al. |
| 7,771,935 B2 | 8/2010 | Liu et al. |
| 7,915,201 B2 | 3/2011 | Franch et al. |
| 7,998,904 B2 | 8/2011 | Liu et al. |
| 8,206,901 B2 | 6/2012 | Freskgard et al. |
| 2002/0048760 A1 | 4/2002 | Drmanac et al. |
| 2002/0055125 A1 | 5/2002 | Charych et al. |
| 2002/0072887 A1 | 6/2002 | Szalma et al. |
| 2002/0081714 A1 | 6/2002 | Jain et al. |
| 2002/0115068 A1 | 8/2002 | Tomlinson et al. |
| 2002/0127598 A1 | 9/2002 | Zhou et al. |
| 2002/0142335 A1 | 10/2002 | Strittmatter |
| 2003/0004122 A1 | 1/2003 | Beigelman et al. |
| 2003/0050453 A1 | 3/2003 | Sorge |
| 2003/0113738 A1 | 6/2003 | Liu et al. |
| 2003/0182068 A1 | 9/2003 | Battersby et al. |
| 2003/0186233 A1 | 10/2003 | Chesnut et al. |
| 2004/0049008 A1 | 3/2004 | Pedersen et al. |
| 2004/0110213 A1 | 6/2004 | Namsaraev |
| 2004/0161741 A1 | 8/2004 | Rabani et al. |
| 2004/0185484 A1 | 9/2004 | Costa et al. |
| 2004/0191812 A1 | 9/2004 | Davydova et al. |
| 2004/0197845 A1 | 10/2004 | Hassibi et al. |
| 2004/0209282 A1 | 10/2004 | Ault-Riche et al. |
| 2005/0025766 A1 | 2/2005 | Liu et al. |
| 2005/0042669 A1 | 2/2005 | Liu et al. |
| 2005/0130173 A1 | 6/2005 | Leamon et al. |
| 2005/0142583 A1 | 6/2005 | Liu et al. |
| 2005/0158765 A1 | 7/2005 | Morgan et al. |
| 2005/0170376 A1 | 8/2005 | Liu et al. |
| 2006/0099592 A1 | 5/2006 | Freskgard et al. |
| 2006/0121470 A1 | 6/2006 | Pedersen |
| 2006/0234231 A1 | 10/2006 | Freskgard et al. |
| 2006/0246450 A1 | 11/2006 | Franch et al. |
| 2006/0269920 A1 | 11/2006 | Freskgard et al. |
| 2006/0292603 A1 | 12/2006 | Gouliaev et al. |
| 2007/0026397 A1 | 2/2007 | Freskgard et al. |
| 2007/0042401 A1 | 2/2007 | Morgan et al. |
| 2007/0224607 A1 | 9/2007 | Morgan et al. |
| 2008/0193983 A1 | 8/2008 | Gouliaev et al. |
| 2008/0305957 A1 | 12/2008 | Thisted et al. |
| 2009/0035824 A1 | 2/2009 | Liu et al. |
| 2009/0143232 A1 | 6/2009 | Pedersen et al. |
| 2009/0149347 A1 | 6/2009 | Liu et al. |
| 2009/0239211 A1 | 9/2009 | Freskgard et al. |
| 2009/0264300 A1 | 10/2009 | Franch et al. |
| 2010/0016177 A1 | 1/2010 | Pedersen et al. |
| 2011/0230419 A1 | 9/2011 | Lundorf et al. |
| 2012/0028812 A1 | 2/2012 | Freskgard et al. |

FOREIGN PATENT DOCUMENTS

| | | |
|---|---|---|
| EP | 0 324 616 B1 | 7/1989 |
| EP | 0 542 770 B1 | 5/1993 |
| EP | 0 604 552 B1 | 7/1994 |
| EP | 0 643 778 B1 | 3/1995 |
| EP | 0 695 305 B1 | 2/1996 |
| EP | 0 766 826 B1 | 4/1997 |
| EP | 0 773 227 A1 | 5/1997 |
| EP | 0 776 330 B1 | 6/1997 |
| EP | 0 778 280 B1 | 6/1997 |
| EP | 0 879 219 B1 | 11/1998 |
| EP | 0 962 527 B1 | 12/1999 |
| EP | 1 324 045 A2 | 7/2003 |
| EP | 1 402 024 B1 | 3/2004 |
| EP | 1 483 585 B1 | 12/2004 |
| EP | 1 514 938 A1 | 3/2005 |
| EP | 1 533 385 A1 | 5/2005 |
| EP | 1 828 381 B1 | 9/2007 |
| EP | 1 832 567 A2 | 9/2007 |
| EP | 2 305 808 | 4/2011 |
| JP | 05292967 | 11/1993 |
| JP | 08000268 | 1/1996 |
| WO | WO 90/05785 | 5/1990 |
| WO | WO 91/05058 | 4/1991 |
| WO | WO 91/19818 | 12/1991 |
| WO | WO 92/00091 | 1/1992 |
| WO | WO 92/02536 | 2/1992 |
| WO | WO 92/22875 | 12/1992 |
| WO | WO 93/03172 | 2/1993 |
| WO | WO 93/06121 | 4/1993 |
| WO | WO 93/20242 | 10/1993 |
| WO | WO 94/08051 | 4/1994 |
| WO | WO 94/13623 | 6/1994 |
| WO | WO 94/24143 | 10/1994 |
| WO | WO 95/04160 | 2/1995 |
| WO | WO 95/06293 | 3/1995 |

(56) References Cited

FOREIGN PATENT DOCUMENTS

| | | |
|---|---|---|
| WO | WO 95/12608 | 5/1995 |
| WO | WO 96/03418 | 2/1996 |
| WO | WO 96/09316 | 3/1996 |
| WO | WO 96/11878 | 4/1996 |
| WO | WO 96/12014 | 4/1996 |
| WO | WO 96/24061 | 8/1996 |
| WO | WO 96/24847 | 8/1996 |
| WO | WO 96/35699 | 11/1996 |
| WO | WO 96/40201 | 12/1996 |
| WO | WO 96/41011 | 12/1996 |
| WO | WO 97/04131 | 2/1997 |
| WO | WO 97/11958 | 4/1997 |
| WO | WO 97/19039 | 5/1997 |
| WO | WO 97/27317 | 7/1997 |
| WO | WO 97/35198 | 9/1997 |
| WO | WO 98/01562 | 1/1998 |
| WO | WO 98/31700 | 7/1998 |
| WO | WO 98/47613 | 10/1998 |
| WO | WO 98/56904 | 12/1998 |
| WO | WO 98/58256 | 12/1998 |
| WO | WO 99/42605 | 8/1999 |
| WO | WO 99/51546 | 10/1999 |
| WO | WO 99/51773 | 10/1999 |
| WO | WO 99/64378 | 12/1999 |
| WO | WO00/20639 | 4/2000 |
| WO | WO 00/21909 | 4/2000 |
| WO | WO 00/23456 | 4/2000 |
| WO | WO 00/23458 | 4/2000 |
| WO | WO 00/24882 | 5/2000 |
| WO | WO 00/32823 | 6/2000 |
| WO | WO 00/40695 | 7/2000 |
| WO | WO 00/47775 | 8/2000 |
| WO | WO 00/61775 | 10/2000 |
| WO | WO 01/00876 | 1/2001 |
| WO | WO 01/07657 | 2/2001 |
| WO | WO 01/07690 | 2/2001 |
| WO | WO 01/53539 | 7/2001 |
| WO | WO 01/56955 | 8/2001 |
| WO | WO 01/90414 | 11/2001 |
| WO | WO 02/03067 | 1/2002 |
| WO | WO 02/10186 | 2/2002 |
| WO | WO 02/34948 | 5/2002 |
| WO | WO 02/40664 | 5/2002 |
| WO | WO 02/074929 | 9/2002 |
| WO | WO 02/074978 | 9/2002 |
| WO | WO 02/083951 | 10/2002 |
| WO | WO 02/099078 | 12/2002 |
| WO | WO 02/102820 | 12/2002 |
| WO | WO 02/103008 | 12/2002 |
| WO | WO 03/025567 | 3/2003 |
| WO | WO 03/062417 | 7/2003 |
| WO | WO 03/076943 | 9/2003 |
| WO | WO 03/078050 | 9/2003 |
| WO | WO 03/078445 | 9/2003 |
| WO | WO 03/078446 | 9/2003 |
| WO | WO 03/078625 | 9/2003 |
| WO | WO 03/078626 | 9/2003 |
| WO | WO 03/078627 | 9/2003 |
| WO | WO 03/082901 | 10/2003 |
| WO | WO 03/106679 | 12/2003 |
| WO | WO 2004/001042 | 12/2003 |
| WO | WO 2004/007529 | 1/2004 |
| WO | WO 2004/009814 | 1/2004 |
| WO | WO 2004/013070 | 2/2004 |
| WO | WO 2004/016767 | 2/2004 |
| WO | WO 2004/024929 | 3/2004 |
| WO | WO 2004/039825 | 5/2004 |
| WO | WO 2004/039962 | 5/2004 |
| WO | WO 2004/042019 | 5/2004 |
| WO | WO 2004/056994 | 7/2004 |
| WO | WO 2004/074429 | 9/2004 |
| WO | WO 2004/074501 | 9/2004 |
| WO | WO 2004/083427 | 9/2004 |
| WO | WO 2004/099441 | 11/2004 |
| WO | WO 2004/110964 | 12/2004 |
| WO | WO 2005/003778 | 1/2005 |
| WO | WO 2005/008240 | 1/2005 |
| WO | WO 2005/026387 | 3/2005 |
| WO | WO 2005/058479 | 6/2005 |
| WO | WO 2005/078122 | 8/2005 |
| WO | WO 2005/090566 | 9/2005 |
| WO | WO 2005/116213 | 12/2005 |
| WO | WO 2006/048025 | 5/2006 |
| WO | WO 2006/053571 | 5/2006 |
| WO | WO 2006/069063 | 6/2006 |
| WO | WO 2006/079061 | 7/2006 |
| WO | WO 2006/128138 | 11/2006 |
| WO | WO 2006/130669 | 12/2006 |
| WO | WO 2006/133312 | 12/2006 |
| WO | WO 2006/135654 | 12/2006 |
| WO | WO 2006/135786 | 12/2006 |
| WO | WO 2006/138560 | 12/2006 |
| WO | WO 2006/138666 | 12/2006 |
| WO | WO 2007/008276 | 1/2007 |
| WO | WO 2007/011722 | 1/2007 |
| WO | WO 2007/016488 | 2/2007 |
| WO | WO 2007/053358 | 5/2007 |
| WO | WO 2007/062664 | 6/2007 |
| WO | WO 2007/124758 | 11/2007 |
| WO | WO 2008/014238 | 1/2008 |
| WO | WO 2008/036273 | 3/2008 |
| WO | WO 2008/054600 | 5/2008 |
| WO | WO 2009/018003 | 2/2009 |
| WO | WO 2009/077173 | 6/2009 |
| WO | WO 2009/152824 | 12/2009 |
| WO | WO 2011/127933 | 10/2011 |

OTHER PUBLICATIONS

Response to European Search Report in European application No. 10184311.8, dated Feb. 6, 2012.
Response to Office Action in European application No. 08169346.7, dated Feb. 10, 2012.
Office Action in European application No. 08169346.7, dated Feb. 24, 2012.
Annex to Office Action in European application No. 08169346.7, dated Feb. 24, 2012.
Response to Office Action in European application No. 09154197.9, dated Aug. 5, 2011.
Office Action in European application No. 09154197.9, dated Sep. 12, 2011.
Annex to Office Action in European application No. 09154197.9, dated Sep. 12, 2011.
European Search Report in European application No. 10183942.1, dated Feb. 6, 2012.
European Search Opinion in European application No. 10183942.1 dated Feb. 6, 2012.
Communication re partial European Search Report in European application No. 10184069.2, dated Feb. 10, 2012.
Partial European Search Report in European application No. 10184069.2, dated Feb. 3, 2012.
Response to Invitation in European application No. 10192717.6, dated Aug. 5, 2011.
Communication re European Search Report in European application No. 10192717.6, dated Oct. 7, 2011.
Partial European Search Report in European application No. 10192717.6, dated Oct. 7, 2011.
Response to Partial European Search Report in European application No. 10192717.6, dated Dec. 8, 2011.
European Search Report in European application No. 10192717.6, dated Jan. 25, 2012.
European Search Opinion in European application No. 10192717.6, dated Jan. 25, 2012.
International Search Report in PCT/DK2011/000031, dated Aug. 23, 2011.
Opposition against EP 1558744 filed by Strawman Limited on Mar. 12, 2012.
Opposition against EP 1558744 filed by HGF on Mar. 14, 2012.
Annex I: Vipergen Technology Paper—The YoctoReactor drug discovery technology platform. 2 pages.—No Date.

(56) References Cited

OTHER PUBLICATIONS

Australian Patents Act 1990-Sectino 32 Regulation 3.6, (Request for a Determination of Dispute between Applicants) and 3.7 Application to Commissioner for Declaration of an Eligible Person.—No Date.
Abravaya, et al. "Detection of point mutations with a modified ligase chain reaction (GAP-LCR)", Nucleic Acids Research, vol. 23, No. 4, pp. 675-682 (1995).
Acevedo, et al. "Template-directed oligonucleotide ligation on hydroxylapatite", Nature, vol. 321, pp. 790-792 (Jun. 19, 1986).
Acevedo, et al., "Non-enzymatic Transcription of an Oligonucleotide 14 Residues Long", J. Mol. Biol., vol. 197, pp. 187-193 (1987).
Acinas, et al. "PCR-Induced Sequence Artifacts and Bias: Insights from Comparison of Two 16S rRNA Clone Libraries Constructed from the Same Sample", Applied and Environmental Microbiology, vol. 71, No. 12, pp. 8966-8969 (2005).
Agarwal, et al. "Total Synthesis of the gene for an alanine transfer ribonucleic acid from yeast", Abstract only, Nature, vol. 227, pp. 27-34 (1970).
Albagli, et al., "Chemical Amplification (CHAMP) by a Continuous, Self-Replicating Oligonucleotide-Based System", J. Am. Chem. Soc., vol. 121, pp. 6954-6955,(1999).
Annex I: Vipergen Technology Paper—The YoctoReactor® drug discovery technology platform. 2 pages.
Annex II: Vipergen Technology Paper—The YoctoReactor drug discovery technology platform. 2 pages. Aug. 2008.
Anonymous. "5,6-Dihydro-Pyrimidines, 2'-Phosphoramidites", Glen Research Report, vol. 10, 1997 (December issue), p. 11.
Anonymous. "Cytofectin GSV Transfection Protocol", Glen Research Report, vol. 10, 1997 (December issue), p. 4.
Anonymous. "More Novel Monomers -4-Thio-dU, 5'-Amino-dT, 2'-F-Pyrimidines", Glen Research Report, vol. 10, 1997 (December issue), p. 10.
Anonymous. "New Fluorescent Reagents—Tamra CPG, Fluorescein-dt", Glen Research Report, vol. 10, 1997 (December issue), p. 7.
Anonymous. "Non-enzymatic Ligation of Single-Stranded and Duplex DNA", Glen Research Report, vol. 10, 1997 (December issue), p. 12.
Anonymous. "Preparing Oligonucleotides for Antisensen Experiments", Glen Research Report, vol. 10, 1997 (December issue), p. 3.
Anonymous. "Q-Supports Reduce Cleavage Time to 2 Minutes", Glen Research Report, vol. 10, 1997 (December issue), p. 9.
Anonymous. "Universal Support Replaces Individual Columns", Glen Research Report, vol. 10, 1997 (December issue), p. 8.
Anonymous. "DCI—A Logical Alternative Aviator", Glen Research Report, vol. 10, No. 1, 1-2 (1997).
Australian Patents Act 19909-Section 32 Regulation 3.6, (Request for a Determination of Dispute Between Applicants) and 3.7 Application to Commissioner for Declaration of an Eligible Person.
Baldwin, "Design, synthesis and use of binary encoded synthetic chemical libraries", Molecular Diversity, vol. 2, pp. 81-88 (1996).
Baldwin, et al. "Synthesis of a Small Molecule Combinatorial Library Encoded with Molecular Tags", J. Am. Chem. Soc., vol. 117, pp. 5588-5589 (1995).
Baran, et al. "Total synthesis of marine natural products without using protecting groups", Nature, vol. 446, pp. 404-408 (2007).
Barany, "Genetic disease detection and DNA amplification using cloned thermostable ligase", Proc. Natl. Acad. Sci., vol. 88, pp. 189-193 (1991).
Barany, "The ligase chain reaction in a PCR world", Genome Res., vol. 1, pp. 5-16 (1991).
Barany, "The *Taq*I star reaction: strand preferences reveal hydrogen-bond donor and acceptor sites in canonical sequence recognition", Gene vol. 65; pp. 149-165 (1988).
Battersby, et al. "Optical encoding of microbeads for gene screening: alternatives to microarrays", Drug Discovery Today, vol. 6, No. 12 (Suppl.), pp. S19-S26 (2001).
Bayer, et al. "Liquid Phase Synthesis of Peptides", Nature, vol. 7; 237, pp. 512-513 (Jun. 30, 1972).

Benner, "Expanding the genetic lexicon: incorporating non-standard amino acids into proteins by ribosome-based synthesis". Trends in Biotechnology, vol. 12, No. 5, pp. 158-163 (May 1994).
Berger, et al., "Universal bases for hybridization, replication and chain termination", Nucleic Acids Research, vol. 28, No. 15, pp. 2911-2914 (2000).
Bittker, et al. "Nucleic acid evolution and minimization by nonhomologous random recombination", Nature Biotechnology, vol. 20, pp. 1024-1029 (Oct. 2002).
Bittker, et al., "Recent advances in the in vitro evolution of nucleic acids", Current Opinion in Chemical Biology, vol. 6, No. 3, pp. 367-374 (2002).
Bëhler, et al., "Template switching between PNA and RNA oligonucleotides", Nature, vol. 376, pp. 578-581 (Aug. 17, 1995).
Bonora, et al. "Large Scale, PEG-Supported DNA Synthesis"; Nucleosides & Nucleotides, vol. 10, No. 1-3, p. 269-273 (1991).
Borman, "Combinatorial chemists focus on small molecules, molecular recognition, and automation", Chemical & Engineering News, pp. 29-54 (Feb. 12, 1996).
Braasch, et al. "Locked nucleic acid (LNA): fine-tuning the recognition of DNA and RNA", Chemistry & Biology, vol. 8, pp. 1-7 (2001).
Braun, et al. "DNA-templated assembly and electrode attachment of a conducting silver wire". Nature, vol. 391, pp. 775-778 (Feb. 19, 1998).
Brennan, et al. "Using T4 RNA Ligase with DNA Substrates", Methods in Enzymology, vol. 100, pp. 38-52 (1983).
Brenner, et al. "Encoded combinatorial chemistry", Proc Natl. Acad. Sci. USA, vol. 89, pp. 5381-5383 (Jun. 1992).
Broude, "Stem-loop oligonucleotides: a robust tool for molecular biology and biotechnology", TRENDS in Biotechnology, vol. 20, No. 6, pp. 249-256 (Jun. 2002).
Bruick, et al., "A simple procedure for constructing 5'-amino terminated oligodeoxynucleotides in aqueous solution", Nucleic Acids Research, vol. 25, No. 6, pp. 1309-1310 (1997).
Bruick, et al. "Template-directed ligation of peptides to oligonucleotides", Chemistry & Biology, vol. 3, No. 1, pp. 49-56 (Jan. 1996).
Buller, "Design and synthesis of a novel DNA-encoded chemical library using Diels-Alder cycloadditions", Bioorg Med. Chem. Lett., vol. 18, pp. 5926-5931 (2008).
Buller, "Discovery of TNF Inhibitors from a DNA-Encoded Chemical Library based on Diels-Alder Cycloaddition", Chemistry & Biology, vol. 16, pp. 1075-1086 (2009).
Buller, "Drug Discovery with DNA-Encoded Chemical Libraries", Bioconjugate Chem., vol. 21, No. 9, pp. 1571-1580, (2010).
Bunin, et al. "Synthesis and Evaluation of 1,4-Benzodiazepine Libraries", Methods in Enzymology, vol. 267, pp. 448-465 (1996).
Bunin, et al. "The combinatorial synthesis and chemical and biological evaluation of a 1,4- benzodiazepine library", Proc. Natl. Acad. Sci. USA, vol. 91, pp. 4708-4712 (May 1994).
Buskirk, et al. "Engineering a Ligand-Dependent RNA Transcriptional Activator", Chemistry & Biology, vol. 11, pp. 1157-1163 (2004). This work is featured in a Research Highlight in Nature Methods, vol. 1, pp. 6-7 (2004).
Calderone, et al., "Nucleic-acid-templated synthesis as a model system for ancient translation", Current Opinion in Chemical Biology, vol. 8, pp. 645-653 (2004).
Calderone, et al. "Directing Otherwise Incompatible Reactions in a Single Solution by Using DNA-Templated Organic Synthesis", Angew. Chem. Int. Ed, vol. 41, No. 21, pp. 4104-4108 (2002).
Canne, et al. "Chemical Protein Synthesis by Solid Phase Ligation of Unprotected Peptide Segments", J. Am. Chem. Soc., vol. 121, pp. 8720-8727 (1999).
Chan, et al., "Intra-tRNA distance measurements for nucleocapsid protein-dependent tRNA unwinding during priming of HIV reverse transcription", Proc. Natl. Acad. Sci. USA, vol. 96, pp. 459-464 (Jan. 1999).
Chen, et al., "Template-directed Synthesis on Oligodeoxycytidylate and Polydeoxycytidylate Templates", J. Mol. Biol., vol. 181, pp. 271-279 (1985).

(56) References Cited

OTHER PUBLICATIONS

Chen, et al. "Enzyme Engineering for Nonaqueous Solvents: Random Mutagenesis to Enchance Activity of Subtilisin E in Polar Organic Media"; Bio/Technology, vol. 9, pp. 1073-1077 (1991) abstract.

Chen, et al. "Enzymes in Nonaqueous Solvents Applications in Carbohydrate and Peptide Preparation", Methods in Biotechnology, vol. 15, pp. 373-374 (2001).

Chu, et al. "Ligation of oligonucleotides to nucleic acids or proteins via disulfide bonds", vol. 16, No. 9, pp. 3671-3691 (1988).

Clark, et al. "Design, synthesis and selection of DNA-encoded small-molecule libraries", Nature Chemistry Biology, vol. 5, No. 9, pp. 647-654 (Sep. 2009).

Clark, "Selecting chemicals: the emerging utility of DNA-encoded libraries", Current Opinion in Chemical Biology, vol. 14, pp. 396-403 (2010).

Colombo, et al. "Synthesis of Leucin-Enkephalin and Methionine-Enkephalin on a p-Alkoxybenzyl-Modified Soluble Support", Hoppe-Seyler's Z. Physiol. Chem., vol. 362, pp. 1385-1391 (Oct. 1981).

Costantino, et al. "Privileged Structures as Leads in Medicinal Chemistry", Current Medicinal Chemistry, vol. 13, pp. 65-85 (2006).

Cotton, et al. "Reactivity of cytosine and thymine in single-base-pair mismatches with hydroxylamine and osmium tetroxide and its application to the study of mutations", Proc Natl. Acad. Sci. USA, vol. 85, pp. 4397-4401 (Jun. 1988).

Cousins, et al. "Identification and Isolation of a Receptor for N-Methyl Alkylammonium Salts: Molecular Amplification in a Pseudo-peptide Dynamic Combinatorial Library", Angew. Chem. Int. Ed., vol. 40, No. 1, pp. 423-427 (2001).

Czarnik, "Encoding strategies in combinatorial chemistry", Proc. Natl. Acad. Sci. USA, vol. 94, pp. 12738-12739 (Nov. 1997).

Czarnik, "Encoding methods for combinatorial chemistry", Current Opinion in Chemical Biology, vol. 1, pp. 60-66 (1997).

Czlapinski, et al. "Nucleic Acid Template-Directed Assembly of Metallosalen-DNA Conjugates", J. Am. Chem. Soc., vol. 123, No. 35, pp. 8618-8169 (2001).

Degn, et al. "Enzyme Activity in Organic Solvent as a Function of Water Activity Determined by Membrane Inlet Mass Spectrometry"; Biotechnology Techniques, vol. 6; No. 2, pp. 161-164-p. 161 (Mar./Apr. 1982).

De Napoli, et al. "PEG-supported Synthesis of Cyclic Oligodeoxyribonucleotides", Nucleosides & Nucleotides, vol. 12, No. 1, pp. 21-30 (1993).

Dewitt, et al. "Diversomers: An approach to nonpeptide, nonoligomeric chemical diversity", Proc. Natl. Acad. Sci. USA, vol. 90, pp. 6909-6913 (Aug. 1993).

"DNA Phosphoramidites & CPG's"; http://www.qualitysystems.com.tw/proligo/dna%20phosphoamidites%20&%20cpg's.htm Dec. 2, 2010.

"Dokl Akad Nauk SSSR", vol. 258, pp. 1242-1245, Krynetskya NF Tumanov YV (1981).

Dolinnaya, et al. "Chemical ligation as a method for the assembly of double-stranded nucleic acids: Modifications and local structure studies", Russian Chemical Bulletin, vol. 45, No. 8, pp. 1787-1809 (Aug. 1996).

Dolinnaya, et al. "Structural and kinetic aspects of chemical reactions in DNA duplexes. Information on DNA local structure obtained from chemical ligation data", Nucleic Acids Research, vol. 19, No. 11, pp. 3073-3080 (1991).

Douglas, et al. "Polymer-Supported Solution Synthesis of Oligosaccharides", J. Am. Chem. Soc., vol. 113, pp. 5095-5097 (1991).

Dower, et al. "In vitro selection as a powerful tool for the applied evolution of proteins and peptides", Current Opinion in Chemical Biology, vol. 6, pp. 390-398 (2002).

Doyon, et al. "Highly Sensitive in Vitro Selections for DNA-Linked Synthetic Small Molecules with Protein Binding Affinity and Specificity", J. Am. Chem. Soc, vol. 125, pp. 12372-12373 (2003).

Doyon, et al. "Highly Sensitive in Vitro Selections for DNA-Linked Synthetic Small Molecules with Protein Binding Affinity and Specificity", J. Am. Chem. Soc, pp. S1-S8 (2003).

Drabovich, et al. "Selection of Smart Small-Molecule Ligands: The Proof of Principle", Analytical Chemistry, vol. 81, No. 1, pp. 490-494 (2009).

Drews, "Drug Discovery: A Historical Perspective", Science, vol. 287, pp. 1960-1964 (2000).

Dreyer, et al. "Enzyme Catalysis in Nonaqueous Media: Past, Present and Future" in Patel (ed.), "Biocatalysis in the Pharmaceutical and Biotechnology Industries", 37 pages (2006).

Ecker, et al. "Rational screening of oligonucleotide combinatorial libraries for drug discovery", Nucleic Acids Research, vol. 21, No. 8, pp. 1853-1856 (1993).

Elghanian, et al. "Selective Colorimetric Detection of Polynucleotides Based on the Distance-Dependent Optical Properties of Gold Nanoparticles", Science, vol. 277, pp. 1078-1081 (Aug. 22, 1997).

Ellman, et al. "Biosynthetic Method for Introducing Unnatural Amino Acids Site-Specifically into Proteins". Methods in Enzymology, vol. 202, pp. 301-336 (1991).

Fack, et al. "Heteroduplex mobility assay (HMA) pre-screening: An improved strategy for the rapid identification of inserts selected from phage-displayed peptide libraries", Molecular Diversity, vol. 5, pp. 7-12 (2000).

Fegan, et al. "Rigid cyanine dye nucleic acid labels", Chem. Commun., pp. 2004-2006 (2008).

Ficht, et al. "As Fast and Selective as Enzymatic Ligations: Upaired Nucleobases Increase the Selectivity of DNA-Controlled Native Chemical PNA Ligation"; ChemBioChem, vol. 6, Issue 11, pp. 2098-2103 (2005) Abstract.

"Finding Reactions in a Haystack: Try'em All, See What Works", Science, vol. 305, p. 1558 (Sep. 10, 2004).

Fredriksson, et al. "Protein detection using proximity-dependent DNA ligation assays", Nature Biotechnology, vol. 20, pp. 473-477 (May 2002).

Frutos, et al. "Demonstration of a word design strategy for DNA computing on surfaces". Nucleic Acids Research, vol. 25, No. 23, pp. 4748-4757 (1997).

Fujimoto, et al., "Template-directed photochemical synthesis of branched oligodeoxynucleotides via 5-carboxyvinyldeoxyuridine", Tetrahedron Letters, vol. 41, pp. 9437-9440 (2000).

Fujimoto, et al., "Template-Directed Photoreversible Ligation of Deoxyoligonucleotides via 5-Vinyldeoxyuridine", J. Am. Chem. Soc., vol. 122, pp. 5646-5647 (2000).

Fujimoto, et al., Template-directed reversible photocircularization of DNA via 5-vinyldeoxycytidine, Tetrahedron Letters, vol. 41, pp. 6451-6454 (2000).

Furka, "Combinatorial Chemistry: 20 years on . . . ", Drug Discovery Today, vol. 7, No. 1, pp. 1-4 (Jan. 2002).

Furka, et al. "Combinatorial Libraries by Portioning and Mixing", Combinatorial Chemistry & High Throughput Screening, vol. 2, pp. 105-122 (1999).

Furlan, et al. "Molecular amplification in a dynamic combinatorial libary using non-covalent interactions". Chem. Commun., pp. 1761-1762 (2000).

Gartner, et al., "Expanding the Reaction Scope of DNA-Templated Synthesis", Angew. Chem. Int. Ed., vol. 41, No. 10, pp. 1796-1800 (2002).

Gartner, et al., "DNA-Templated Organic Synthesis and Selection of a Library of Macrocycles", Science, vol. 305, pp. 1601-1605 (Sep. 10, 2004).

Gartner, et al. "Multistep Small-Molecule Synthesis Programmed by DNA Templates". J. Am. Chem. Soc., vol. 124, No. 35, pp. 10304-10306 (2002).

Gartner, et al., "The Generality of DNA-Templated Synthesis as a Basis for Evolving Non-Natural Small Molecules", J. Am. Chem. Soc., vol. 123, No. 28, pp. 6961-6963 (2001).

Gartner, et al. "Two Enabling Architectures for DNA-Templated Organic Synthesis". Angew. Chem. Int. Ed., vol. 42, No. 12, pp. 1370-1375 (2003).

(56) References Cited

OTHER PUBLICATIONS

Geysen, et al. "Combinatorial Compound Libraries for Drug Discovery: An Ongoing Challenge", Nature Reviews Drug Discovery, vol. 2, pp. 222-230 (Mar. 2003).
Gordon, et al. "Applications of Combinatorial Technologies to Drug Discovery. 2. Combinatorial Organic Synthesis, Library Screening Strategies, and Future Directions". Journal of Medicinal Chemistry, vol. 37, No. 10, pp. 1385-1401 (May 13, 1994).
Gorin, et al. "Reactivity-Dependent PCR: Direct, Solution-Phase in Vitro Selection for Bond Formation", J. Am. Chem. Soc., vol. 131, pp. 9189-9191 (2009).
Grange, et al. "Detection of point mutations in type I collagen by RNase digestion of RNA/RNA hybrids", Nucleic Acids Research, vol. 18, No. 14, pp. 4227-4236 (1990).
Grubina, et al. "DNA-Templated Synthesis of a Synthetic Small Molecule Library", The Nucleus, vol. LXXXII, No. 5, pp. 10-14 (Jan. 2004).
Gruen, et al. "An in vivo selection system for homing endonuclease activity", Nucleic Acids Research, vol. 30, No. 7 e29, 6 pages (2002).
Gryaznov, et al., "Template controlled coupling and recombination of oligonucleotide blocks containing thiophosphoryl groups", Nucleic Acids Research, vol. 21, No. 6, pp. 1403-1408 (1993).
Gryaznov, et al., "Chemical Ligation of Oligonucleotides in the Presence and Absence of a Template", J. Am. Chem. Soc., vol. 115, No. 9, pp. 3808-3809 (1993).
Gryaznov, et al., "Enhancement of selectivity in recognition of nucleic acids via chemical autoligation", Nucleic Acids Research, vol. 22, No. 12, pp. 2366-2369 (1994).
Gumport, et al. "T4 RNA Ligase as a Nucleic Acid Synthesis and Modification Reagent", Elsevier North Holland, Inc., pp. 314-345 (1981).
Guo, et al. "Preparation of Encoded Combinatorial Libraries for Drug Discovery", Methods in Molecular Biology, Combinatorial Library Methods and Protocols, pp. 23-39 (2002).
Halpin, et al. "DNA display I. Sequence-Encoded Routing of DNA Populations", PLoS Biology, vol. 2, Issue 7, pp. 1015-1021 (Jul. 2004).
Halpin, et al. "DNA Display II. Genetic Manipulation of Combinatorial Chemistry Libraries for Small-Molecule Evolution", PLoS Biology, vol. 2, Issue 7, pp. 1022-1030 (Jul. 2004).
Halpin, et al., "DNA Display III. Solid-Phase Organic Synthesis on Unprotected DNA", PLoS Biology, vol. 2, Issue 7, pp. 1031-1038 (Jul. 2004).
Hansen, et al. "A Yoctoliter-Scale DNA Reactor for Small-Molecule Evolution", J. Am. Chem. Soc., vol. 131, pp. 1322-1327 (2009).
Harada, et al. "In vitro selection of optimal DNA substrates for T4 RNA ligase", Proc. Natl. Acad. Sci. USA, vol. 90, pp. 1576-1579 (Feb. 1993).
Harada, et al. "Unexpected substrate specificity of T4 DNA ligase revealed by in vitro selection", Nucleic Acids Research, vol. 21, No. 10, pp. 2287-2291 (1993).
Harada, et al. "In Vitro Selection of Optimal DNA Substrates for Ligation by a Water-Soluble Carbodiimide", J Mol Evol, vol. 38, pp. 558-560 (1994).
Herpin, et al. "Synthesis of a 10 000 Member 1,5-Benzodiazepine-2-one Library by the Directed Sorting Method", J. Comb. Chem., vol. 2, No. 5, pp. 513-521 (2000).
Herrlein, et al. "Selective chemical autoligation on a double-stranded DNA template", *Nucleic Acids Research*, vol. 22, No. 23, pp. 5076-5078 (1994).
Higgins, et al. "Addition of oligonucleotides to the 5'-terminus of DNA by T4 RNA ligase", Nucleic Acids Research, vol. 6, No. 3, pp. 1013-1024 (Mar. 1979).
Higgins, et al. "DNA-Joining Enzymes: A Review", Methods in Enzymology, vol. 68, pp. 50-71 (1979).
Hinton, et al. "T4 RNA Ligase Joins 2'-Deoxyribonucleoside 3', 5'-Bisphosphates to Oligodeoxyribonucleotides", Biochemistry, vol. 17, No. 24, pp. 5091-5097 (1978).
Holmes, "Model Studies for New o-Nitrobenzyl Photolabile Linkers: Substituent Effects on the Rates of Photochemical Cleavage", J. Org. Chem., vol. 62, No. 8, pp. 2370-2380 (1997).
Housby, et al. "Fidelity of DNA ligation: a novel experimental approach based on the polymerisation of libraries of oligonucleotides", Nucleic Acids Research, vol. 26, No. 18, pp. 4259-4266 (1998).
Hsu, et al. "Detection of DNA point mutations with DNA mismatch repair enzymes" Carcinogenesis, vol. 15, No. 8, pp. 1657-1662 (1994).
Inoue, et al. "A nonenzymatic RNA polymerase model", Science, vol. 219, pp. 859-862 (Feb. 18, 1983).
Inoue, et al. Oligomerization of (Guanosine 5'-phosphor)-2-methylimidazolide on Poly(C), J. Mol. Biol., vol. 162, pp. 201-217 (1982).
Ito, et al. "Tag-Reporter and Resin Capture—Release Strategy in Oligosaccharide Synthesis", Chem. Eur. J., vol. 8, No. 14, pp. 3076-3084 (2002).
James, et al. "The Fidelity of Template-Directed Oligonucleotide Ligation and the Inevitability of Polymerase Function", Origins of Life and Evolution of the Biosphere, vol. 29, pp. 375-390 (1999).
Janda, "Tagged versus untagged libraries: Methods for the generation and screening of combinatorial chemical libraries", Proc. Natl. Acad. Sci. USA, vol. 91, pp. 10779-10785 (Nov. 1994).
Jäschke, et al. "Evolution of DNA and RNA as catalysts for chemical reactions"; Current Opinion in Chemical Biology, vol. 4, pp. 257-262 (2000).
Jäschke, et al. "Synthesis and properties of oligodeoxyribonucleotide—polyethylene glycol conjugates", Nucleic Acids Research, vol. 22, No. 22, pp. 4810-4817 (1994).
Jones, et al. "Enzymes in organic synthesis. 22. Effects of organic solvents on horse liver alcohol dehydrogenase-catalyzed reduction"; Can. J. Chem., vol. 60, pp. 335-338 (1982).
Kahn, "DNA Ligases": http://adnadn.umd.edu/biochem/kahn/molmachines/replication/DNA%20ligase.htm, 4 pages downloaded Dec. 10, 2009.
Kanagawa, Bias and Artifacts in Multitemplate Polymerase Chain Reactions (PCR), Journal of Bioscience and Bioengineering, vol. 96, No. 4, pp. 317-323 (2003).
Kanan, et al. "Reaction Discovery Enabled by DNA-Templated Synthesis and In Vitro Selection", Supplementary Information, pp. 1-20 (2004).
Kanan, et al. "Reaction discovery enabled by DNA-templated synthesis and in vitro selection", Nature, vol. 431, pp. 545-549 (Sep. 30, 2004).
Keiler, et al., "Role of peptide tagging system in degradation of proteins synthesized from damaged messenger RNA", Science, vol. 271, pp. 990-993 (Feb. 16, 1996).
Kerr, et al. "Encoded Combinatorial Peptide Libraries Containing Non-Natural Amino Acids", J. Am. Chem. Soc., vol. 115, pp. 2529-2531 (1993).
Kinoshita, et al. "Enzymatic synthesis of code regions for encoded combinatorial chemistry (ECC)", Nucleic Acids Symposium Series, vol. 34, pp. 201-202 (1995).
Kinoshita, et al. "Strand Ligation in a Double-stranded DNA by T4 RNA Ligase", Chemistry Letters, vol. 9, pp. 797-798 (1996).
Klekota, et al. "Selection of DNA-Binding Compounds via Multistage Molecular Evolution". Tetrahedron 55, pp. 11687-11697 (1999).
Klibanov, "Why are enzymes less active in organic solvent than in water?"; Trends in Biotechnology; vol. 15, Issue 3, pp. 97-101; (Mar. 1, 1997) Abstract.
Krishna, "Developments and trends in enzyme catalysis in nonconventional media", Biotechnology Advances; vol. 20; Issues 3-4, pp. 239-267 (Nov. 2002) Abstract.
Krug, et al. "Reversal of T4 RNA Ligase", Biochemistry, vol. 21, No. 8, pp. 1858-1864 (1982).
Kurz, et al. "cDNA—Protein Fusions: Covalent Protein—Gene Conjugates for the In Vitro Selection of Peptides and Proteins", Chembiochem, vol. 2, pp. 666-672 (2001).
Kurz, et al. "An Efficient Synthetic Strategy for the Preparation of Nucleic Acid-Encoded Peptide and Protein Libraries for In Vitro

(56) References Cited

OTHER PUBLICATIONS

Evolution Protocols", Fourth International Electronic Conference on Synthetic Organic Chemistry (ECSOC-4), www.mdpi.org/ecsoc-4.htm, 5 pages, Sep. 1-30, 2000.

Kurz, et al. "Psoralen photo-crosslinked mRNA-puromycin conjugates: a novel template for the rapid and facile preparation of mRNA-protein fushions", Nucleic Acids Research, vol. 28, No. 18, 5 pages (2000).

Lebl, "Parallel Personal Comments on "Classical" Papers in Combinatorial Chemistry", J. Comb. Chem., vol. 1, pp. 3-24 (1999).

Lehman, "DNA Ligase: Structure, Mechanism, and Function; The joining of DNA chains by DNA ligase is an essential component of DNA repair, replication, and recombination", Science vol. 186, pp. 790-797 (Nov. 29, 1974).

Leitzel, et al. "Template-Directed Ligation: From DNA Towards Different Versatile Templates", The Chemical Record, vol. 1, pp. 53-62 (2001).

Letsinger, et al. "Chemical and photochemical ligation of oligonucleotide blocks", Nucleosides & Nucleotides, vol. 16, Nos. 5-6, pp. 643-652 (1997).

Lewis, et al. "Ligation of oligonucleotides by pyrimidine dimers—a missing 'link' in the origin of life?", Nature, vol. 298, pp. 393-396 (Jul. 22, 1982).

Li, et al. "DNA-Catalyzed Polymerization", J. Am. Chem. Soc., vol. 124, No. 5, pp. 746-747, (2002).

Li, et al. "Stereoselectivity in DNA-Templated Organic Synthesis and Its Origins". J. Am. Chem. Soc., vol. 125, No. 34, pp. 10188-10189 (2003).

Li, et al. "DNA-Templated Organic Synthesis: Nature's Strategy for Controlling Chemical Reactivity Applied to Synthetic Molecules", Angew. Chem. Int. Ed., vol. 43, pp. 4848-4870 (2004).

Li, et al. "Translation of DNA into Synthetic N-Acyloxazolidines", J. Am. Chem. Soc., vol. 126, pp. 5090-5092 (2004).

"Ligase", Answers.com: http://www.answers.com/topic/ligase, 15 pages [accessed Dec. 10, 2009].

Lim, et al. "Synthesis of DNA Dumbbells: Chemical vs. Enzymatic Ligation of Self-Complementary Oligonucleotides", Nucleosides, Nucleotides and Nucleic Acids; vol. 16, Issue 1 & 2, pp. 41-51 (Jan. 1997) Abstract only.

Lindström, et al. "An orthogonal oligonucleotide protecting group strategy that enables assembly of repetitive or highly structured DNAs"; Nucleic Acids Research, vol. 30, No. 19, p. e101 (Oct. 1, 2002).

Liu, "The Chemistry and Chemical Biology of Molecular Evolution", Liu Group Research Summary from the website of Professor David R. Liu, obtained from the website in Feb. 2005.

Liu, "The Chemistry and Chemical Biology of Molecular Evolution", website of Dr. D. R. Liu, publicly available Mar. 1, 2001. http://web.archive.org/web/20010301175107/http://evolve.havard.edu.

Liu, "The Chemistry and Chemical Biology of Molecular Evolution", website of Dr. D. R. Liu, publicly available Oct. 15, 2003. http://web.archive.org/web/20031015114255/http://evolve.havard.edu.

Liu, "The Chemistry and Chemical Biology of Molecular Evolution", website of Dr. D. R. Liu, publicly available Nov. 20, 2002. http://web.archive.org/web/20021120104204/http://evolve.havard.edu.

Liu, "The Chemistry of Molecular Evolution", website of Dr. D. R. Liu, publicly available Oct. 15, 2000. http://web.archive.org/web/20001015144553/http://evolve.havard.edu.

Liu, et al. "Denaturing high performance liquid chromatography (DHPLC) used in the detection of germline and somatic mutations", Nucleic Acids Research, vol. 26, No. 6, pp. 1396-1400 (1998).

Liu, et al., "DNA-Templated Synthesis as a Basis for the Evolution of Synthetic Molecules.", ORGN 612, Division of Organic Chemistry, The 225th ACS National Meeting, New Orleans, LA, 1 page (Mar. 23-27, 2003).

Liu, et al. "Engineering a tRNA and aminoacyl-tRNA synthetase for the site-specific incorporation on unnatural amino acids into proteins in vivo". Proc. Natl. Acad. Sci. USA, vol. 94, pp. 10092-10097 (Sep. 1997).

Liu, et al. "Optimized Synthesis of RNA-Protein Fusions for in vitro Protein Selection", Methods in Enzymology, vol. 318, pp. 268-293 (2000).

Liu, et al. "Progress toward the evolution of an organism with an expanded genetic code", Proc. Natl. Acad. Sci. USA, vol. 96, pp. 4780-4785 (Apr. 1999).

Liu, et al. "Template-directed photoligation of oligodeoxyribonucleotides via 4-thiothymidine", Nucleic Acids Research, vol. 26, 13, pp. 3300-33044 (1998).

Liu, "The Development of Amplifiable and Evolvable Unnatural Molecules", Harvard University, Department of Chemistry and Chemical Biology, Grant No. N00014-00-1-0596, 4 pages, Report dated Aug. 4, approved for public release.

Liu, "Translating DNA into Synthetic Molecules", PLoS Biology, vol. 2, Issue 7, pp. 905-906 (Jul. 2004).

Lobanov, TRENDS in Biotechnology, vol. 20, No. 2, pp. 86-87 (Feb. 2002).

Lockhart, et al. "Expression monitoring by hybridization to high-density oligonucleotide arrays", Nature Biotechnology, vol. 14, pp. 1675-1680 (Dec. 1996).

Loughlin, "Biotransformations in organic synthesis"; Bioresource Technology, vol. 74, pp. 49-62 (2000).

Lowe, et al. "Combinatorial Libraries for Studying Molecular Recognition", URL: http://www.iupac.org/symposia/proceedings/phuket97/lowe.html, 7 pages, downloaded in Jun. 2005.

Loweth, et al. "DNA-Based Assembly of Gold Nanocrystals", Angew. Chem. Int. Ed., vol. 38, No. 12, pp. 1808-1812 (1999).

Luebke, et al. "Nonenzymatic ligation of double-helical DNA by alternate-strand triple helix formation"; Nucleic Acids Research; vol. 20, No. 12, pp. 3005-3009 (1992).

Luo, et al. "Analysis of the Structure and Stability of a Backbone-Modified Oligonucleotide: Implications for Avoiding Product Inhibition in Catalytic Template-Directed Synthesis", J. Am. Chem. Soc., vol. 120, No. 13, pp. 3019-3031 (1998).

Luther, et al. "Surface-promoted replication and exponential amplification of DNA analogues". Nature, vol. 396, pp. 245-248 (Nov. 19, 1998).

MacLean, et al. "Encoded combinatorial chemistry: Synthesis and screening of a library of highly functionalized pyrrolidines", Proc. Natl. Acad. Sci. USA, vol. 94, pp. 2805-2810 (Apr. 1997).

Magliery, et al. "Expanding the Genetic Code In Vitro and In Vivo", The Genetic Code and the Origin of Life, Ed. Ribas de Pouplana, L. Landes Bioscience, In Press, pp. 221-249 (2004).

Makara, et al. "Improving success rates for lead generation using affinity binding technologies", Current Opinion in Biotechnology, vol. 16, pp. 666-673 (2005).

Mannocci, et al. "DNA-encoded affinity maturation libraries", 2nd International Symposium on DNA Encoded Chemical Libraries, 23 pages (Aug. 20, 2010).

Mannocci, "DNA-Encoded Chemical Libraries", Diss. ETH No. 18153, 172 pages (2009).

Margulies, et al., "Genome sequencing in microfabricated high-density picolitre reactors", Nature, vol. 437, pp. 376-380 (Sep. 15, 2005).

Mashal, et al. "Detection of mutations by cleavage of DNA heteroduplexes with bacteriophage resolvases", Nature Genetics, vol. 9, pp. 177-183 (Feb. 1995).

Matsuda, et al. "Low fidelity DNA synthesis by human DNA polymerase-η", Nature, vol. 404, pp. 1011-1013 (Apr. 27, 2000).

Matsuura, et al. "Construction of Glyco-Clusters by Self-Organization of Site-Specifically Glycosylated Oligonucleotides and Their Cooperative Amplification of Lectin-Recognition", J. Am. Chem. Soc., vol. 123, No. 2, pp. 357-358 (2001).

McCoy, et al. "T4 Ribonucleic Acid Ligase Joins Single-Strand Oligo(deoxyribonucleotides)", Biochemistry, vol. 19, No. 4, pp. 635-642 (1980).

McGregor, et al. "Interaction-Dependent PCR: Identification of Ligand-Target Pairs from Libraries of Ligands and Libraries of Targets in a Single Solution-Phase Experiment", J. Am. Chem. Soc., vol. 132, pp. 15522-15524 (2010).

(56) References Cited

OTHER PUBLICATIONS

Melkko, et al. "Lead discovery by DNA-encoded chemical libraries", Drug Discovery Today, vol. 12, Nos. 11/12, pp. 465-471 (Jun. 2007).
Mendel, et al. "Site-directed mutagenesis with an expanded genetic code", Annu. Rev. Biophys. Biomol. Struc., vol. 24, pp. 435-462 (1995).
Miller, "DNA as a template for reaction discovery", Nature Biotechnology, vol. 22, No. 11, pp. 1378-1379 (Nov. 2004).
Mirkin, "Programming the Assembly of Two- and Three-Dimensional Architectures with DNA and Nanoscale Inorganic Building Blocks", Inorg. Chem., vol. 39, No. 11, pp. 2258-2272.
Mudrakovskaya, et al. "Solid-Phase Enzymatic Synthesis of Oligoribonucleotides", Bioorg Khim, vol. 17, No. 6, pp. 469-472 (1991).
Mutter, et al. "Functionalized polyethylene glycols and polypeptides in organic synthesis and catalysis", Reactive Polymers, vol. 6, pp. 99-107 (1987).
Myers, et al. "Detection of Single Base Substitutions by Ribonuclease Cleavage at Mismatches in RNA:DNA Duplexes", Science, vol. 230, pp. 1242-1246 (Dec. 13, 1985).
Nazarenko, et al. "A closed tube format for amplification and detection of DNA based on energy transfer", Nucleic Acids Research, vol. 25, No. 12, pp. 2516-2521 (1997).
Needels, et al. "Generation and screening of an oligonucleotide-encoded synthetic peptide library", Proc. Natl. Acad. Sci. USA, vol. 90, pp. 10700-10704 (Nov. 1993).
Nemoto, et al. "In vitro virus: bonding of mRNA bearing puromycin at the 3-'terminal end to the C-terminal end of its encoded protein on the ribosome in vitro", FEBS Letters, vol. 414, pp. 405-408 (1997).
Nestler, et al. "A General Method for Molecular Tagging of Encoded Combinatorial Chemistry Libraries", J. Org. Chem., vol. 59, No. 17, pp. 4723-4724 (1994).
Nielsen, "Combinatorial chemistry and automation", DDT, vol. 1, No. 11, pp. 458-460 (Nov. 1996).
Nielsen, et al. "Synthetic Methods for the Implementation of Encoded Combinatorial Chemistry", J. Am. Chem. Soc., vol. 115, pp. 9812-9813 (1993).
Nikolaiev, et al. "Peptide-Encoding for Structure Determination of Nonsequenceable Polymers Within Libraries Synthesized and Tested on Solid-Phase Supports", Peptide Research, vol. 6, No. 3, pp. 161-170 (1993).
Nishigaki, et al. "Y-ligation: An efficient method for ligating single-stranded DNAs and RNAs with T4 RNA ligase", Molecular Diversity, vol. 4, pp. 187-190 (1998).
O'Donovan, et al. "Blind Analysis of Denaturing High-Performance Liquid Chromatography as a Tool for Mutation Detection", Genomics, vol. 52, pp. 44-49 (1998).
Ohlmeyer, et al. "Complex synthetic chemical libraries indexed with molecular tags". Proc. Natl. Acad. Sci. USA, vol. 90, pp. 10922-10926 (Dec. 1993).
"Organic Chemistry", Wikipedia, [accessed Dec. 10, 2009]: http://en.wikipedia.org/wiki/organic_chemistry (10 pages).
"Orthogonal Protection Protecting Group", Wikipedia: http://en.Wikipedia.org/wiki/Protecting_group#Orthogonal_protection [accessed Apr. 15, 2010] (1 page).
Otto, et al. "Recent developments in dynamic combinatorial chemistry", Current Opinion in Chemical Biology, vol. 6, pp. 321-327 (2002).
Pavia, "The Chemical Generation of Molecular Diversity". http://www.netsci.org/Science/Combichem/feature01.html, 10 pages (access Nov. 2, 2004).
Persichetti, et al. "Cross-Linked Enzyme Crystals (CLECs) of Thermolysin in the Synthesis of Peptides", J. Am. Chem. Soc., vol. 117, No. 10, pp. 2732-2737 (1995).
Piccirilli, "RNA seeks its maker", Nature, vol. 376, pp. 548-549 (Aug. 17, 1995).
Pochet, et al. "Solid-supported ligation primer", Nucleic Acids Research, vol. 16, No. 4, p. 1619 (1988).
Polsky-Cynkin, et al., "Use of DNA Immobilized on Plastic and Agarose Supports to Detect DNA by Sandwich Hybridization", Clin. Chem., vol. 31, No. 9, pp. 1438-1443 (1985).
Porco, Jr. "Synthesis undressed", Nature, vol. 446, pp. 383-385 (Mar. 22, 2007).
Purmal, et al. "A new affinity reagent for the site-specific, covalent attachment of DNA to active-site nucleophiles: application to the EcoRI and RsrI restriction and modification enzymes", Nucleic Acids Research; vol. 20, No. 14, pp. 3713-3719 (1992).
Ramström, et al. "In situ Generation and Screening of a Dynamic Combinatorial Carbohydrate Library Against Concanavalin A", ChemBioChem, vol. 1, pp. 41-48 (2000).
Rembold, et al., "Single-Strand Regions of Poly(G) Act as Templates for Oligo(C) Synthesis", J. Mol. Evol., vol. 38, pp. 205-210 (1994).
Roberts, et al. "Simultaneus selection, amplification and isolation of a pseudo-peptide receptor by an immobilised N-methyl ammonium ion template". Chem. Commun., pp. 938-939 (2002).
Roberts, et al. "RNA-peptide fusions for the in vitro selection of peptides and proteins". Proc Natl Acad Sci USA, vol. 94, pp. 12297-12302 (Nov. 1997).
Robertson, "Direct Evolution Process for Robust Enzyme Catalysis in Organic Solvents"; 13 pages, Report date: Sep. 1996.
Robinson, "A Synthesis of Tropinone", Journal of the Chemical Society Transactions, vol. 111, pp. 762-768 (1917).
Rodriguez, et al. "Template-Directed Extension of a Guanosine 5'-Phosphate Covalently Attached to an Oligodeoxycytidylate Template", J Mol Evol, vol. 33, pp. 477-482 (1991).
Romaniuk, et al. "Joining of RNA Molecules with RNA Llgase", Methods in Enzymology, vol. 100, pp. 52-59 (1983).
Rosenbaum, et al. "Efficient and Sequence-Specific DNA-Templated Polymerization of Peptide Nucleic Acid Aldehydes". J. Am. Chem. Soc. vol. 125, 13924-13925 (2003).
Saiki, et al. "Genetic analysis of amplified DNA with immobilized sequence-specific oligonucleotide probes", Proc. Natl. Acad. Sci. USA vol. 86, pp. 6230-6234 (Aug. 1989).
Sakurai, et al. "DNA-Templated Functional Group Transformations Enable Sequence-Programmed Synthesis Using Small-Molecule Reagents", J. Am.Chem. Soc., vol. 127, No. 6, pp. 1660-1661 (2005).
Salas, et al. "Biosynthetic Polydeoxynucleotides as Direct Templates for Polypeptide Synthesis", The Journal of Biological Chemistry, vol. 243, No. 6, pp. 1012-1015 (Mar. 10, 1968).
Sarmento, et al. "Cardosins A and B, two new enzymes available for peptide synthesis", Journal of Molecular Catalysis B: Enzymatic, vol. 5, pp. 327-330 (1998).
Scheuermann, et al. "DNA-encoded chemical libraries", Journal of Biotechnology, vol. 126, pp. 568-581 (2006).
Scheuermann, et al. "DNA-Encoded Chemical Libraries: A Tool for Drug Discovery and for Chemical Biology", ChemBioChem, vol. 11, No. 7, pp. 931-937 (2010).
Schmidt, et al. "Information transfer from DNA to peptide nucleic acids by template-directed syntheses", Nucleic Acids Research, vol. 25, No. 23, pp. 4792-4796 (1997).
Schmidt, et al., "Information transfer from peptide nucleic acids to RNA by template-directed syntheses", Nucleic Acids Research, vol. 25, No. 23, pp. 4792-4796 (1997).
Schmitz, et al. "Solid-Phase Enzymatic Synthesis of Oligonucleotides", Organic Letters, vol. 1, No. 11, pp. 1729-1731 (1999).
Schoenleber, et al. "Photochemical Release of Amines by C,N-Bond Cleavage", Synlett, No. 4, pp. 501-504 (2003).
Schultz, et al. "The Combinatorial Library: A Multifunctional Resource", Biotechnol. Prog. 1996, 12, 729-743.
Schwartz, et al. Template Directed Synthesis of Novel, Nucleic Acid-Like Structures, Science, vol. 228, pp. 585-587 (May 3, 1985).
Shabarova, et al. "Chemical ligation of DNA: the first non-enzymatic assembly of a biologically active gene", Nucleic Acids Research, vol. 19, No. 15, pp. 4247-4251 (1991).
Sharifian, "Errors induced during PCR amplification", 53 pages (May 30, 2010).
Shchepinov, et al. "Trityl Tags for Encoding in Combinatorial Synthesis", Tetrahedron, vol. 56, pp. 2713-2724 (2000).
Shuman, "DNA Ligases: Progress and Prospects"; http://www.jbc.org/content/284/26/17365.ful, 7 pages downloaded Feb. 10, 2009.

(56) References Cited

OTHER PUBLICATIONS

Smith, et al., "DNA-guided assembly of proteins as a pathway to an assembler", (wadsworth.org/albcon97/abstract/krummena.htm) The 1997 Albany Conference: Biomolecular Motors and Nanomachines, 1 page (1997).
Snyder, et al. "Ordered Multistep Synthesis in a Single Solution Directed by DNA Templates", Angew. Chem. Int. Ed, vol. 44, pp. 7379-7382 (2005).
Sokolova, et al. "Chemical reactions within DNA duplexes Cyanogen bromide as an effective oligodeoxyribonucleotide coupling agent"; FEBS Letters, vol. 232, No. 1, pp. 153-155; (May 1988).
Still, "Career-In-Review (CIR)", BJ Wright, Synthesis Literacy Group, Columbia University Chemistry, 22 pages (Mar. 30, 2007).
Storhoff, et al., "Programmed Materials Synthesis with DNA", Chem. Rev., vol. 99, No. 7, pp. 1849-1862 (1999).
Summerer, et al., "DNA-Templated Synthesis: More Versatile than Expected", Angew. Chem. Int. Ed., vol. 41, No. 1, pp. 89-90 (2002).
Tabor, "DNA-Ligases"; Current Protocols in Molecular Biology, Suppl. 8, p. 3.14.1-3.14.4 (1987).
Takemori, et al. "Stabilization of Enzyme Activity by an Organic Solvent", Nature, vol. 215, pp. 417-419 (Jul. 22, 1967) Abstract only.
Tamura, et al., "Oligonucleotide-directed peptide synthesis in a ribosome- and ribozyme-free system", Proc Natl. Acad. Sci. USA, vol. 98, No. 4, pp. 1393-1397 (Feb. 13, 2001).
Tan, et al. Natural-product inhibitors of human DNA ligase I, Biochem. J., vol. 314, pp. 993-1000 (1996).
Tan, et al. "Ligand discovery using encoded combinatorial libraries", Current Opinion in Drug Discovery & Development, vol. 3, No. 4, pp. 439-453 (2000).
Tanaka, et al. "Synthesis of a Novel Nucleoside for Alternative DNA Base Pairing through Metal Complexation", J. Org. Chem., vol. 64, No. 14, pp. 5002-5003 (1999).
Tessier, et al. "Ligation of Single-Stranded Oligodeoxyribonucleotides by T4 RNA Ligase", Analytical Biochemistry, vol. 158, pp. 171-178 (1986).
Tse, et al. "Translation of DNA into a Library of 13,000 Synthetic Small-Molecule Macrocycles Suitable for In Vitro Selection", J Am Chem Soc., vol. 130, No. 46, pp. 15611-15626 (Nov. 19, 2008).
Uhlenbeck, et al. "T4 RNA Ligase", The Enzymes, vol. XV pp. 31-58 (1982).
Unknown, "Science & Technology: Concentrates", Chem. & Eng. News, vol. 82, No. 40, p. 31 (2004).
Vágner, et al. "Enzyme-mediated spatial segregation on individual polymeric support beads: Application to generation and screening of encoded combinatorial libraries", Proc. Natl. Acad. Sci. USA, vol. 93, pp. 8194-8199 (Aug. 1996).
Vaisman, et al. "Human DNA Polymerase t Promiscuous Mismatch Extension", The Journal of Biological Chemistry, vol. 276, No. 33, pp. 30615-30622 (Aug. 17, 2001).
Visscher, et al., "Template-Directed Oligomerization Catalyzed by a Polynucleotide Analog", Science, vol. 244, pp. 329-331 (Apr. 21, 1989).
Visscher, et al. "Template-Directed Synthesis of Acyclic Oligonucleotide Analogues", J Mol Evol, vol. 28, pp. 3-6 (1988).
Visscher, et al., "Oligomerization of deoxynucleoside-bisphosphate dimers: template and linkage specificity", Origins of Life and Evolution of the Biosphere, vol. 19, pp. 3-6 (1989).
Vratskikh, et al. "Solid-phase synthesis of oligoribonucleotides using T4 RNA ligase and T4 polynucleotide kinase", Biochimie, vol. 77, pp. 227-232 (1995).
Wagner, et al. "Mutation detection using immobilized mismatch binding protein (MutS)" Nucleic Acids Research, vol. 23, No. 19, pp. 3944-3948 (1995).
Walder, et al. "Complementary carrier peptide synthesis: General strategy and implications for prebiotic origin of peptide synthesis", Proc. Natl. Acad. Sci. USA, vol. 78, No. 1, pp. 51-55 (Jan. 1979).
Wang, et al. "Circular RNA oligonucleotides. Synthesis, nucleic acid binding properties, and a comparison with circular DNAs"; Nucleic Acids Research, vol. 22, No. 12; pp. 2326-2333 (1994).

Wang, et al. "A New Functional Suppressor tRNA/Aminoacyl-tRNA Synthetase Pair for the in Vivo Incorporation of Unnatural Amino Acids into Proteins", J. Am. Chem. Soc., vol. 122, No. 20, pp. 5010-5011 (2000).
Washington, et al. "Mismatch Extension Ability of Yeast and Human DNA Polymerase η", The Journal of Biological Chemistry, vol. 276, No. 3, pp. 2263-2266 (Jan. 19, 2001).
Waybright, et al., "Oligonucleotide-Directed Assembly of Materials: Defined Oligomers", J. Am Chem Soc., vol. 123, No. 9, pp. 1828-1833 (2001).
Website of prof. David R. Liu, publicly available Apr. 19, 2001.
Website of prof. David R. Liu, publicly available Apr. 23, 2003.
Website of prof. David R. Liu, publicly available Aug. 1, 2003.
Website of prof. David R. Liu, publicly available Aug. 2, 2002.
Website of prof. David R. Liu, publicly available Dec. 16, 2003.
Website of prof. David R. Liu, publicly available Feb. 10, 2004.
Website of prof. David R. Liu, publicly available Feb. 15, 2001.
Website of prof. David R. Liu, publicly available Feb. 8, 2003.
Website of prof. David R. Liu, publicly available Jun. 4, 2002.
Website of prof. David R. Liu, publicly available Jun. 6, 2003.
Website of prof. David R. Liu, publicly available Mar. 1, 2001.
Website of prof. David R. Liu, publicly available Mar. 11, 2000.
Website of prof. David R. Liu, publicly available Mar. 27, 2003.
Website of prof. David R. Liu, publicly available Mar. 31, 2001.
Website of prof. David R. Liu, publicly available Nov. 20, 2002.
Website of prof. David R. Liu, publicly available Nov. 29, 2002.
Website of prof. David R. Liu, publicly available Nov. 30, 2001.
Website of prof. David R. Liu, publicly available Oct. 15, 2000.
Website of prof. David R. Liu, publicly available Oct. 15, 2003.
Website of prof. David R. Liu, publicly available Oct. 17, 2002.
Website of prof. David R. Liu, publicly available Sep. 23, 2001.
Website of prof. David R. Liu, publicly available Sep. 24, 2002.
Weiss, et al. "Enzymatic Breakage and Joining of Deoxyribonucleic Acid, I. Repair of Single- Strand Breaks in DNA by an Enzyme System from *Escherichia coli* Infected with T4 Bacteriophage", Proc. Natl. Acad. Sci. USA, vol. 57, pp. 1021-1028 (1967).
Weizman, et al. "2,2'-Bipyridine Ligandoside: A Novel Building Block for Modifying DNA with Intra-Duplex Metal Complexes". J. Am. Chem. Soc., vol. 123, No. 14, pp. 3375-3376 (2001).
Whitesides, et al. "Enzymes as Catalysts in Organic Synthesis", Aldrichimica Acta., vol. 16, No. 2, pp. 27-33 (1983).
Winzeler, et al. "Fluorescence-Based Expression Monitoring Using Microarrays", Methods Enzymol., vol. 306, pp. 3-18 (1999).
Wong, et al. "Branch capture reactions: displacers derived from asymmetric PCR"; Nucleic Acids Research, vol. 19, No. 9, pp. 2251-2259 (1991).
Xu, et al. "Non-enzymatic Ligation of Single-Stranded and Duplex DNA", Abstract, Glen Research Catalog, Tetrahedron Letters, vol. 38, pp. 5595-5598 (1997).
Xu, et al. "High sequence fidelity in a non-enzymatic DNA autoligation reaction", Nucleic Acids Research, vol. 27, No. 3, pp. 875-881 (1999).
Xu, et al. "Nonenzymatic autoligation in direct three-color detection of RNA and DNA point mutations", Nature Biotechnology, vol. 19, pp. 148-152 (Feb. 2001).
Xu, et al. "Rapid and Selective Selenium-Mediated Autoligation of DNA Strands", J. Am. Chem. Soc., vol. 122, No. 37, pp. 9040-9041 (2000).
Zhan, et al. "Chemical Amplification through Template-Directed Synthesis", J. Am. Chem. Soc., vol. 119, No. 50, pp. 12420-12421 (1997).
Zhu, et al. "A Primer-dependent Polymerase Function of *Pseudomonas aeruginosa* ATP-dependent DNA ligase (LigD)", The Journal of Biological Chemistry, vol. 280, No. 1, pp. 418-427 (Jan. 7, 2005).
Zuckerman, et al. "Discovery of Nanomolar Ligands for 7-Transmembrane G-Protein-Coupled Receptors from a Diverse N-(Substituted) Glycine Peptoid Library", J. Med. Chem., vol. 37, No. 17, pp. 2678-2685 (1994).
International Search Report from PCT No. PCT/DK02/00419 dated Jun. 25, 2003.
International Preliminary Examination Report from PCT No. PCT/DK02/00419 dated Jan. 28, 2004.

(56) References Cited

OTHER PUBLICATIONS

European Office Action from European Application No. EP 02740409.4 dated Sep. 1, 2005.
Reply to European Office Action from European Applicant No. 02740409.4 dated Jun. 16, 2006.
Intent to Grant from European Application No. EP 02740409.4 printed Oct. 13, 2006.
Decision to Grant from European Application No. EP 02740409.4 dated Jul. 26, 2007.
Extended European Search Report from European Application No. 07114663.3 dated May 25, 2009.
Extended European Search Report from European Application No. 10 18 4311 dated Feb. 28, 2011.
International Search Report from PCT No. PCT/DK03/00172 dated Nov. 3, 2003.
Office Action from European Application No. 03709676.5 dated Feb. 23, 2005.
Reply to 1st Office Action from European Application No. 30709676.5 dated Jun. 30, 2005.
2nd Office Action from European Application No. 03709676.5 dated Aug. 26, 2005.
Reply to 2nd Office Action from European Application No. 03709676.5 dated Sep. 13, 2005.
3rd Office Action from European Application No. 03709676.5 dated Sep. 30, 2005.
Reply to 3rd Office Action from European Application No. 03709676.5 dated May 19, 2006.
Intent to Grant from European Application No. 03709676.5 dated Oct. 9, 2006.
Amendment after Intention to Grant from European Application No. 03709676.5 dated Nov. 16, 2007.
Decision to Grant from European Application No. 03709676.5 dated Oct. 23, 2008.
European Search Report from European Application No. 08 16 9346 mailed Apr. 13, 2010.
Response filed in European Application No. 08169346.7 mailed Mar. 23, 2011.
1st Office Action from European Application No. 08169346.7 mailed Apr. 19, 2011.
International Search Report from PCT Application No. PCT/DK03/00516 mailed Feb. 18, 2004.
1st Office Action from European Application No. 03766117.0 dated Mar. 24, 2009.
Reply to 1st Office Action from European Application No. 03766117.0 dated Jan. 8, 2010.
2nd Office Action from European Application No. 03766117.0 dated Feb. 16, 2010.
Reply to 2nd Office Action from European Application No. 03766117.0 dated Aug. 20, 2010.
3rd Office Action from European Application No. 03766117.0 dated Nov. 19, 2010.
Reply to 3rd Office Action from European Application No. 03766117.0 dated May 23, 2011.
4th Office Action from European Application No. 03766117.0 dated Jun. 9, 2011.
International Search Report for PCT Application No. PCT/DK03/00921 Jun. 22, 2004.
1st Office Action for European Application No. 03767480.1 dated May 7, 2007.
Reply to 1st Office Action for European Application No. 03767480.1 dated Mar. 19, 2008.
2nd Office Action for European Application No. 03767480.1 dated Jun. 18, 2008.
Reply to 2nd Office Action for European Application No. 03767480.1 dated Feb. 6, 2009.
Intent to Grant for European Application No. 03767480.1 dated Mar. 30, 2009.
Amendment after Intention to Grant for European Application No. 03767480.1 dated Jul. 22, 2009.
Decision to Grant for European Application No. 03767480.1 dated Nov. 5, 2009.
European Search Report for European Application No. 09 17 7376 dated Feb. 24, 2011.
International Search Report for PCT Application No. PCT/DK03/00417 mailed Feb. 10, 2004.
1st Office Action for European Application No. 03729906.6 mailed May 17, 2006.
Reply to 1st Office Action for European Application No. 03729906.6 mailed Mar. 9, 2007.
2nd Office Action for European Application No. 30729906.6 mailed Sep. 22, 2009.
Reply to 2nd Office Action for European Application No. 03729906.6 mailed May 6, 2010.
International Search Report for PCT Application No. PCT/DK2004/000116 mailed Aug. 23, 2004.
1st Office Action for European Application No. 04713515.7 mailed Oct. 19, 2006.
Reply to 1st Office Action for European Application No. 04713515.7 mailed Aug. 20, 2007.
2nd Office Action for European Application No. 04713515.7 mailed Mar. 31, 2008.
Reply to 2nd Office Action for European Application No. 04713515.7 mailed Dec. 5, 2008.
3rd Office Action for European Application No. 04713515.7 mailed Sep. 6, 2010.
Reply to 3rd Office Action for European Application No. 04713515.7 mailed Jun. 21, 2011.
International Search Report for International Application No. PCT/DK2004/000117 mailed Aug. 19, 2004.
1st Office Action for European Application No. 04713517.3 dated Dec. 22, 2006.
Reply to 1st Office Action for European Application No. 04713517.3 dated Oct. 19, 2007.
2nd Office Action for European Application No. 04713517.3 dated Sep. 23, 2008.
Reply to 2nd Office Action for European Application No. 04713517.3 dated Jul. 13, 2009.
3rd Office Action for European Application No. 04713517.3 dated Feb. 14, 2011.
International Search Report for International Application No. PCT/2004/000195 mailed Dec. 27, 2004.
1st Office Action for European Application No. 04722237.7 dated Mar. 2, 2006.
Reply to 1 st Office Action for European Application No. 04722237.7 dated Dec. 20, 2006.
2nd Office Action for European Application No. 04722237.7 dated Feb. 28, 2007.
Reply to 2nd Office Action for European Application No. 04722237.7 dated Oct. 19, 2007.
Intent to Grant for European Application No. 04722237.7 dated Jan. 18, 2008.
Amendment to Grant for European Application No. 04722237.7 dated Nov. 11, 2008.
Decision to Grant for European Application No. 04722237.7 dated Feb. 5, 2009.
European Search Report for European Application No. 09154197 mailed Sep. 15, 2010.
International Search Report for International Application No. PCT/DK03/00739 mailed Aug. 30, 2004.
Amendment after ESR for European Application No. 03757752.5 dated Feb. 14, 2006.
1st Office Action for European Application No. 03757752.5 dated Mar. 16, 2006.
Reply to 1st Office Action for European Application No. 03757752.5 dated Jan. 12, 2006.
2nd Office Action for European Application No. 03757752.5 dated Feb. 15, 2007.
Reply to 2nd Office Action for European Application No. 03757752.5 dated Aug. 15, 2007.
Summons for European Application No. 03757752.5 dated Aug. 11, 2008.

(56) References Cited

OTHER PUBLICATIONS

Letter for Oral Proceeding for European Application No. 03757752.5 dated Dec. 15, 2008.
Telephone Summary for European Application No. 03757752.5 dated Dec. 23, 2008.
Letter for Oral Proceeding for European Application No. 03757752.5 dated Jan. 2, 2009.
Oral Proceedings for European Application No. 03757752.5 dated Jan. 8, 2009.
3rd Office Action for European Application No. 03757752.5 dated Jan. 14, 2009.
Reply to 3rd Office Action for European Application No. 03757752.5 dated Jul. 17, 2009.
Intent to Grant for European Application No. 03757752.5 dated Mar. 30, 2010.
Decision to Grant for European Application No. 03757752.5 dated May 19, 2011.
Request for Corrections for European Application No. 03757752.5 dated Nov. 9, 2010.
Office Action for Japanese Application No. 2005-501801 dated Apr. 6, 2010.
Office Action for Japanese Application No. 2005-501801 dated May 31, 2011.
Australian Application No. 2003273792.
Examination Report for Australian Application No. 2003273792 dated May 6, 2011.
International Search Report for PCT/DK2004/000630 mailed Feb. 14, 2005.
1st Office Action for European Application No. 04762850.8 dated Dec. 6, 2006.
Reply to 1st Office Action for European Application No. 04762850.8 dated Oct. 18, 2007.
2nd Office Action for European Application No. 04762850.8 dated Jan. 24, 2008.
Reply to 2nd Office Action for European Application No. 04762850.8 dated Sep. 2, 2008.
Intent to Grant for European Application No. 04762850.8 dated Dec. 10, 2008.
Amendment after Grant for European Application No. 04762850.8 dated Jul. 17, 2009.
Decision to Grant for European Application No. 04762850.8 dated Oct. 8, 2009.
International Search Report for International Application No. PCT/DK2005/000199 mailed Jan. 23, 2006.
1st Office Action for European Application No. 05715120.1 dated Apr. 12, 2007.
Reply to 1st Office Action for European Application No. 05715120.1 dated Feb. 1, 2008.
2nd Office Action for European Application No. 05715120.1 dated Mar. 25, 2008.
Reply to 2nd Office Action for European Application No. 05715120.1 dated Jan. 9, 2009.
Intent to Grant for European Application No. 05715120.1 dated May 7, 2009.
Amendment after Grant for European Application No. 05715120.1 dated Sep. 3, 2009.
Decision to Grant for European Application No. 05715120.1 dated Oct. 1, 2009.
International Search Report for International Application No. PCT/DK2005/000106 mailed Sep. 12, 2005.
1st Office Action for European Application No. 05700655.3 dated Jun. 19, 2007.
Reply to 1st Office Action for European Application No. 05700655.3 dated Apr. 11, 2008.
2nd Office Action for European Application No. 05700655.3 dated Sep. 12, 2008.
Reply to 2nd Office Action for European Application No. 05700655.3 dated Jul. 9, 2009.
3rd Office Action for European Application No. 05700655.3 dated Aug. 12, 2009.
Reply to 3rd Office Action for European Application No. 05700655.3 dated Feb. 9, 2010.
Intent to Grant for European Application No. 05700655.3 dated Mar. 31, 2010.
Amendment after Grant for European Application No. 05700655.3 dated Nov. 11, 2010.
Decision to Grant for European Application No. 05700655.3 dated Dec. 2, 2010.
International Search Report for International Application No. PCT/DK2006/000685 mailed Jun. 14, 2007.
1st Office Action for European Application No. 06818144.5 dated Dec. 11, 2008.
Reply to 1st Office Action for European Application No. 06818144.5 dated Oct. 30, 2009.
Intent to Grant for European Application No. 06818144.5 dated Feb. 23, 2010.
Amendment after Grant for European Application No. 06818144.5 dated Oct. 7, 2010.
Decision to Grant European Application No. 06818144.5 dated Nov. 5, 2010.
European Search Report for European Application No. 10 19 2716 mailed May 24, 2011.
Invitation to Identify Subject Matter for European Application No. 10 192 717.6 dated Jun. 1, 2011.
International Search Report for International Application No. PCT/DK2009/050129 mailed Aug. 21, 2009.
Communication pursuant to Rule 161(1) and 162 for European Application No. 09765460.2 dated Mar. 14, 2011.
Response to Rule 161(1) and 162 for European Application No. 09765460.2 dated Apr. 18, 2011.
Millward, S.W. et al. "A General Route for Post-Translational Cyclization of mRNA Display Libraries", *Journal of the American Chemical Society*: vol. 127, 14142-14143, (2005).
Millward, S.W. et al. "Design of Cyclic Peptides That Bind Protein Surfaces with Antibody-Like Affinity", *ACS Chemical Biology*: vol. 2, No. 9, 625-634, (2007).
Giebel, L.B. et al. "Screening of Cyclic Peptide Phage Libraries Identifies Ligands That Bind Streptavidin with High Affinities", *Biochemistry*: vol. 34, No. 47; 15430-15435, (1995).
Ladner, R.C. "Constrained peptides as binding entities", *Elsevier Science Ltd., Trends in Biotechnology*: vol. 13, 426-430, (1995).
Koivunen, E. et al. "Phage Libraries Displaying Cyclic Peptides with Different Ring Sizes: Ligand Specificities of the RGD-Directed Integrins", *Bio/Technology*: vol. 13, 265-270, (1995).
Office Action in European patent application No. 10184311.8, dated Mar. 19, 2012, with Annex.
Office Action in Israel patent application No. 207672, dated Jan. 15, 2012, with English translation.
Response to OA in Israel patent application No. 207672, dated Jun. 14, 2012.
Office Action in Israel patent application No. 207673, dated Jan. 15, 2012, with English translation.
Response to OA in Israel patent application No. 207673, dated Jun. 14, 2012.
Response to OA in Canadian patent application No. 2,544,153, dated Mar. 26, 2012.
Appeal filed for Indian patent application No. 178/MUMNP/2007, dated Nov. 15, 2011.
Office Action in Chinese patent application No. 200380104764.5, dated Feb. 29, 2012, with translation of text of notification.
Response to OA in Chinese patent application No. 200380104764.5, dated Jul. 16, 2012.
Office Action in Japanese patent application No. P2010-226107, dated Jul. 10, 2012, with English translation.
Office Action in European patent application No. 10192716.8, dated Jul. 30, 2012.
Response to OA in European patent application No. 07114663.3, dated Jul. 4, 2012.
Office Action in European patent application No. 07114663.3, dated Jul. 23, 2012.
Official Communication in European patent application No. 09154197.9, dated Aug. 7, 2012.

(56) References Cited

OTHER PUBLICATIONS

Response submitted Apr. 21, 2010 to Non-final Rejection re U.S. Appl. No. 12/330,709.
Supplemental response submitted Jun. 2, 2010 re U.S. Appl. No. 12/330,709.
Ex parte Quyale Action dated Jul. 27, 2010 re U.S. Appl. No. 12/330,709.
Response of Jan. 10, 2011 to Ex parte Quayle Action re U.S. Appl. No. 12/330,709.
Notice of Allowance dated Mar. 3, 2011 re U.S. Appl. No. 12/330,709.
RCE filed Jun. 2, 2011 re U.S. Appl. No. 12/330,709.
Office Action dated Sep. 17, 2012 re U.S. Appl. No. 12/330,709.
Response dated Feb. 18, 2013 to Office Action re U.S. Appl. No. 12/330,709.
Non-final rejection dated Mar. 27, 2013 re U.S. Appl. No. 12/330,709.
Response submitted Aug. 27, 2013 re U.S. Appl. No. 12/330,709.
Final rejection dated Oct. 28, 2013 re U.S. Appl. No. 12/330,709.
Non-final Rejection dated Feb. 8, 2007 re U.S. Appl. No. 10/507,121.
Response submitted Jun. 7, 2007 to Non-final Rejection re U.S. Appl. No. 10/507,121.
Final Rejection dated Sep. 7, 2007 re U.S. Appl. No. 10/507,121.
RCE filed Feb. 13, 2008 re U.S. Appl. No. 10/507,121.
Notice of Allowance dated Mar. 20, 2008 re U.S. Appl. No. 10/507,121.
Issue Notification for U.S. Appl. No. 10/507,121 dated Jul. 30, 2008.
Non-final Rejection dated Jan. 27, 2010 re U.S. Appl. No. 12/179,323.
Response submitted Jun. 24, 2010 to Non-final Rejection re U.S. Appl. No. 10/507,121.
Final Rejection dated Sep. 15, 2010 re U.S. Appl. No. 12/179,323.
Notice of Appeal submitted Mar. 15, 2011 re U.S. Appl. No. 12/179,323.
RCE submitted Oct. 17, 2011 re U.S. Appl. No. 12/179,323.
Non-final Rejection dated Jul. 3, 2013 re U.S. Appl. No. 12/179,323.
First Restriction Requirement dated Apr. 4, 2008 re U.S. Appl. No. 10/523,006.
Response to first Restriction Requirement submitted Oct. 1, 2008 re U.S. Appl. No. 10/523,006.
Second Restriction Requirement dated Dec. 9, 2009 re U.S. Appl. No. 10/523,006.
Response to second Restriction Requirement submitted May 5, 2010 re U.S. Appl. No. 10/523,006.
Third Restriction Requirement dated Aug. 3, 2010 re U.S. Appl. No. 10/523,006.
Response to third Restriction Requirement submitted Feb. 1, 2011 re U.S. Appl. No. 10/523,006.
P104US00 Non-final Rejection dated Mar. 16, 2011 re U.S. Appl. No. 10/523,006.
Response submitted Sep. 16, 2011 to non-final rejection re U.S. Appl. No. 10/523,006.
Final rejection dated Feb. 6, 2012 re U.S. Appl. No. 10/523,006.
RCE Submitted Aug. 6, 2012 re U.S. Appl. No. 10/523,006.
Response submitted Oct. 11, 2013 re U.S. Appl. No. 10/523,006.
Restriction Requirement dated Aug. 2, 2010 re U.S. Appl. No. 10/539,288.
Response to Restriction Requirement submitted Jan. 31, 2011 re U.S. Appl. No. 10/539,288.
Non-final Rejection dated Apr. 25, 2011 re U.S. Appl. No. 10/539,288.
Response after Non-final rejection submitted Oct. 25, 2011 re U.S. Appl. No. 10/539,288.
Final rejection dated Dec. 22, 2011 re U.S. Appl. No. 10/539,288.
Notice of Appeal filed Jun. 19, 2012 re U.S. Appl. No. 10/539,288.
RCE filed Aug. 20, 2012 re U.S. Appl. No. 10/539,288.
Non final rejection dated Sep. 21, 2012 re U.S. Appl. No. 10/539,288.
Response after Non-final rejection submitted Feb. 28, 2013 re U.S. Appl. No. 10/539,288.
Non-final rejection dated Apr. 16, 2013 re U.S. Appl. No. 10/539,288.
Response to Non-final rejection submitted Sep. 16, 2013 re U.S. Appl. No. 10/539,288.
Restriction Requirement dated Jan. 4, 2008 re U.S. Appl. No. 10/518,056.
Response to Restriction Requirement submitted Jun. 2, 2008 re U.S. Appl. No. 10/518,056.
Non-final Rejection dated Oct. 8, 2008 re U.S. Appl. No. 10/518,056.
Response after Non-final Rejection submitted Feb. 17, 2009 re U.S. Appl. No. 10/518,056.
Final Rejection dated May 27, 2009 re U.S. Appl. No. 10/518,056.
1st Restriction requirement of Oct. 5, 2011 re U.S. Appl. No. 12/095,778.
Response dated Mar. 5, 2012 to 1st Restriction Requirement re U.S. Appl. No. 12/095,778.
2nd Restriction requirement dated Jun. 27, 2012 re U.S. Appl. No. 12/095,778.
Response submitted Dec. 27, 2012 to 2nd Restriction Requirement re U.S. Appl. No. 12/095,778.
Office Action dated Apr. 15, 2013 re U.S. Appl. No. 12/095,778.
Response dated May 15, 2013 to Restriction Requirement re U.S. Appl. No. 12/095,778.
Non-final rejection dated Oct. 8, 2013 re U.S. Appl. No. 12/095,778.
Adang et al., "The Contribution of Combinatorial Chemistry to Lead Generation: AnInterim Analysis", Current Medicinal Chemistry 2001, 8, 985-998.
Affleck, "Solutions for library encoding to create collections of discrete compounds", Chemical Biology, 2001, 5:257-263.
Bain et al., "Biosynthetic site-specific incorporation of a non-natural amino acid into a polypeptide", J. Am. Chem. Soc., 1989, 111, 8013-8014.
Barnes et al., "Recent developments in the encoding and deconvolution of combinatorial libraries", Chemical Biology 2000, 4:346-350.
Chen et al., "Total Synthesis of Naturally Occurring Prostaglandin F2a on a Non-Cross-Linked Polystyrene Support", Tetrahedron Letters 39 (1998) 3943-3946.
Coe et al., "Solution-phase combinatorial chemistry", Molecular Diversity, 4: 31-38, 1999.
Dolle, "Comprehensive Survey of Combinatorial Library Synthesis: 2000", Journal of Combinatorial Chemistry, 2001, vol. 3, No. 6, pp. 477-517.
Dolle, "Comprehensive Survey of Combinatorial Library Synthesis: 2001", Journal of Combinatorial Chemistry, 2002, vol. 4, No. 5, pp. 369-418.
Dolle, "Comprehensive Survey of Combinatorial Library Synthesis: 2002", Journal of Combinatorial Chemistry, 2003, vol. 5, No. 6, pp. 693-753.
Furka et al., "General method for rapid synthesis of multicomponent peptide mixtures", Int. J. Peptide Protein Res., 37, 1991, 487-493.
Gallop et al., "Applications of Combinatorial Technologies to Drug Discovery. 1. Background and Peptide Combinatorial Libraries", Journal of Medicinal Chemistr-y, 1994, vol. 37, No. 9, pp. 1233-1251.
Guillen Schlippe et al.,"In Vitro Selection of Highly Modified Cyclic Peptides That Act as Tight Binding Inhibitors", J. Am. Chem. Soc. 2012, 134, 10469-10477.
Han et al., "Liquid-phase combinatorial synthesis", Proc. Natl. Acad. Sci. USA, vol. 92, pp. 6419-6423, Jul. 1995.
www.wikipedia.org/wiki/DNA-encoded chemical library Oct. 2, 2012, pp. 1-12.
http://www2.umt.edu/medchem/teaching/medchem/mclect14.htmThompson C. M., Medicinal Chemistry, lecture 14, Pharmaceutical Sciences 621 & Chemistry 569.
Li et al., "Kinetics of RNA Degradation by specific base catalysis of transesterification involving the 2'-hydroxyl group", J. Am. Chem. Soc., 1999, 121, pp. 5364-5372.
Ma et al., "In Vitro Selection of Unnatural Cyclic Peptide Libraries via mRNA Display", Book Ribosome Display and Related Technologies, ch. 21, pp. 367-390.
MacLean et al., "Glossary of terms used in combinatorial chemistry", Pure Appl. Chem., vol. 71, No. 12, pp. 2349-2365, 1999.
Meier et al, "Combinatorial Methods, Automated Synthesis and High-Throughput Screening in Polymer Research: The Evolution Continues", Macromol. Rapid Commun. 2004, 25, 21-33.

(56) References Cited

OTHER PUBLICATIONS

Chorghade, "Drug discovery and development", 2006, ISBN-13: 978-0-471-39848-6, Published by John Wiley & Sons, Inc., Hoboken, New Jersey.
Needels et al., "Generation and screening of an oligonucleotide-encoded syntheticpeptide library", Proc. Natl. Acad. Sci. USA, vol. 90, pp. 10700-10704, Nov. 1993.
Ni et al., "Versatile Approach to Encoding Combinatorial Organic Syntheses Using Chemically Robust Secondary Amine Tags", J. Med. Chem. 1996, 39, 1601-1608.
Nicolaou et al., "Radiofrequency Encoded CombinatorialChemistry", Angew. Chem. Int. Ed. Engl., 1995, 34, No. 20, pp. 2289-2291.
Noren et al., "A general method for site-specific incorporation of unnatural aminoacids into protein", Science, American Association for the advancement of science, Washington, DC, vol. 244, 1989, pp. 182-188.
Starck et al., "The puromycin route to assess stereo- and regiochemical constraints on peptide bond formation in eukaryotic ribosomes", J. Am. Chem. Soc., 2003, 125, 8090-8091.
Studer et al., "Fluorous Synthesis: A Fluorous-Phase Strategy for Improving Separation Efficiency in Organic Synthesis", 1997, Science 275, pp. 823-826.
Terrett et al., "Combinatorial synthesis the design of compound libraries and their application to drug discovery", Tetrahedron, 1995, vol. 51, No. 30., pp. 8135-8173.
Website: "Combinatorial chemistry", http://www.ukessays.co.uk/essays/chemistry/combinatorial-chemistry.php, Oct. 29, 2012, pp. 1-11.
Wermuth et al., "Glossary of terms used in medical chemistry", Pure & Appl. Chem, 1998, vol. 70, No. 5, pp. 1129-1143.
Ymane et al., "Discrimination between D- and L-Tyrosyl transfer ribonucleic acids in peptide chain elongation", Biochemistry, vol. 20, No. 25, Dec. 8, 1981, pp. 7059-7064.
Lipinski et al., "Experimental and computational approaches to estimate solubility and permeability in drug discovery and development settings", Adv. Drug Deliv. Rev., vol. 46 (1-3), 2001, pp. 3-26.
Lipinski, "Lead- and drug-like compounds: the rule-of-five revolution", Drug Discovery Today: Technologies, vol. 1, No. 4, 2004, pp. 337-341.
Kleiner et al., "Small-molecule discovery from DNA-encoded chemical libraries", Chem. Soc. Rev., 2011, 40, pp. 5707-5717.
http://en.wikipedia.org/wiki/Scaffold_protein.
Balkenhohl et al., "Combinatorial synthesis of small organic molecules", Angew Chem Int. Ed Engl. 1996, 35, pp. 2288-2337.
Strachan et al., "Human Molecular Genetics", 2nd edition, textbook published by Wiley-Liss, 1999.
Barrio et al., "Synthesis of modified nucleoside 3',5'-bisphophates and their incorporation into oligoribonucleotides with T4 RNA Ligase", Biochemistry, vol. 17, No. 11, 1978.
Chan et al., "Altered DNA ligase I activity in Bloom's syndrome cells", Nature, vol. 325, pp. 357-359 , 1987.
Cranston et al., "Studies on ribonucleic acid ligase", J.Biol.Chem., vol. 249, No. 23, pp. 7447-7456, 1974.
England et al., "Enzymatic oligoribonucleotide synthesis with T4 RNA ligase", Biochemistry, vol. 17, No. 11., 1978.
Gassen et al., "Synthesis by polymer-bound ribonuclease of the termination codons U-A-A, U-A-G, and U-G-A" Biochemical and biophysical research communications, vol. 44, No. 6, pp. 1410-1415, 1971.
Haseth et al., "Interaction of *Escherichia coli* host factor protein with oligoriboadenylates", Biochemistry, 19, pp. 6138-6446, 1980.
Hoffman et al., "Polynucleotide phosphorylase covalently bound to cellulose and ith use in the preparation of homopolynucleotides", Biochemical and biophysical research communications, vol. 41, No. 3, pp. 710-714, 1970.
Anonymous. "DCI—A Logical Alternative Aviator", Glen Research, vol. 10, No. 1, 1-12 (1997).
Walder, JA., et al. "Complementary carrier Peptide Synthesis: General Strategy and Implications for Prebiotic Origin of Peptide Synthesis", Department of Chemistry, and Department of Biochemistry and Molecular Biology, Northwestern University, Evanston, Illinois 60201, 1979 (B).
Response to Office Action in EP 07114663.3 dated May 17, 2013.
3rd Office Action in European patent application No. 07114663.3 dated Jun. 3, 2013.
Response to 1st Office Action of Mar. 19, 2012 in EP 10184311.8 submitted Jan. 18, 2013.
2nd Office action dated Feb. 6, 2013 in EP 10184311.8.
Response to 2nd Office Action of Feb. 24, 2012 in EP 08169346.7 submitted Dec. 21, 2012.
3rd Office Action dated Jan. 29, 2013 in EP 08169346.7.
Response to 4th Office Action dated Jun. 9, 2011 in EP 03766117.0 submitted Mar. 14, 2012.
5th Office Action from European Appllication No. 03766117.0 dated May 31, 2012.
Office Action from European Application No. 03766117.0 dated Mar. 26, 2013.
Decision to Grant dated Oct. 10, 2013 re European patent appliction No. 09154197.9.
Response to oppositions against EP 1558744 submitted Dec. 5, 2012.
Written submissions re EP 1558744 submitted Sep. 11, 2013 by proprietor.
Written submissions re EP 1558744 submitted Sep. 12, 2013 by opponent.
Response to ESR of Feb. 6, 2012 re European Patent Application No. 10183942.1 submitted Jan. 9, 2013.
1st Office Action for European Patent Application No. 10183942.1 dated Feb. 11, 2013.
Decision to Grant EP 10183942.1 dated Nov. 14, 2013.
European Search Report issued Jun. 6, 2012 re EP 10184069.2.
Response dated Apr. 12, 2013 to European Search Report issued in European Patent Application No. 10184069.2.
1st Office Action for European Patent Application No. 10184069.2 dated Jul. 3, 2013.
EESR Office Action in European patent application No. 10192716.8 dated Jul. 3, 2013.
Invitation to identify subject matter for search Response to ESR dated Jan. 25, 2012 submitted Dec. 5, 2012.
Invitation to identify subject matter for search Office Action dated Jul. 16, 2013 re European patent application No. 10192717.6.
European Office Action from EP 09765460.2 dated May 7, 2012.
Response to office action re 09765460.2 submitted Feb. 22, 2013.
Communication pursuant to Rule 161(1) and 162 for European Application No. 11720372.9 dated Dec. 12, 2012.
Notice of Acceptance for Australian Application No. 2003273792 dated Jun. 22, 2011.
Office action of Aug. 20, 2012 re Canadian patent application No. 2,544,153.
Notice of Allowance of Sep. 3, 2012 re Chinese patent application No. 200380104764.5.
Office Action in Israeli patent application No. 207672 dated May 28, 2013.
Office Action in Israeli patent application No. 207673 dated May 28, 2013.
Office Action of Jan. 29, 2013 re Japanese patent application No. 2010-226107.
Decision of dismissal of amendment dated Aug. 20, 2013 re Japanese patent application No. 2010-226107.
Restriction Requirement P101US00 Restriction Requirement dated Apr. 6, 2005 re U.S. Appl. No. 10/175,539.
Response to Restriction Requirement P101US00 Response to Restriction Requirement submitted May 6, 2005 re U.S. Appl. No. 10/175,539.
Non-final Rejection 1012_2005 P101US00 Non-final Rejection dated Oct. 13, 2005 re U.S. Appl. No. 10/175,539.
Response after Non-final Rejection 1012_2005 P101US00 Response submitted Apr. 13, 2006 to Non-final Rejection re U.S. Appl. No. 10/175,539.
Final Rejection 0517_2006 P101US00 Final Rejection dated May 19, 2006 re U.S. Appl. No. 10/175,539.
Notice of Appeal filed Nov. 20, 2006 re U.S. Appl. No. 10/175,539.
RCE submitted Feb. 20, 2007 re U.S. Appl. No. 10/175,539.

(56) References Cited

OTHER PUBLICATIONS

Non-final Rejection dated May 14, 2007 re U.S. Appl. No. 10/175,539.
Response submitted Sep. 13, 2007 to Non-final Rejection to U.S. Appl. No. 10/175,539.
Quayle Action dated Nov. 27, 2007 re U.S. Appl. No. 10/175,539.
Response submitted Feb. 27, 2008 to Quayle Action re U.S. Appl. No. 10/175,539.
Notice of Allowance dated May 15, 2008 re U.S. Appl. No. 10/175,539.
Amendment after Notice of Allowance dated Oct. 16, 2008 re U.S. Appl. No. 10/175,539.
Amendment after Notice of Allowance dated May 13, 2009.
Issue Notification dated May 12, 2010 re U.S. Appl. No. 10/75,539.
Non-final Rejection dated Oct. 27, 2009 re U.S. Appl. No. 12/330,709.
Response submitted Jul. 27, 2010 to Non-final Action Apr. 5, 2010 re U.S. Appl. No. 10/525,817.
Non-final rejection Jan. 5, 2011 re U.S. Appl. No. 10/525,817.
Interview Summary dated Sep. 29, 2011 re U.S. Appl. No. 10/525,817.
Response submitted Jul. 5, 2011 to Non-final Action re U.S. Appl. No. 10/525,817.
Examiner's amendment communication dated May 12, 2011 re U.S. Appl. No. 10/525/817.
Notice of Allowance dated Oct. 14, 2011 re U.S. Appl. No. 10/525,817.
Notice of Allowance dated Jan. 19, 2012 re U.S. Appl. No. 10/525,817.
RCE dated Mar. 21, 2012 re U.S. Appl. No. 10/525,817.
Notice of Allowance dated Mar. 30, 2012 re U.S. Appl. No. 10/525,817.
Issue Notification dated Jun. 6, 2012 re U.S. Appl. No. 10/525,817.
Restriction Requirement of Jun. 25, 2008 re U.S. Appl. No. 11/402,957.
Response submitted Aug. 25, 2008 to Restriction Requirement re U.S. Appl. No. 11/402,957.
Non-final Rejection dated Nov. 28, 2008 re U.S. Appl. No. 11/402,957.
Response submitted May 15, 2009 to Non-final Rejection re U.S. Appl. No. 11/402,957.
Non-final Rejection dated Jul. 6, 2009 re U.S. Appl. No. 11/402,957.
Response submitted Dec. 7, 2009 to Non-final Rejection re U.S. Appl. No. 11/402,957.
Final Rejection dated Feb. 16, 2010 re U.S. Appl. No. 11/402,957.
Response submitted Jul. 28, 2010 to Final Rejection re U.S. Appl. No. 11/402,957.
Notice of Appeal dated Aug. 16, 2010 re U.S. Appl. No. 11/402,957.
Notice of Allowance dated Sep. 2, 2010 re U.S. Appl. No. 11/402,957.
RCE dated Dec. 2, 2010 re U.S. Appl. No. 11/402,957.
Second Notice of Allowance dated Apr. 29, 2011 re U.S. Appl. No. 11/402,957.
RCE dated Jul. 28, 2011 re U.S. Appl. No. 11/402,957.
Third Notice of Allowance dated Oct. 31, 2011 re U.S. Appl. No. 11/402,957.
RCE dated Dec. 13, 2011 re U.S. Appl. No. 11/402,957.
Preliminary amendment Nov. 21, 2012 re U.S. Appl. No. 11/402,957.
Non-final Rejection dated May 22, 2013 re U.S. Appl. No. 11/402,957.
Response to Non-final rejection submitted Sep. 23, 2013 re U.S. Appl. No. 11/402,957.
Restriction Requirement dated May 14, 2013 re U.S. Appl. No. 13/455,223.
Response submitted Aug. 14, 2013 to Restriction Requirement re U.S. Appl. No. 13/455,223.
Non-final rejection dated Nov. 15, 2013 re U.S. Appl. No. 13/455,223.
First Restriction Requirement dated Feb. 4, 2009 re U.S. Appl. No. 10/572,644.
Reponse submitted Jul. 29, 2009 to First Restriction Requirement re U.S. Appl. No. 10/572,644.
Non-final rejection dated Oct. 29, 2009 re U.S. Appl. No. 10/572,644.
Response submitted Apr. 28, 2010 to Non-final rejection re U.S. Appl. No. 10/572,644.
Second Restriction Requirement dated Jul. 21, 2010 re U.S. Appl. No. 10/572,644.
Response submitted Jan. 19, 2011 to Second Restriction Requirement re U.S. Appl. No. 10/572,644.
Non-final rejection dated Mar. 31, 2011 re U.S. Appl. No. 10/572,644.
Response submitted Sep. 30, 2011 to Non final rejection re U.S. Appl. No. 10/572,644.
Final rejection dated Jan. 9, 2012 re U.S. Appl. No. 10/572,644.
Notice of Appeal filed Jul. 6, 2012 re U.S. Appl. No. 10/572,644.
RCE of Sep. 6, 2012 re U.S. Appl. No. 10/572,644.
Non-final rejection dated Mar. 30, 2009 re U.S. Appl. No. 10/593,868.
Response submitted Jul. 28, 2009 to Non-final rejection re U.S. Appl. No. 10/593,868.
Notice of Allowance dated Nov. 16, 2009 re U.S. Appl. No. 10/593,868.
Amendments after Notice of Allowance Feb. 16, 2010 re U.S. Appl. No. 10/593,868.
Issue Notification dated Apr. 7, 2010 re U.S. Appl. No. 10/593,868.
Restriction Requirement dated Apr. 7, 2011 re U.S. Appl. No. 10/589,551.
Response submitted Oct. 7, 2011 to Restriction Requirement re U.S. Appl. No. 10/589,551.
Non-final rejection dated Oct. 26, 2011 re U.S. Appl. No. 10/589,551.
Notice of Appeal filed Oct. 27, 2009 re U.S. Appl. No. 10/518,056.
Amendments after Notice of Appeal submitted Nov. 17, 2009 re U.S. Appl. No. 10/518,056.
Advisory Action dated Jan. 7, 2010 re U.S. Appl. No. 10/518,056.
RCE filed Mar. 22, 2010 re U.S. Appl. No. 10/518,056.
Non-final Rejection mailed Mar. 31, 2008 re U.S. Appl. No. 10/545,795.
Response after Non-final Rejection submitted Sep. 30, 2008.
Final Rejection dated Jan. 27, 2009 re U.S. Appl. No. 10/545,795.
Notice of Appeal filed Jul. 27, 2009 re U.S. Appl. No. 10/545,795.
Amendments after Notice of Appeal submitted Sep. 28, 2009 re U.S. Appl. No. 10/545,795.
Advisory Action dated Sep. 29, 2009 re U.S. Appl. No. 10/545,795.
Second amendment after Notice of Appeal submitted Sep. 28, 2009 re U.S. Appl. No. 10/545,795.
Advisory Action dated Oct. 21, 2009 re U.S. Appl. No. 10/545,795.
RCE submitted Oct. 27, 2009 re U.S. Appl. No. 10/545,795.
Non-final Rejection dated Mar. 30, 2010 re U.S. Appl. No. 10/545,795.
Non-final Rejection dated Nov. 16, 2009 re U.S. Appl. No. 10/545,795.
Interview summary dated Jul. 15, 2010 re U.S. Appl. No. 10/545,795.
Interview summary dated Jul. 30, 2010 re U.S. Appl. No. 10/545,795.
Response after Non-final Rejection dated Aug. 30, 2010 re U.S. Appl. No. 10/545,795.
Final Rejection dated Feb. 1, 2011 re U.S. Appl. No. 10/545,795.
Notice of Appeal filed Jul. 27, 2011 re U.S. Appl. No. 10/545,795.
Restriction Requirement dated Jul. 31, 2008 re U.S. Appl. No. 10/546,538.
Response to Restriction Requirement filed Dec. 24, 2008 re U.S. Appl. No. 10/546,538.
Non-final Rejection dated Jun. 10, 2009 re U.S. Appl. No. 10/546,538.
Response after Non-final Rejection submitted Dec. 9, 2009 re U.S. Appl. No. 10/546,538.
Final Rejection dated Jun. 8, 2010 re U.S. Appl. No. 10/546,538.
Notice of Appeal filed Dec. 8, 2010 re U.S. Appl. No. 10/546,538.
Appeal dismissed dated Jul. 20, 2011 re U.S. Appl. No. 10/546,538.
Restriction requirement mailed Apr. 24, 2012 re U.S. Appl. No. 13/179,283.
Response submitted Jul. 23, 2012 to restriction requirement re U.S. Appl. No. 13/179,283.
Non-final rejection dated Jul. 31, 2012 re U.S. Appl. No. 13/179,283.

(56) References Cited

OTHER PUBLICATIONS

Response of Jan. 30, 2013 to Non final rejection re U.S. Appl. No. 13/179,283.
Final rejection dated Apr. 11, 2013 re U.S. Appl. No. 13/179,283.
Notice of Appeal filed Sep. 11, 2013 re U.S. Appl. No. 13/179,283.
Restriction Requirement of Apr. 21, 2008 re U.S. Appl. No. 10/549,619.
Response filed Sep. 22, 2009 to Restriction Requirement re U.S. Appl. No. 10/549,619.
Non-final Rejection 0428_2009 re U.S. Appl. No. 10/549,619.
Response after Non-final Rejection submitted Oct. 26, 2009 re U.S. Appl. No. 10/549,619.
Interview summary Mar. 3, 2010 re U.S. Appl. No. 10/549,619.
Notice of Allowance re U.S. Appl. No. 10/549,619.
Amendments after Notice of Allowance Oct. 6, 2010 re U.S. Appl. No. 10/549,619.
Second amendment after Notice of Allowance Oct. 21, 2012 re U.S. Appl. No. 10/549,619.
Issue Notification of Mar. 9, 2011 re U.S. Appl. No. 10/549,619.
First Restriction Requirement dated May 7, 2007 re U.S. Appl. No. 10/525,817.
Response submitted to First Restriction Requirement Sep. 10, 2007 re U.S. Appl. No. 10/525,817.
Second Restriction Requirement dated Nov. 26, 2007 re U.S. Appl. No. 10/525,817.
Response to second Restriction Requirement submitted Feb. 29, 2008 re U.S. Appl. No. 10/525,817.
Third Restriction Requirement dated Jul. 6, 2009 re U.S. Appl. No. 10/525,817.
Response to third Restriction Requirement submitted Oct. 5, 2009 re U.S. Appl. No. 10/525,817.
Non-final rejection dated Mar. 29, 2010 re U.S. Appl. No. 10/525,817.
Supplemental Non-final Action dated Apr. 2, 2010 re U.S. Appl. No. 10/525,817.
Balasubramanian, "Solid phase chemical technologies for combinatorial chemistry", J. Cell. Biochem. Suppl., 37, 2001, pp. 28-33.
Balasubramanian, "The science of chemical discovery: probing the unknown with new technologies", DDT, vol. 5, No. 12, Dec. 2000, pp. 533-534.
piercenet.com/method/avidin-biotin-interaction retrieved Nov. 5, 2013.
Schreiber, "The small-molecule approach to biology—Chemical genetics and diversity-oriented organic synthesis make possible the systematic exploration of biology", C&EN, Mar. 3, 2003, pp. 51-61.
Wills et al., "Recent developments in linker design and application", Current Opinion in Chemical Biology, 2003, 7, pp. 346-352.
Bain et al., "Regioselective Ligation of Oligoribonucleotides using DNA Splints", Nucl. Acids Res., vol. 20, No. 16, 4372, 1992.
Boger & Goldberg "Chapter 10: Multi-step Solution Phase Combinatorial Synthesis" in Combinatorial Chemistry, ed. Hicham Fenniri, Oxford University Press (Oxford, England), 2000, pp. 303-326.
Cheng et al., Novel Solution Phase Strategy for the Synthesis of Chemical Libraries Containing Small Organic Molecules, J. Am. Chem. Soc., vol. 118, 2567-2573, 1996.
Clark et al., "Design, Synthesis and Selection of DNA-encoded Small-molecule Libraries", Nat. Chem. Biol., vol. 5, No. 9, 647-654, 2009.
Curran, "Strategy-Level Separations in Organic Synthesis: From Planning to Practise", Angew. Chem. Int. Ed., vol. 37, 1174-1196, 1998.
Declaration by Dr. Dennis Benjamin (including curriculum vitae), Sep. 11, 2013.
Frutos et al. "Enzymatic Ligation Reactions of DNA "Words" on Surfaces for DNA Computing", J. Am. Chem. Soc., vol. 120, No. 40, 10277-10282, 1998.
Gait, "Chapter 1: An Introduction to Modern Methods of DNA Synthesis": Van Boom & Wreesman, "Chapter 7: Chemical Synthesis of Small Oligoribonucleotides in solution"; and Beckett & Uhlenbeck, "Chapter 8: Enzymatic Synthesis of Oligoribonucleotides", in Oligonucleotide Synthesis: A Practical Approach, ed. M.J. Gait, IRL Press (Oxford, England and Washington, DC), 1984, pp. 1-22, 153-183, and 185-197.
Gartner et al., "Expanding the Reaction Scope of DNA-Templated Synthesis", Angew. Chem. Int. Ed., vol. 41, No. 10, 1796-1800, 2002.
Gartner et al., "Multistep Small-Molecule Synthesis Programmed by DNA Templates", J. Am. Chem. Soc., vol. 124, No. 35, 10304-10306 (including Supporting Information, pp. 1-4).
Glen Research Report, "Advances in RNA Synthesis and Structural Analysis", vol. 11, No. 2, Dec. 1998.
Harrison et al., "Synthesis and Hybridization Analysis of a Smal Library of Peptide-oligonucleotide Conjugates", Nucl. Acids Res., vol. 26, No. 13, 3136-3145, 1998.
Hausch et al., "Libraries of Multifunctional RNA Conjugates for the Selection of New RNA Catalysts", Bioconjugate Chem., vol. 8, 885-890, 1997.
Hill et al., "Diels-Alder Bioconjugation of Diene-Modified Oligonucleotides", J. Org. Chem., vol. 66, 5352-5358, 2001.
Itakura et al., "Expression in *Escherichia coli* of a Chemically Synthesized Gene for the Hormone Somatostatin", Science, vol. 198, 1056-1063, 1977.
Janda, "Tagged Versus Untagged Libraries: Methods for the Generation and Screening of Combinatorial Chemical Libraries," PNAS USA, vol. 91, 10779-10785, 1994.
Kelemen et al., "Hypersensitive Substrate for Ribonucleases", Nucl. Acids. Res., vol. 27, No. 18, 3696-3701, 1999.
Kempe et al., Chemical and Enzymatic Biotin-labeling of Oligodeoxyribonucleotides, Nucl. Acids Res., vol. 13, No. 1, 45-57, 1985.
Kinoshita et al., "Enzymatic Synthesis of Sequencing Primers Based on a Library of Tetramers", Chem. Express, No. 7, 149-152, 1992.
Kinoshita et al., "Strand Ligation in a double-stranded DNA by T4 RNA Ligase", Chem. Lett., No. 9, 797-798, 1996.
Kitamura et al., "Construction of Block-Shuffled Libraries of DNA for Evolutionary Protein Engineering: Y-Ligation-Based Block Shuffling", Prot. Engineering, vol. 15, No. 10, 843-853, 2002.
Kitamura et al., "Development of Systemic in vitro Evolution and its Application to Generation of Peptide-Aptamer-Based Inhibitors of Cathepsin E", J. Mol. Biol., vol. 387, 1186-1198, 2009.
Moore et al. "Site-specific Modification of Pre-mRAN: the 2'-hydroxyl Groups at the Splice Sites", Science, vol. 256, No. 5059, 992-997, 1992.
Nielsen et al., "Synthetic Methods for the Implementation of Encoded Combinatorial Chemistry", J. Am. Chem. Soc., vol. 115, 9812-9813, 1993 with supplementary Materials (pp. 1-7).
Nielsen et al., "Towards Chemical Implementation of Encoded Combinatorial Libraries", Methods: A Companion to Meth: Enzymol., vol. 6, 361-371, 1994.
Roux et al., "Optimization and troubleshooting in PCR", PCR Methods Appl., vol. 4, No. 5, S185-S194, Apr. 1995.
Schmitz et al., "Solid-phase Enzymatic Synthesis of Oligonucleotides", Org. Lett., vol. 1, 1729-1731, 1999.
Seelig et al., "Site-directed Modification of Enzymatically Synthesized RNA: Transcription Initiation and Diels-Alder Reaction, " Tetrahed. Lett., vol. 38, 7729-7732, 1997.
Seo et al., "Click Chemistry to Construct Fluorescent Oligonucelotides for DNA sequencing", J. Org. Chem., vol. 68, 609-612, 2003.
Sherlin et al., "Chemical and Enzymatic Synthesis of tRNAs for High-throughput Crystallization", RNA, vol. 7, No. 11, 1671-1678, 2001.
Tabuchi et al., "An Efficient Ligation Method in the Making of an in vitro Virus for in vitro Protein Evolution, " Biol., Proced. Online, vol. 4, No. 1, 49-54, 2002.
Verma et al., "Modified Oligonucleotides: Synthesis and Strategy for Users", Annu. Rev. Biochem., vol. 67, 99-134, 1998.
Woiwode et al., "Synthetic Compound Libraries Displayed in the Surface of Encoded Bacteriophage", Chem. Biol., vol. 847-858, Sep. 2003.

(56) References Cited

OTHER PUBLICATIONS

Wojczewski et al., "Fluorescen Oligonucleotides—Versatile Tools as Probes and Primers for DNA and RNA Analysis", Synlett, No. 10, 1667-1678, 1999.

Wong & Whitesides, "Enzymes in Synthetic Organic Chemistry", Tetrahedron Organic Chemistry Series vol. 12, Pergamon, Elsevier Science Lrd. (Oxford, England) 1994, pp. XIII-XV, 1-40, and 329-334.

Zhang et al., "Solution-Phase Preparation of a 560-Compound Library of Individual Pure Mappicine Analogous by Fluorous Mixture Synthesis", J. Am. Chem. Soc., vol. 124, 10443-10450, 2002.

Kiebom, "Enzymes that do not work ini organic solvents: Too polar substrates give too tight enzyme-product complexes", Recl. Trav. Chim. Pays-Bas, 107, pp. 347-348, 1988.

Middleton et al., "Synthesis and purification of oligoribonucleotides using T4 RNA ligase and reverse-phase chromatography", Analytical Biochemistry, 144, pp. 110-117, 1985.

Narang, "DNA synthesis", Tetrahedron, vol. 39, No. 1, pp. 3-22, 1983.

Neilson et al., "Synthesis of biologically active portions of an intercistronic region by use of a new 3'-phosphate incorporation method to protect 3'-OH and their binding to ribosomes", Eur. J. Biochem., 99, pp. 429-439, 1979.

Ochoa et al., "Enzymatic synthesis of polynucleotides", J.Biol. Chem., vol. 236, 12, pp. 3303-3311, 1961.

Willis et al., "DNA ligase I deficiency in Bloom's syndrome", Nature, vol. 325, pp. 355-357, 1987.

Kurz et al. Psoralen photo-crosslinked mRNA puromycin conjugates: a novel template for the rapid and facile preparation of mRNA-protein fusions. Nucleic Acids Res. Sep. 15, 2000; 28(18): E83.

d'Angelo et al., "HIV-1 integrase: the next target for AIDS therapy?", Pathol. Biol. 2001, 49, pp. 237-246.

\* cited by examiner

Fig. 1
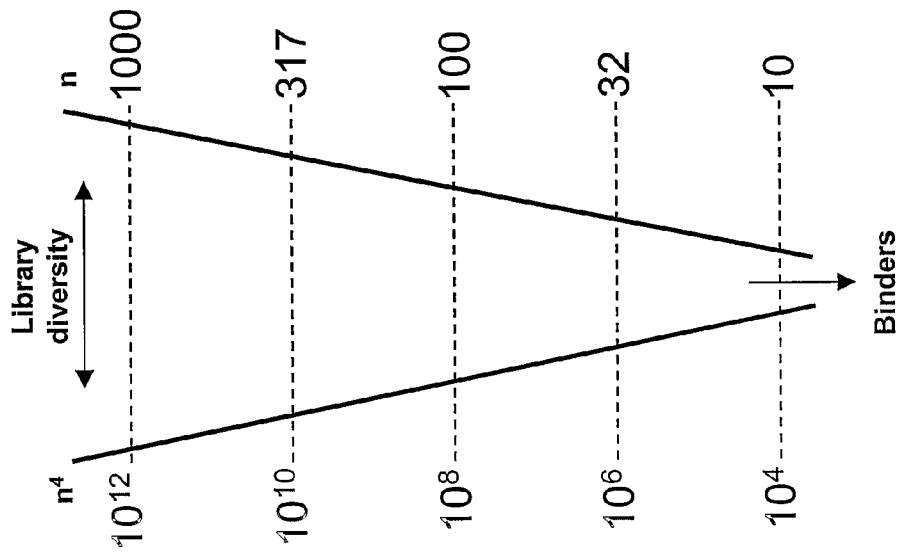
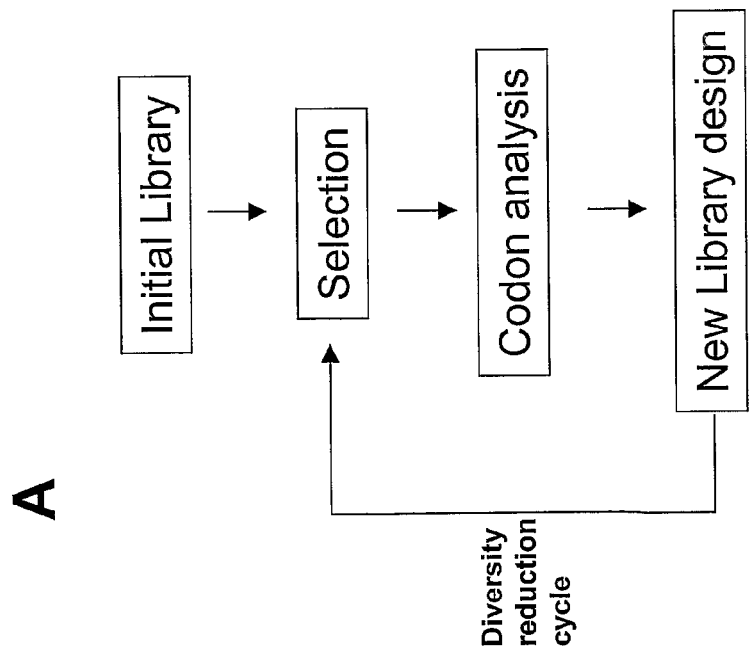

Fig. 5
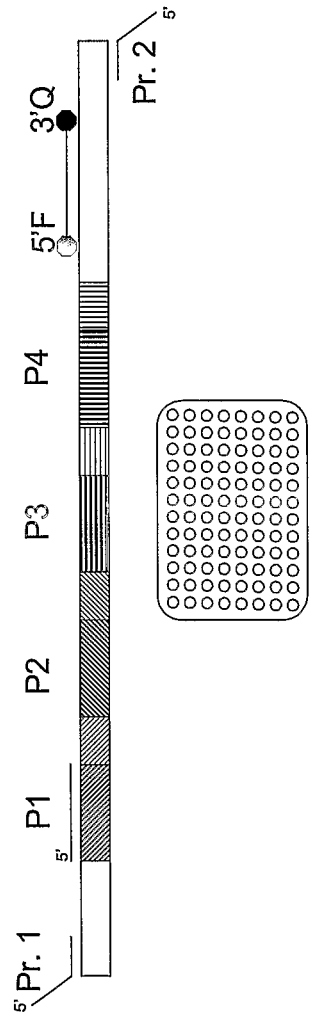
Panel A
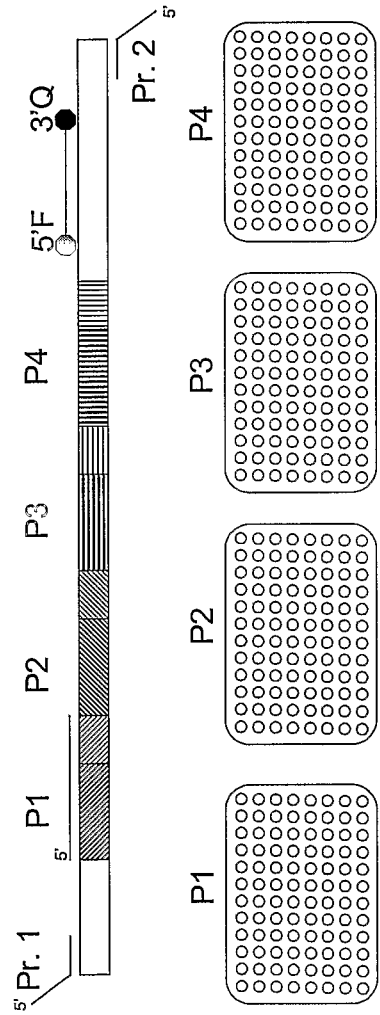
Panel B

METHOD FOR PRODUCING SECOND-GENERATION LIBRARY

This application is a Continuation of U.S. Ser. No. 10/546,538, filed 26 Jun. 2006; which is a National Stage Application of PCT/DK2004/000117, filed 23 Feb. 2004, which claims benefit of PA 2003 00268, filed 21 Feb. 2003 in Denmark, PA 2003 00269, filed 21 Feb. 2003 in Denmark, U.S. Ser. No. 60/448,480, filed 21 Feb. 2003; U.S. Ser. No. 60/448,460, filed 21 Feb. 2003; PA 2003 01356, filed 18 Sep. 2003 in Denmark and U.S. Ser. No. 60/504,748, filed 22 Sep. 2003, and which applications are incorporated herein by reference. To the extent appropriate, a claim of priority is made to each of the above disclosed applications.

Various patent and non-patent references cited in the present application are hereby incorporated by reference in their entirety.

TECHNICAL FIELD OF THE INVENTION

The invention relates to a method for producing a second-generation compound library with an improved desired property profile. In nature and artificial methods based on the natural system, the parent genotype is carried on to the offspring and results in a phenotype in which the exact type and sequence of amino acids is retained, unless a mutation and/or recombination has occurred. The present method only retains the identity of chemical entities, e.g. amino acids, while the sequence wholly or partly is scrambled. The result is a focused second-generation library with lower diversity.

BACKGROUND OF THE INVENTION

The biological evolution is based on the survival of specific genotypes that encode phenotypes with the most suitable functionalities in a certain environment. In all living species DNA programs the genotype. DNA serves two important functions in the natural selection process. One function is obviously to encode for the type of nucleotides used and the other function is to encode for the specific order of nucleotide sequences in a nucleic acid sequence. The strategy used in nature, i.e. encoding for the exact type as well as the precise sequence of nucleotides, ensures an extremely similarity between the progeny and its parents. Thus, conserving almost the exact sequence and type of the nucleotides is absolutely essential in order to create offspring with a high functionality. The changes in the genotype from one generation to another, which allow for evolution, are determined by the random mutation rate and recombination between the two parent's genotypes.

The natural selection cannot afford too many changes in the DNA from one generation to the next in order to secure survival of the species. Therefore, nature has evolved sophisticated means to proofread the copying of the DNA from the parents to its progeny and secured that the characteristics of phenotype from one generation to the next is carried only by the DNA.

Within the art of selecting ligands from a library of encoded polypeptides associated with a corresponding identifier nucleic acid sequence, the method of nature is used. Thus, when more than a single library generation is needed, the identifier nucleic acid sequences (genotype) carries the information from one generation to the next.

WO 93/03172 A1 discloses a method for identifying a polypeptide ligand having a desired property in a polypeptide library. In a first step, a translatable mRNA mixture is provided, which is mixed with a mixture of ribosome complexes to form a translation product attached to the mRNA strand responsible for the formation thereof. In a second step the ribosome complexes binding to a target are partitioned from and remainder of the library. In a third step, an amplification of mRNA strands of the partitioned ribosome complexes, which has bound to the target follows. The amplified mRNA strands are used for the production of a second generation library, which is subjected to a renewed contact with the target. The method is repeated a sufficient number of times until the size of the library has narrowed to a small pool of high affinity binders.

In WO98/31700 A1 a method for selecting a DNA molecule, which encodes for a desired protein, is disclosed. The method implies the initial presence of a pool of candidates RNA molecules, which subsequently is translated into a corresponding pool of RNA-protein fusions. Subsequently the mRNA-protein fusion products are subjected to a selection process, i.e. the fusion products are presented for a target molecule, and a new pool of complexes capable of binding to the target are partitioned. From the new pool of complexes, the mRNAs are recovered and amplified for use in a subsequent round of library generation. Xu, L. et al *Chemistry & Biology*, Vol. 9, 933-942, August 2002 discloses a practical embodiment in which a library of more than $10^{12}$ unique mRNA-protein fusion products through ten rounds of library generation and selection are used to identify a high affinity binding protein.

The preparation of libraries of synthetic molecules associated with a corresponding identifier nucleic acid sequence, and the selection of synthetic molecules from such libraries, have been the subject of various patent applications. When two or more generations of libraries are needed, the identifier nucleic acid sequence is used as carrier between an initial library and the next generation library.

Thus, in WO 00/23458A1 libraries of complexes comprising non-natural molecules attached to corresponding nucleic acid sequences are suggested. After a selection of the library has been conducted, the nucleic acid sequences of successful complexes are amplified by PCR and a new library is prepared from these nucleic acid sequences. The same method of carrying information from an initial library to the next library is applied in WO 02/074929A2 and WO 02/103008A2.

The present invention provides a new method for evolving encoded molecules. The method is based on the identification of chemical entities used in the synthesis of reaction products of successful complexes and the application, at least in part, of these chemical entities in the preparation of the next generation library. The utilization of preferable chemical entities and the exclusion of certain undesired chemical entities in the next library generation generally imply that the next generation library has a smaller size compared to the size of the initial library, thereby, at the same time, retaining the desirable encoded molecules in the library.

SUMMARY OF THE INVENTION

The present invention concerns a method for producing a composition of molecules with an improved desired property, said method comprising the steps of: providing an initial library comprising a plurality of different encoded molecules associated with a corresponding identifier nucleic acid sequence, wherein each encoded molecule comprises a reaction product of multiple chemical entities and the identifier nucleic acid sequence comprises codons identifying said chemical entities; subjecting the initial library to a condition partitioning members having encoded molecules displaying a predetermined property from the remainder of the initial library; identifying codons of the identifier nucleic acid sequences of the partitioned members of the initial library; and preparing a second-generation library of encoded molecules using the chemical entities coded for by the codons of the partitioned members of the initial library or a part thereof.

The present invention relates to a novel approach to perform evolution of molecules with a desired property, said approach being different from the approach of nature and the prior art. The invention is based on the selecting of chemical entities, the counterpart of amino acids in Nature, instead of the precise sequence of chemical entities. This new approach is powerful in ex vivo conditions when high functionality of the off spring is not vital for success and when the number of chemical entities relative to the number of reactants used in each encoded molecule is high.

The method disclosed herein will be increasingly effective as the library size increases. This is due to the fact that more chemical entities is used when a library size is increased, when the number of reactions for the formation of the encoded is fixed and the fact that different chemical entities tend to be involved in encoded molecules having the desired property. The chemical entities, which are part of the final selected molecules, will be enriched in each round of selection. Finally, when the diversity has been extensively reduced, the enriched molecules are decoded from the identifier nucleic acid sequence comprising the codons of the chemical entities that have participated in the formation of the encoded molecule.

The strategy of performing enrichment of chemical entities instead of specific combinations of chemical entities more efficiently search the chemical space for all combinations of chemical entities that are eager to show a certain property, such as a binding ability towards a target. Thus, chemical entities having a certain impact on the formation of encoded molecules is allowed in a new library to recombine in each new library generation. In a certain aspect of the invention, the recombination is random, i.e. once a chemical entity has qualified as being of interest it is allowed in every position of the reaction sequence. In another aspect of the invention, the recombination is semi-random, i.e. once a chemical entity is qualified as being of interest it is used in a certain position in the reaction sequence of the encoded molecule. In still a further aspect of the invention, the amount of the chemical entity used in a subsequent library generation is dependent on the frequency and the amount of the partitioned library members.

The present invention may be of special interest when a group of chemical entities are selected from a larger pool of chemical entities in the formation of a first library. Selecting chemical entities resulting in encoded molecules having a certain property in a first library and spiking with remaining chemical entities of the pool allows for the formation of a second-generation library not necessarily of a smaller size but enriched in encoded molecules having a certain property.

The second-generation library may be formed of a reaction product of the chemical entities without attaching the reaction product to a nucleic acid. In an embodiment of such second-generation library the individual reaction products are formed in discrete reaction compartments in accordance with traditional combi-chem technology. In a certain aspect of the invention, the second-generation library is prepared as the first generation library, i.e. the second-generation library comprises a plurality of different encoded molecules associated with a corresponding identifier nucleic acid sequence, wherein each encoded molecule comprises a reaction product of multiple chemical entities and the identifier nucleic acid sequence comprises codons identifying said chemical entities.

In a preferred aspect of the invention, it comprises subjecting the second-generation library to a condition partitioning members having encoded molecules displaying a predetermined property from the remainder of the second-generation library. The second-generation library may be partitioned as to the same property or a different property. Notably, the second-generation library can be screening against the same target or a different target.

After the partitioning of the second-generation library, the invention comprises the step of deducing the identity of the encoded molecule(s) using the identifier nucleic acid sequence, when present. Optionally, a third or further generation library may be formed and screened before the final deducing step is performed. In a certain embodiment, the decoding includes that the codons of the identifier nucleic acid sequence is decoded to establish the synthesis history of the encoded molecules. The synthesis history includes the identity of the chemical entities used and the point in time they enter the sequence of reactions resulting in the encoded molecule.

The encoded molecule is preferably a reaction product in which multiple chemical entity precursors have participated. The encoded molecule may have any chemical structure. Generally, the multiple chemical entities are precursors for a structural unit appearing in the encoded molecule. However, the chemical entities may also perform a chemical reaction with the nascent encoded molecule, which result in an altering or removal of chemical groups. In certain aspects of the invention, the encoded molecule is a scaffolded molecule, i.e. various chemical entities have reacted with a chemical core structure like steroid, benzodiazepine, retinol, camphor, ephedrine, penicillin, cannabinol, coumarin, oxazol, etc. In certain other aspects of the invention the encoded molecule is fully or partly a polymer. The polymer may be of a type which occurs naturally or may be a non-naturally occurring polymer. Nature only has the possibility of preparing $\alpha$-polypeptides using the recognition of a codon of an mRNA strand by the anticodon of a charged tRNA. In some aspects of the invention, the encoded molecule is not a $\alpha$-peptide. Notably, in some aspects of the invention, the chemical entities are reacted without enzymatic interaction to produce the encoded molecule.

The encoded molecule can be associated with the nucleic acid sequence identifier in any appropriate way. In a certain aspect of the invention, the encoded molecule associated with the corresponding identifier nucleic acid sequence is a bifunctional complex. The bifunctional complex may be formed by covalent or non-covalent attachment of the encoded molecule to the identifier nucleic acid sequence. In another aspect of the invention, an identifier nucleic acid sequence is physically a distinct entity separated from the encoded molecule, wherein the identifier identifies the spatial position of an encoded molecule, e.g. in the same compartment in which an encoded molecule is formed a corresponding identifier oligonucleotide is generated.

The conditions partitioning complexes of interests from the remainder of the library may be chosen from a variety of possibilities. In one aspect the condition relates to physical parameters, so that complexes displaying a physical stability under e.g. certain temperature conditions, certain acidic conditions, certain radiation conditions etc. are selected from the library. In other aspects of the invention the condition for partitioning the desired complexes includes subjecting the initial library to a molecular target and partitioning complexes binding to this target. The molecular target may be any compound of interest. Exemplary targets are proteins, carbohydrates, polysaccharides, hormones, receptors, antibodies, viruses, antigens, cells, tissues etc.

In certain aspects the target is immobilized on a solid support, such as column material and contacted with the candidate complexes in a fluid media followed by a partitioning of the complexes capable of binding to the target under the contacting conditions used. Typically the binding complexes are eluted from the column using increased stringency conditions.

The complexes as such or only the identifier part is harvested after the partitioning step. Usually the identifier nucleic acid sequences are amplified prior to the identification step. The amplification is suitably performed applying polymerise chain reaction (PCR). The amplified identifiers may be explicitly or implicitly identified. When the codons are identified explicitly, the sequence and identity of nucleotides in the codon is made known to the experimenter, whereas, when the codons of the identifiers are implicitly identified, the experimenter is not presented for the information.

Any suitable method for identifying codons may be used. In a certain aspect of the invention, traditional sequencing, e.g. by using a modification of the Sangers method or pyrosequencing methods, identifies the codons. In another aspect of the invention, the codons of the identifier nucleic acid sequences of the partitioned members of the initial library are identified by contacting said identifier nucleic acid sequences with a pool of nucleic acid fragments under conditions allowing for hybridisation.

The pool of nucleic acid fragments may be immobilized or in solution. In a certain aspect of the invention, the pool of nucleic acid fragments comprises a plurality of single stranded nucleic acid probes immobilized in discrete areas of a solid support, wherein the nucleic acid probes are capable of hybridising to a codon of the identifier nucleic acid sequence comprising codons. The nucleic acid probes may be positioned on a microarray, such that the identity of the codons is revealed by observing the discrete areas of the support in which a hybridisation event has occurred.

The nucleic acid probe can be directly hybridised to the identifier or the nucleic acid probe of the array is hybridised to an identifier nucleic acid sequence through an adapter oligonucleotide having a sequence complementing the probe as well as one or more codons of the identifier nucleic acid sequence. The probe may identify a single codon of an identifier or a probe of the array is capable of hybridising to two codons of the identifier nucleic acid sequence or a sequence complementary to said sequence. The ability to hybridise two or more codons makes it possible to study the influences of neighbouring chemical entities on each other. In a certain aspect, a nucleic acid probe of the array is capable of hybridising to all codons of an identifier nucleic acid sequence. This latter option will fully decode the identity of the encoded molecule. Usually however, a fully decoding is only possible for a relative small library size, as it presupposes a nucleic acid probe for each member of the library.

When single codons are detected, useful information about a certain codon may be gathered by detecting the codon together with a framing sequence identifying the position in the reaction history of the chemical entity corresponding to said codon.

As an example, if a library of complexes is prepared from 100 chemical entities and the three reactions, i.e. each identifier comprises 4 codons, the library size is $10^8$. For most practical uses $10^8$ is in the excess of what is possible to detect on an array, especially if multiple determinations for each identifier are considered necessary to obtain a high accuracy. However, an array of just 100 probes complementary to the 100 codons will reveal important information prior to or subsequent to a selection. In the event a framing sequence is detected together with the codon an array of 400 probes is needed.

A suitable method for identifying an hybridisation event is to use a label. Therefore, in a preferred embodiment, the existence of a hybridisation event is measured through labelling of the identifier nucleic acid sequence, or an amplification product thereof. When the label emits light, the hybridisation event is measured by the emission of light in a scanner. To reveal the relative abundance of each chemical entity in the library of encoded molecules, the relative intensity of light in each discrete spot is measured.

The measurement of a hybridisation event may be conducted by various methods known in the art. In the event the label emits lights, the presence or absence of a hybridisation event may be measured in a scanner, e.g. a confocal scanner. The scanner may be connected with computer software, which is able to quantify the amount of lights measured. The amount of light measured correlates with the amount of identifier annealed to the probes. Thus, it is possible to measure not only the presence or absence of one or more codons of an identifier; it is also possible to measure the relative amount of the codons in one or more identifiers.

After the complexes have been partitioned and the specific codons have been identified on the microarray, the information can be used to design optimized libraries including chemical entities based on both the selection data and the chemical structure. The microarray analysis will first of all detect which chemical entities pass the partitioning step. Secondly, the relative intensity on the microarray will reflect the relative binding affinity of the chemical entities. Finally, the structures of the chemical entities are directly identified due to the position of the probes on the array. For instance, chemical entities that are strongly selected in a partitioning process but possess some unfavourable chemical structure can be excluded in the next generation of library. Similarly, chemical entities that are weekly selected in a partitioning process but possess some favourable chemical structure can be included in the next generation of library. Thus, the next generation library design can be based both on a rational choice of chemical entities with lead-like structures and the selection pressure detected on the microarray.

Another method of identifying codons includes that nucleic acid fragments are primer oligonucleotides, and the identification involves subjecting the hybridisation complex between the primer oligonucleotides and the identifier nucleic acid sequences to a condition allowing for an extension reaction to occur when the primer is sufficient complementary to a part of the identifier nucleic acid sequence, and evaluating based on measurement of the extension reaction, the presence, absence, or relative abundance of one or more codons.

The extension reaction requires a primer, a polymerase as well as a collection of deoxyribonucleotide triphosphates (abbreviated dNTP's herein) to proceed. An extension product may be obtained in the event the primer is sufficient complementary to an identifier oligonucleotide for a polymerase to recognise the double helix as a substrate. After binding of the polymerase to the double helix, the deoxyribonucleotide triphosphates (blend of dATP, dCTP, dGTP, and dTTP) are incorporated into the extension product using the identifier oligonucleotide as identifier. The conditions allowing for the extension reaction to occur usually includes a suitable buffer. The buffer may be any aqueous or organic solvent or mixture of solvents in which the polymerase has a sufficient activity. To facilitate the extension process the polymerase and the mixture of dNTP's are generally included in a buffer which is added to the identifier oligonucleotide and primer mixture. An exemplary kit comprising the polymerase and the nNTP's for performing the extension process comprises the following: 50 mM KCl; 10 mM Tris-HCl at pH 8.3; 1.5 mM MgCl2; 0.001% (wt/vol) gelatin, 200 μM dATP; 200 μM dTTP; 200 μM dCTP; 200 μM dGTP; and 2.5 units *Thermus aquaticus* (Taq) DNA polymerase I (U.S. Pat. No. 4,889,818) per 100 microliters (μl) of buffer.

The primer may be selected to be complementary to one or more codons or parts of such codons. The length of the primers may be determined by the length of the codons, however, the primers usually are at least about 11 nucleotides in length, more preferred at least 15 nucleotides in length to allow for an efficient extension by the polymerase. The presence or absence of one or more codons is indicated by the presence of or absence of an extension product. The extension product may be measured by any suitable method, such as size fractioning on an agarose gel and staining with ethidium bromide.

In a preferred embodiment the admixture of identifier oligonucleotide and primer is thermocycled to obtain a sufficient number of copies of the extension product. The thermocycling is typically carried out by repeatedly increasing and decreasing the temperature of the mixture within a temperature range whose lower limit is about 30 degrees Celsius (30° C.) to about 55° C. and whose upper limit is about 90° C. to about 100° C. The increasing and decreasing can be continuous, but is preferably phasic with time periods of relative temperature stability at each of temperatures favouring polynucleotide synthesis, denaturation and hybridization.

When a single complex is analysed in accordance with the present method, the result may be used to verify the presence or absence of a specific chemical entity during the formation of the display molecule. The formation of an extension product is indicative of the presence of an oligonucleotide part complementary to the primer in the identifier oligonucleotide. Conversely, the absence of an extension product is indicative of the absence of an oligonucleotide part complementary to the primer in the identifier oligonucleotide. Selecting the sequence of the primer such that it is complementary to one or more codons will therefore provide information of the structure of the encoded molecule coded for by this codon(s).

In a preferred aspect of the invention, in the mixture of the identifier oligonucleotide and the primer oligonucleotide, a second primer complementary to a sequence of the extension product is included. The second primer is also termed reverse primer and ensures an exponential increase of the number of produced extension products. The method using a forward and reverse primer is well known to skilled person in the art and is generally referred to as polymerase chain reaction (abbreviated PCR) in the present application with claims. In one embodiment of the invention the reverse primer is annealed to a part of the extension product downstream, i.e. near the 3"end of the extension product, or a part complementing the coding part of the identifier oligonucleotide. In another embodiment, the first primer (forward primer) anneals to an upstream position of the identifier oligonucleotide, preferably before the coding part, and the reverse primer anneals to a sequence of the extension product complementing one or more codons or parts thereof.

The amplicons resulting from the PCR process may be stained during or following the reaction to ease the detection. A staining after the PCR process may be prepared with e.g. ethidium bromide or a similar staining agent. As an example, amplicons from the PCR process is run on an agarose gel and subsequently stained with ethidium bromide. Under UV illumination bands of amplicons becomes visible. It is possible to incorporate the staining agent in the agarose gel or to allow a solution of the staining agent to migrate through the gel. The amplicons may also be stained during the PCR process by an intercalating agent, like CYBR. In presence of the intercalating agent while the amplification proceeds it will incorporate in the double helix. The intercalation agent may then be made visible by irradiation by a suitable source.

The intensity of the staining is informative of the relative abundance of a specific amplicon. Thus, it is possible to quantify the occurrence of a codon in an identifier oligonucleotide. When a library of bifunctional complexes has been subjected to a selection the codons in the pool of identifier oligonucleotides which has been selected can be quantified using this method. As an example a sample of the selected identifier oligonucleotides is subjected to various PCR amplifications with different primers in separate compartments and the PCR product of each compartment is analysed by electrophoresis in the presence of ethidium bromide. The bands that appear can be quantified by a densitometric analysis after irradiation by ultraviolet light and the relative abundance of the codons can be measured.

Alternatively, the primers may be labelled with a suitable small molecule, like biotin or digoxigenin. A PCR-ELISA analysis may subsequently be performed based on the amplicons comprising the small molecule. A preferred method includes the application of a solid support covered with streptavidin or avidin when biotin is used as label and anti-digoxigenin when digoxigenin is used as the label. Once captured, the amplicons can be detected using an enzyme-labelled avidin or anti-dixigenin reporter molecule similar to a standard ELISA format.

To avoid laborious post-PCR handling steps required to evaluate the amplicons, it is in a certain embodiment preferred to measure the extension process "real time". Several real time PCR processes has been developed and all the suitable real time PCR process available to the skilled person in the art can be used in the evaluating step of the present invention and are include in the present scope of protection. The PCR reactions discussed below are of particular interest.

The monitoring of accumulating amplicons in real time has been made possible by labelling of primers, probes, or amplicons with fluorogenic molecules. The real time PCR amplification is usually performed with a speed faster than the conventional PCR, mainly due to reduced cycles time and the use of sensitive methods for detection of emissions from the fluorogenic labels. The most commonly used fluorogenic oligoprobes rely upon fluorescent resonance energy transfer (FRET) between fluorogenic labels or between one fluorophor and a dark or "black-hole" non-fluorescent quencher (NFQ), which disperse energy as heat rather than fluorescence. FRET is a spectroscopic process by which energy is passed between molecules separated by 10-100 Å that have overlapping emission and absorption spectra. An advantage of many real time PCR methods is that they can be carried out in a closed system, i.e. a system which does not need to be opened to examine the result of the PCR. A closed system implies a reduced result turnaround, minimisation of the potential for carry-over contamination and the ability to closely scrutinise the essay's performance.

The real time PCR methods currently available to the skilled person can be classified into either amplicon sequence specific or non-specific methods. The basis for the non-specific detection methods is a DNA-binding fluorogenic molecule. Included in this class are the earliest and simplest approaches to real time PCR. Ethidium bromide, YO-PRO-1, and SYBR® green 1 all fluorescence when associated with double stranded DNA which is exposed to a suitable wavelength of light. This approach requires the fluorescent agent to be present during the PCR process and provides for a real time detection of the fluorescent agent as it is incorporated into the double stranded helix.

The amplicons sequence specific methods includes, but are not limited to, the TaqMan®, hairpin, LightCycler®, Sunrise®, and Scorpion® methods. The LightCycler® method also designated "HybProbes" make use of a pair of adjacent, fluorogenic hybridisation oligonucleotide probes. A first, usually the upstream oligoprobe is labelled with a 3' donor fluorophore and the second, usually the downstream probe is commonly labelled with either a Light cycler Red 640 or Red 705 acceptor fluorophore a the 5' terminus so that when both oligoprobes are hybridised the two fluorophores are located in close proximity, such as within 10 nm, of each other. The close proximity provides for the emission of a fluorescence when irradiated with a suitable light source, such a blue diode in case of the LightCycler®. The region for annealing of the probes may be any suitable position that does not interfere with the primer annealing. In a suitable setup, the site for binding the probes are positioned downstream of the codon region on the identifier oligonucleotide. Alternatively, when a reverse primer is used, the region for annealing the probes may be at the 3' end of the strand complementing the identifier oligonucleotide. Another embodiment of the LightCycler method includes that the pair of oligonucleotide probes are annealed to one or more codons and primer sites exterior to the coding part of the identifier oligonucleotide are used for PCR amplification.

The TaqMan® method, also referred to as the 5' nuclease or hydrolysis method, requires an oligoprobe, which is attached to a reporter fluorophor, such as 6-carboxy-fluoroscein, and a quencher fluorophore, such as 6-carboxy-tetramethyl-rhodamine, at each end. When in close proximity, i.e. annealed to an identifier oligonucleotide, or a sequence complementing the identifier oligonucleotide, the quencher will "hijack" the emissions that have resulted from the excitation of the reporter. As the polymerase progresses along the relevant strand, it displaces and the hydrolyses the oligoprobe via its 5'→3' endonuclease activity. Once the reporter is removed from the extinguishing influence of the quencher, it is able to release excitation energy at a wavelength that can be monitored by a suitable instrument, such as ABI Prism® 7700. The fractional cycle number at which the real-time fluorescence signal mirrors progression of the reaction above the background noise is normally used as an indicator of successful identifier oligonucleotide amplification. This threshold cycle ($C_T$) is defined as the PCR cycle in which the gain in fluorescence generated by the accumulating amplicons exceeds 10 standard deviations of the mean base line fluorescence. The $C_T$ is proportional to the number of identifier oligonucleotide copies present in the sample. The TaqMan probe is usually designed to hybridise at a position downstream of a primer binding site, be it a forward or a reverse primer. When the primer is designed to anneal to one or more codons of the identifier oligonucleotide, the presence of these one or more codons is indicated by the emittance of light. Furthermore, the quantity of the identifier oligonucleotides comprising the one or more codons may be measured by the $C_T$ value.

The Hairpin method involves an oligoprobe, in which a fluorophore and a quencher are positioned at the termini. The labels are hold in close proximity by distal stem regions of homologous base pairing deliberately designed to create a hairpin structure which result in quenching either by FRET or a direct energy transfer by a collisional mechanism due to the intimate proximity of the labels. When direct energy transfer by a collision mechanism is used the quencher is usually different from the FRET mechanism, and is suitably 4-(4'-dimethylamino-phenylazo)-benzene (DABCYL). In the presence of a complementary sequence, usually downstream of a primer, or within the bounds of the primer binding sides in case of more than one a single primer, the oligoprobe will hybridise, shifting into an open configuration. The fluorophore is now spatially removed from the quencher's influence and fluorescence emissions are monitored during each cycle. In a certain aspect, the hairpin probe may be designed to anneal to a codon in order to detect this codon if present on the identifier oligonucleotide. This embodiment may be suitable if codons only differs from each other with a single or a few nucleotides, because is in well-known that the occurrence of a mismatch between a hairpin oligoprobe and its target sequence has a greater destabilising effect on the duplex than the introduction of an equivalent mismatch between the target oligonucleotide and a linear oligoprobe. This is probably because the hairpin structure provides a highly stable alternate conformation.

The Sunrise and Scorpion methods are similar in concept to the hairpin oligoprobe, except that the label becomes irreversible incorporated in to the PCR product. The Sunrise method involves a primer (commercially available as Amplifluor™ hairpin primers) comprising a 5' fluorophore and a quencher, e.g. DABCYL. The labels are separated by complementary stretches of sequence that create a stem when the sunrise primer is closed: At the 3' terminus is a target specific primer sequence. In a preferred embodiment the target sequence is a codon, optionally more codons. The sunrise primer's sequence is intended to be duplicated by the nascent complementary stand and, in this way, the stem is destabilised, the two fluorophores are held apart, usually between 15 and 25 nucleotides, and the fluorophore is free to emit its excitation energy for monitoring. The Scorpion primer resembles the sunrise primer, but derivate in having a moiety that blocks duplication on the signalling portion of the scorpion primer. The blocking moiety is typically hexethylene glycol. In addition to the difference in structure, the function of the scorpion primers differs slightly in that the 5' region of the oligonucleotide is designed to hybridise to a complementary region within the amplicons. In a certain embodiment the complementary region is a codon on the identifier oligonucleotide. The hybridisation forces the labels apart disrupting the hairpin and permitting emission in the same way as the hairpin probes.

After the selection has been performed the codon profile is indicative of the chemical entities that have been used in the synthesis of encoded molecules having a certain property, such as an affinity towards a target. In the event the selection has been sufficient effective it may be possible directly to deduce a part or the entire structure of encoded molecules with the desired property. Alternatively, it may be possible to deduce a structural unit appearing more frequently among the encoded molecules after the selection, which gives important information to the structure-activity-relationship (SAR). If the selection process has not narrowed the size of the library to a manageable number, the formation of a second-generation library is useful. In the formation of the second-generation library chemical entities, which have not been involved in the synthesis of encoded molecules that have been successful in the selection may be omitted, thus limiting the size of the new library and at the same time increasing the concentration of complexes with the requested property, e.g. the ability to bind to a target. The second-generation library may then be subjected to more stringent selection conditions to allow only the encoded molecules with a higher affinity to bind to the target. The second-generation library may also be generated using the chemical entities coded for in addition to certain chemical entities suspected of increasing the performance of the final encoded molecule. The indication of certain successful chemical entities may be obtained from the SAR. The use in a second-generation library of chemical entities, which have proved to be interesting for further investigation in a preceding library, may thus entail a shuffling with new chemical entities that may focus the second-generation library in a certain desired direction.

An Example of implicit identification of codons includes that the nucleic acid fragment is associated with a chemical entity precursor capable of being transferred to a recipient reactive group. The recipient reactive group may be a part of a chemical scaffold and the chemical entity precursor may add a structural unit to said scaffold. It is preferred that the nucleic acid fragment codes for the chemical entity. In some aspects of the present invention each member of the nucleic acid fragment pool comprises an anticodon, which identifies the chemical entity. When a plurality of chemical entities are present the anticodon is preferably unique, i.e. a unique correspondence between the chemical entities and the associated anticodons exists.

The identifier nucleic acid sequence comprises codons, which may be able to pair with one or more anticodons of the pool of nucleic acid fragments. The pairing between one or more codons of an identifier nucleic acid sequence and one or more anticodons is preferably specific, i.e. the one or more codons of the identifier nucleic acid sequence are only recognized by particular anticodons. The nucleic acid fragment containing more than one anticodon can encode for scaffold molecules where each anticodon encodes for specific chemical entities of that scaffold molecule. The specific pairing makes it possible implicitly to decode the codon of an identifier nucleic acid sequence. In the method according to the invention, non-specific pairing between codons and anticodons can be cleaved with an enzyme or chemically treated to break the double stranded nucleotides. The non-pairing region can be cleaved using enzymes that cleaves specifically nucleotide sequences with mismatches. Notably, the enzyme is selected from T4 endonuclease VII, T4 endonuclease I, CEL I, nuclease S1, or variants thereof. The cleavage is preferable used when more than one codon and anticodon is involved in pairing between the identifier nucleic acid sequence and the nucleic acid fragment.

The pool of nucleic acid fragments associated with a chemical entity may comprise anticodons complemented by codons of one or more identifier nucleic acid sequence as well as anticodons which are not complemented by codons on any identifier nucleic acid sequence. In other words, the amount of genetic information contained in the anticodons of the pool is larger than the amount of genetic information complemented by the codons.

The contacting of the one or more identifier nucleic acid sequences with the pool of nucleic acid fragments are usually conducted at conditions, which allow for hybridisation, i.e. conditions at which cognate nucleic acid sequences can anneal to each other. To facilitate the recovery of nucleic acid fragments, which have annealed to the identifier nucleic acid sequences, the identifier nucleic acid sequences are usually immobilized on a solid support. Examples of suitable solid supports include beads and column material, e.g. beads and column material associated with a second part of the affinity pair to bind identifier nucleic acid sequences attached to the first part of the molecular affinity pair. In certain aspects of the invention the solid support is associated with streptavidin and the identifier nucleic acid sequences are attached to biotin.

When the identifier nucleic an acid sequences are immobilized on a solid support the pool of nucleic acid fragments is typically present in a mobile phase, i.e. dissolved in a liquid. The identifier nucleic acids will hybridise to these nucleic acid fragments in the pool which are sufficient complementary to a particular part of an identifier nucleic acid sequence for a binding to occur. Fragments not finding any complementing sequence will remain in the solution. In the event, the identifier nucleic acid sequences are segregated into codons and the fragments comprises anticodons, the anticodons which are able to anneal to a codons will be caught while fragments not having a cognate codon will be maintained in the mobile phase. When codons and anticodons are present in the method of the present invention, specific hybridisation implies that the tendency of an anticodon to cross-hybridise to another codon will be impede or avoided. To avoid cross-hybridisation, codons may be designed such that each codon is distinguished from all other codons be one, two or more mismatching nucleotides.

The mobile phase is subsequently separated from the solid phase e.g. by washing, and the enriched pool of fragments is recovered. The recovery of the nucleic acid fragments are usually done by subjecting the hybrid to denaturing conditions, i.e. conditions which separate the two strands. If the parent nucleic acid sequences are immobilized on beads, the separation of the fragments can be effected using denaturing conditions and centrifugation/spinning.

The enriched pool of nucleic acid fragments associated with a chemical entity may be used directly to prepare a next generation library of complexes, in which each member of the library comprises an encoded molecule and the nucleic acid sequence which codes for this molecule. In one embodiment of the invention, building blocks comprising a particular transferable chemical entity associated with an anti-codon corresponding to the anticodons of the detected fragments are used in the generation of the next generation library. In another embodiment, additional building blocks are added having modified transferable chemical entities in order to improve on a certain property of the encoded molecule.

The complexes may be prepared by various known methods starting from the nucleic acid fragment comprising the anticodon and the chemical entity, as disclosed above. According to a particular method, the next generation library is formed by a) mixing under hybridisation conditions, nascent bifunctional complexes comprising a chemical entity or a reaction product of chemical entities, and an identifier nucleic acid sequence comprising codon(s) identifying said chemical entities, with the recovered nucleic acid fragments, said fragments comprising an oligonucleotide sufficient complementary to at least a part of the identifier nucleic acid sequence to allow for hybridisation, a transferable chemical entity and an anticodon identifying the chemical entity, to form hybridisation products; and b) transferring the chemical entities of the nucleic acid fragments to the nascent bifunctional complexes through a reaction involving a reactive group of the nascent bifunctional complex, in conjunction with a transfer of the genetic information of the anticodon.

Preferably, the above method for preparing the next generation library comprises the further step of c) separating the components of the hybridisation product and recovering the complexes. If further chemical entities are intended to participate in the formation of the encoded molecule of the nascent complex, steps a) through c) are repeated as appropriate using the recovered complexes in step c) as the nascent bifunctional complexes in step a) of the next round.

The genetic information of the anticodon may be transferred to the nascent complex by a variety of methods. According to a first embodiment the genetic information of the anticodon is transferred by enzymatically extending the oligonucleotide identifier region to obtain a codon attached to the bifunctional complex having received the chemical entity. A second embodiment implies that genetic information of the anti-codon is transferred to the nascent complexes by hybridisation to a cognate codon of the nascent complex.

According to the first embodiment, the enriched pool of fragments comprises an affinity oligonucleotide sufficient complementary to an identifier region of the nascent complex, said oligonucleotide being distinct from the anticodon. Accordingly, the oligonucleotide identifier region of the nascent complex anneals to the affinity oligonucleotide of the building block to form the hybridisation product, while the anti-codon remains single stranded. Subsequently, the chemical entity is transferred to the recipient reactive group of the complex to form the encoded molecule prior to, simultaneously with, or subsequent to the enzymatically extension of the hybridisation product using the anticodon as identifier. Specific examples of suitable enzymes are polymerases and ligases, which requires dNTPs and oligonucleotides, respectively as substrates. The method for forming the complexes according to this first embodiment is the subject PCT/DK03/00739, the content thereof being incorporated herein by reference.

According to the second embodiment, the anticodon form part of the affinity oligonucleotide, i.e. the anticodon is a part of or the entire affinity oligonucleotide. Initially, a plurality of identifiers comprising different codons and/or different order of codons is provided. The identifiers are associated with a recipient reactive group, i.e. the reactive group may be covalently attached to the identifier or attached by hybridisation. Notably, a codon of the identifier may be used for the attachment of a building block harbouring the reactive group. The identifiers are subsequently contacted with the enriched pool of building blocks, i.e. nucleic acid fragments associated with a transferable chemical entity. The mixture of identifiers and building blocks are maintained at hybridisation conditions to anneal the anticodon of the building blocks to the cognate codon of the identifier. After or simultaneously with the annealing step, the chemical entity is transferred to the recipient reactive group of the identifier. The method for forming the complexes according to the second embodiment is the subject of various patent applications, including WO 02/103008, WO 02/074929, Danish patent application No. PA 2002 01347, and U.S. provisional patent application No. 60/409,968. The content of these patent applications are incorporated herein by reference in their entirety.

The new generation of library complexes may be used in a partition step, in which the library of complexes is subjected to a condition partitioning complexes displaying a predetermined property from the remainder of the next generation library, as explained above. Thus, using the present method, it is possible to repeat the partitioning procedure a desired number of times using still more stringent conditions, until a single or a few encoded molecules are identified which display the desired property to a high extent. When the partitioning is based on an affinity assay, the library of encoded molecules are increasingly narrowed in size from one generation to the next and at the same time the high affinity binders are increased in concentration.

The outcome of a codon analysis will be dependent of the enrichment factor in the selection process. An efficient and specific selection will generate a large difference between the specific binders compared to the background. Still, there will be a large amount of molecules in the background that will reduce the possibility to obtain measurable differences between the binders and the background in the codon analysis procedure. If the enrichment factor (or too large library) is not good enough to distinguish a specific binder among the background binders, the signal in the codon analysis will probably not be detectable. However, there will be a continuing of binders that use a certain chemical entity in a certain position. These "non optimal" binders (a certain important chemical entity in one position and less important in the other position) will be many due to the diversity obtained when only one (or a few) positions are important in the selection process. Therefore, the sum of all molecules with a preferable chemical entity in a certain position will be larger than the sum of all molecules with a non-binding chemical entity, which will make the codon analysis easier.

This invention may involve an extensive analysis of all the chemical entities in a library and how they are involved in the binding to targets. This information can be used both to design new libraries and in the final process where the lead structures are produced and pre-clinical candidates are picked. The extensive data obtained in the codon analysis can for instance be used for selecting candidates with the appropriate specificity. This can be done if selection has been performed on a family of proteins where one of the members is the target.

The invention enables pharmacophore identification and transformation into small molecule drugs. In cases where peptide-like libraries is used, the peptide/petidomimetic lead to small molecule conversion process is supported by medicinal chemistry and cheminformatics and guided by matching the pharmacophore derived from massive structure activity relationship (SAR) data information from the codon analysis. A "pharmacophore" is a description of the structural criteria a molecule must fulfil in order that it is active against a specified biological receptor. These criteria are usually the 3D spatial relationships of a set of chemical features, and sometimes include the steric boundaries, within which the molecule must fit. There is a set of software methods, which automatically infers such pharmacophores, given a SAR, in the absence of direct macromolecular structural data.

The extensive SAR information obtained using the codon analyses described in this invention can be combined with molecular modeling technologies to refine for example pharmacophore models and the plausible interactions between the potential binders and a target.

The codon analysis is also a valuable experimental tool for SAR on weak binders. The codon analysis measures the abundance of chemical entities after a selection in all binding molecules. Thus, even week binders, which there might be many of, is detected even though the detected codon is selected in many different combinations. The selection procedure can also be tuned to enrich predominately for weak binders, which will simplify the codon analysis data.

This invention is also suitable for replacing the laborious task of extracting SAR information by hand with an automated process using suitable algorithm and software programs. The codon analysis (e.g. array or QPCR measurements) can be directly feed into a data handling software program that use both the codon abundances and structural data to generate SAR information and potential pharmacophore models.

The SAR information and potential pharmacophore models obtained from the codon analysis can be used to design focused libraries in an array format allowing massive and parallel testing. Thus, the selection procedure and codon analysis can be seen as a diversity reduction step to allow a complete test of potential binders in an array format.

Various methods for identifying the codons of the identifiers of step iii) are disclosed herein. When a pool of partitioned identifier nucleic acid sequences is subjected to the identification step it is normally not practically to decode a sufficient number of sequences comprising the entire "genome" of an encoded molecule to ensure that all interesting encoded molecules have been revealed. Therefore, a modified sequencing technique preferably identifies the codons in each position occurring with the highest frequency. The next generation library is then build using in each position the chemical entities occurring with the highest frequency.

In a certain embodiment of the invention, the codon identification step uses the entire population of identifier nucleic acid sequences in the analysis and informs the experimenter of the relative abundance of each codon in a certain position. The codon information may be obtained using microarray, QPCR, or any equivalent method for revealing the identity of codons. In contrary, sequencing a subset of identifier nucleic acid sequences only provides the experimenter with a limited insight as to the population of codons and the corresponding encoded molecules.

DETAILED DESCRIPTION OF THE INVENTION

Complex

The complex comprises an encoded molecule and an identifier oligonucleotide. The identifier comprises codons that identify the encoded molecule. Preferably, the identifier oligonucleotide identifies the encoded molecule uniquely, i.e. in a library of complexes a particular identifier is capable of distinguishing the molecule it is attached to from the rest of the molecules.

The encoded molecule and the identifier may be attached directly to each other or through a bridging moiety. In one aspect of the invention, the bridging moiety is a selectively cleavable linkage.

The identifier oligonucleotide may comprise two or more codons. In a preferred aspect the identifier oligonucleotide comprises three or more codons. The sequence of each codon can be decoded utilizing the present method to identify reactants used in the formation of the encoded molecule. When the identifier comprises more than one codon, each member of a pool of chemical entities can be identified and the order of codons is informative of the synthesis step each member has been incorporated in.

In a certain embodiment, the same codon is used to code for several different chemical entities. In a subsequent identification step, the structure of the encoded molecule can be deduced taking advantage of the knowledge of different attachment chemistries, steric hindrance, deprotection of orthogonal protection groups, etc. In another embodiment, the same codon is used for a group of chemical entities having a common property, such as a lipophilic nature, a certain attachment chemistry etc. In a preferred embodiment, however, the codon is unique i.e. a similar combination of nucleotides does not appear on the identifier oligonucleotide coding for another chemical entity. In a practical approach, for a specific chemical entity, only a single combination of nucleotides is used. In some aspects of the invention, it may be advantageous to use several codons for the same chemical entity, much in the same way as Nature uses up to six different codons for a single amino acid. The two or more codons identifying the same chemical entity may carry further information related to different reaction conditions.

The sequence of the nucleotides in each codon may have any suitable length. The codon may be a single nucleotide or a plurality of nucleotides. In some aspects of the invention, it is preferred that each codon independently comprises four or more nucleotides, more preferred 4 to 30 nucleotides. In some aspects of the invention the lengths of the codons vary.

A certain codon may be distinguished from any other codon in the library by only a single nucleotide. However, to facilitate a subsequent decoding process and to increase the ability of the primer to discriminate between codons it is in general desired to have two or more mismatches between a particular codon and any other codon appearing on identifier oligonucleotide. As an example, if a codon length of 5 nucleotides is selected, more than 100 nucleotide combinations exist in which two or more mismatches appear. For a certain number of nucleotides in the codon, it is generally desired to optimize the number of mismatches between a particular codon relative to any other codon appearing in the library.

The identifier oligonucleotide will in general have at least two codons arranged in sequence, i.e. next to each other. Two neighbouring codons may be separated by a framing sequence. Depending on the encoded molecule formed, the identifier may comprise further codons, such as 3, 4, 5, or more codons. Each of the further codons may be separated by a suitable framing sequence. Preferably, all or at least a majority of the codons of the identifier are separated from a neighbouring codon by a framing sequence. The framing sequence may have any suitable number of nucleotides, e.g. 1 to 20. Alternatively, codons on the identifier may be designed with overlapping sequences.

The framing sequence, if present, may serve various purposes. In one setup of the invention, the framing sequence identifies the position of the codon. Usually, the framing sequence either upstream or downstream of a codon comprises information which positions the chemical entity and the reaction conditions in the synthesis history of the encoded molecule. The framing sequence may also or in addition provide for a region of high affinity. The high affinity region may ensure that a hybridisation event with an anti-codon will occur in frame. Moreover, the framing sequence may adjust the annealing temperature to a desired level.

A framing sequence with high affinity can be provided by incorporation of one or more nucleobases forming three hydrogen bonds to a cognate nucleobase. Examples of nucleobases having this property are guanine and cytosine. Alternatively, or in addition, the framing sequence may be subjected to backbone modification. Several back bone modifications provides for higher affinity, such as 2'-O-methyl substitution of the ribose moiety, peptide nucleic acids (PNA), and 2'-4' O-methylene cyclisation of the ribose moiety, also referred to as LNA (Locked Nucleic Acid).

The sequence comprising a codon and an adjacent framing sequence has in a certain aspect of the invention a total length of 11 nucleotides or more, preferably 15 nucleotides or more. A primer may be designed to complementary to the codon sequence as well as the framing sequence. The presence of an extension reaction under conditions allowing for such reaction to occur is indicative of the presence of the chemical entity encoded in the codon as well as the position said chemical entity has in the entire synthesis history of the encoded molecule.

The identifier may comprise flanking regions around the coding section. The flanking regions can also serve as priming sites for amplification reactions, such as PCR or as binding region for oligonucleotide probe. The identifier may in certain embodiments comprise an affinity region having the property of being able to hybridise to a building block.

It is to be understood that when the term identifier oligonucleotide is used in the present description and claims, the identifier oligonucleotide may be in the sense or the anti-sense format, i.e. the identifier can be a sequence of codons which actually codes for the encoded molecule or can be a sequence complementary thereto. Moreover, the identifier may be single-stranded or double-stranded, as appropriate.

The encoded molecule part of the complex is generally of a structure expected of having an effect according to the property sought for, e.g. the encoded molecule has a binding affinity towards a target. When the target is of pharmaceutical importance, the encoded molecule is generally a possible drug candidate. The complex may be formed by tagging a library of different possible drug candidates with a tag, e.g. a nucleic acid tag identifying each possible drug candidate. In another embodiment of the invention, the molecule formed by a variety of reactants which have reacted with each other and/or a scaffold molecule. Optionally, this reaction product may be post-modified to obtain the final molecule displayed on the complex. The post-modification may involve the cleavage of one or more chemical bonds attaching the encoded molecule to the identifier in order more efficiently to display the encoded molecule.

The formation of an encoded molecule generally starts by a scaffold, i.e. a chemical unit having one or more reactive groups capable of forming a connection to another reactive group positioned on a chemical entity, thereby generating an addition to the original scaffold. A second chemical entity may react with a reactive group also appearing on the original scaffold or a reactive group incorporated by the first chemical entity. Further chemical entities may be involved in the formation of the final reaction product. The formation of a connection between the chemical entity and the nascent encoded molecule may be mediated by a bridging molecule. As an example, if the nascent encoded molecule and the chemical entity both comprise an amine group a connection between these can be mediated by a dicarboxylic acid. A synthetic molecule is in general produced in vitro and may be a naturally occurring or an artificial substance. Usually, a synthetic molecule is not produced using the naturally translation system in an in vitro process.

The chemical entities that are precursors for structural additions or eliminations of the encoded molecule may be attached to a building block prior to the participation in the formation of the reaction product leading the final encoded molecule. Besides the chemical entity, the building block generally comprises an anti-codon. In some embodiments the building blocks also comprise an affinity region providing for affinity towards the nascent complex.

Thus, the chemical entities are suitably mediated to the nascent encoded molecule by a building block, which further comprises an anticodon. The anti-codon serves the function of transferring the genetic information of the building block in conjunction with the transfer of a chemical entity. The transfer of genetic information and chemical entity may occur in any order. The chemical entities are preferably reacted without enzymatic interaction in some aspects of the invention. Notably, the reaction of the chemical entities is preferably not mediated by ribosomes or enzymes having similar activity. In other aspects of the invention, enzymes are used to mediate the reaction between a chemical entity and a nascent encoded molecule.

According to certain aspects of the invention the genetic information of the anti-codon is transferred by specific hybridisation to a codon on a nucleic acid identifier. Another method for transferring the genetic information of the anti-codon to the nascent complex is to anneal an oligonucleotide complementary to the anti-codon and attach this oligonucleotide to the complex, e.g. by ligation. A still further method involves transferring the genetic information of the anti-codon to the nascent complex by an extension reaction using a polymerase and a mixture of dNTPs.

The chemical entity of the building block may in most cases be regarded as a precursor for the structural entity eventually incorporated into the encoded molecule. In other cases the chemical entity provides for the eliminations of chemical units of the nascent encoded molecule. Therefore, when it in the present application with claims is stated that a chemical entity is transferred to a nascent encoded molecule it is to be understood that not necessarily all the atoms of the original chemical entity is to be found in the eventually formed encoded molecule. Also, as a consequence of the reactions involved in the connection, the structure of the chemical entity can be changed when it appears on the nascent encoded molecule. Especially, the cleavage resulting in the release of the entity may generate a reactive group which in a subsequent step can participate in the formation of a connection between a nascent complex and a chemical entity.

The chemical entity of the building block comprises at least one reactive group capable of participating in a reaction which results in a connection between the chemical entity of the building block and another chemical entity or a scaffold associated with the nascent complex. The number of reactive groups which appear on the chemical entity is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections, are typically present on scaffolds. Non-limiting examples of scaffolds are opiates, steroids, benzodiazepines, hydantoines, and peptidylphosphonates.

The reactive group of the chemical entity may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a chemical reagent or an enzyme. The cleavage results in a transfer of the chemical entity to the nascent encoded molecule or in a transfer of the nascent encoded molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage is conducted as a simultaneous reaction, i.e. either the chemical entity of the building block or the nascent encoded molecule is a leaving group of the reaction. In some aspects of the invention, it is appropriate to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational spaced sampled by the reactive group is optimized for a reaction with the reactive group of the nascent encoded molecule.

The encoded molecules may have any chemical structure. In a preferred aspect, the encoded molecule can be any compound that may be synthesized in a component-by-component fashion. In some aspects the synthetic molecule is a linear or branched polymer. In another aspect the synthetic molecule is a scaffolded molecule. The term "encoded molecule" also comprises naturally occurring molecules like α-polypeptides etc, however produced in vitro usually in the absence of enzymes, like ribosomes. In certain aspects, the synthetic molecule of the library is a non-α-polypeptide.

The encoded molecule may have any molecular weight. However, in order to be orally available, it is in this case preferred that the synthetic molecule has a molecular weight less than 2000 Daltons, preferably less than 1000 Dalton, and more preferred less than 500 Daltons.

The size of the library may vary considerably pending on the expected result of the inventive method. In some aspects, it may be sufficient that the library comprises two, three, or four different complexes. However, in most events, more than two different complexes are desired to obtain a higher diversity. In some aspects, the library comprises 1,000 or more different complexes, more preferred 1,000,000 or more different complexes. The upper limit for the size of the library is only restricted by the size of the vessel in which the library is comprised. It may be calculated that a vial may comprise up to $10^{14}$ different complexes.

Methods for Forming Libraries of Complexes The encoded molecules associated with an identifier oligonucleotide having two or more codons that code for reactants that have reacted in the formation of the molecule part of the complex may be formed by a variety of processes. Generally, the preferred methods can be used for the formation of virtually any kind of encode molecule. Suitable examples of processes include prior art methods disclosed in WO 93/20242, WO 93/06121, WO 00/23458, WO 02/074929, and WO 02/103008, the content of which being incorporated herein by reference as well as methods of the present applicant not yet public available, including the methods disclosed in PCT/DK03/00739 filed 30 Oct. 2003 which entered the U.S. National phase as U.S. Ser. No. 10/525,817 and was published in the U.S. as US2006/0099592, and DK PA 2003 00430 filed 20 Mar. 2003. Any of these methods may be used, and the entire content of the patent applications are included herein by reference.

The methods disclosed in PCT/DK03/00739 relate to a method for obtaining a bifunctional complex comprising a display molecule part and a coding part, wherein a nascent bifunctional complex comprising a chemical reaction site and a priming site for enzymatic addition of a tag is reacted at the chemical reaction site with one or more reactants, and provided with respective tag(s) identifying the reactant(s) at the priming site using one or more enzymes.

Enzymes are in general substrate specific, entailing that the enzymatic addition of a tag to the priming site is not likely to interfere with the display molecule being formed. Thus, the application of protection groups on the coding part as well as the nascent display molecule can be avoided for this reason. However, it may be desired for other reasons to protect the growing display molecule. Enzymes are available having an activity in aqueous and organic media. The vast majority of enzymes, however, have a higher activity in an aqueous media compared to an organic media. Therefore, prior to or subsequent to the providing of the tag it may be desired to change the media in order to obtain applicable conditions for the reaction of the reactant at the chemical reaction site.

Generally, the display molecule part is formed by more than a single round of reaction between one or more reactants and the chemical reaction site. In a certain aspect of the invention, the nascent bifunctional complex reacted with one or more reactants and provided with respective tag(s) is reacted further one or more times with one or more reactant(s) and is provided with respective identifying tag(s) to produce a reaction product as one part of the bifunctional complex and an identifying part comprising tags which codes for the identity of the reactants which have participated in the formation of the reaction product.

In a certain aspect of the invention, a round or cycle of reaction implies that a single reactant is reacted with the chemical reaction site and that a respective tag identifying the reactant is provided at the priming site for enzymatic addition. In another aspect of the invention, a round of reaction implies that multiple reactants are reacted at the chemical reaction site and that tags identifying one or more, but not necessarily all, reactants are provided at the priming site for enzymatic addition. The reaction at the chemical reaction site and the addition of tags may occur in any order, i.e. the reaction may occur subsequent to, simultaneously with, or previous to the tag addition. The choice of order may among other things be dependent on the enzyme type, the reaction conditions, and the type of reactant.

The nascent bifunctional complex comprises a chemical reaction site and a priming site for enzymatic addition of a tag. Optionally, the nascent bifunctional complex also comprises a linking moiety, which connects the chemical reaction site with the priming site.

The linking moiety may serve various purposes, such as distancing the priming site from the chemical reaction site sufficient from each other to allow an enzyme to perform the tag addition and provide for a hybridisation region. In an aspect of the invention, the linking moiety is a nucleic acid sequence. The length of the oligonucleotide is preferably suitable for hybridisation with a complementing oligonucleotide, i.e. the number of nucleotides in the linking moiety is suitably 8 or above. In a certain embodiment, the linking moiety is attached to the chemical reaction site via a spacer comprising a selectively cleavable linker to enable a detachment of the display molecule from the coding part in a step subsequent to the formation of the final bifunctional complex. A nascent bifunctional complex is also referred to as a growing complex and specifies an initial or intermediate complex to be processed according to the method of the present invention. An intermediate complex designates an initial complex that has been subjected to one or more rounds of reactant reaction and tag addition.

The chemical reaction site may comprise a single or multiple reactive groups capable of reacting with one or more reactants. In a certain aspect the chemical reaction site comprises a scaffold having one or more reactive groups attached. Examples of suitable reactive groups include amine, carboxylic acid, thio, aldehyde, and hydroxyl groups. Examples of scaffolds include benzodiazepines, steroids, hydantiones, piperasines, diketopiperasines, morpholines, tropanes, cumarines, qinolines, indoles, furans, pyrroles, oxazoles, amino acid precursors, and thiazoles. Furthermore, the reactive groups of the chemical reaction site may be in a pro-form that has to be activated before a reaction with the reactant can take place. As an example, the reactive groups can be protected with a suitable group, which needs to be removed before a reaction with the reactant can proceed. A display molecule in the present description with claims indicates a chemical reaction site that has been reacted with one or more reactants.

The reactants of the present invention include free reactants as well as reactants which comprises a functional entity and a nucleic acid sequence. The free reactant participates in the reaction with the chemical reaction site and may give rise to a chemical structure of the final display molecule.

The free reactant is generally not attached to a nucleic acid unless a nucleic acid component is intended in the final display molecule. The free reactant may have any chemical structure and preferably comprises a reactive group or a precursor therefore, which will enable a reaction with a chemical reaction site. Examples of reactive groups include hydroxyl groups, carboxylic acid groups, thiols, isocyanates, amines, esters, and thioesters. Optionally, a further reactant occurs to mediate a connection between the free reactant and the chemical reaction site.

The coding part of the nascent bifunctional complex is formed by addition of at least one tag to a priming site using one or more enzymes. Further tags may be attached to a previous tag so as to produce a linear or branched identifier. As long as at least one tag of the identifier is attached by an enzymatic catalysed reaction, further tags may be provided using chemical means or enzymatic means at the discretion of the experimenter. In a certain embodiment of the invention, all tags are provided using an enzymatic catalysed reaction. A tag suitably comprises recognition units, i.e. units which may be recognized by recognition groups. The recognition unit possess an ability to carry information so as to identify a reactant. A variety of different kinds of recognition exist in nature. Examples are antibodies, which recognise an epitope, proteins which recognise another protein, mRNA which recognise a protein, and oligonucleotides which recognise complementing oligonucleotide sequences. Generally, it is preferred that the tag is a sequence of nucleotides.

The coding part of the bifunctional complex is in a preferred aspect of the invention amplifiable. The capability of being amplified allows for the use of a low amount of bifunctional complex during a selection process. In the event, the tag is a protein, the protein may be amplified by attaching the mRNA which has encoded the synthesis thereof, generating the cDNA from the mRNA and subjecting said mRNA to a translation system. Such system is disclosed in WO 98/31700, the content of which is incorporated herein by reference. An alternative method for amplifying a protein tag is to use phage displayed proteins. In general, however, the tag is a sequence of nucleotides, which may be amplified using standard techniques like PCR. When two or more tags are present in a linear identifying oligonucleotide, said oligonucleotide generally consist of a certain kind of backbone structure, so as to allow an enzyme to recognise the oligonucleotide as substrate. As an example the back bone structure may be DNA or RNA.

The priming site of a nascent bifunctional complex is capable of receiving a tag. The chemical identity of the priming site depends among other things on the type of tag and the particular enzyme used. In the event the tag is a polynucleotide, the priming site generally comprises a 3'-OH or 5'-phosphate group of a receiving nucleotide, or functional derivatives of such groups. Enzymes which may be used for enzymatic addition of a tag to the priming site include an enzyme selected from polymerase, ligase, and recombinase, and a combination of these enzymes.

The reaction between the chemical reaction site and the one or more reactants may take place under suitable conditions that favours the reaction. In some aspects of the invention, the reaction is conducted under hybridisation conditions, i.e. an annealing between two complementing oligonucleotides remains during the reaction conditions. In other aspects of the invention, the reaction is conducted under denaturing conditions to allow for suitable condition for the reaction to occur. In the event, the coding part of the growing complex comprises an oligonucleotide; said oligonucleotide is in an aspect of the invention in a double stranded form during the reaction to reduce the likelihood of side reactions between components of the oligonucleotide and reactants.

The tag identifying a reactant can be added to the priming site using any appropriate enzyme. In a certain embodiment, a tag is provided at the priming site of the nascent bifunctional complex utilizing an enzymatic extension reaction. The extension reaction may be performed by a polymerase or a ligase or a combination thereof. The extension using a polymerase is suitably conducted using an anti-tag oligonucleotide as template.

The anti-tag oligonucleotide is annealed at the 3' end of the oligonucleotide part of the nascent bifunctional complex with a single stranded overhang comprising an anti-codon, which identifies the reactant. The anti-codon of the anti-tag can be transcribed to the identifier part using a polymerase and a mixture of dNTPs. Alternatively, a ligase is used for the addition of the tag using one or more oligonucleotides as substrates. The ligation can be performed in a single stranded or a double stranded state depending on the enzyme used. In general it is preferred to ligate in a double stranded state, i.e. oligonucleotides to be ligated together are kept together by a complementing oligonucleotide, which complements the ends of the two oligonucleotides.

Examples of suitable enzymes include DNA polymerase, RNA polymerase, Reverse Transcriptase, DNA ligase, RNA ligase, Taq DNA polymerase, Pfu polymerase, Vent polymerase, HIV-1 Reverse Transcriptase, Klenow fragment, or any other enzyme that will catalyze the incorporation of complementing elements such as mono-, di- or polynucleotides. Other types of polymerases that allow mismatch extension could also be used, such for example DNA polymerase η. (Washington et al., (2001) JBC 276: 2263-2266), DNA polymerase τ. (Vaisman et al., (2001) JBC 276: 30615-30622), or any other enzyme that allow extension of mismatched annealed base pairs. In another aspect, when ligases are used, suitable examples include Taq DNA ligase, T4 DNA ligase, T4 RNA ligase, T7 DNA ligase, and *E. coli* DNA ligase. The choice of the ligase depends to a certain degree on the design of the ends to be joined together. Thus, if the ends are blunt, T4 RNA ligase may be preferred, while a Taq DNA ligase may be preferred for a sticky end ligation, i.e. a ligation in which an overhang on each end is a complement to each other.

The tag added to the priming site of the nascent bifunctional complex holds information as to the reactant. In the present invention with claims, the information relating to the reactant will be termed codon. Apart from a combination of the nucleotides coding for the identity of the reactant, a tag may comprise further nucleotides. In a certain aspect of the invention, a tag comprises a framing sequence. The framing sequence may serve various purposes, such as an annealing region for anti-tags and/or as a sequence informative of the point in time of the synthesis history the associated reactant has reacted.

The association between the codon and the identity of the reactant may vary dependent on the desired output. In a certain embodiment, the codon is used to code for several different reactants. In a subsequent identification step, the structure of the display molecule can be deduced taking advantage of the knowledge of the different attachment chemistries, steric hindrance, deprotection of orthogonal protection groups, etc. In another embodiment, the same codon is used for a group of reactants having a common property, such as a lipophilic nature, molecular weight, a certain attachment chemistry, etc. In a preferred embodiment however, the codon is unique, i.e. a similar combination of nucleotides does not identify another reactant.

In a practical approach, for a specific reactant, only a single combination of nucleotides is used. In some aspects of the invention, it may be advantageous to use several different codons for the same reactant. The two or more codons identifying the same reactant may carry further information related to different reaction conditions. In another aspect of the invention, a single codon specifies two or more reactants.

In one aspect of the invention, each bifunctional complex is prepared by simultaneous or sequentially tagging and reaction of reactant as illustrated in the scheme below: x-X->ax-XA->1 ax-XA1

Capital letters represent reactant or chemical reaction site. Lower case letters represent tags.

A scaffold "X" is linked to a tag "x". A reactant is linked to "X" e.g. "A" and so is a tag for that fragment e.g. "a". Suitably, the tag is unique.

The coding part of the eventually formed bifunctional complex will contain all the codons. The sequence of each of the codons is used to decipher the structure of the reactants that have participated in the formation of the displayed molecule, i.e. the reaction product. The order of the codons can also be used to determine the order of incorporation of the reactants. This may be of particular interest when a linear polymer is formed, because the exact sequence of the polymer can be determined by decoding the encoding sequence. Usually, to facilitate the decoding step, a constant or binding region is transferred to the bifunctional complex together with the codon. The constant region may contain information about the position of the related reactant in the synthesis pathway of the display molecule.

The invention also relates to a method for identifying a display molecule having a preselected property, comprising the steps of: subjecting the library produced according to the method indicated above to a condition, wherein a display molecule or a subset of display molecules having a predetermined property is partitioned from the remainder of the library, and identifying the display molecule(s) having a preselected function by decoding the coding part of the complex.

The above method, generally referred to as selection, involves that a library is subjected to a condition in order to select display molecules having a property which is responsive to this condition. The condition may involve the exposure of the library to a target. The bifunctional complexes having an affinity towards this target may be partitioned form the remainder of the library by removing non-binding complexes and subsequent eluting under more stringent conditions the complexes that have bound to the target. Alternatively, the coding part of the bifunctional complex can be cleaved from the display molecule after the removal of non-binding complexes and the coding part may be recovered and decoded to identify the display molecule.

It is possible to perform a single or several rounds of selection against a specific target with a subsequently amplification of the selected variants. These obtained variants are then separately tested in a suitable assay. The selection condition can be stringent and specific to obtain binding molecules in one selection rounds. It may be advantageously to perform the method using a single round of selection because the number and diversity of the potential binders are larger compared to procedures using further selections where potential binders may be lost. In another embodiment the selection procedure involves several round of selection using increasing stringency conditions. Between each selection an amplification of the selected complex may be desirable.

The coding part can be amplified using PCR with primers generating two unique cut-sites. These cut-sites can be used for multimerization of the coding region by cloning into a suitable vector for sequencing. This approach will allow simultaneously sequencing of many encoding regions. Alternatively, the PCR product is directly cloned into a suitable vector using for example TA cloning. In still another approach the identity of the display molecule is established by applying the PCR product to a suitable microarray.

It is within the capability of the skilled person in the art to construct the desired design of an oligonucleotide. When a specific annealing temperature is desired it is a standard procedure to suggest appropriate compositions of nucleic acid monomers and the length thereof. The construction of an appropriate design may be assisted by software, such as Vector NTI Suite or the public database at the internet address www.nwfsc.noaa.gov/protocol/oligoTMcalc.html. The conditions which allow hybridisation of two oligonucleotides are influenced by a number of factors including temperature, salt concentration, type of buffer, and acidity. It is within the capabilities of the person skilled in the art to select appropriate conditions to ensure that the contacting between two oligonucleotides is performed at hybridisation conditions. The temperature at which two single stranded oligonucleotides forms a duplex is referred to as the annealing temperature or the melting temperature. The melting curve is usually not sharp indicating that the annealing occurs over a temperature range.

In one embodiment of the methods disclosed in PCT/DK03/00739 is a second mode of that invention, a method for generating a complex comprising a display molecule part and a coding part, wherein a nascent bifunctional complex comprising a chemical reaction site and a priming site for enzymatic addition of a tag is reacted at the chemical reaction site with one or more reactants and provided at the priming site with respective tags identifying the one or more reactants using one or more enzymes.

The lack of a covalent link between the reactive part and the coding part of the building block implies that a library is to be produced by a split-and-mix strategy. In a first step a nascent bifunctional complex is dispensed in one or more separate compartment and subsequently exposed to a reactant in each compartment, which reacts at the chemical reaction site, and an agent which provides the tag identifying said reactant at the priming site. The agent providing the tag includes an enzyme and a substrate therefore. In a certain embodiment of the invention, the tag is provided by extending over an anticodon using a polymerase. In another embodiment of the invention, the tag is provided at the priming site by ligation of a codon oligonucleotide, which holds information as to the identity of the reactant.

When the enzyme is a polymerase, the substrate is usually a blend of triphosphate nucleotides selected from the group comprising dATP, dGTP, dTTP, dCTP, rATP, rGTP, rTTP, rCTP, rUTP. Substrates for ligases are oligo- and polynucleotides, i.e. nucleic acids comprising two or more nucleotides. An enzymatic ligation may be performed in a single or double stranded fashion. When a single stranded ligation is performed, a 3' OH group of a first nucleic acid is ligated to a 5' phosphate group of a second nucleic acid. A double stranded ligation uses a third oligonucleotide complementing a part of the 3' end and 5' end of the first and second nucleic acid to assist in the ligation. Generally, it is preferred to perform a double stranded ligation.

In some embodiments of the invention, a combination of polymerase transcription and ligational coupling is used. As an example, a gap in an otherwise double stranded nucleic acid may be filled-in by a polymerase and a ligase can ligate the extension product to the upstream oligonucleotide to produce a wholly double stranded nucleic acid.

Mode 2 is conducted in separate compartments for each reaction, as discussed above. Thus, the addition of a tag occurs without competing nucleic acids present and the likelihood of cross-encoding is reduced considerable. The enzymatic addition of a tag may occur prior to, subsequent to, or simultaneous with the reaction. In some aspects of the invention, it is preferred to add the tag to the nascent bifunctional complex prior to the reaction, because it may be preferable to apply conditions for the reaction which are different form the conditions used by the enzyme. Generally, enzyme reactions are conducted in aqueous media, whereas the reaction between the reactant and the chemical reaction site for certain reactions is favoured by an organic solvent. An appropriate approach to obtain suitable condition for both reactions is to conduct the enzyme reaction in an aqueous media, lyophilize and subsequent dissolve or disperse in a media suitable of the reaction at the chemical reactive site to take place. In an alternative approach, the lyophilization step may be dispensed with as the appropriate reaction condition can be obtained by adding a solvent to the aqueous media. The solvent may be miscible with the aqueous media to produce a homogeneous reaction media or immiscible to produce a bi-phasic media.

The reactant according to the second mode may be a free reactant or a zipper building block. A free reactant is not attached to a code identifying another part of the reactant. In most cases, a free reactant comprises a chemical structure comprising one, two or more reactive groups, which can react with the chemical reaction site. A zipper building block is a functional entity which is attached to a chemical entity that binds in the vicinity of the chemical reaction site. The binding chemical entity may be an oligonucleotide which hybridises to a linking moiety of the nascent bifunctional complex prior to the reaction. The hybridisation event will increase the proximity between the functional entity and the chemical reaction site, thereby reducing the possibility of side reactions and promote the reaction due to a high local concentration.

The nascent bifunctional complex is constructed having the encoding method in mind. Thus, if a polymerase is used for the encoding, a region of hybridisation is usually provided in the linker moiety. The region of hybridisation will allow for a binding region of a complementing oligonucleotide comprising an anti-codon to hybridise to the nascent bifunctional complex. The binding region serves as a binding site for a polymerase, which then may produce an extension product using the anti-codon oligonucleotide as template. When a ligase is used for the encoding, the priming site of the nascent bifunctional complex comprises one or more nucleotides which the ligase may consider as a substrate. In a single stranded ligation an oligonucleotide present in the media and bearing information as to the identity of the reactive group will be ligated to the nascent bifunctional molecule. A double stranded ligation requires the priming site of the nascent bifunctional complex to be able to hybridise to a complementing oligonucleotide prior to ligation. Suitably, the priming site comprises one, two, or more nucleotides, to which a complementing oligonucleotide can hybridise. The complementing oligonucleotide hybridise in the other end to the codon oligonucleotide, which holds the information of a particular reactant.

The linker moiety of the nascent bifunctional complex may comprise information relating to the identity of the chemical reaction site. In an applicable approach, the linker moiety comprises a codon informative of the identity of the chemical reaction site.

The oligonucleotides bearing the information on the pertinent reactant, may, apart from the combination of nucleotides identifying the reactant, comprise flanking regions. The flanking regions may serve as binding regions capable of hybridising to the nascent bifunctional complex. The binding region may be designed so as to hybridise promiscuous to more than a single nascent bifunctional complex. Alternatively, the binding region on the coding oligonucleotide is capable of being ligated to a binding region the nascent bifunctional complex using a splint oligonucleotide as mediator.

The invention may be performed by reacting a single reactant with the nascent bifunctional complex and add the corresponding tag. However, in general it is preferred to build a display molecule comprising the reaction product of two of more reactants. Thus, in a certain aspect of the invention a method is devised for obtaining a bifunctional complex composed of a display molecule part and a coding part, said display molecule part being the reaction product of reactants and the chemical reaction site of the initial complex. In an aspect of the invention, two alternating parallel syntheses are performed so that the tag is enzymatical linked to the nascent bifunctional complex in parallel with a reaction between a chemical reaction site and a reactant. In each round the addition of the tag is followed or preceded by a reaction between reactant and the chemical reaction site. In each subsequent round of parallel syntheses the reaction product of the previous reactions serves as the chemical reaction site and the last-incorporated tag provides for a priming site which allows for the enzymatical addition a tag. In other aspects of the invention, two or more tags are provided prior to or subsequent to reaction with the respective reactants.

The coding part comprising all the tags may be transformed to a double stranded form by an extension process in which a primer is annealed to the 3' end of the oligonucleotide and extended using a suitable polymerase. The double strandness may be an advantage during subsequent selection processes because a single stranded nucleic acid may perform interactions with a biological target in a way similar to aptamers.

In a certain aspect of mode 2 a method is devised for generating a library of bifunctional complexes comprising a display molecule part and a coding part. The method comprises the steps of providing in separate compartments nascent bifunctional complexes, each comprising a chemical reaction site and a priming site for enzymatic addition of a tag and performing in any order reaction in each compartment between the chemical reaction site and one or more reactants, and addition of one or more respective tags identifying the one or more reactants at the priming site using one or more enzymes.

The nascent bifunctional complexes in each compartment may be identical or different. In the event the nascent bifunctional complex differs at the chemical reaction site, the nascent bifunctional complex suitable comprises a codon identifying the structure of the chemical reaction site. Similar, the reactants applied in each compartment may be identical or different as the case may be. Also, the reaction conditions in each compartment may be similar or different.

Usually, it is desired to react the complex with more than a single reactant. In a certain aspect of the invention, the content of two or more compartments are pooled together and subsequently split into an array of compartments for a new round of reaction. Thus, in any round subsequent to the first round, the end product of a preceding round of reaction is used as the nascent bifunctional complex to obtain a library of bifunctional complexes, in which each member of the library comprises a reagent specific reaction product and respective tags which codes for the identity of each of the reactants that have participated in the formation of the reaction product. Between each round of reaction the content of the compartments is in an aspect of the invention mixed together and split into compartments again. In other aspects of the invention the content of a compartment is after having received a codon but before a reaction has occurred divided into further compartments in which a further codon is received and a reaction occurs with the two reactants that have been encoded. In another aspect of the invention, more than two codons are encoded before a reaction between chemical reaction site and reactants are allowed to take place. In the alternative, two or more reactions are allowed to occur before an encoding with the respective tags is initiated.

The individual codons may be distinguished from another codon in the library by only a single nucleotide. However, to facilitate a subsequent decoding process it is in general desired to have two or more differences between a particular codon and any other codon. As an example, if a codon/anti-codon length of 5 nucleotides is selected, more than 100 nucleotide combinations exist in which two or more differences appear. For a certain number of nucleotides in the codon, it is generally desired to optimize the number of differences between a particular codon/anticodon relative to any other codon/anticodon appearing in the library. An oligonucleotide codon may comprise any suitable number of nucleotides, such as from 2 to 100, 3 to 50, 4 to 20 or 5 to 15 nucleotides.

The reactant can be a free reactant or a zipper building block. The reactant serves the function of being a precursor for the structural entity eventually incorporated in to the displayed molecule part. There structure of a reactant may after reaction with a chemical reaction site become changed in a subsequent round. In the event the reactant is a zipper building block, a cleavage of the linkage between the functional entity and the oligonucleotide is normally conducted after reaction. An exception is in the final round, in which the cleavage can be dispensed with. The cleavage can occur subsequent to or simultaneously with the reaction with the chemical reaction site. The cleavage may generate a reactive group which in a subsequent step can participate in the formation of a connection between the nascent display molecule and a reactant.

The free reactant or the functional entity of the zipper building block preferably comprises at least one reactive group capable of participating in a reaction which results in a connection to the chemical reaction site of the nascent bifunctional molecule. The number of reactive groups which appear on the free reactant and the functional entity is suitably one to ten. A free reactant or a functional entity featuring only one reactive group is used i.a. in the end positions of polymers or scaffolds, whereas functional entities having two reactive groups are suitable for the formation of the body part of a polymer or scaffolds capable of being reacted further. Two or more reactive groups intended for the formation of connections, are typically present on scaffolds. A scaffold is a core structure, which forms the basis for the creation of multiple variants. The variant forms of the scaffold are typically formed through reaction of reactive groups of the scaffold with reactive groups of other reactants, optionally mediated by fill-in groups or catalysts. The functional entities or free reactants to be connected to the scaffold may contain one, two or several reactive groups able to form connections. Examples of scaffolds include steroids, hydantions, benzodiazepines, etc.

The reactive group of the free reactant or the functional entity attached to a nucleic acid comprising a zipper region, i.e. a region promiscuously binding to a linking moiety of the nascent bifunctional complex, may be capable of forming a direct connection to a reactive groups of the chemical reactive site or the reactant may be capable of forming a connection to a reactive group of the chemical reactive site through a bridging fill-in group. It is to be understood that not all the atoms of the reactive groups are necessarily maintained in the connection formed. Rather the reactive groups are to be regarded as precursors for the structure of the connection.

When a zipper building block is used, a cleavage may be performed after or simultaneously with the formation of the connection between the chemical reaction site and the functional entity. The cleavage can be performed in any appropriate way. In an aspect of the invention the cleavage involves usage of a reagent or enzyme. The cleavage results in a transfer of the functional entity to the nascent bifunctional complex or in a transfer of the complex to the functional entity of the zipper building block. In some cases it may be advantageous to introduce new chemical groups as consequence of the cleavage. The new chemical groups may be used for further reaction in a subsequent cycle, either directly or after having been activated. In other cases it s desirable that no trace of the linker remains after the cleavage. In some aspects of the invention it may not be desired to cleave on or more chemical bonds. As an example, it may be desirable to maintain the connection between the zipper domain and the functional entity in the last round.

In some aspects of the invention, the connection and the cleavage is conducted as a simultaneous reaction, i.e. either the functional entity of the zipper building block or the chemical reactive site of the nascent bifunctional complex is a leaving group of the reaction. In some aspects of the invention, it is preferred to design the system such that the cleavage occurs simultaneously because this will reduce the number of steps and the complexity. The simultaneous connection and cleavage can also be designed such that either no trace of the linker remains or such that a new chemical group for further reaction is introduced, as described above. In other aspects of the invention, it is preferred to conduct separate cross-linking and cleavage steps because the stepwise approach allows for mastering each sub step and for a reduction of the likelihood of non-specific transfer.

The attachment of the functional entity to the oligonucleotide comprising a zipping domain is usually conducted through a linker. Preferably the linker connects the functional entity with the oligonucleotide at a terminal nucleotide or a nucleotide 1 or two nucleotides down the oligonucleotide. The attachment of the functional entity can be at any entity available for attachment, i.e. the functional entity can be attached to a nucleotide of the oligonucleotide at the nucleobase, or the back bone. In general, it is preferred to attach the functional entity at the phosphor of the internucleoside linkage or at the nucleobase.

In a certain aspect of the invention, the reactive group of the functional entity is attached to the oligonucleotide, optionally through a suitable spacer. The reactive group is preferably of a type which is able to create a connection to the nascent display molecule by either direct reaction between the respective reactive groups or by using a suitable fill-in group. The reactive group coupling the functional entity with the oligonucleotide is preferably cleaved simultaneously with the establishment of the connection. The functional entity may in some cases contain a second reactive group able to be involved in the formation of a connection in a subsequent cycle. The second reactive group may be of a type which needs activation before it is capable of participating in the formation of a connection.

Preferably at least one linker remains intact after the cleavage step. The at least one linker will link the display molecule to the coding part, i.e. the part comprising the one or more tags identifying the various reactant that have participated in the formation of the display molecule. It may be desired to connect the display molecule part to the coding part of the bifunctional complex through a space comprising a selectively cleavable linker. The selectively cleavable linker is designed such that it is not cleaved under conditions which result in a transfer of a function entity to the chemical reaction site.

The cleavable linkers may be selected from a large plethora of chemical structures. Examples of linkers includes, but are not limited to, linkers having an enzymatic cleavage site, linkers comprising a chemical degradable component, and linkers cleavable by electromagnetic radiation. Cleavable linkers of particular interest are currently linkers that can be cleaved by light. A suitable example includes an o-nitro benzyl group positioned between the display molecule and the coding part of the bifunctional complex.

In the event two or more reactants are reacted with the chemical reactive site, the codons of the coding part may be separated by a constant region or a binding region. One function of the binding region may be to establish a platform at which an enzyme, such as polymerase or ligase can recognise as a substrate. Depending on the encoded molecule formed, the identifier may comprise further codons, such as 3, 4, 5, or more codons. Each of the further codons may be separated by a suitable binding region. Preferably, all or at least a majority of the codons of the identifier are separated from a neighbouring codon by a binding sequence. The binding region may have any suitable number of nucleotides, e.g. 1 to 20.

The binding region, if present, may serve various purposes besides serving as a substrate for an enzyme. In one setup of the invention, the binding region identifies the position of the codon. Usually, the binding region either upstream or downstream of a codon comprises information which allows determination of the position of the codon. In another setup, the binding regions have alternating sequences, allowing for addition of building blocks from two pools in the formation of the library. Moreover, the binding region may adjust the annealing temperature to a desired level.

A binding region with high affinity can be provided by incorporation of one or more nucleobases forming three hydrogen bonds to a cognate nucleobase. Examples of nucleobases having this property are guanine and cytosine. Alternatively, or in addition, the binding region may be subjected to backbone modification. Several backbone modifications provides for higher affinity, such as 2'-O-methyl substitution of the ribose moiety, peptide nucleic acids (PNA), and 2'-4'-O-methylene cyclisation of the ribose moiety, also referred to as LNA (Locked Nucleic Acid).

The identifier may comprise flanking regions around the codons. The flanking region can encompass a signal group, such as a fluorophor or a radio active group to allow for detection of the presence or absence of a complex or the flanking region may comprise a label that may be detected, such as biotin. When the identifier comprises a biotin moiety, the identifier may easily be recovered.

The flanking regions can also serve as priming sites for amplification reactions, such as PCR. Usually, the last cycle in the formation of the bifunctional complex includes the incorporation of a priming site. A region of the bifunctional complex close to the display molecule, such as a nucleic acid sequence between the display molecule and the codon coding for the scaffold molecule, is usually used for another priming site, thereby allowing for PCR amplification of the coding region of the bifunctional complex.

The library of tagged entities may involve $10\text{-}10^{20}$ or $10\text{-}10^{14}$ or $10\text{-}10^2$ or $10\text{-}10^3$ or $10^2\text{-}10^3$ or $10^2\text{-}10^4$ or $10^3\text{-}10^8$ or $10^3\text{-}10^8$ or $10^3\text{-}10^{10}$ or $10^3\text{-}10^{14}$ or $10^5\text{-}10^8$ or $10^5\text{-}10^{10}$ or $10^5\text{-}10^{14}$ or $10^8\text{-}10^{14}$ or $10^{14}\text{-}10^{20}$ entities.

Below five presently preferred embodiments are described. A first embodiment disclosed in more detail in WO 02/103008 is based on the use of a polymerase to incorporate unnatural nucleotides as building blocks. Initially, a plurality of identifier oligonucleotides is provided. Subsequently primers are annealed to each of the identifiers and a polymerase is extending the primer using nucleotide derivatives, which have appended chemical entities. Subsequent to or simultaneously with the incorporation of the nucleotide derivatives, the chemical entities are reacted to form a reaction product. The encoded molecule may be post-modified by cleaving some of the linking moieties to better present the encoded molecule.

Several possible reaction approaches for the chemical entities are apparent. First, the nucleotide derivatives can be incorporated and the chemical entities subsequently polymerised. In the event the chemical entities each carry two reactive groups, the chemical entities can be attached to adjacent chemical entities by a reaction of these reactive groups. Exemplary of the reactive groups are amine and carboxylic acid, which upon reaction form an amide bond. Adjacent chemical entities can also be linked together using a linking or bridging moiety. Exemplary of this approach is the linking of two chemical entities each bearing an amine group by a bi-carboxylic acid. Yet another approach is the use of a reactive group between a chemical entity and the nucleotide building block, such as an ester or a hoister group. An adjacent building block having a reactive group such as an amine may cleave the interspaced reactive group to obtain a linkage to the chemical entity, e.g. by an amide linking group.

A second embodiment for obtainment of complexes disclosed in WO 02/103008 pertains to the use of hybridisation of building blocks to an identifier and reaction of chemical entities attached to the building blocks in order to obtain a reaction product. This approach comprises that identifiers are contacted with a plurality of building blocks, wherein each building block comprises an anti-codon and a chemical entity. The anti-codons are designed such that they recognise a sequence, i.e. a codon, on the identifier. Subsequent to the annealing of the anti-codon and the codon to each other a reaction of the chemical entity is effected.

The identifier may be associated with a scaffold. Building blocks bringing chemical entities in may be added sequentially or simultaneously and a reaction of the reactive group of the chemical entity may be effected at any time after the annealing of the building blocks to the identifier.

A third embodiment for the generation of a complex includes chemical or enzymatic ligation of building blocks when these are lined up on a identifier. Initially, identifiers are provided, each having one or more codons. The identifiers are contacted with building blocks comprising anti-codons linked to chemical entities. The two or more anti-codons annealed on an identifier are subsequently ligated to each other and a reaction of the chemical entities is effected to obtain a reaction product. The method is disclosed in more detail in DK PA 2003 00430 filed 20 Mar. 2003.

A fourth embodiment makes use of the extension by a polymerase of an affinity sequence of the nascent complex to transfer the anti-codon of a building block to the nascent complex. The method implies that a nascent complex comprising a scaffold and an affinity region is annealed to a building block comprising a region complementary to the affinity section. Subsequently, the anti-codon region of the building block is transferred to the nascent complex by a polymerase. The transfer of the chemical entity may be transferred prior to, simultaneously with or subsequent to the transfer of the anti-codon. This method is disclosed in detail in PCT/DK03/00739, which entered the U.S. National phase as U.S. Ser. No. 10/525,817 and was published in the U.S. as US 2006/0099592.

A fifths embodiment also disclosed in PCT/DK03/00739 comprises reaction of a reactant with a reaction site on nascent bifunctional molecule and addition of a nucleic acid tag to the nascent bifunctional molecule using an enzyme, such as a ligase. When a library is formed, usually an array of compartments is used for reaction of reactants and enzymatic addition of tags with the nascent bifunctional molecule.

Thus, the codons are either pre-made into one or more identifiers before the encoded molecules are generated or the codons are transferred simultaneously with the formation of the encoded molecules.

After or simultaneously with the formation of the reaction product some of the linkers to the identifier may be cleaved, however, usually at least one linker is maintained to provide for the complex.

Nucleotides

The nucleotides used in the present invention may be linked together in a sequence of nucleotides, i.e. an oligonucleotide. Each nucleotide monomer is normally composed of two parts, namely a nucleobase moiety, and a backbone. The backbone may in some cases be subdivided into a sugar moiety and an internucleoside linker.

The nucleobase moiety may be selected among naturally occurring nucleobases as well as non-naturally occurring nucleobases. Thus, "nucleobase" includes not only the known purine and pyrimidine hetero-cycles, but also heterocyclic analogues and tautomers thereof. Illustrative examples of nucleobases are adenine, guanine, thymine, cytosine, uracil, purine, xanthine, diaminopurine, 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5-bromouracil, pseudo-isocytosine, 2-hydroxy-5-methyl-4-triazolopyridine, isocytosine, isoguanine, inosine and the "non-naturally occurring" nucleobases described in Benner et al., U.S. Pat. No. 5,432,272. The term "nucleobase" is intended to cover these examples as well as analogues and tautomers thereof. Especially interesting nucleobases are adenine, guanine, thymine, cytosine, 5-methylcytosine, and uracil, which are considered as the naturally occurring nucleobases in relation to therapeutic and diagnostic application in humans.

Examples of suitable specific pairs of nucleobases are shown below:

Natural Base Pairs

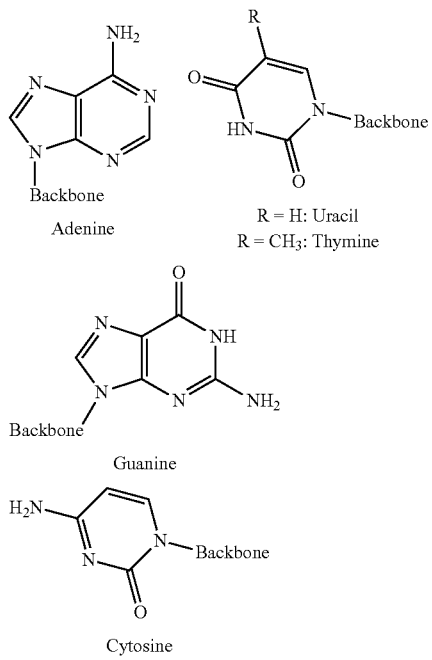

Synthetic Base Pairs

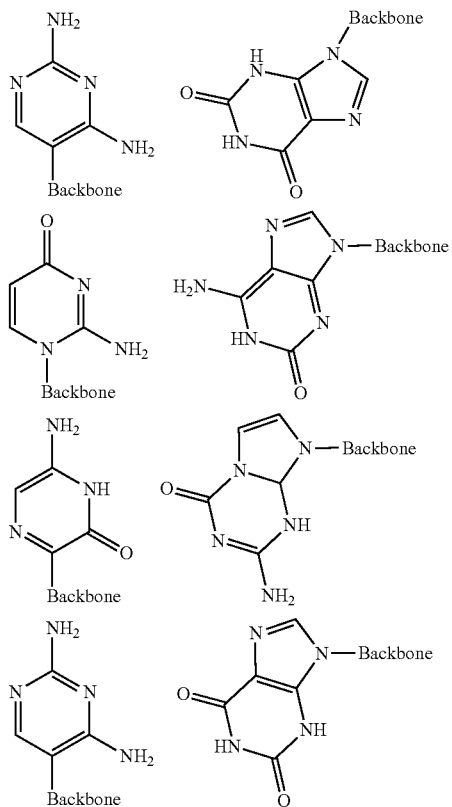

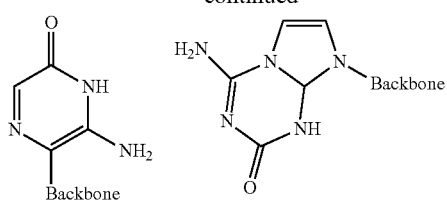
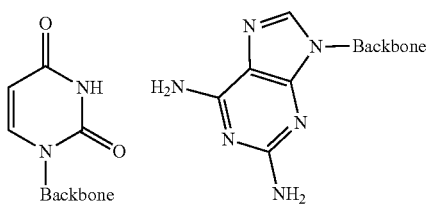
Synthetic purine bases pairing with natural pyrmidines
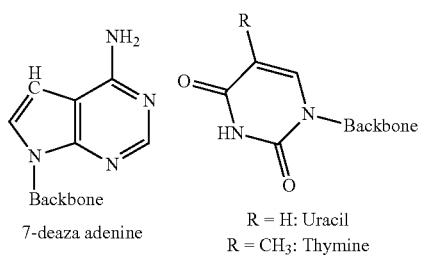
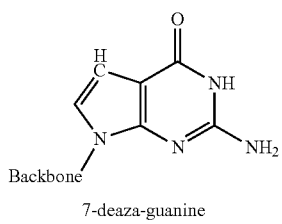
7-deaza-guanine
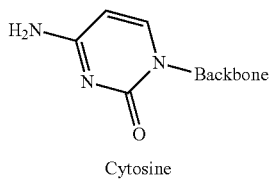
Cytosine
Suitable examples of backbone units are shown below (B denotes a nucleobase):
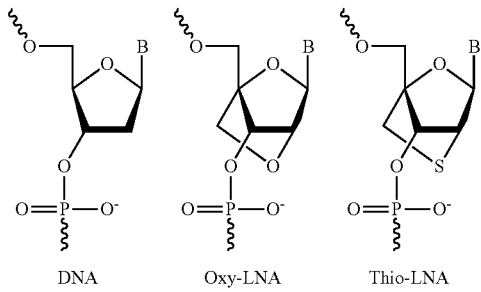
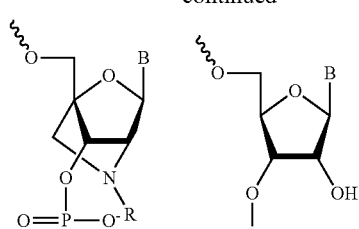
Amino-LNA
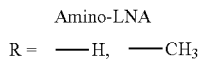
RNA
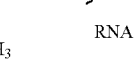
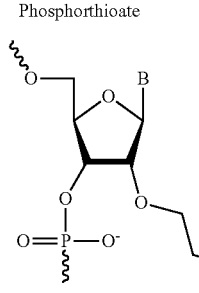
Phosphorthioate
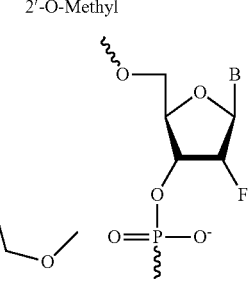
2'-O-Methyl
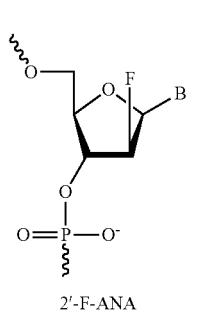
2'-MOE
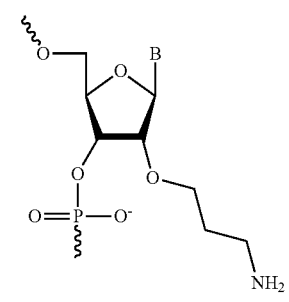
2'-Fluoro
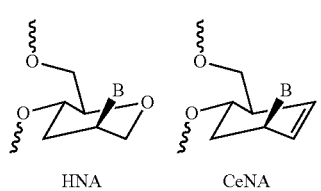
2'-F-ANA    2'-AP
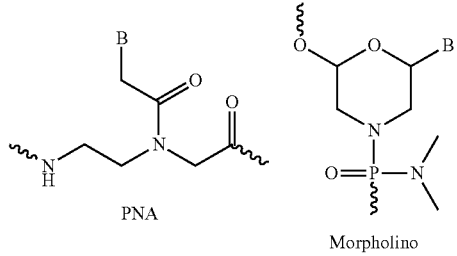
HNA   CeNA   PNA   Morpholino

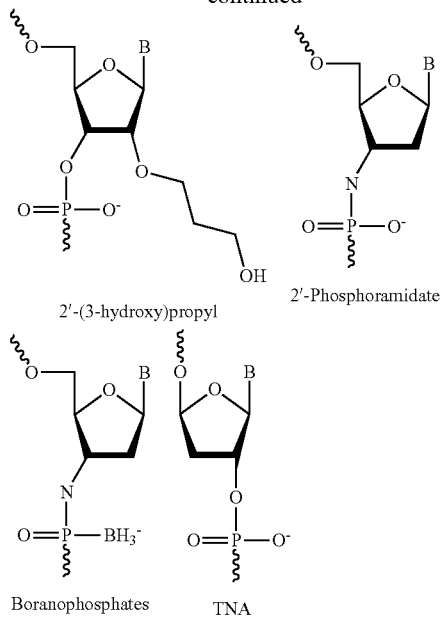

2'-(3-hydroxy)propyl

2'-Phosphoramidate

Boranophosphates

TNA

The sugar moiety of the backbone is suitably a pentose but may be the appropriate part of a PNA or a six-member ring. Suitable examples of possible pentoses include ribose, 2'-deoxyribose, 2'-O-methyl-ribose, 2'-flour-ribose, and 2'-4'-O-methylene-ribose (LNA). Suitably the nucleobase is attached to the 1' position of the pentose entity.

An internucleoside linker connects the 3' end of preceding monomer to a 5' end of a succeeding monomer when the sugar moiety of the backbone is a pentose, like ribose or 2-deoxyribose. The internucleoside linkage may be the natural occurring phosphodiester linkage or a derivative thereof. Examples of such derivatives include phosphorothioate, methylphosphonate, phosphoramidate, phosphotriester, and phosphodithioate. Furthermore, the internucleoside linker can be any of a number of non-phosphorous-containing linkers known in the art.

Preferred nucleic acid monomers include naturally occurring nucleosides forming part of the DNA as well as the RNA family connected through phosphodiester linkages. The members of the DNA family include deoxyadenosine, deoxyguanosine, deoxythymidine, and deoxycytidine. The members of the RNA family include adenosine, guanosine, uridine, cytidine, and inosine. Inosine is a non-specific pairing nucleoside and may be used as universal base because inosine can pair nearly isoenergetically with A, T, and C. Other compounds having the same ability of non-specifically base-pairing with natural nucleobases have been formed. Suitable compounds which may be utilized in the present invention includes among others the compounds depicted below Examples of Universal Bases

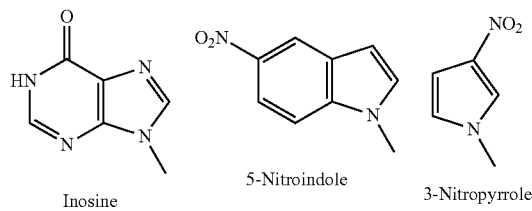

Inosine

5-Nitroindole

3-Nitropyrrole

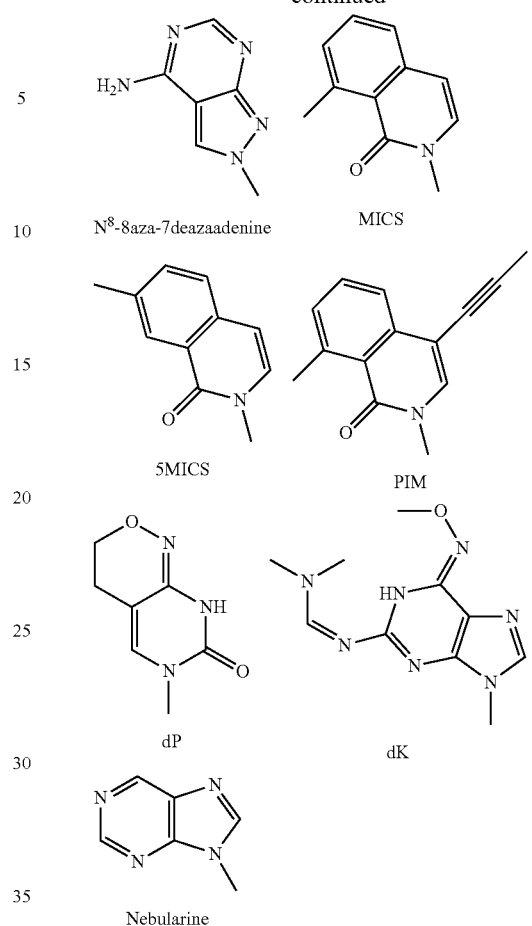

$N^8$-8aza-7deazaadenine

MICS

5MICS

PIM dP dK

Nebularine

Building Block

The chemical entities or reactants that are precursors for structural additions or eliminations of the encoded molecule may be attached to a building block prior to the participation in the formation of the reaction product leading to the final encoded molecule. Besides the chemical entity, the building block generally comprises an anti-codon.

The chemical entity of the building block comprises at least one reactive group capable of participating in a reaction, which results in a connection between the chemical entity of the building block and another chemical entity or a scaffold associated with the nascent complex. The connection is facilitated by one or more reactive groups of the chemical entity. The number of reactive groups, which appear on the chemical entity, is suitably one to ten. A building block featuring only one reactive group is used i.a. in the end positions of polymers or scaffolds, whereas building blocks having two reactive groups are suitable for the formation of the body part of a polymer or scaffolds capable of being reacted further. One, two or more reactive groups intended for the formation of connections are typically present on scaffolds.

The reactive group of the building block may be capable of forming a direct connection to a reactive group of the nascent complex or the reactive group of the building block may be capable of forming a connection to a reactive group of the nascent complex through a bridging fill-in group. It is to be understood that not all the atoms of a reactive group are necessarily maintained in the connection formed. Rather, the reactive groups are to be regarded as precursors for the structure of the connection.

The subsequent cleavage step to release the chemical entity from the building block can be performed in any appropriate way. In an aspect of the invention the cleavage involves usage of a reagent or an enzyme. The cleavage results in a transfer of the chemical entity to the nascent encoded molecule or in a transfer of the nascent encoded molecule to the chemical entity of the building block. In some cases it may be advantageous to introduce new chemical groups as a consequence of linker cleavage. The new chemical groups may be used for further reaction in a subsequent cycle, either directly or after having been activated. In other cases it is desirable that no trace of the linker remains after the cleavage.

In another aspect, the connection and the cleavage are conducted as a simultaneous reaction, i.e. either the chemical entity of the building block or the nascent encoded molecule is a leaving group of the reaction. In general, it is preferred to design the system such that the connection and the cleavage occur simultaneously because this will reduce the number of steps and the complexity. The simultaneous connection and cleavage can also be designed such that either no trace of the linker remains or such that a new chemical group for further reaction is introduced, as described above.

The attachment of the chemical entity to the building block, optionally via a suitable spacer can be at any entity available for attachment, e.g. the chemical entity can be attached to a nucleobase or the backbone. In general, it is preferred to attach the chemical entity at the phosphor of the internucleoside linkage or at the nucleobase. When the nucleobase is used for attachment of the chemical entity, the attachment point is usually at the 7 position of the purines or 7-deaza-purins or at the 5 position of pyrimidines. The nucleotide may be distanced from the reactive group of the chemical entity by a spacer moiety. The spacer may be designed such that the conformational space sampled by the reactive group is optimized for a reaction with the reactive group of the nascent encoded molecule or reactive site.

The anticodon complements the codon of the identifier oligonucleotide sequence and generally comprises the same number of nucleotides as the codon. The anticodon may be adjoined with a fixed sequence, such as a sequence complementing a framing sequence.

Various specific building blocks are envisaged. Building blocks of particular interest are shown below.

Building Blocks Transferring a Chemical Entity to a Recipient Nucleophilic Group The building block indicated below is capable of transferring a chemical entity (CE) to a recipient nucleophilic group, typically an amine group. The bold lower horizontal line illustrates the building block comprising an anti-codon and the vertical line illustrates a spacer. The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold

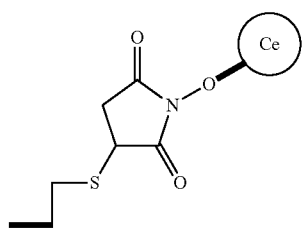

The 5-membered substituted N-hydroxysuccinimid (NHS) ring serves as an activator, i.e. a labile bond is formed between the oxygen atom connected to the NHS ring and the chemical entity. The labile bond may be cleaved by a nucleophilic group, e.g. positioned on a scaffold, to transfer the chemical entity to the scaffold, thus converting the remainder of the fragment into a leaving group of the reaction. When the chemical entity is connected to the activator through a carbonyl group and the recipient group is an amine, the bond formed on the scaffold will an amide bond. The above building block is the subject of WO03078627A2, the content of which is incorporated herein in their entirety by reference.

Another building block, which may form an amide bond, is

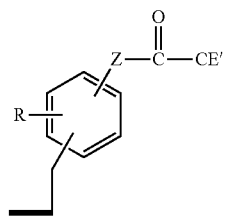

R may be absent or $NO_2$, $CF_3$, halogen, preferably Cl, Br, or I, and Z may be S or O. This type of building block is disclosed in WO03078626A2. The content of this patent application is incorporated herein in the entirety by reference.

A nucleophilic group can cleave the linkage between Z and the carbonyl group thereby transferring the chemical entity —(C=O)—CE' to said nucleophilic group.

Building Blocks Transferring a Chemical Entity to a Recipient Reactive Group Forming a C=C Bond A building block as shown below is able to transfer the chemical entity to a recipient aldehyde group thereby forming a double bond between the carbon of the aldehyde and the chemical entity

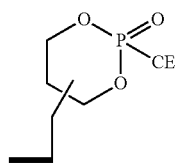

The above building block is disclosed in WO03078445A2, the content of which being incorporated herein in the entirety by reference.

Building Blocks Transferring a Chemical Entity to a Recipient Reactive Group Forming a C—C Bond The below building block is able to transfer the chemical entity to a recipient group thereby forming a single bond between the receiving moiety, e.g. a scaffold, and the chemical entity.

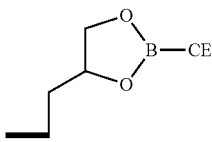

The above building block is disclosed in WO03078445A2, the content of which being incorporated herein in the entirety by reference.

Another building block capable of transferring a chemical entity to a receiving reactive group forming a single bond is

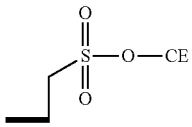

The receiving group may be a nucleophile, such as a group comprising a hetero atom, thereby forming a single bond between the chemical entity and the hetero atom, or the receiving group may be an electronegative carbon atom, thereby forming a C—C bond between the chemical entity and the scaffold. The above building block is disclosed in WO03078446A2, the content of which is incorporated herein by reference.

The chemical entity attached to any of the above building blocks may be a selected from a large arsenal of chemical structures. Examples of chemical entities are H or entities selected among the group consisting of a $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^8$ substituted with 0-3 $R^9$.

where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from —$N_3$, —CNO, —C(NOH)$NH_2$, —NHOH, —NHN$HR^6$, —C(O)$R^6$, —Sn$R^6_3$, —B(O$R^6)_2$, —P(O)(O$R^6)_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from —F, —Cl, —Br, and —I; and $R^7$ is independently selected from —$NO_2$, —COO$R^6$, —CO$R^6$, —CN, —OSi$R^6_3$, —O$R^6$ and —$NR^6_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from —F, —Cl, —$NO_2$, —$R^3$, —O$R^3$, —Si$R^3_3$ $R^9$ is =O, —F, —Cl, —Br, —I, —CN, —$NO_2$, —O$R^6$, —$NR^6_2$, —$NR^6$—C(O)$R^8$, —$NR^B$—C(O)O$R^8$, —S$R^6$, —S(O)$R^6$, —S(O)$_2R^6$, —COO$R^6$, —C(O)$NR^6_2$ and —S(O)$_2NR^6_2$.

Cross-Link Cleavage Building Blocks

It may be advantageous to split the transfer of a chemical entity to a recipient reactive group into two separate steps, namely a cross-linking step and a cleavage step because each step can be optimized. A suitable building block for this two-step process is illustrated below:

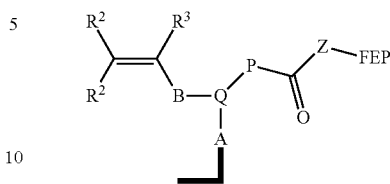

Initially, a reactive group appearing on the chemical entity precursor (abbreviated FEP) reacts with a recipient reactive group, e.g. a reactive group appearing on a scaffold, thereby forming a cross-link. Subsequently, a cleavage is performed, usually by adding an aqueous oxidising agent such as $I_2$, $Br_2$, $Cl_2$, $H^+$, or a Lewis acid. The cleavage results in a transfer of the group HZ-FEP— to the recipient moiety, such as a scaffold.

In the above formula

Z is O, S, $NR^4$

Q is N, $CR^1$

P is a valence bond, O, S, $NR^4$, or a group $C_{5-7}$arylene, $C_{1-6}$alkylene, $C_{1-6}$O-alkylene, $C_{1-6}$S-alkylene, $NR^1$-alkylene, $C_{1-6}$alkylene-O, $C_{1-6}$alkylene-S option said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^9$, $C_1$-$C_3$ alkylene-$NR^4C(O)OR^9$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^9$ substituted with 0-3 $R^9$, B is a group comprising D-E-F, in which D is a valence bond or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, E is, when present, a valence bond, O, S, $NR^4$, or a group $C_{1-6}$alkylene, $C_{1-6}$alkenylene, $C_{1-6}$alkynylene, $C_{5-7}$arylene, or $C_{5-7}$heteroarylene, said group optionally being substituted with 1 to 4 group $R^{11}$, F is, when present, a valence bond, O, S, or $NR^4$, A is a spacing group distancing the chemical structure from the complementing element, which may be a nucleic acid, $R^1$, $R^2$, and $R^3$ are independent of each other selected among the group consisting of H, $C_1$-$C_6$ alkyl, $C_2$-$C_6$ alkenyl, $C_2$-$C_6$ alkynyl, $C_4$-$C_6$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^9$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^9$ substituted with 0-3 $R^9$, FEP is a group selected among the group consisting of H, $C_1$-$C_6$ alkyl, $C_2$-$C_6$ alkenyl, $C_2$-$C_6$ alkynyl, $C_4$-$C_8$ alkadienyl, $C_3$-$C_7$ cycloalkyl, $C_3$-$C_7$ cycloheteroalkyl, aryl, and heteroaryl, said group being substituted with 0-3 $R^4$, 0-3 $R^5$ and 0-3 $R^9$ or $C_1$-$C_3$ alkylene-$NR^4_2$, $C_1$-$C_3$ alkylene-$NR^4C(O)R^8$, $C_1$-$C_3$ alkylene-$NR^4C(O)OR^8$, $C_1$-$C_2$ alkylene-O—$NR^4_2$, $C_1$-$C_2$ alkylene-O—$NR^4C(O)R^8$, $C_1$-$C_2$ alkylene-O—$NR^4C(O)OR^8$ substituted with 0-3 $R^9$, where $R^4$ is H or selected independently among the group consisting of $C_1$-$C_6$ alkyl, $C_2$-$C_6$ alkenyl, $C_2$-$C_6$ alkynyl, $C_3$-$C_7$ cycloalkyl, $C_3$-$C_7$ cycloheteroalkyl, aryl, heteroaryl, said group being substituted with 0-3 $R^9$ and $R^5$ is selected independently from $-N_3$, $-CNO$, $-C(NOH)NH_2$, $-NHOH$, $-NHNHR^6$, $-C(O)R^6$, $-SnR^6_3$, $-B(OR^6)_2$, $-P(O)(OR^6)_2$ or the group consisting of $C_2$-$C_6$ alkenyl, $C_2$-$C_6$ alkynyl, $C_4$-$C_8$ alkadienyl said group being substituted with 0-2 $R^7$, where $R^6$ is selected independently from H, $C_1$-$C_6$ alkyl, $C_3$-$C_7$ cycloalkyl, aryl or $C_1$-$C_6$ alkylene-aryl substituted with 0-5 halogen atoms selected from $-F$, $-Cl$, $-Br$, and $-I$; and $R^7$ is independently selected from $-NO_2$, $-COOR^6$, $-COR^E$, $-CN$, $-OSiR^6_3$, $-OR^6$ and $-NR^6_2$.

$R^8$ is H, $C_1$-$C_6$ alkyl, $C_2$-$C_6$ alkenyl, $C_2$-$C_6$ alkynyl, $C_3$-$C_7$ cycloalkyl, aryl or $C_1$-$C_6$ alkylene-aryl substituted with 0-3 substituents independently selected from $-F$, $-Cl$, $-NO_2$, $-R^3$, $-OR^3$, $-SiR^3_3$ $R^9$ is $=O$, $-F$, $-Cl$, $-Br$, $-I$, $-CN$, $-NO_2$, $-OR^6$, $-NR^6_2$, $-NR^6-C(O)R^8$, $-NR^6-C(O)OR^8$, $-SR^6$, $-S(O)R^6$, $-S(O)_2R^6$, $-COOR^6$, $-C(O)NR^6_2$ and $-S(O)_2NR^6_2$.

In a preferred embodiment Z is O or S, P is a valence bond, Q is CH, B is $CH_2$, and $R^1$, $R^2$, and $R^3$ is H. The bond between the carbonyl group and Z is cleavable with aqueous $I_2$.

Partitioning Conditions

The partition step may be referred to as a selection or a screen, as appropriate, and includes the screening of the library for encoded molecules having predetermined desirable characteristics. Predetermined desirable characteristics can include binding to a target, catalytically changing the target, chemically reacting with a target in a manner which alters/modifies the target or the functional activity of the target, and covalently attaching to the target as in a suicide inhibitor.

The target can be any compound of interest. E.g. the target can be a protein, peptide, carbohydrate, polysaccharide, glycoprotein, hormone, receptor, antigen, antibody, virus, substrate, metabolite, transition state analogue, cofactor, inhibitor, drug, dye, nutrient, growth factor, cell, tissue, etc. without limitation. Particularly preferred targets include, but are not limited to, angiotensin converting enzyme, renin, cyclooxygenase, 5-lipoxygenase, IIL-1 0 converting enzyme, cytokine receptors, PDGF receptor, type II inosine monophosphate dehydrogenase, β-lactamases, integrin, and fungal cytochrome P-450. Targets can include, but are not limited to, bradykinin, neutrophil elastase, the HIV proteins, including tat, rev, gag, int, RT, nucleocapsid etc., VEGF, bFGF, TGFIβ, KGF, PDGF, thrombin, theophylline, caffeine, substance P, IgE, sPLA2, red blood cells, glioblastomas, fibrin clots, PBMCs, hCG, lectins, selectins, cytokines, ICP4, complement proteins, etc.

Encoded molecules having predetermined desirable characteristics can be partitioned away from the rest of the library while still attached to the identifier nucleic acid sequence by various methods known to one of ordinary skill in the art. In one embodiment of the invention the desirable products are partitioned away from the entire library without chemical degradation of the attached nucleic acid identifier such that the identifiers are amplifiable. The identifiers may then be amplified, either still attached to the desirable encoded molecule or after separation from the desirable encoded molecule.

In a preferred embodiment, the desirable encoded molecule acts on the target without any interaction between the nucleic acid attached to the desirable encoded molecule and the target. In one embodiment, the bound complex-target aggregate can be partitioned from unbound complexes by a number of methods. The methods include nitrocellulose filter binding, column chromatography, filtration, affinity chromatography, centrifugation, and other well known methods.

Briefly, the library of complexes is subjected to the partitioning step, which may include contact between the library and a column onto which the target is immobilised. Identifier nucleic acids associated with undesirable encoded molecules, i.e. encoded molecules not bound to the target under the stringency conditions used, will pass through the column. Additional undesirable encoded molecules (e.g. encoded molecules which cross-react with other targets) may be removed by counter-selection methods. Desirable complexes are bound to the column and can be eluted by changing the conditions of the column (e.g., salt, pH, surfactant, etc.) or the identifier.

Additionally, encoded molecules which react with a target can be separated from those products that do not react with the target. In one example, a chemical compound which covalently attaches to the target (such as a suicide inhibitor) can be washed under very stringent conditions. The resulting complex can then be treated with proteinase, DNAse or other suitable reagents to cleave a linker and liberate the nucleic acids which are associated with the desirable chemical compound. The liberated nucleic acids can be amplified.

In another example, the predetermined characteristic of the desirable product is the ability of the product to transfer a chemical group (such as acyl transfer) to the target and thereby inactivate the target. One could have a product library where all of the products have a thioester chemical group. Upon contact with the target, the desirable products will transfer the chemical group to the target concomitantly changing the desirable product from a thioester to a thiol. Therefore, a partitioning method which would identify products that are now thiols (rather than thioesters) will enable the selection of the desirable products and amplification of the nucleic acid associated therewith.

There are other partitioning and screening processes, which are compatible with this invention that are known to one of ordinary skill in the art. In one embodiment, the products can be fractionated by a number of common methods and then each fraction is then assayed for activity. The fractionization methods can include size, pH, hydrophobicity, etc.

Inherent in the present method is the selection of encoded molecules on the basis of a desired function; this can be extended to the selection of molecules with a desired function and specificity. Specificity can be required during the selection process by first extracting identifier nucleic acid sequences of chemical compounds which are capable of interacting with a non-desired "target" (negative selection, or counter-selection), followed by positive selection with the desired target. As an example, inhibitors of fungal cytochrome P-450 are known to cross-react to some extent with mammalian cytochrome P-450 (resulting in serious side effects). Highly specific inhibitors of the fungal cytochrome could be selected from a library by first removing those products capable of interacting with the mammalian cytochrome, followed by retention of the remaining products which are capable of interacting with the fungal cytochrome.

BRIEF DESCRIPTION OF THE FIGURES

FIG. 1 illustrates the overall process of building block evolution.

FIG. 5 discloses two embodiments of using a Taqman probe (5' nuclease probe) in the measurement of the presence or absence of a certain codon.

DETAILED DESCRIPTION OF THE FIGURES

FIG. 1A Shows the principle steps in BB evolution. An initial library of desired size is produced. This initial library is subjected to a selection process where encoded molecules that associate with a target of interest are enriched. The encoding identifier oligonucleotide is preferably amplified and the used in the codon analysis step. This step monitors the relative abundance of each codon in the selected library. The information obtained in this analysis is used to design a new enriched library, which contains the preferable chemical entities and their corresponding codons. This new library is then subjected to a new selection process to select for binders. This diversity reduction cycle can be repeated until the desirable result is obtained and the binders have been obtained.

FIG. 1B shows how the diversity of a library ($n^4$) is reduced by reducing the number of chemical entities (n) in the library. Thus, by removing chemical entities not involved in the encoded molecules partitioned, a reduction in library diversity can be obtained to allow the identification of binders.

Figure 2:
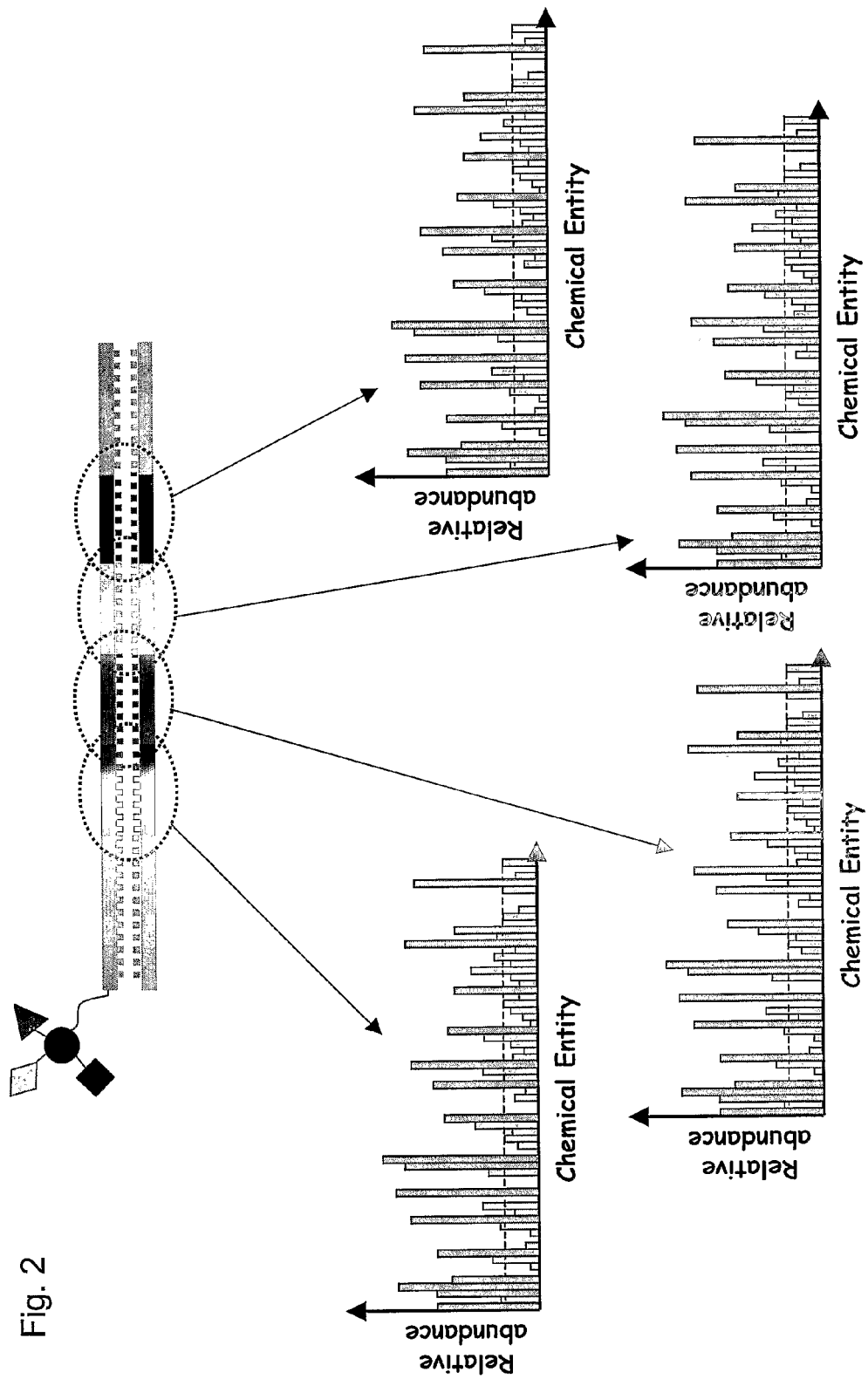
FIG. 2 shows the distribution of codon in different positions in an output from a selection.

The identifier oligonucleotide that encodes for the display molecule is composed of codons and associated with the encoded molecule, as shown in FIG. 2. These codons possess information about the chemical entities in the encoded molecule. Each of these codon positions can be analysed for the precise sequence, which will reflect which chemical entities that have been enrich for in the selection process. The relative amount can also be obtained by comparing the signal in the measuring procedure (e.g. QPCR and array analysis). Each codon position will have its own fingerprint on which chemical entities that the selected display molecules possess. These fingerprints in each position can subsequently be used to put together a new more focused library with a lower and more enrich diversity that can be subjected to another round of selection. This can then repeated until the preferable encoded molecules have been obtained.

Figure 3:
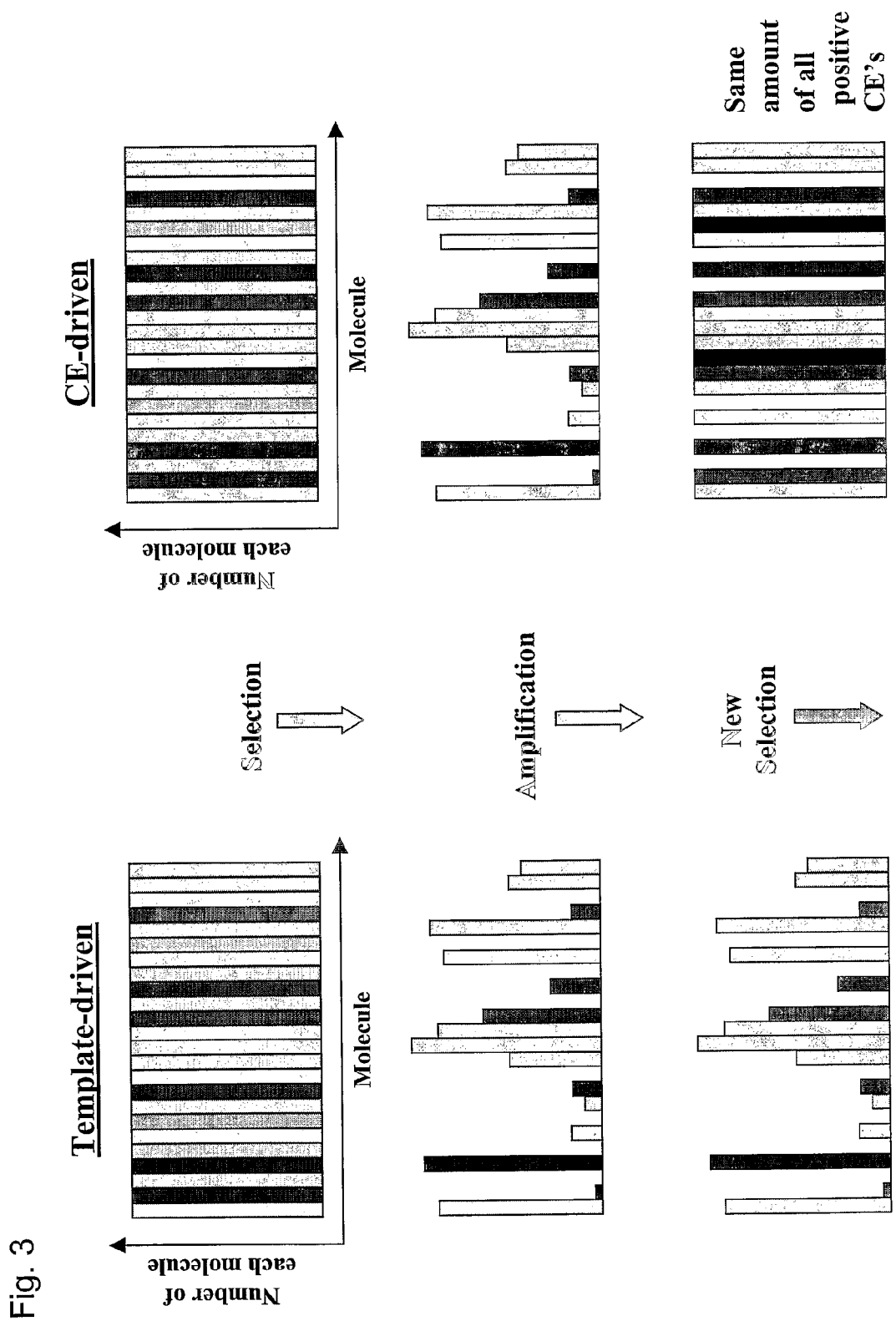
FIG. 3 shows the difference between identifier driven and building block driven evolution.

FIG. 3 illustrates the main difference between identifier and chemical entity (CE) evolution. In both cases the initial selection starts on a library with certain diversity. After the first round of selection the encoding identifiers are amplified where the distribution is maintained. This distribution is then transferred to the next generation which is used in a new selection. Thus, the strongest binders that were enriched in the first round of selection will be present at a relatively higher concentration compared to the weaker binders and the background. In the CE-driven evolution the codon analysis is used to design a new library. In this example, the new library is constructed to contain all the chemical entities that were identified as a positive signal in the analysis. In other words, all the chemical entities that were not detected through the codon analysis were excluded in the new library. The new library is designed to have an equal amount of each selected chemical entity, which will generate all the possible display molecules at the same concentration. This will allow all binders to compete at the same concentration and potentially retain a more diverse set of binders in each round of selection. This is especially important for small molecules here not only the affinity is of interest.

Figure 4:
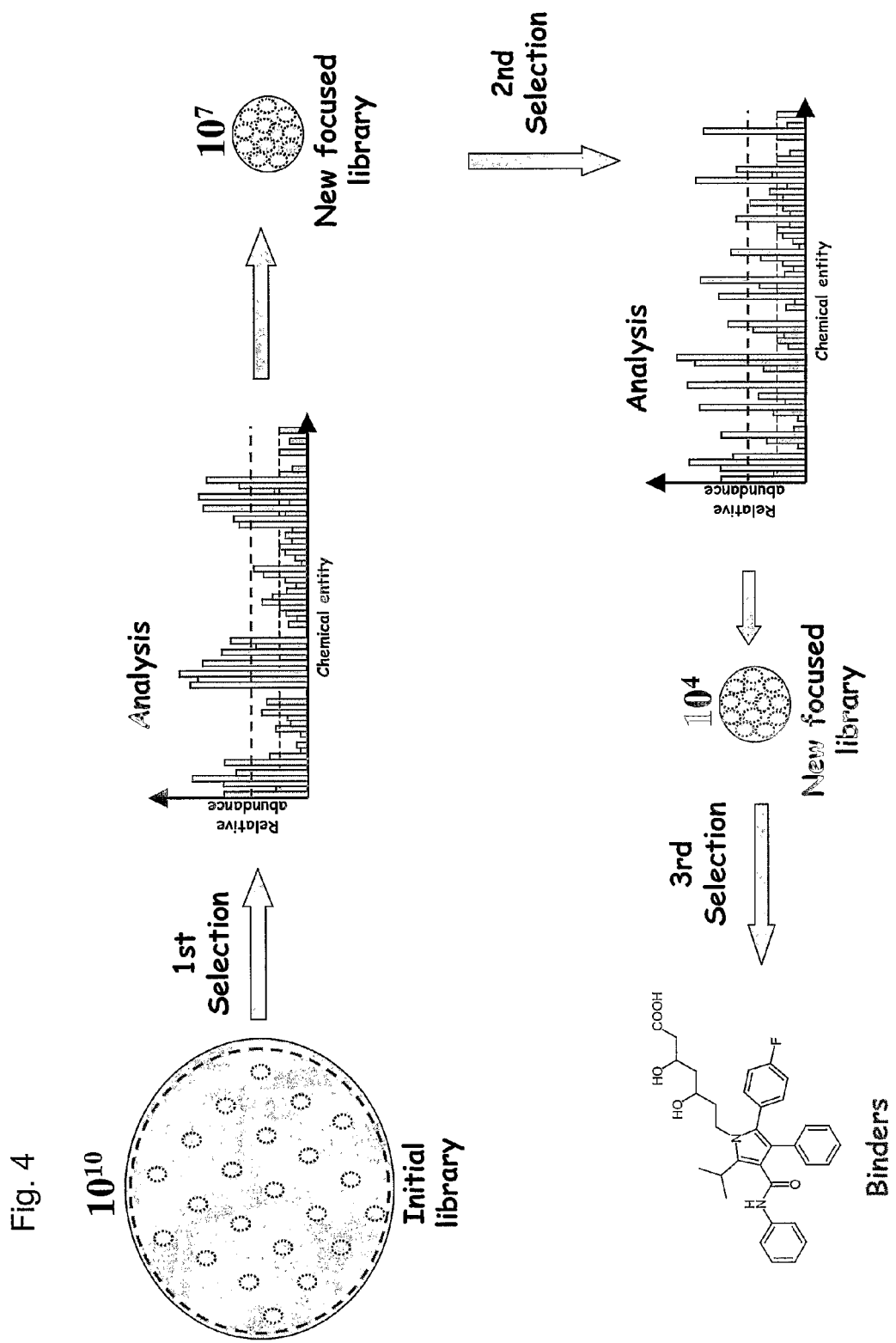
FIG. 4 shows a method for reducing the library diversity through codon analysis.

FIG. 4. This illustrates the process where the diversity is reduced through the codon analysis. An initial library of $10^{10}$ (e.g. 317*317*317*317) library members is subjected to a selection. The enrich identifier oligonucleotides are amplified and used in the codon analysis. The codon analysis result is used to design a new $10^7$ (e.g. 57*57*57*57) library where the enriched chemical entities are included. This new library is the again subjected to a selection process. The identifier oligonucleotides are amplified and used for codon analysis. This new codon analysis results is again used to design a new $10^4$ (e.g. 10*10*10*10) library where the enriched chemical entities are included. Finally a last selection step is performed in this reduced diversity library to identify the binders.

A preferred embodiment of the invention utilizing a universal Taqman probe is shown in FIG. 5. Four codons are shown (P1 through P4; bold pattern) along with framing sequences (light pattern). A universal Taqman probe anneals to a region adjacent to the codon region, but within the amplicon defined by the universal PCR primers Pr. 1 and Pr. 2. These primers could be the same as used for amplification of the identifier oligonucleotides encoding binders after an enrichment process on a specific target. However, are minimal length identifiers preferred during the encoding process, the region involved in Taqman probe annealing could be appended to the library identifier oligonucleotides by e.g. overlap PCR, ligation, or by employing a long downstream PCR primer containing the necessary sequences. The added length corresponding to the region necessary for annealing of the Taqman probe would be form 20 to 40 nts depending on the type of TaqMan probe and $T_A$ of the PCR primers. The Q-PCR reactions are preferably performed in a 96- or 384-well format on a real-time PCR thermocycling machine.

Panel A shows the detection of abundance of a specific codon sequence in position one. Similar primers are prepared for all codon sequences. For each codon sequence utilized to encode a specific BB in the library a Q-PCR reaction is performed with a primer oligonucleotide complementary to the codon sequence in question. A downstream universal reverse primer Pr. 2 is provided after the Taqman probe to provide for an exponential amplification of the PCR amplicon. The setup is most suited for cases where the codon constitutes a length corresponding to a length suitable for a PCR primer.

Panel B shows the detection of abundance of a specific codon sequence in a specific codon position using a primer, which is complementing a codon and a framing sequence. Similar primers are used for all the codons and framing sequences. For each codon sequence utilized to encode a specific BB at a specific codon position in the library a Q-PCR reaction is performed with an oligo complementary to the codon sequence in question as well as a short region up- or downstream of the codon region which ensures extension of the primer in a PCR reaction only when annealed to the codon sequence in that specific codon position. The number of specific primers and Q-PCR reactions needed to cover all codon sequences in all possible codon positions equals the number of codon sequences times the number of codon positions. Thus, monitoring the abundance of 96 different codon sequences in 4 different positions can be performed in a single run on four 96 wells micro titre plates (as shown in Panel B) or a single 384 well plate on a suitable instrument. This architecture allows for the decoding of a $8.5 \times 10^7$ library of different encoded molecules.

Quantification is performed relative to the amount of full-length PCR product obtained in a parallel control reaction on the same input material performed with the two external PCR primers Pr. 1+Pr. 2. Theoretically, a similar rate of accumulation of this control amplicon compared to the accumulation of a product utilizing a single codon+sequence specific primer would indicate a 100% dominance of this particular sequence in the position in question.

Although the setups shown in Panel A and B employ a Taqman probe strategy, other detection systems (SYBR green, Molecular Beacons etc.) could be utilized. In theory, multiplex reactions employing up to 4 different fluorofors in the same reaction could increase throughput correspondingly.

An example of how a deconvolution process of a library of encoded molecules occurs is described in the following. Imagine that at the end of a selection scheme a pool of 3 ligand families (and the corresponding coding identifiers) are dominating the population and present at approx. the same concentration. Three different chemical entities are present in the first position of the encoded compounds, and each of these chemical entities are present in combination with one unique chemical entity out of 3 different chemical entities in position P2. Only one chemical entity in position 3 gives rise to active binders, whereas any of a 20% subset of chemical entities (e.g. determined by charge, size or other characteristics) is present in position 4. The outcome of the initial codon profile analysis would be: 3 codon sequences are equally dominating in position P1, 3 other codon sequences in position P2, 1 unique codon sequence is dominant in P3 whereas somewhat similarly increased levels of 20% of the codon sequences (background levels of the remaining 80% sequences) are seen in P4. In such cases it could be relevant to use an iterative Q-PCR ("IQPCR") strategy to perform a further deconvolution of a library after selection. Again with reference to the example above, by taking the PCR products from the 3 individual wells that contained primers giving the high yields in position P1, diluting the product appropriately and performing a second round of Q-PCR on each of these identifier oligonucleotides separately, it would be possible to deduce which codon sequence(s) is preferred in P2 when a given codon sequence is present in P1.

Figure 9:
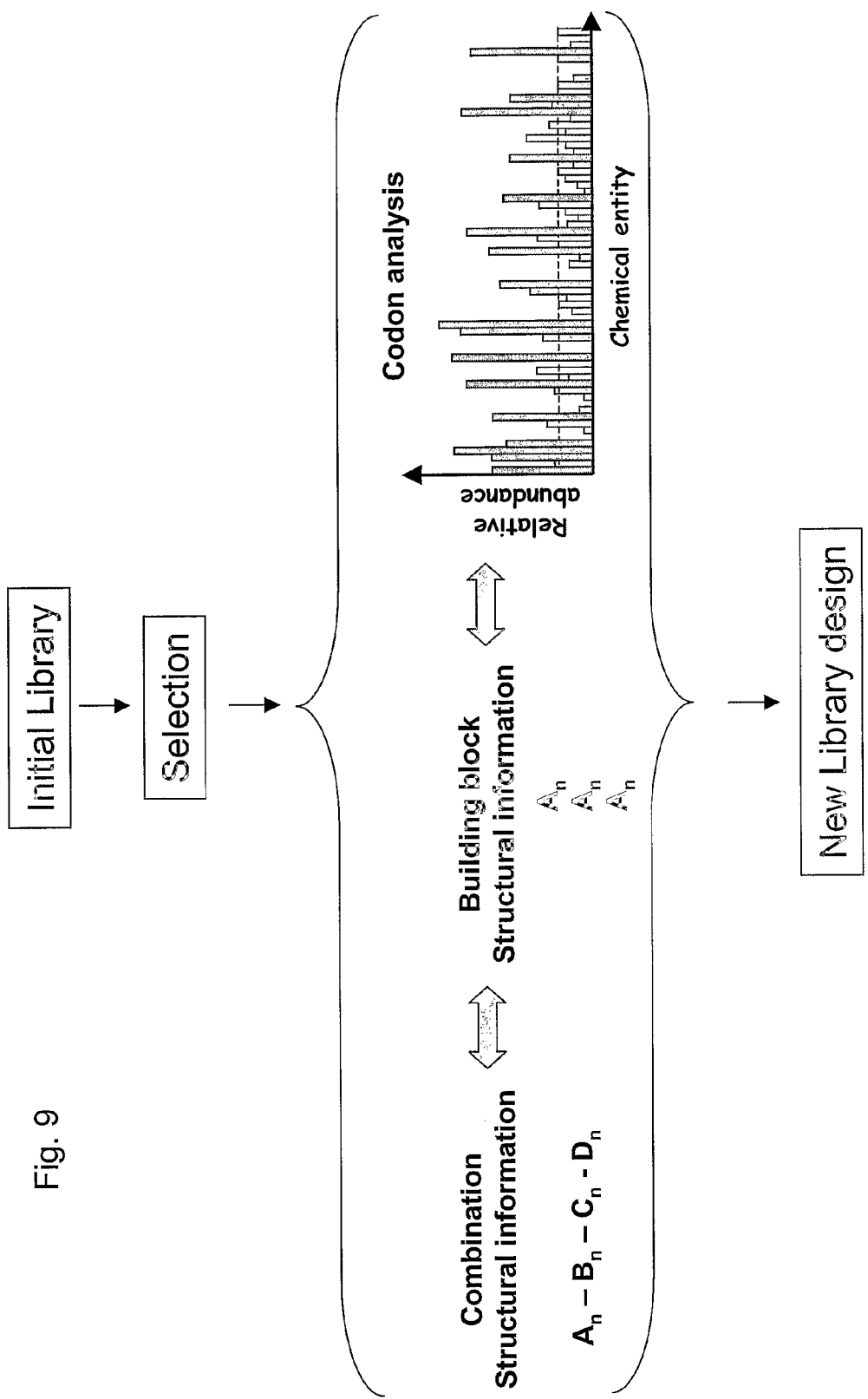
FIG. 9 discloses a scheme relating to combined structural information and codon abundances in library design.

FIG. 9. This figure illustrates the possibility to combine structural information about the chemical entities and the relative abundance when designing a new more focused library. The structural information about the chemical entities can be used at least in two ways. First the similarities between the chemical entities in each position can be used to choose chemical entities to a new library. Secondly, the combination of the selected chemical entities can be analyzed to investigate possible pattern that generate potential ligands. This is especially useful if the binding site or the structure of a known ligand is known. Any type of structural analysis tool can be used that generate information about the structure of separate chemical entities or combination of chemical entities (the potential binders). By combining these three analysis approaches a more focused library can be generated that potentially will contain more specific binders compare to background binders. This new focused library can be used in another round of selection to reduce the diversity. This procedure can be repeated until the desired binders have been identified.

Figure 10:
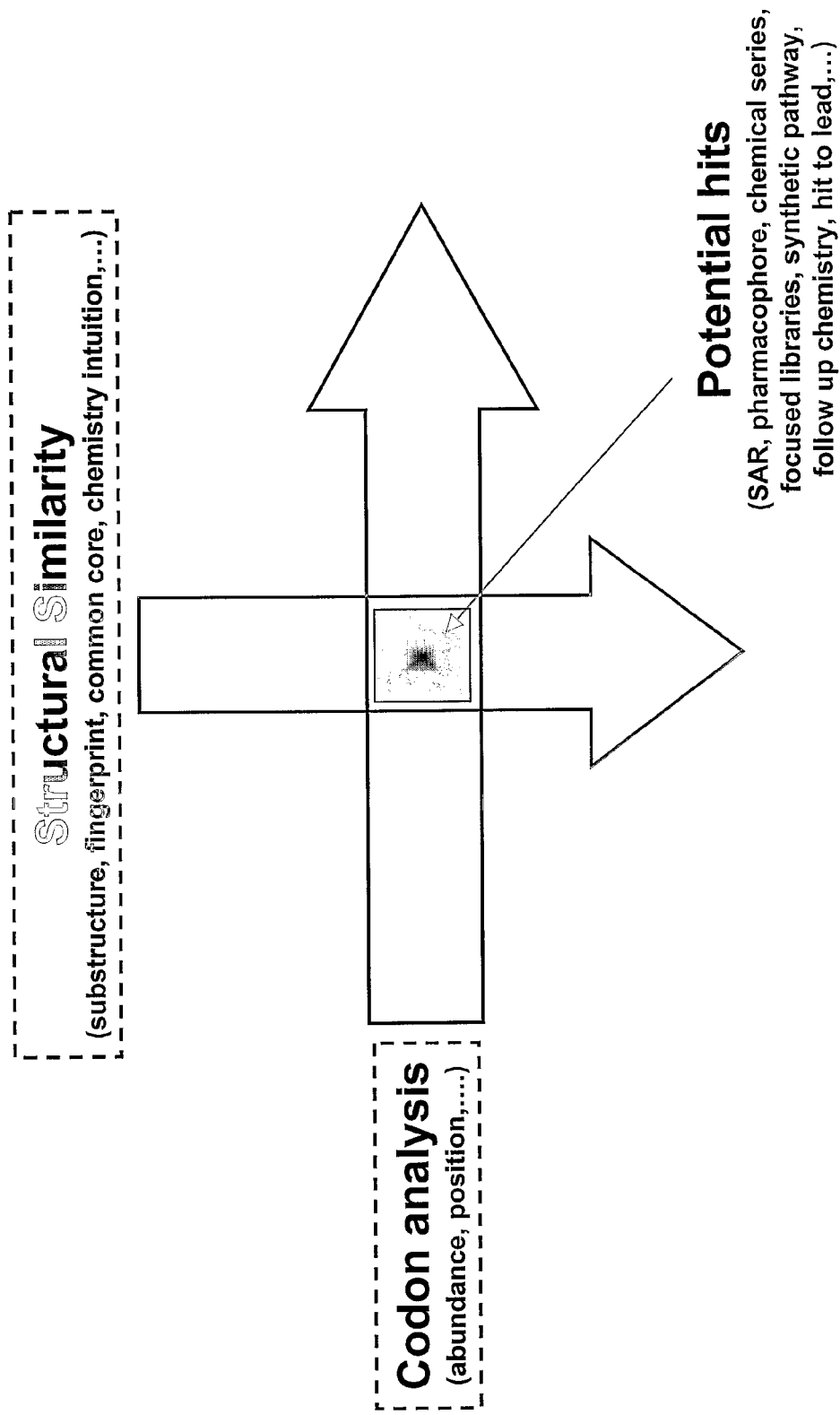
FIG. 10 discloses a relationship between codon analysis and structural information.

FIG. 10. This figure shows how the combination of codon analysis and structural information can generate valuable information. This invention allows the performance of structure activity relationship analysis (SAR) where the relative abundance in the codon analysis will represent the activity parameter (e.g. $IC_{50}$ values) in the SAR measurements. Pharmacophore models can be generated, focused libraries can be designed, certain follow up chemistry can be used and information in the hit to lead process can be used.

Figure 11:
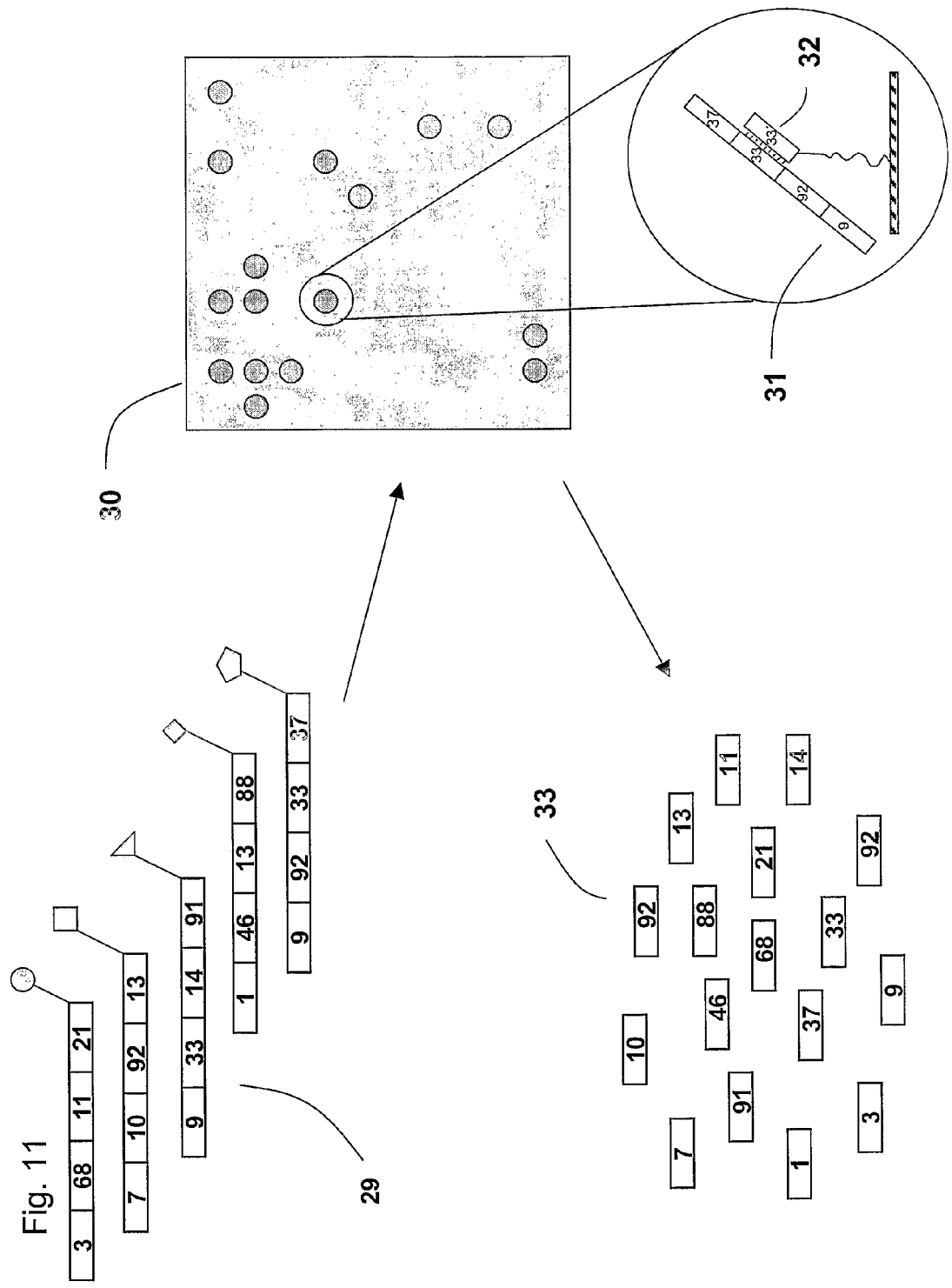
FIG. 11 shows the detection of single codons of identifiers.

FIG. 11 shows an array detection system in which a single codon is detected. Initially a library of selected complexes (29), i.e. complexes comprised of the initial library, which display a certain property, is provided as disclosed above. The initial library of complexes is prepared from e.g. 100 codons and identifiers having 4 codons in sequence, which theoretical gives a library of $10^8$ complexes. The selected complexes are subjected to amplification to amplify the identifiers of the selected complexes and the amplification products are added to an array (30). The array (30) comprises probes (32) complementary to each of the codons of the identifiers (31). At hybridisation conditions the PCR products of the identifiers are annealed to the cognate probes of the array and in a suitable scanner the spatial position of the annealed probes are detected to elucidate the codons (33) of the identifier. The quantity of each codons may be measured to find codons abundant in more than one identifier and/or codons leading to encoded molecules with high affinity. The information may be used for decoding of the encoded molecule of the complexes displaying the desired property or the information may be used for selection of building blocks, which is to be added in a next round of library formation.

Figure 12:
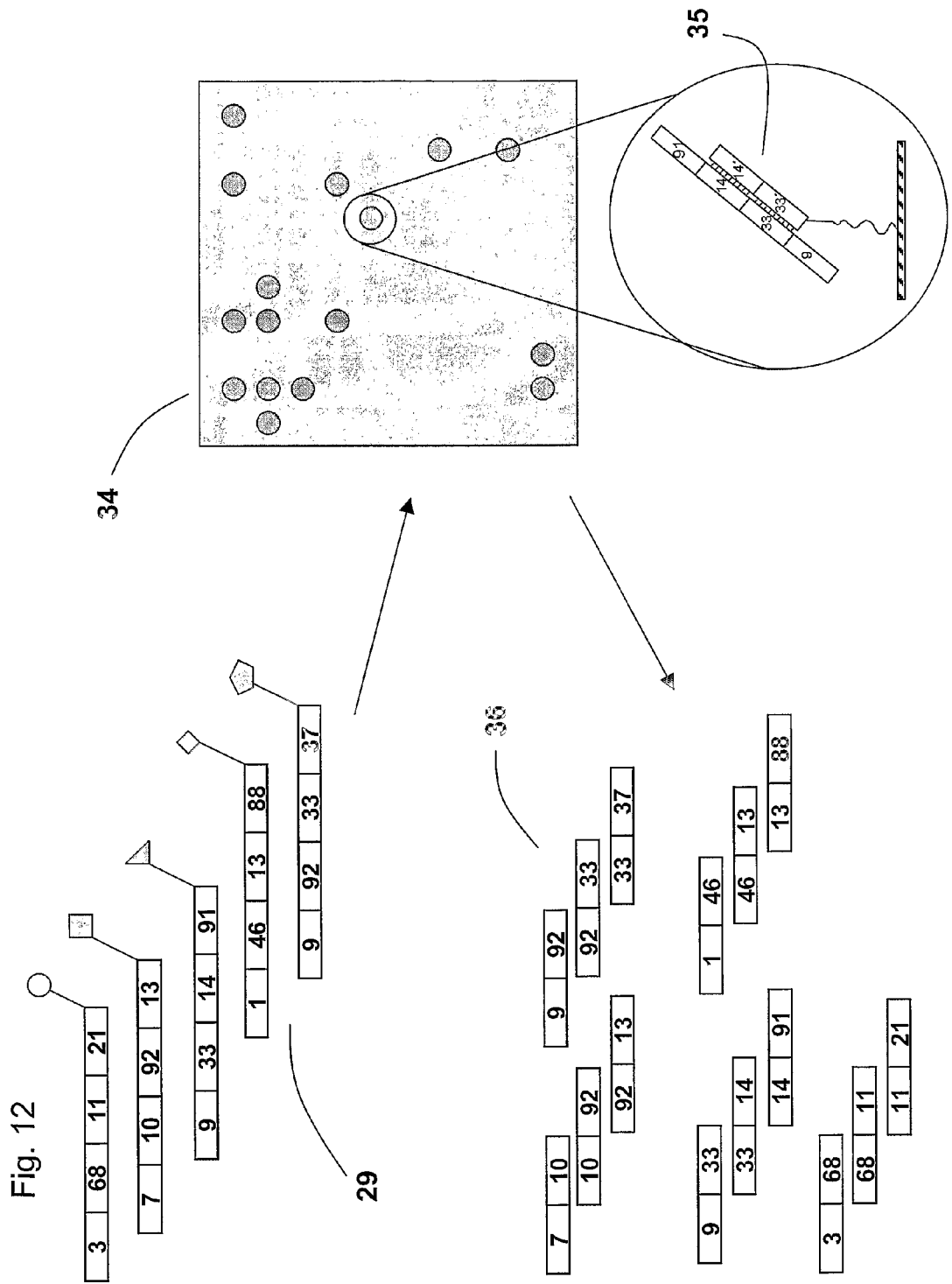
FIG. 12 shows the detection of codon pairs of identifiers.

FIG. 12 discloses an array detection system for establishing codons pairs, i.e. codons in the vicinity of each other. Initially (as shown in this example) a library of complexes is prepared from 100 different codons deposited on an identifier in a sequence of four, making the total amount of combinations possible $10^8$. The initial library is subjected to a condition in order to select a sub-library (29) displaying a desired property. The identifiers of the sub-library are amplified by a PCR reaction and the reaction product is added under hybridisation conditions to an array (34). The array is designed with probes (35) capable of detecting two codons at a time. To cover all possible combinations of a library based on 100 different codons $10^4$ probes are needed, which is practically feasible with the current technology.

The detection of the codons may be conducted quantitatively, i.e. the relative abundance of each of the codon pairs may be determined. The detection on the array may be used to reconstruct the selected identifiers (36) as three overlapping codon pair detections depict the entire identifier. In the event the same codon pair appears on more than one identifier, the information on the relative abundance of each codon pair maybe used to decipher the sequence of codons of the selected identifiers as it can be assumed that each codon pair of the same identifier appears in the same amounts in the PCR products added to the array.

Figure 13:
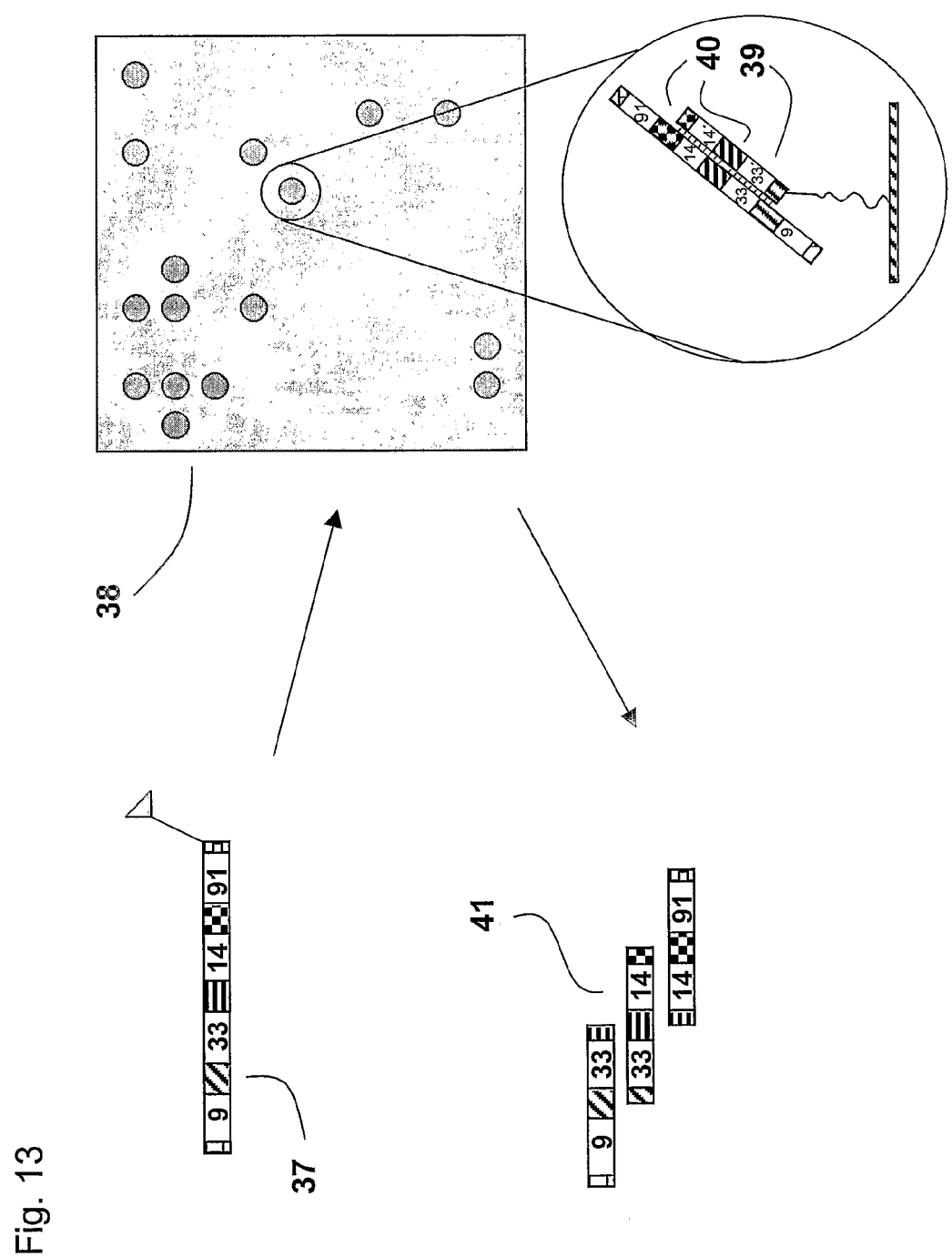
FIG. 13 shows the detection of codon pairs at specific codon positions.

FIG. 13 discloses an array for detecting codon pairs at specific codon positions. Initially, a library of complexes comprising identifiers with framing sequences is provided. The framing sequence is specific for each position of the codons on the identifier. Four times more probes on the microarray is needed per each codon if the position of the codons also should be detected in the analysis which is practically feasible with current technology. The position is detected due to the framing sequences next to each codon. The initial library is subjected to a selection process to isolate complexes (37) having a desired property. The selected complexes are amplified by a PCR reaction and the reaction products are added to an array (38). The array comprises probes capable of detecting codon pairs as wells as the framing sequences (40) between the codons. The framing sequence determines the position of the codon in the reaction history, i.e. it is possible to deduct which chemical entity that reacted at which point in time of the synthesis history of the encoded molecule, thus making it possible to reconstruct the structure of the encoded molecule.

The detection of the codon pairs may be conducted quantitatively, i.e. the relative abundance of each of the codon pairs may be determined. The detection on the array may be used to reconstruct the selected identifiers (41) as three overlapping codon pair detections depict the entire identifier. In the event the same codon pair appears on more than one identifier, the information on the relative abundance of each codon pair maybe used to decipher the sequence of codons of the selected identifiers as it can be assumed that each codon pair of the same identifier appears in the same amounts in the PCR products added to the array.

Figure 14:
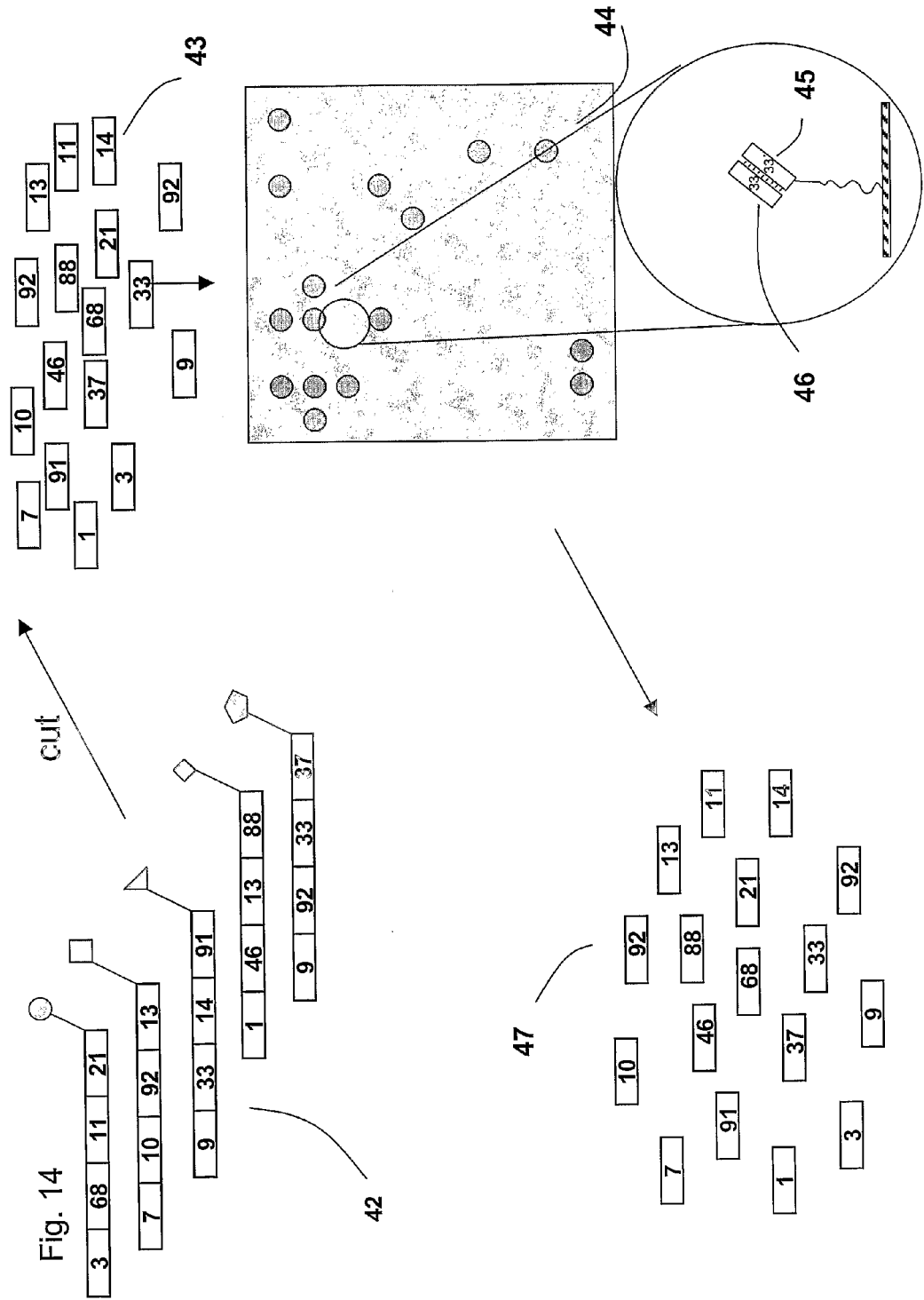
FIG. 14 shows the detection of single codons of identifiers after the separation of the individual codons.

FIG. 14 shows an array detection system in which a single codon is detected. Initially a library of selected complexes (42), i.e. complexes comprised of the initial library which display a certain property, is provided as disclosed above. The initial library of complexes is prepared from e.g. 100 codons and identifiers having 4 codons in sequence, which theoretical gives a library of $10^8$ complexes. The selected complexes are subjected to amplification to amplify the identifiers of the selected complexes and the amplification products are treated with suitable reagents to cut between the individual codons (43). The individual codon is the applied to the array. The array (44) comprises probes (45) complementary to each of the codons of the identifiers (46). At hybridisation conditions the PCR products of the identifiers are annealed to the cognate probes of the array and in a suitable scanner the spatial position of the annealed probes are detected to elucidate the codons (47) of the identifier. The quantity of each codon may be measured to find codons abundant in more than one identifier and/or codons leading to encoded molecules with high affinity. The information may be used for decoding of the encoded molecule of the complexes displaying the desired property or the information may be used for selection of building blocks, which is to be added in a next round of library formation.

Figure 15:
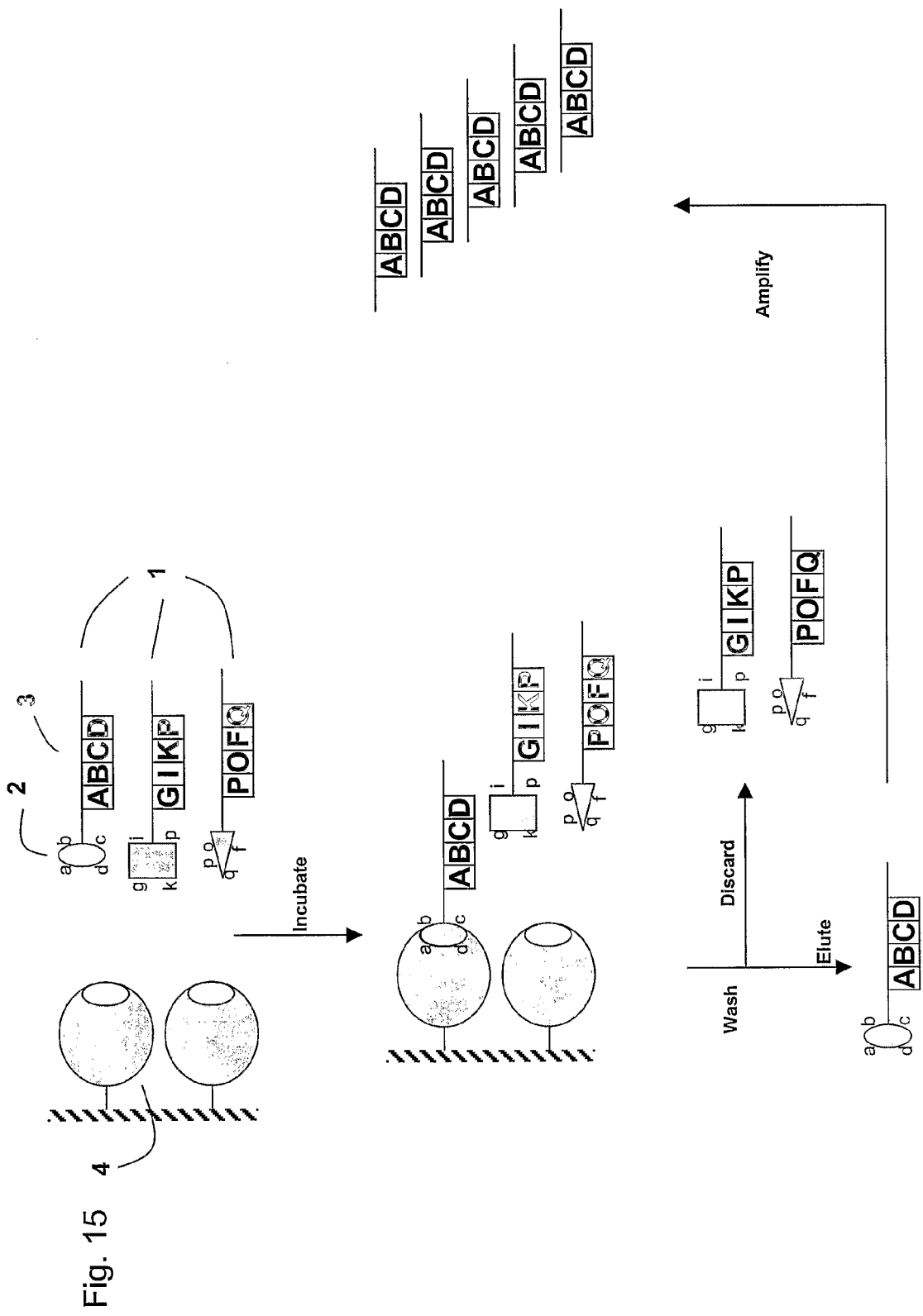
FIG. 15 discloses a method for selecting from a library, complexes capable of binding to a target molecule.

FIG. 15 discloses a method for selection of a suitable complex in several steps. In a first step the library of complexes 1 is provided. Each member of the library comprises an encoded molecule 2 composed of four chemical entities which is attached to an identifier oligonucleotide 3, which comprises four codons. The initial library shown comprises three complexes. In a second step the library of complexes is incubated with immobilized target molecules 4. The encoded molecule having an affinity towards the target molecule is bound to the immobilized target whereas encoded molecules not having affinity towards the target under the conditions used remains in the liquid media. The complexes remaining in the liquid media are discarded by a washing process, while the bound complexes remain attached to the immobilized target molecules. The washing process is usually conducted using mild stringency conditions in the initial rounds of selection. In later stage selections the working stringency conditions are usually increased to allow only high affinity binders to remain attached to the target. Subsequent to the washing step the complexes having affinity towards the target molecule are recovered. The recovery process usually requires high stringency conditions to detach the encoded molecule from the immobilized target. The selected sub-library resulting from the elution is subjected to an amplification process. The amplification of the identifier nucleic acid sequence of the selected complexes is usually performed using the PCR method. Preferably, a modification of the PCR method is followed such that a biotin molecule is attached to one of the primers to obtain a handle for subsequent immobilization. The result of the amplification step is multiple copies of the identifier nucleic acid sequences, which codes for the encoded molecules which have survived the selection step.

Figure 16:
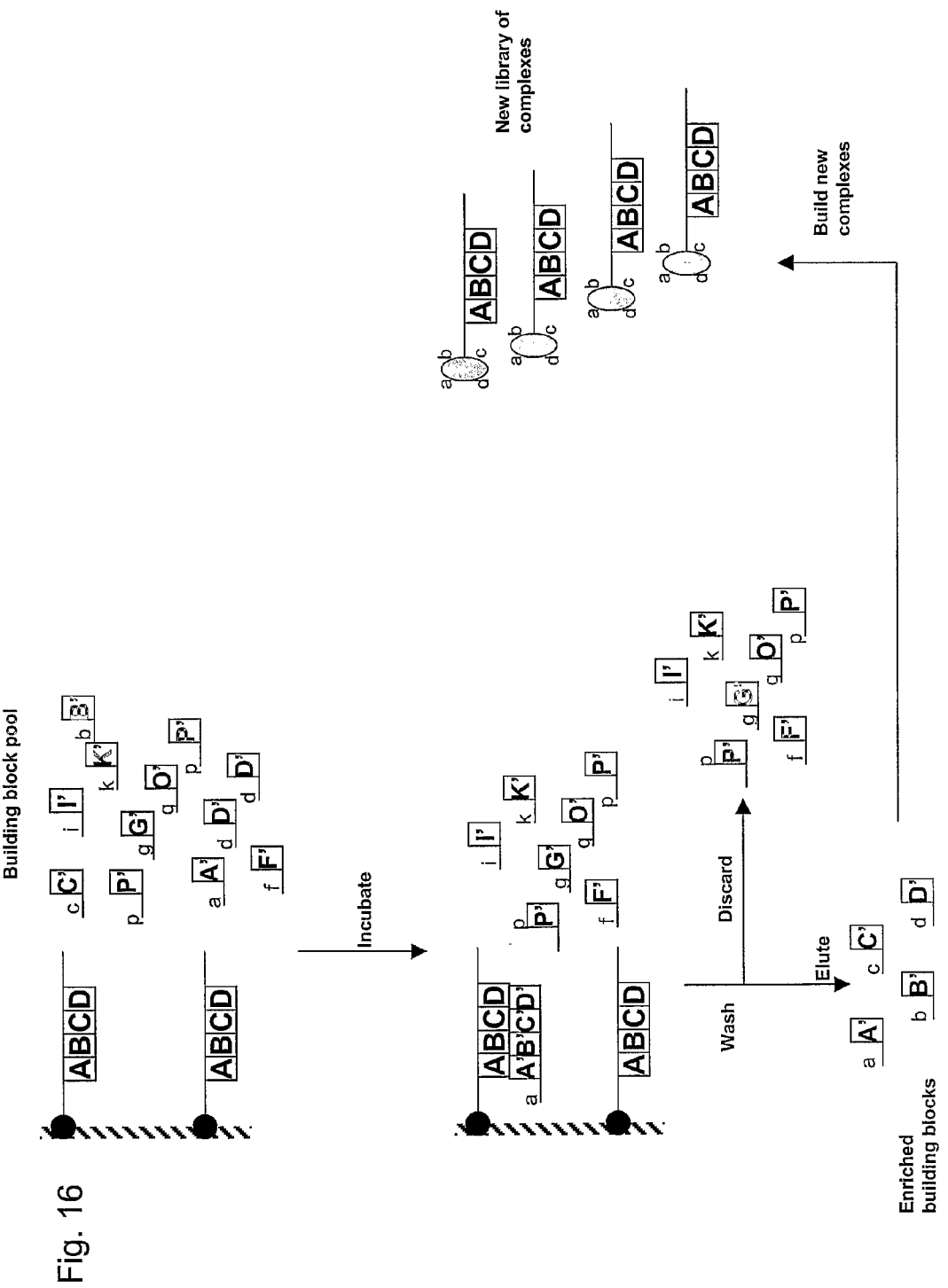
FIG. 16 discloses a method for enriching specific nucleic acid fragments and the utility of these fragments for the generation of a new library.

FIG. 16 discloses an enrichment process of building blocks. The building blocks can be used for generation of a new library. Initially, identifier nucleic acid sequences are immobilized on solid support. In one aspect of the invention the identifier nucleic acid sequences are the product of the selection procedure described in FIG. 1. Each codon of the identifier nucleic acid sequence is identified with an uppercase letter, i.e. A, B, C, or D. The immobilized identifier acid sequences are contacted with the pool of building blocks under hybridisation conditions. Each of the building blocks are illustrated with an sequence complementary to a codon which may or may nor be present on the identifier nucleic acid sequence. The complementary sequences are indicated with a apostrophe, e.g. A', B', etc. The transferable chemical entity of a building block is illustrated with a lowercase letter. The conditions providing for hybridisation of the complementing sequences of the pool of building blocks to the immobilised identifier nucleic acid sequence are preferably such that cognate nucleic acid sequences are hybridised to each other while sequences not recognizing any immobilized sequence remain in aqueous media. The immobilized sequences of the identifier nucleic acid sequences are thus used as bait in catching building blocks with complementing sequences. Following the incubation step, non-binding building bocks are removed by washing, whereby the part of the pool of building blocks not being able to find a complementing sequence is discarded. The building blocks attached to the immobilized nucleic acid sequences are detached using dehybridisation conditions. The diminished pool of building blocks may be used in a subsequent round for preparing a new library of complexes, in which the encoded molecule comprises a reaction product comprising additions from chemical entities attached to the enriched building blocks. Because the order of building blocks which have participated in the formation of the encoded molecules successful in the selection procedure, is not preserved by the method for enriching building blocks a scrambling of the encoded molecules may be obtained in some of the methods described herein for obtaining a library of complexes. In some applications of the library it will be an advantage to have a scrambling of the building blocks because and increased diversity is obtained.

Figure 17:
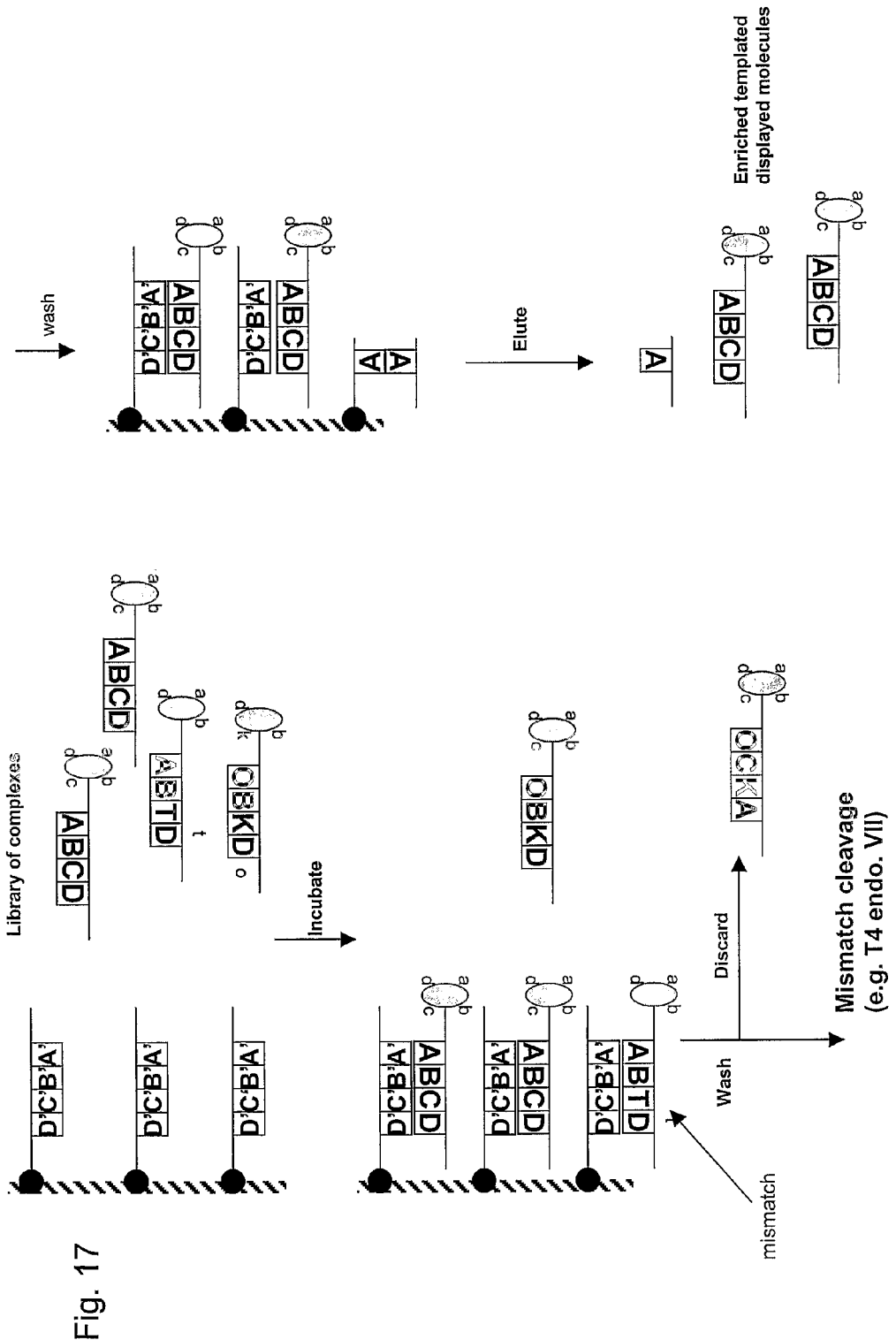
FIG. 17 discloses a method for reducing the diversity of a library of complexes.

FIG. 17 discloses a method for reducing the diversity of the library of complexes resulting from the method described in FIG. 16. In some of the applications of the library the diversity induced by scrambling of the building blocks are not desired. In a first step the sequences complementary to the identifier acid sequences used in FIG. 16 are provided and immobilized on a suitable solid support. In one aspect of the invention the complementary sequence is obtained from the PCR product resulting from the method according to FIG. 15. Alternatively, the complementing sequence may be obtained by extending the identifier nucleic acid sequence using a suitable primer, optionally attached to a handle such as a biotin or dinitrophenol. In a second step the immobilized complementary sequence is incubated with the scrambled library under conditions, which provide for hybridisation between the complementary sequence and members of the library having affinity towards this sequence. Members of the library not having affinity to the complementary sequences remains in the media and is discarded, while members of the library being able to hybridise to the immobilized nucleic acid sequences is recovered. Occasionally, nucleic acids not perfectly matching with the complementary sequence immobilized on the solid support are caught. In one aspect of the invention the hybridisation products, prior to the recovery step, are treated with an enzyme capable of recognizing mismatching nucleotides and cleaving the double stranded helix in which they are situated. An example of an enzyme with this ability is T4 endonuclease VII. After the treatment with the enzyme, complexes displaying a hybridisation toward the immobilized sequence are eluted under dehybridisation conditions. Nucleotide sequences remaining from the cleavage by the enzyme will also be present in the new library, however, these sequences will not have any effect of a subsequent selection because no molecule is attached thereto.

EXAMPLES

Example 1

Enrichment of Nucleic Acid Fragments

A codon was included in the oligonucleotide sequence shown below. The codon is underlined and the boldface sequences represent the "framing" regions next to each codon. These framing regions can be used for specifying the position of each codon.

```
                                    (SEQ ID NO: 1)
Biotin-AATTCCGGAACATACTAGTCAACATGA-3'
```

This identifier oligonucleotide was immobilized on streptavidin beads using standard protocols, i.e. 600 µmol identifier oligonucleotide with 5'-dT biotin in 50 µl 100 mM Mes pH 6.0 was mix with 50 µl SA-magnetic beads (Roche). The mixture was washed 2-3 times with 100 mM MES pH 6.0 to remove non-bound identifier oligonucleotides. To reduce background binding, the oligos and beads was incubated at RT for 10 min on shaker, then incubated on ice for 10 min while rotating the tube. Finally, the sample was washed with 100 mM MES 4 times in 800 µl at 60° C.

In the case where a PCR product is immobilized, the complementing (non-sense) strand is removed using 10 mM NaOH. This will generate single-stranded DNA with the selected codons. The same procedure described in this example can be used for a collection of different identifier nucleic acid molecules that contain one or more codons. The codons in the identifier nucleic acid molecules can be the same or different determined from the enrichment performed on the initial library.

The immobilized identifier nucleic acid molecule was mixed with the pool of nucleic acid fragments shown below. This pool of fragments illustrates an original pool that was used for generating an initial library of complexes. Each fragment may possess in the 3'-end a specific chemical entity that is encoded by the codon sequence. These nucleic acid fragments contain a specific sequence in the codon region (underlined) while the framing region shown in boldface is identical among the fragments. Thus, the pool of fragments represents different codons in the same position of the identifier nucleic acid.

```
1.
                                    (SEQ ID NO: 2)
CGT GTG ATC GAA CTC GTG TG GTATGATCAGTTGTACT-5'

2.
                                    (SEQ ID NO: 3)
CGT GTG ATC GAA CTC GTG TG GTATCTAGTCGGTTACT-5'

3.
                                    (SEQ ID NO: 4)
CGT GTG ATC GAA CTC GTG TG GTATTCGAGTGTTTACT-5'

4.
                                    (SEQ ID NO: 5)
CGT GTG ATC GAA CTC GTG TG GTATAGCTCATGGTACT-5'
```

Figure 18A:
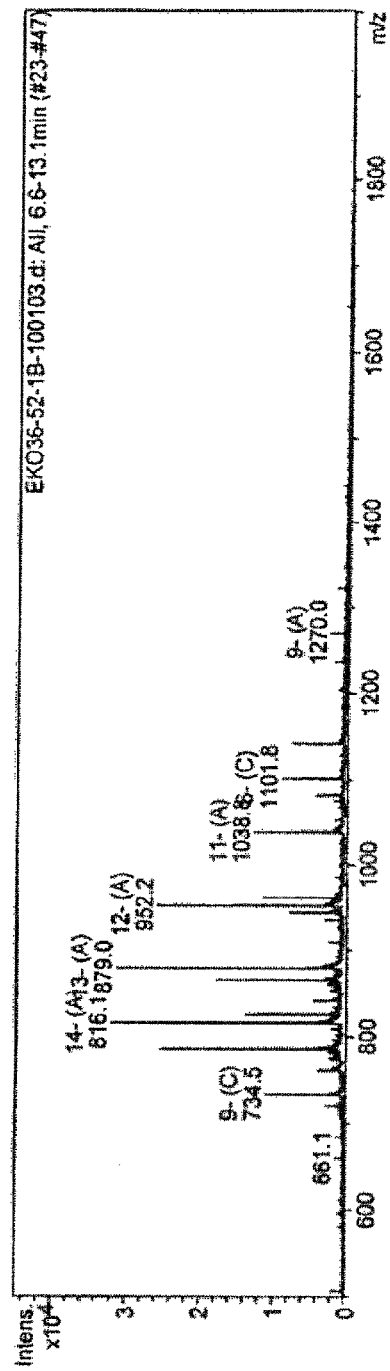
FIG. 18 shows mass spectrograms for (A) eluted fragments and controls (B) with the correct sequence, codon 1, and (C) with the incorrect sequence, codon 3.

The nucleic acid fragments are mixed with the immobilized identifier nucleic acid using 600 µmol of each nucleic acid fragment mixed with the immobilized identifier nucleic acid molecules (100 mM MES pH 6.0, 150 mM NaCl)). The mixture was incubated at 25° C. for 30 minutes in a shaker. The non-hybridized fragments were removed by 4 times washing in 800 µl 100 mM MES, 150 mM NaCl. This step should separate the complementing fragments (bound) encoding for the select chemical entities from the non-complementing fragments (non-bound) encoding for chemical entities that were not effective in the preceding selection process. The annealed fragments are eluted from the immobilized identifier nucleic acid molecules by re-suspending the beads in 25 µl 60° C. $H_2O$ and incubating for 2 min at 60° C. The enriched fragments were purified on a micro-spin gel filtration column (BiRad). The eluted fragments were prepared for mass spectroscopy (MS) analysis by mixing in half volume of ion exchanger resin and incubating minimum 2 h at 25° C. on a shaker. After incubation the resin was removed by centrifugation and 15 µl of the supernatant was mixed with 7 µl of water, 2 µl of piperidine and imidazole (each 625 mM) and 24 µl acetonitrile. The sample was analysed using a Mass Spectroscopy instrument (Bruker Daltonics, Esquire 3000plus). The result for the MS analysis is shown in FIG. 18A, with components A-C characterized as set forth below.

| Component | Deconvoluted Mass | Molecule | Absolute Abundance | Relative Abundance | |
|---|---|---|---|---|---|
| A | 11438.39 | [M − H]− | 112674 | 96.98 | → HATCH |
| B | 8663.73 | [M − H]− | 61649 | 53.06 | |
| C | 6616.63 | [M − H]− | 41245 | 35.50 | |

The mass from the correct complementary fragment (number 1) is obtained in the MS analysis (11438.39, expected 11439 Da) No masses for the other fragments (number 2-4)

could not be found in the MS spectra (expected masses; 11415, 11430, 11424 Da). This result shows that the right fragment is strongly enriched and other fragments with the wrong codon sequences are removed. The enrichment is possible even when the "spacing" region (boldface) is identical in each fragment.

Figure 18B:
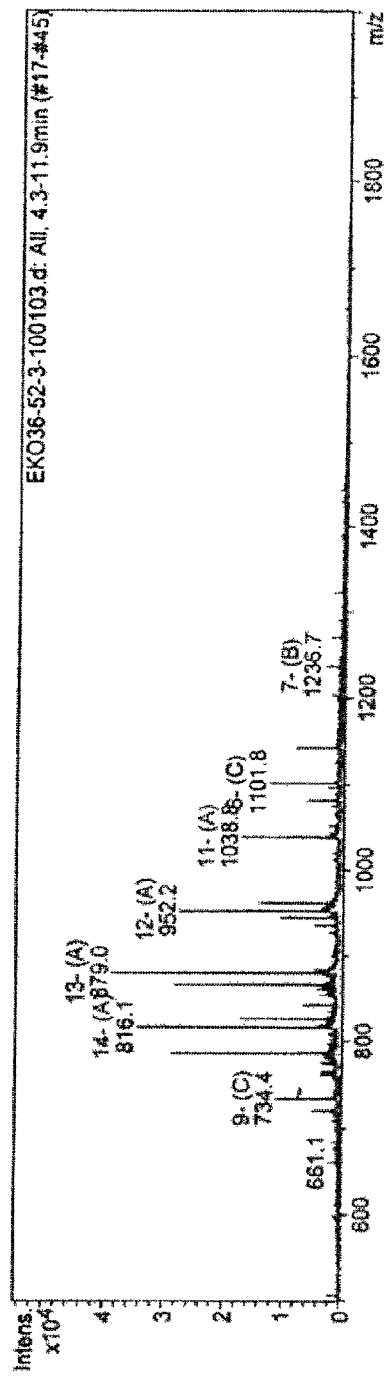

Two control experiments were also performed to validate the enrichment protocol. In the first experiment, the fragment with the correct codon sequence (number 1) was mixed with the immobilized identifier molecule as described above. The sample was washed end eluted also as described above and prepared for MS analysis. The result from the MS analysis is shown in FIG. 18B, with components A-C characterized as set forth below.

| Component | Deconvoluted Mass | Molecule | Absolute Abundance | Relative Abundance |
|---|---|---|---|---|
| A | 11438.39 | [M – H]– | 127110 | 96.21 → HATCH |
| B | 8663.73 | [M – H]– | 82800 | 62.67 |
| C | 6616.63 | [M – H]– | 51480 | 38.97 |

The result indicates that the fragment with the correct sequence (number 1) anneals to the immobilized identifier molecules and is eluted under the conditions used in this example. The expected mass (11439) correlate well with the experimental mass, 11438.39 Da.

Figure 18C:
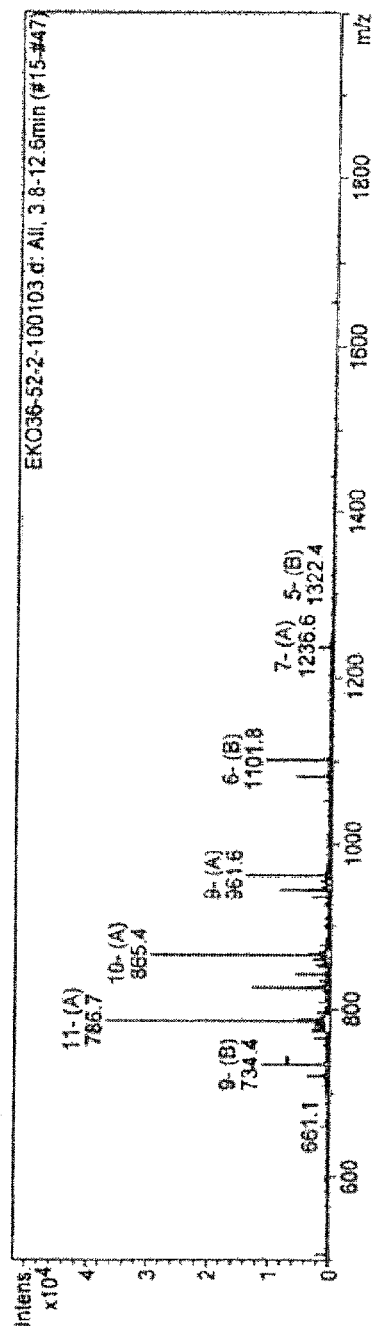

In the other control experiment, a fragment with a wrong codon sequence (number 3) was allow to bind to the immobilized identifier molecule as described above. Again, the eluted sample was prepared and analysed with MS. The result is shown in FIG. 18C, with components A-C characterized as set forth below.

| Component | Deconvoluted Mass | Molecule | Absolute Abundance | Relative Abundance |
|---|---|---|---|---|
| A | 11438.39 | [M – H]– | 89308 | 96.60 - EK0SQ |
| B | 8663.73 | [M – H]– | 41963 | 45.39 - PRIH |
| C | 6616.63 | [M – H]– | 13651 | 14.77 - EK01 |

In this experiment, no mass was found that corresponded to the expected mass (11430) of the tested building block (number 1). Again, thisshows that fragments with a anticodon sequence different from the enriched codons in the identifier nucleic acid molecules are not captured using this approach.

The enriched fragments obtained using this strategy may then be used to generate a new library of encoded molecules. This new library will contain encoded molecules composed of the enriched chemical entities. Thus, the library size have been reduced due to the removal of chemical entities not involved in binding encoded molecules, and enriched in chemical entities that are highly represented in the encoded molecules which binds to the target molecule.

Example 1 shows the possibility of enriching for specific building block molecules, i.e. nucleic acid fragments associated with transferable chemical entities. The same procedure can be used for a larger pool of building block than four as used herein. The codon design will determine the maximum number of building blocks that can be used. The sequence in the codon region should be large enough to allow discrimination in the annealing step. Various conditions can be used to increase the stringency in the annealing step. Parameters such as temperature, salt, pH, form amide concentration, time and other conditions could be used.

Example 2 (Model)

Multiple Codon Selection in a Library

This example describes the enrichment of building blocks using an identifier nucleic acid (identifier) molecule with multiple codons. These codons encode for a displayed molecule (DM) that are attached to the identifier molecule before the selection is performed. The library size is determined both by the number of different chemical entities and the total number of chemical entities. The identifier molecule shown below contains three codons. The codons, which codes for the displayed molecule are indicated with underlines and the region separating (framing region) the codons in boldface. The size of the codons can be varied dependent on the diversity need in the library and the optimal setup for chemical entity enrichment. The framing region can also be varied dependent on the discrimination needed to distinguish the precise position of a codon in the identifier molecule. The framing region will also be important for the generation of the library. This can be understood when the encoding is accomplished by extension of the encoding region as disclosed in DK PA 2002 01955 and U.S. 60/434,425, incorporated herein by reference. There need to be a perfect match in the 3'-end in order to get efficient extension with a polymerase or a ligase. The size of this spacing/framing region should be long enough to form a complementing region to allow extension with a polymerase or ligase. Preferably, the spacing region should be between 3 and 6 nucleotides. The codon region together with the spacing region will also be useful when codons are to be identified using a micro array setup. The identifier molecule with the right codon sequences will hybridize to the array and be detected.

The sequence below represents an enriched identifier molecule attached to the displayed molecule (DM). This identifier molecule has been enriched due to the fact that the DM binds to the target molecule in the selection process. In practice, more than one enriched identifier molecules will be obtained when using a library of displayed molecules attached to its identifier sequence.

(SEQ ID NO: 6)
DM-GCACACTAGCTTGAGCACACTGACACATGGAGATCACATGCTTCGA

CAATGCAGGACTCCCG-CAGCTTTACGATCCCGCAGGTAACCGT

This identifier molecule is amplified with two primers (below) using a standard PCR reaction. For example, 500 nM of each primer, 2.5 units Taq polymerase, 0.2 mM of each NTP, in a PCR buffer (50 mM KCl, 10 mM Tris-Cl, 3 mM DTT, 1.5 mM MgCl$_2$, 0.1 mg/ml BSA). Run 25 cycles (94° C. melt for 30 seconds, 55° C. anneal for 45 seconds, 72° C. extension for 60 seconds).

(SEQ ID NO: 7)
B-GCACACTAGCTTGAGCACACTGACA-3'

(SEQ ID NO: 8)
CGAAATGCTAGGGCGTCCATTGGCA-5'

This will amplify the identifier molecule from the selection process and add a biotin in the 5'-end of one of the strand (below). This amplified product is then immobilized on a solid support, streptavidin beads for example. This can be performed identical as describe in example 1.

When the identifier molecules have been immobilized and the excess has been removed by a washing step (as describe in example 1), the complementing non-sense stand is removed by incubating in 10 NaOH for about 2 min and washed with 100 mM Mes buffer, pH 6.0. This procedure will generate the strand shown below where the codon regions are exposed to allow hybridization with the complementing sequences.

(SEQ ID NO: 9)
B-GCACACTAGCTTGAGCACACTGACACATGGAGATCACATGCTTCGAC

AATGCAGGACTCCCG-CAGCTTTACGATCCCGCAGGTAACCGT

The next step is to protect the complementing sequences outside the codons to prevent the binding of the building block to these sequences. This can be performed by adding "blocking" oligonucleotides that has a complementing sequence. This is shown below.

B-
(SEQ ID NO: 9)
GCACACTAGCTTGAGCACACTGACACATGGAGATCACATGCTTCGACAAT

GCAGGACTCCCG-CAGCTTTACGATCCCGCAGGTAACCGT (SEQ ID NO: 10)
CGTGTGATCGAACTCGTGTGACTGT (SEQ ID NO: 11)
CGAAATGCTAGGGCGTCCATT-

GGCA

Next, the pool of different building blocks is added and is allowed annealing to the codon region in the identifier region. The position of annealing is determined by the spacing region shown in boldface. The stringency is adjusted to only allow hybridization of the correct building block in the right position. This can be accomplished by mixing the right component together using various conditions. The condition can for example include the presence of salt, formamide and various buffers adjusted to suitable pH and temperature. Below is the correct building block that will anneal to the enriched identifier molecules. These building blocks is annealed and eluted as described in example 1.

(SEQ ID NO: 12)
CE-CGTGTGATCGAACTCGTGTGACTGTGTACCTCTAGTGTAC

The next pool of building blocks is blocked with an oligonucleotide that also protects the first codon. This is necessary to prevent binding of the building blocks in that codon.

B-
(SEQ ID NO: 9)
GCACACTAGCTTGAGCACACTGACACATGGAGATCACATGCTTCGACAAT

GCAGGACTCCCG-CAGCTTTACGATCCCGCAGGTAACCGT (SEQ ID NO: 13)
CGTGTGATCGAACTCGTGTGACTGTGTAIIIIIIIII (SEQ ID NO: 14)
CGAAATGCTAGGGCGTCCATT-

GGCA

Again, the library of building blocks is added to enrich for the selected codons. Below is the building block with the correct sequence. These building blocks is annealed and eluted as described in example 1.

(SEQ ID NO: 15)
CE-CGTGTGATCGAACTCGTGTGACTGTGTAIIIIIIIIITACGAAGCT

GTTACG

Finally, the identifier molecule is protected with a blocking oligo that expose only the last codon.

B--
(SEQ ID NO: 9)
GCACACTAGCTTGAGCACACTGACACATGGACATCACATGCTTCGACAAT

GCAGGACTCCCG-CAGCTTTACGATCCCGCAGGTAACCGT (SEQ ID NO: 16)
CGTGTGATCGAACTCGTGTGACTGTGTAIIIIIIIIITACIIIIIIIII (SEQ ID NO: 17)
CGAAATGCTAGGGCGTCCATTGG-

CA

A new pool of building blocks is added and allowed hybridizing to the identifier molecule. These building blocks is annealed and eluted as described in example 1.

(SEQ ID NO: 18)
CE-CGTGTGATCGAACTCGTGTGACTGTGTAIIIIIIIIITACIIIIIII

IIIACGTCCTGAGGGCGT

The enrichment of each library of building blocks are performed in separate tubes in order to keep the libraries of building block separated. The enrichment is performed with building blocks loaded with chemical entities (CE).

Example 3

Template Versus Chemical Entity Evolution

Figure 19A:
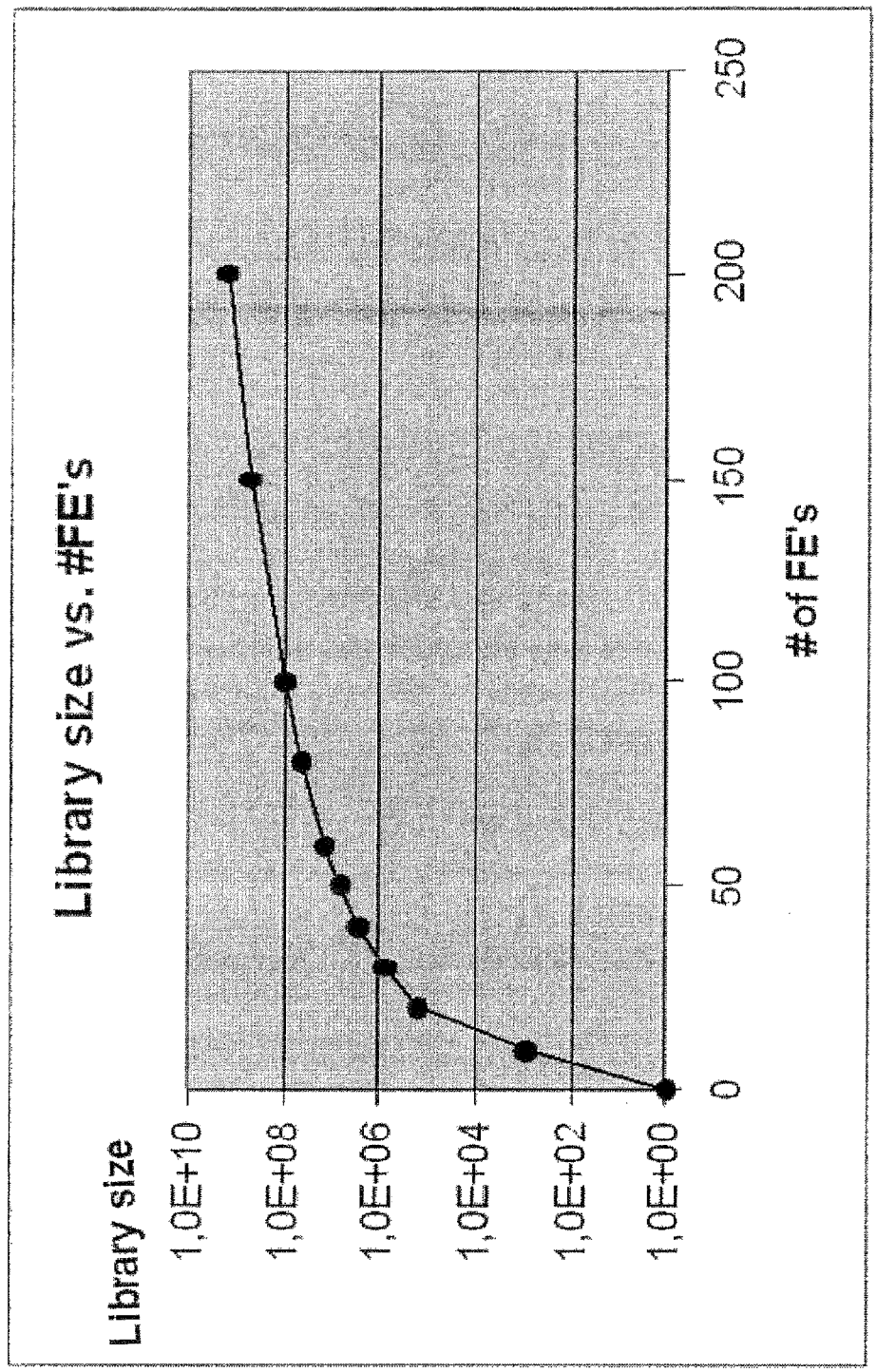
FIG. 19 shows (A) the relationship of library size to number of functional entities (FE) for an encoded molecule library as discussed in Example 3, and (B) the relationship of library size to number of amino acids for a protein library.

FIG. 19A illustrates the relationship between the number of chemical entitles and the library size. The example below is calculated on that the final encoded molecules contains four chemical entities that is individually encoded by the corresponding building block ($n^4$, where n is the number of building blocks). The graph shows that the diversity decreases dramatically with the reduction of the total number of building blocks. If the number of different building can be reduced to about 20-30 (library size of $16*10^3$ and $81*10^4$, respectively) in the selection process, then the library size for the final round of selection is low enough for identification of the binding molecules.

Figure 19B:
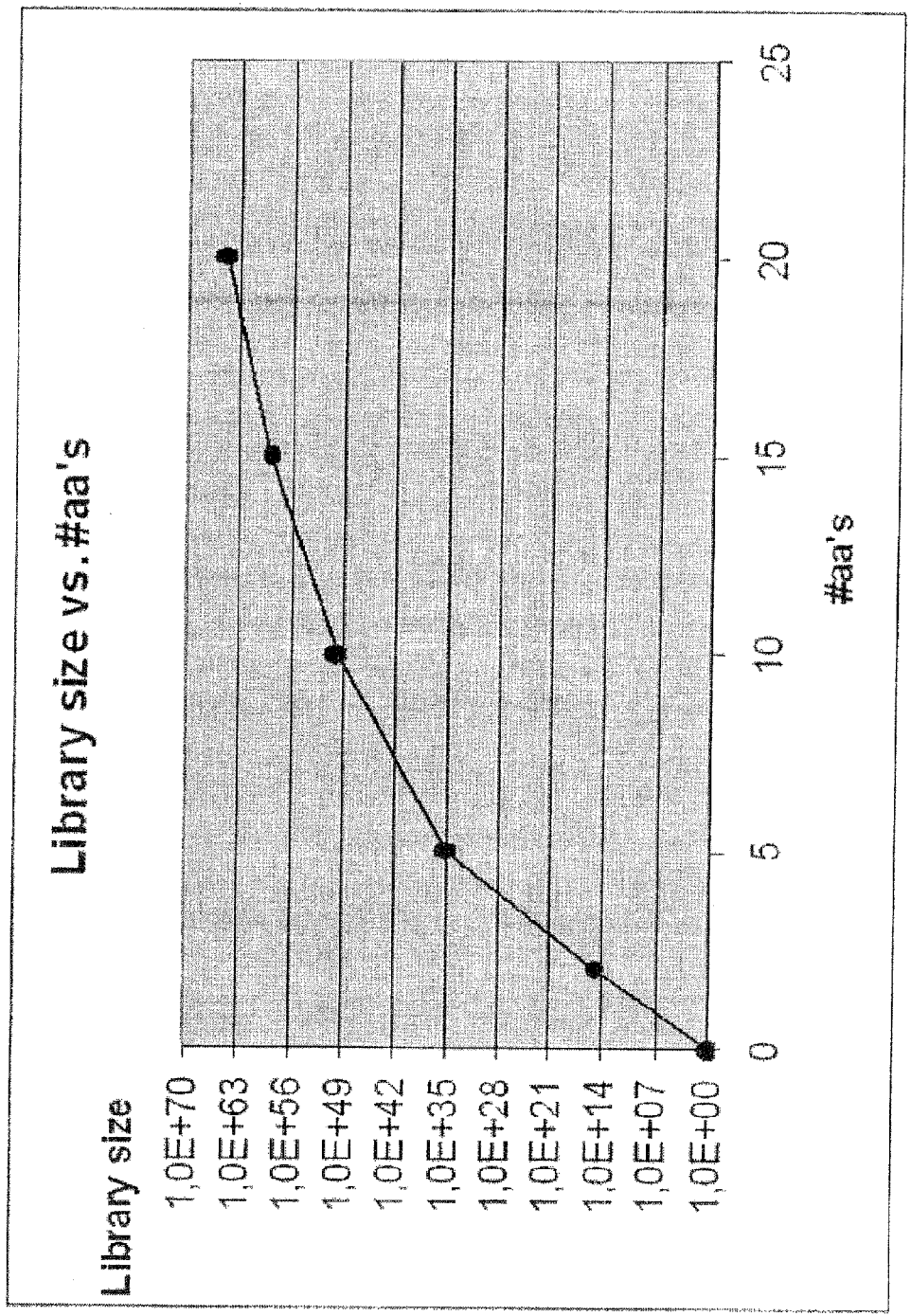

When the same analysis is performed on a protein another situation is obtained. FIG. 19B relates to a very small protein (50 amino acids in length). The diversity is enormous when all amino acids are included in the library. The size of the library is also decreasing with the total number of amino acids, but not to the same extent as show above for a small molecule. Even when the different amino acids are reduced to 2, the library size is huge ($1.2\ 10^{15}$). This shows that amino acid enrichment is impossible on protein. This is even more pronounced for mid-size protein which contains about 300 amino acids.

Example 4

Codon Analysis

This example illustrates one possibility to perform codon analysis on a whole population of different identifier oligonucleotides. The analysis can also be performed using array where the probe oligonucleotides (complementary to the codons) are immobilized in discreet areas and the signal is monitored dependent on the amount of identifiers oligonucleotides are hybridised in each specific area. Codon analysis can also be performed using standard sequencing using a polymerase extension step.

In FIG. 5, Four codons are shown (P1 through P4; bold pattern) along with flanking regions (light pattern). A universal Taqman probe anneals to a region adjacent to the codon region, but within the amplicon defined by the universal PCR primers Pr. 1 and Pr. 2. These primers could be the same as used for amplification of the identifier oligonucleotides encoding binders after an enrichment process on a specific target. However, are minimal length identifiers preferred during the encoding process, the region involved in Taqman probe annealing could be appended to the library identifier oligonucleotides by e.g. overlap PCR, ligation, or by employing a long down-stream PCR primer containing the necessary sequences. The added length corresponding to the region necessary for annealing of the Taqman probe would be form 20 to 40 nts depending on the type of TaqMan probe and $T_A$ of the PCR primers. The Q-PCR reactions are preferably performed in a 96- or 384-well format on a realtime PCR thermocycling machine.

FIG. 5, panel A, shows the detection of abundance of a specific codon sequence in position one. Similar primers are prepared for all codon sequences. For each codon sequence utilized to encode a specific BB in the library a Q-PCR reaction is performed with a primer oligonucleotide complementary to the codon sequence in question. A downstream universal reverse primer Pr. 2 is provided after the Taqman probe to provide for an exponential amplification of the PCR amplicon. The setup is most suited for cases where the codon constitutes a length corresponding to a length suitable for a PCR primer.

FIG. 5, panel B shows the detection of abundance of a specific codon sequence in a specific codon position using a primer which is complementing a codon and a framing sequence. Similar primers are used for all the codons and framing sequences. For each codon sequence utilized to encode a specific BB at a specific codon position in the library a Q-PCR reaction is performed with an oligo complementary to the codon sequence in question as well as a short region up- or downstream of the codon region which ensures extension of the primer in a PCR reaction only when annealed to the codon sequence in that specific codon position. The number of specific primers and Q-PCR reactions needed to cover all codon sequences in all possible codon positions equals the number of codon sequences times the number of codon positions. Thus, monitoring the abundance of 96 different codon sequences in 4 different positions can be performed in a single run on four 96 wells micro titre plates (as shown in FIG. 5, panel B) or a single 384 well plate on a suitable instrument. This architecture allows for the decoding of a $8.5^{x}10^7$ library of different encoded molecules.

Quantification is performed relative to the amount of full-length PCR product obtained in a parallel control reaction on the same input material performed with the two external PCR primers Pr. 1+Pr. 2. Theoretically, a similar rate of accumulation of this control amplicon compared to the accumulation of a product utilizing a single codon+sequence specific primer would indicate a 100% dominance of this particular sequence in the position in question.

Although the setups shown in FIG. 5, panel A and B employ a Taqman probe strategy, other detection systems (SYBR green, Molecular Beacons etc.) could be utilized. In theory, multiplex reactions employing up to 4 different fluorofors in the same reaction could increase throughput correspondingly.

An example of how a deconvolution process of a library of encoded molecules occurs is described in the following. Imagine that at the end of a selection scheme a pool of 3 ligand families (and the corresponding coding identifiers) are dominating the population and present at approx. the same concentration. Three different chemical entities are present in the first position of the encoded compounds, and each of these chemical entities are present in combination with one unique chemical entity out of 3 different chemical entities in position P2. Only one chemical entity in position 3 gives rise to active binders, whereas any of a 20% subset of chemical entities (e.g. determined by charge, size or other characteristica) are present in position 4. The outcome of the initial codon profile analysis would be: 3 codon sequences are equally dominating in position P1, 3 other codon sequences in position P2, 1 unique codon sequence is dominant in P3 whereas somewhat similarly increased levels of 20% of the codon sequences (background levels of the remaining 80% sequences) are seen in P4. In such cases it could be relevant to use an iterative Q-PCR ("IQPCR") strategy to perform a further deconvolution of a library after selection. Again with reference to the example above, by taking the PCR products from the 3 individual wells that contained primers giving the high yields in position P1, diluting the product appropriately and performing a second round of Q-PCR on each of these identifier oligonucleotides separately, it would be possible to deduce which codon sequence(s) is preferred in P2 when a given codon sequence is present in P1.

```
                     Identifiers used for Q-PCR quantification

P1                        P2
5'-CAGCTTGGACACCACGTCATACTAGCTGCTAGAGATGTGGTGATATTAGTGTGTGACGATGGTACGCACAAGTACGAACGTGCA
P3                        P4
TCAGAGAGGACGAGCAGGACCTGGAACCTGGTGC*TTCCTCCACCACGTCTCTGAC-3'  (SEQ ID NO: 19)

GGAAGAAGACAGAAGACCTG  (SEQ ID NO: 20)   CTCGACCACTGCAGGTGGAGCTCC  (SEQ ID NO: 21)

TCAGGAGTCGAGAACTGAAG  (SEQ ID NO: 22)   CGTGCTTCCTCTGCTGCACCACCG  (SEQ ID NO: 23)

TGTGTACGTCAACACGTCAG  (SEQ ID NO: 24)   CCTGGTGTCGAGGTGAGCAGCAGC  (SEQ ID NO: 25)

TGTGGAACTACCATCCAAGG  (SEQ ID NO: 26)   CTCGACGAGGTCCATCCTGGTCGC  (SEQ ID NO: 27)

CCATCCAACATCGTTGGAAG  (SEQ ID NO: 28)   CGTGAGGAGCAGGTCCTCCTGTCG  (SEQ ID NO: 29)

AACCTGTCCTGTGAGATCTG  (SEQ ID NO: 30)   CCTGACACTGGTCGTGGTCGAGGC  (SEQ ID NO: 31)
```

| Identifiers used for Q-PCR quantification |
|---|
| TCACGAAGCTGGATGATGAG (SEQ ID NO: 32) CCATCTCGACGACCTGCTCCTGGG (SEQ ID NO: 33) |
| TAGCATCGATCGAACGTAGG (SEQ ID NO: 34) CCACGAGGTCTCCACTGGTCCAGG (SEQ ID NO: 35) |
| TCGAAGCTACTGTCGAGATG (SEQ ID NO: 36) CCACTGAGCTGCTCCTCCAGGTGG (SEQ ID NO: 37) |

| Oligos for identifier synthesis: |
|---|
| FPv2: CAGCTTGGACACCACGTCATAC (SEQ ID NO: 38) |
| RPv2: GTCAGAGACGTGGTGGAGGAA (SEQ ID NO: 39) |
| Temp1-1: CAGCTTGGACACCACGTCATACTAGCTGCTAGAGATGTGGTGATATTAGTGTGTGACGAT (SEQ ID NO: 40) |
| Temp1-2: CAGCTTGGACACCACGTCATACGGAAGAAGACAGAAGACCTGATATTAGTGTGTGACGAT (SEQ ID NO: 41) |
| Temp1-3: CAGCTTGGACACCACGTCATACTCAGGAGTCGAGAACTGAAGATATTAGTGTGTGACGAT (SEQ ID NO: 42) |
| Temp1-4: CAGCTTGGACACCACGTCATACTGTGTACGTCAACACGTCAGATATTAGTGTGTGACGAT (SEQ ID NO: 43) |
| Temp1-5: CAGCTTGGACACCACGTCATACTGTGGAACTACCATCCAAGGATATTAGTGTGTGACGAT (SEQ ID NO: 44) |
| Temp1-6: CAGCTTGGACACCACGTCATACCCATCCAACATCGTTGGAAGATATTAGTGTGTGACGAT (SEQ ID NO: 45) |
| Temp1-7: CAGCTTGGACACCACGTCATACAACCTGTCCTGTGAGATCTGATATTAGTGTGTGACGAT (SEQ ID NO: 46) |
| Temp1-8: CAGCTTGGACACCACGTCATACTCACGAAGCTGGATGATGAGATATTAGTGTGTGACGAT (SEQ ID NO: 47) |
| Temp1-9: CAGCTTGGACACCACGTCATACTAGCATCGATCGAACGTAGGATATTAGTGTGTGACGAT (SEQ ID NO: 48) |
| Temp1-10: CAGCTTGGACACCACGTCATACTCGAAGCTACTGTCGAGATGATATTAGTGTGTGACGAT (SEQ ID NO: 49) |
| Temp2: GTCCTCTCTGATGCACGTTCGTACTTGTGCGTACCATCGTCACACACTAATATC (SEQ ID NO: 50) |
| Temp3-1: GAACGTGCATCAGAGAGGACGAGCAGGACCTGGAACCTGGTGCAATTCCAGCTTCTAGGAAGACT (SEQ ID NO: 51) |
| Temp3-2: GAACGTGCATCAGAGAGGACTCGACCACTGCAGGTGGAGCTCCAATTCCAGCTTCTAGGAAGACT (SEQ ID NO: 52) |
| Temp3-3: GAACGTGCATCAGAGAGGACGTGCTTCCTCTGCTGCACCACCGAATTCCAGCTICTAGGAAGACT (SEQ ID NO: 53) |
| Temp3-4: GAACGTGCATCAGAGAGGACCTGGTGTCGAGGTGAGCAGCAGCAATTCCAGCTTCTAGGAAGACT (SEQ ID NO: 54) |
| Temp3-5: GAACGTGCATCAGAGAGGACTCGACGAGGTCCATCCTGGTCGCAATTCCAGCTTCTAGGAAGACT (SEQ ID NO: 55) |
| Temp3-6: GAACGTGCATCAGAGAGGACGTGAGGAGCAGGTCCTCCTGTCGAATTCCAGCTTCTAGGAAGACT (SEQ ID NO: 56) |
| Temp3-7: GAACGTGCATCAGAGAGGACCTGACACTGGTCGTGGTCGAGGCAATTCCAGCTTCTAGGAAGACT (SEQ ID NO: 57) |
| Temp3-8: GAACGTGCATCAGAGAGGACCATCTCGACGACCTGCTCCTGGGAATTCCAGCTTCTAGGAAGACT (SEQ ID NO: 58) |
| Temp3-9: GAACGTGCATCAGAGAGGACCACGAGGTCTCCACTGGTCCAGGAATTCCAGCTTCTAGGAAGACT (SEQ ID NO: 59) |
| Temp3-10: GAACGTGCATCAGAGAGGACCACTGAGCTGCTCCTCCAGGTGGAATTCCAGCTTCTAGGAAGACT (SEQ ID NO: 60) |
| Temp4: GTCAGAGACGTGGTGGAGGAAGTCTTCCTAGAAGCTGGAATT (SEQ ID NO: 61) |

Taqman MGB probe binding region: * = AATTCCAGCTTCTAGGAAGAC

Synthesis of Identifier Oligonucleotides:

The 10 identifier oligonucleotides were assembled in 10 separate 50 µl PCR reactions each containing 0.05 µmol of the oligos Q-Temp1-X, Q-Temp2, Q-Temp3-X and QTemp4 (x=1 through 10) and 25 µmol of the external primers FPv2 and RPv2 with TA=53° C. The 160 bp products were gel-purified using QiAquick Gel Extraction Kit from QIAGEN (Cat. No. 28706) and quantified on spectrophotometer. As a control, 20 ng of each of the identifiers (as estimated from these measurements) were loaded on an agarose gel.

Preparation of Samples for Q-PCR:

Sample A: Generated by mixing 20 ng from each identifier oligonucleotide prep. Volume was adjusted to 50 µl. Concentration: 4 ng/µl=38.46 fmol/µl (160 bp×650 Da/bp=1.04×10⁵ g/mol. 1 ng=9.615 fmol). Diluted to $10^7$ copies/5 µl (0.00332 fmol/µl).

Sample B: 20 ng/20 µl stocks of each identifier were prepared. The sample was mixed as follows:
5 µl undil. Identifier #10
5 µl 2× dil. Identifier #9
5 µl 4× dil. Identifier #8
5 µl 8× dil. Identifier #7
5 µl 16× dil. Identifier #6
5 µl 32× dil. Identifier #5
5 µl 64× dil. Identifier #4
5 µl 128× dil. Identifier #3
5 µl 256× dil. Identifier #2
5 µl 512× dil. Identifier #1
Concentration: 10 ng/50 µl=0.20 ng/µl=1.923 fmol/µl.
Diluted 579.2-fold to $10^7$ copies/5 µl (0.00332 fmol/µl).

Standard curve: The samples for the standard curve was prepared by diluting Sample A 116.55-fold to $10^9$ copies/5 µl (0.33 fmol/μl) and subsequently performing a 10-fold serial dilution of this sample. 5 μl was used for each PCR reaction. The standard curve is shown in FIG. 2.

Q-PCR Reactions

For 5 ml premix (for one 96-well plate):
2.5 ml Taqman Universal PCR Master Mix (Applied Biosystems; includes Taq polymerase, dNTPs and optimized Taq pol. buffer)
450 μl RPv2 (10 μmol/ul)
25 μl Taqman probe (6-FAM-TCCAGCTTCTAGGAAGAC-MGBNFQ (SEQ ID NO:62); 50 μM; Applied Biosystems)
1075 μl H2O 40.5 μl premix was aliquoted into each well and 4.5 μl of relevant upstream PCR primer (FPv2 (for standard curve) or one of the codon specific primers listed below; 10 μmol/μl) and 5 μl sample (H2O in wells for negative controls) was added. The codon-specific PCR primers were: (Tm calculations shown are from Vector NTI; matched to Tm for RPv2 (67.7° C.))

| | | |
|---|---|---|
| P1-1: | GTCATACTAGCTGCTAGAGATGTGGTGATA | (SEQ ID NO: 63) 66.8° C. |
| P1-2: | CATACGGAAGAAGACAGAAGACCTGATA | (SEQ ID NO: 64) 67.8° C. |
| P1-3: | TCATACTCAGGAGTCGAGAACTGAAGATA | (SEQ ID NO: 65) 67.6° C. |
| P1-4: | CATACTGTGTACGTCAACACGTCAGATA | (SEQ ID NO: 66) 67.4° C. |
| P1-5: | CATACTGTGGAACTACCATCCAAGGATA | (SEQ ID NO: 67) 68.0° C. |
| P1-6: | CCATCCAACATCGTTGGAAGAT | (SEQ ID NO: 68) 67.8° C. |
| P1-7: | CATACAACCTGTCCTGTGAGATCTGATA | (SEQ ID NO: 69) 67.7° C. |
| P1-8: | ATACTCACGAAGCTGGATGATGAGATA | (SEQ ID NO: 70) 67.3° C. |
| P1-9: | CATACTAGCATCGATCGAACGTAGGATA | (SEQ ID NO: 71) 68.1° C. |
| P1-10: | TCATACTCGAAGCTACTGTCGAGATGATA | (SEQ ID NO: 72) 68.2° C. |
| P2-1: | ATATTAGTGTGTGACGATGGTACGCA | (SEQ ID NO: 73) 67.8° C. |
| P3-1: | ACAAGTACGAACGTGCATCAGAGA | (SEQ ID NO: 74) 67.7° C. |
| P4-1: | CGAGCAGGACCTGGAACCT | (SEQ ID NO: 75) 67.7° C. |
| P4-2: | TCGACCACTGCAGGTGGA | (SEQ ID NO: 76) 68.3° C. |
| P4-3: | GCTTCCTCTGCTGCACCA | (SEQ ID NO: 77) 66.7° C. |
| P4-4: | GGTGTCGAGGTGAGCAGCA | (SEQ ID NO: 78) 69.1° C. |
| P4-5: | CGACGAGGTCCATCCTGGT | (SEQ ID NO: 79) 68.6° C. |
| P4-6: | GTGAGGAGCAGGTCCTCCTGT | (SEQ ID NO: 80) 68.0° C. |
| P4-7: | CTGACACTGGTCGTGGTCGA | (SEQ ID NO: 81) 68.8° C. |
| P4-8: | CATCTCGACGACCTGCTCCT | (SEQ ID NO: 82) 67.9° C. |
| P4-9: | ACGAGGTCTCCACTGGTCCA | (SEQ ID NO: 83) 68.3° C. |
| P4-10: | ACTGAGCTGCTCCTCCAGGT | (SEQ ID NO: 84) 66.5° C. |

Thermocycling/measurement of fluoresence was performed on an Applied Biosystems ABI Prism 7900HT real-time instrument utilizing the standard cycling parameters:
95° C. 10 min;
40 cycles of
95° C. 15 sec;
60° C. 1 min
All samples were run in duplicate.

Results

Figure 6:
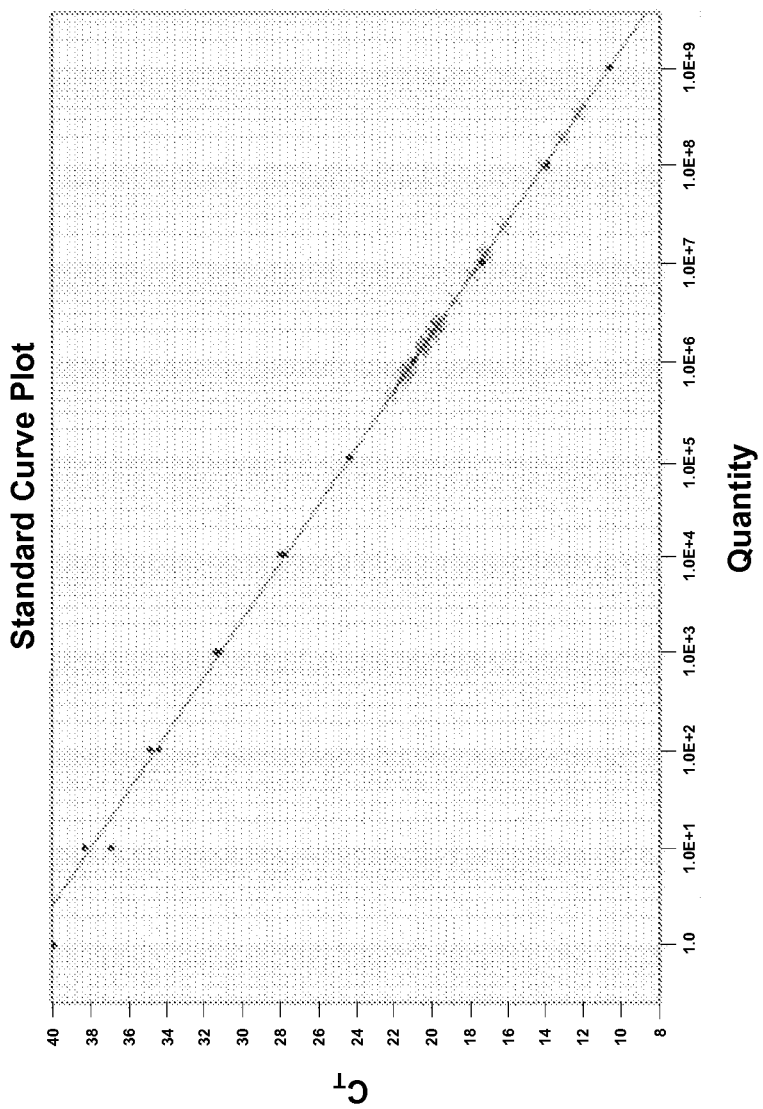
FIG. 6 shows a standard curve referred to in example 4.

FIG. 6 shows the standard curve calculated by the 7900HT system software. The log of the starting copy number was plotted against the measured $C_T$ value. The relationship between $C_T$ and starting copy number was linear in the range from 10 to $10^9$ identifier copies.

This standard curve was utilized by the system software to calculate the quantity in the "unknown" samples as shown below.

TABLE I

Figure 7:
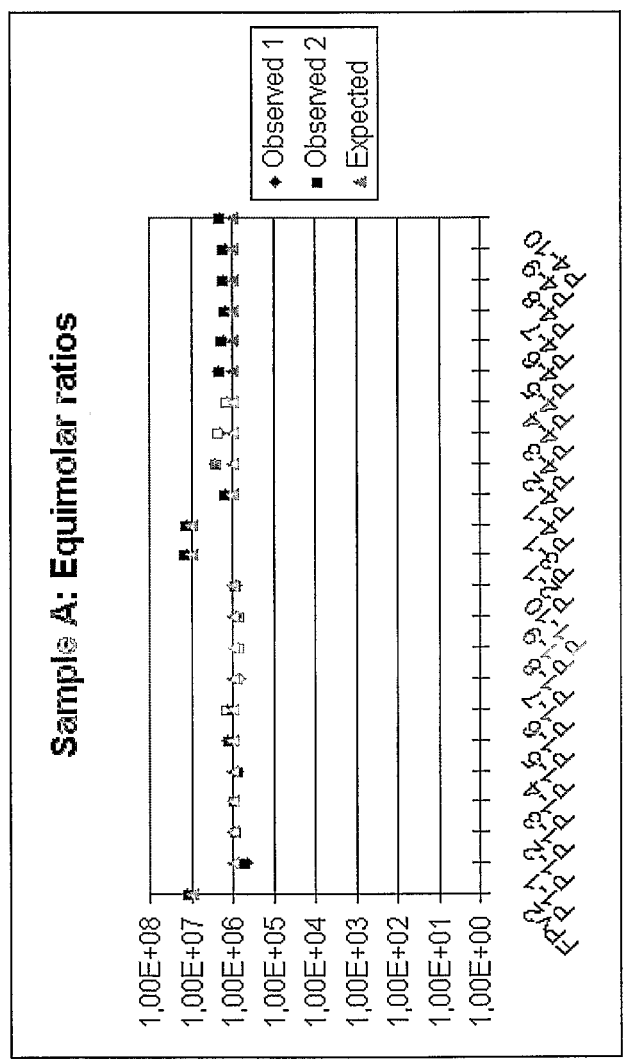
FIG. 7 shows a result of example 4.

Sample A (Shown graphically in FIG. 7)

| Sample A: Equimolar ratios | Observed A | Observed B | Expected |
|---|---|---|---|
| FPv2 | 12539947.00 | 11977503.00 | 10000000 |
| P1-1 | 445841.90 | 480382.03 | 1000000 |
| P1-2 | 884840.70 | 847478.56 | 1000000 |
| P1-3 | 1013073.56 | 948770.00 | 1000000 |
| P1-4 | 764187.94 | 741304.40 | 1000000 |
| P1-5 | 1352874.60 | 1275155.50 | 1000000 |
| P1-6 | 1284075.60 | 1337928.50 | 1000000 |
| P1-7 | 658161.80 | 747371.56 | 1000000 |
| P1-8 | 742187.20 | 653874.00 | 1000000 |
| P1-9 | 824587.75 | 705785.75 | 1000000 |
| P1-10 | 813550.75 | 836037.90 | 1000000 |
| P2-1 | 13145159.00 | 14482606.00 | 10000000 |
| P3-1 | 13263911.00 | 12773780.00 | 10000000 |
| P4-1 | 1430704.80 | 1472576.80 | 1000000 |
| P4-2 | 2681652.00 | 2481824.80 | 1000000 |
| P4-3 | 1933106.80 | 2085476.40 | 1000000 |
| P4-4 | 1359684.40 | 1364621.40 | 1000000 |
| P4-5 | 2206709.80 | 2065813.60 | 1000000 |
| P4-6 | 1652718.10 | 1873777.20 | 1000000 |
| P4-7 | 1468208.10 | 1416153.00 | 1000000 |
| P4-8 | 1664467.50 | 1581067.00 | 1000000 |
| P4-9 | 1462520.60 | 1594593.80 | 1000000 |
| P4-10 | 2020088.20 | 1912277.40 | 1000000 |

TABLE II

Figure 8:
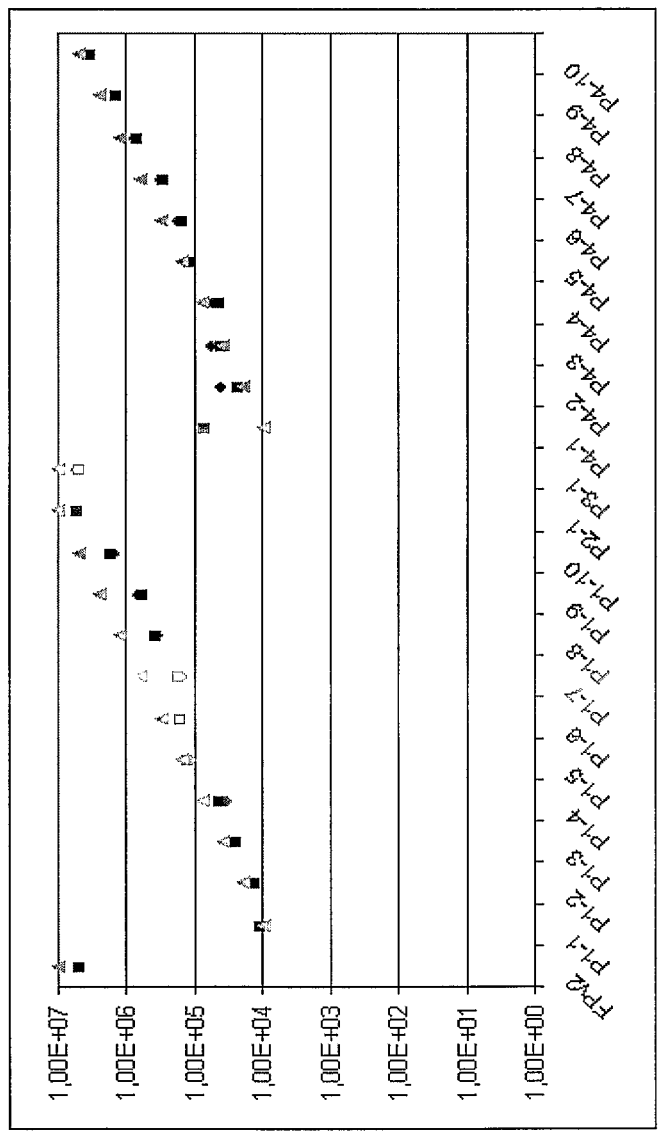
FIG. 8 discloses a result of example 4.

Sample B (Shown graphically in FIG. 8)

| Sample B: 2-fold dil. | Observed A | Observed B | Expected |
|---|---|---|---|
| FPv2 | 4.97E+06 | 5.05E+06 | 10000000 |
| P1-1 | 9955.07 | 10899.97 | 9765.625 |
| P1-2 | 12732.32 | 13469.12 | 19531.25 |
| P1-3 | 25542.8 | 25419.85 | 39062.5 |
| P1-4 | 34748.89 | 44070.81 | 78125 |
| P1-5 | 110881.41 | 123734.13 | 156250 |
| P1-6 | 163687.44 | 166220.5 | 312500 |

TABLE II-continued

Sample B (Shown graphically in FIG. 8)

| Sample B: 2-fold dil. | Observed A | Observed B | Expected |
|---|---|---|---|
| P1-7 | 156993.81 | 172005.64 | 625000 |
| P1-8 | 343176.78 | 374809.13 | 1250000 |
| P1-9 | 646619.44 | 576151 | 2500000 |
| P1-10 | 1.49E+06 | 1.72E+06 | 5000000 |
| P2-1 | 5.19E+06 | 5.37E+06 | 10000000 |
| P3-1 | 5.29E+06 | 5.09E+06 | 10000000 |
| P4-1 | (no signal) | 70223.8 | 9765.625 |
| P4-2 | 42103.32 | 22733.17 | 19531.25 |
| P4-3 | 54480.62 | 39663.62 | 39062.5 |
| P4-4 | 51293.07 | 43950.9 | 78125 |
| P4-5 | 137946.95 | 115027.34 | 156250 |
| P4-6 | 174134.64 | 156442.55 | 312500 |
| P4-7 | 316505.78 | 283856.84 | 625000 |
| P4-8 | 737661.44 | 691296.75 | 1250000 |
| P4-9 | 1.42E+06 | 1.45E+06 | 2500000 |
| P4-10 | 3.72E+06 | 3.52E+06 | 5000000 |

The results of the experiments show the possibility of accurately quantification of identifier oligonucleotides down to or even below 10 copies with a 9 fold dynamic range, and reliable relative quantification of the tested codons in various positions in the identifier oligonucleotide.

Example 5

Codon Analysis

Another possibility to analyse codons in identifier oligonucleotides is to use array format with attached probe oligonucleotides.

Six adaptors with the different anti-codon sequences in all three positions were designed. All the adaptors contain a probe binding sequence (20 nucleotides) that allows discrete binding on the microarray. Probe design is known in the art. Adaptors harbouring one to three deletions in the spacing region were used as negative controls to ensure that only the framing region is responsible for the hybridization of the identifier. Thus, the negative controls contain another framing sequence. The identifier oligonucleotide harbours the complementing codon sequence and the position directing framing regions.

```
Adaptor oligonucleotides
                                          (SEQ ID NO: 85)
3' CTCATCGGAAGGGCTCGTAACGGTGGGTTTGGGGGCTGGGTTTGG GGCGTGGGTTTGGGCGG-5'
                                          (SEQ ID NO: 86)
3' TTTGGTAGCTGAGTGCCCTAGGCTGGGTTTGGGCGGTGGGTTTGG GGGCTGGGTTTGGGGCG-5'
                                          (SEQ ID NO: 87)
3' TAACTGGTTTGACGCCACGCGCGTGGGTTTGGGGCGTGGGTTTGG GCGGTGGGTTTGGGGGC-5'
                                          (SEQ ID NO: 88)
3' TAATTGAGCTGACGGCGCACGGCTGGGTTTGGGCGTGGGTTTGGG GCTGGGTTTGGGGCG-5'
                                          (SEQ ID NO: 89)
3' TGTTGCTACTCTGGCCCGAGGCTGGGTTTGGGCTGGGTTTGGGCT GGGTTTGGGGCG-5'
                                          (SEQ ID NO: 90)
3' ACGGGATAACAACGCAGCCTGGCTGGGTTTGGGTGGGTTTGGGTG

GGTTTGGGGCG-5'

Identifier Oligonucleotide
                                          (SEQ ID NO: 91)
Biotin-5' GCCACCCAAACCCCCG
```

GenFlex hybridisation and scanning. Prior to hybridization, the Adaptor mix (100 µM final concentration for each of the adaptor oligonucleotides) in a hybridization buffer (100 mM MES, 1 M NaCl, 20 mM EDTA, 0.01% Tween 20, 1×Denhardt's), was heated to 95° C. for 5 min and subsequently cooled and maintained at 40° C. for 5 min before loading onto the Affymetrix GenFlex probe array cartridge. The probe array was then incubated for 2 h at 45° C. at constant rotation (60 rpm). The remaining Adaptor mix was removed from the GenFlex cartridge, and replaced with the identifier in a hybridization buffer (100 mM MES, 1 M NaCl, 20 mM EDTA, 0.01% Tween 20, 1×Denhardt's). The identifier hybridisation mix was heated to 95° C. for 5 min and subsequently cooled and maintained at 40° C. for 5 min before loading onto the Affymetrix GenFlex probe array cartridge and hybridised for 2 h at 45° C. at constant rotation (60 rpm). The washing and staining procedure was performed in the Affymetrix Fluidics Station. The probe array was exposed to 2 washes in 6×SSPE-T at 25° C. followed by 12 washes in 0.5×SSPE-T at 40° C. The biotinylated Identifier oligonucleotide was stained with a streptavidin-phycoerythrin conjugate, final concentration 2 µg/µl (Molecular Probes, Eugene, Oreg.) in 6×SSPE-T for 10 min at 25° C. followed by 6 washes in 6×SSPE-T at 25° C.

Figure 20:
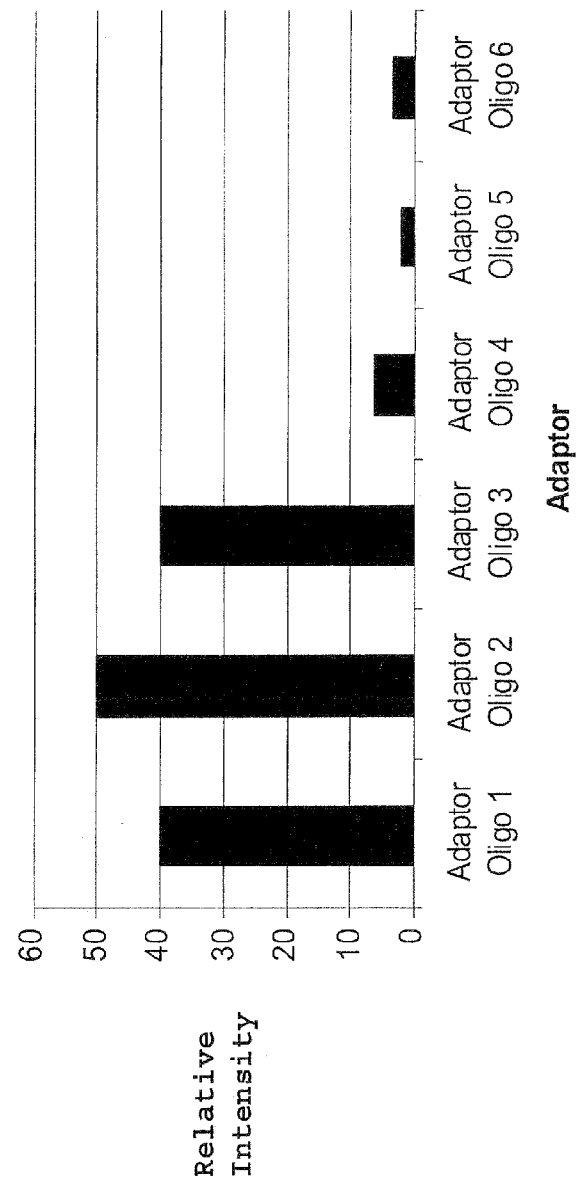
FIG. 20 shows the ability of probe to distinguish the same codon when flanked by different sequences as discussed in example 5.

The probe arrays were scanned at 560 nm using a confocal laser-scanning microscope with an argon ion laser as the excitation source (Hewlett Packard GeneArray Scanner G2500A). The readings from the quantitative scanning were analysed by the Affymetrix Gene Expression Analysis Software. The results are depicted in FIG. 20.

The Array analysis shows that the codons including the framing regions are able to distinguish between the different probe oligonucleotides. The designed probes will only detect codons with the correct framing region allowing distinguishing first of the right codon and secondly as to which position the codon is positioned. Only one deletion in both framing regions reduces significantly the hybridization of the identifier. Thus, the framing sequence may be used to obtain information about the position of a specific codon and the point in the reaction history when a given reaction of a chemical entity has occurred. The information obtained in this example using either QPCR or array codon analysis as example can be used to generate a new more focused library. The signal from the QPCR analysis or the array analysis can directly be used to combine preferable chemical entities.

Example 6

Generation of a Second-Generation Library

The information obtained from a codon analysis performed according to the principles described in Examples 4 or 5 can be utilized for assembly a new more focused library. Sequence information can also be used to design a second-generation library with reduced diversity. This example illustrates how sequence data can be utilized to make a more focused library with the enriched chemical entities. Identical strategy can be based on the codon analysis methods described in Examples 4 or 5.

A 700-member library was generated composing of 4×25×7 chemical entities. The library generation protocol is described below with the sequence information and chemical entity structure.

General arrangement of each complex composed of display molecule and identifier oligonucleotide in the library generation:

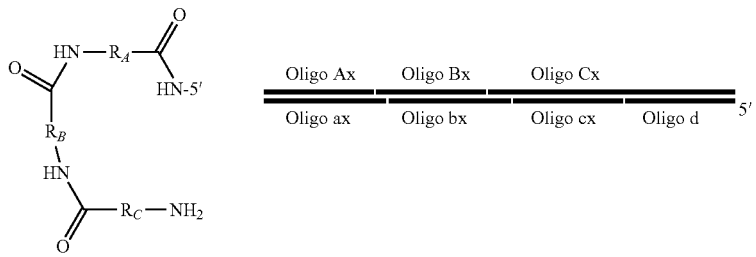

Specific codons in each oligo (Ax, Bx, Cx) was used and can be designed by using a specific nucleotide sequence for each chemical entity. In this particular setup, two complementary oligonucleotides (e.g. oligo Ax and oligo ax) containing a particular codon are allow to hybridize before the ligation step. The ligation of each codon oligonucleotide in each position is ligated with that attachment of the encoded chemical entity.

Overview of the Library Generation Procedure:

First Round of Library Generation (Round A):

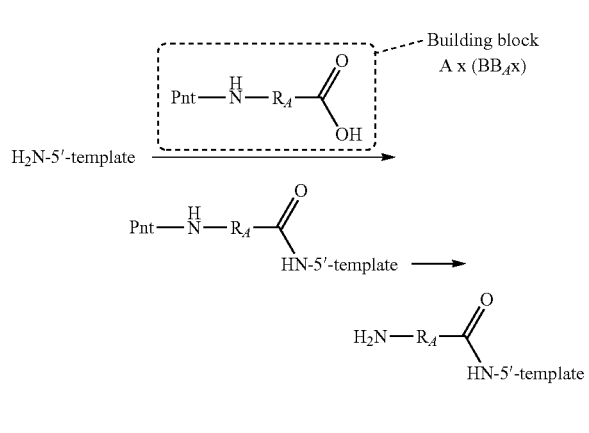

"Pnt" corresponds to pentenoyl—an amine protecting group. "R" can by any molecule fragment. The chemical used in library generation comprise a primary (shown) or a secondary amine.

Second Round of Library Generation (Round B):

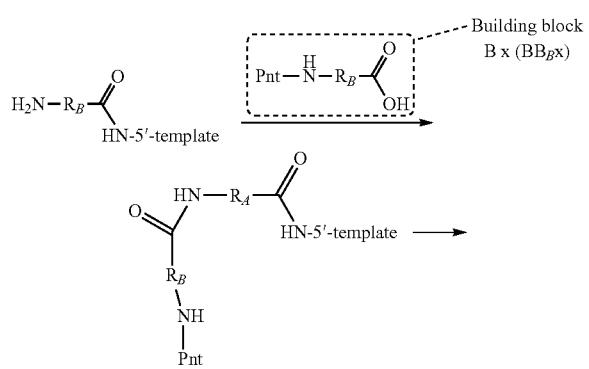

-continued

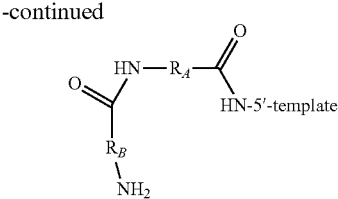

Third Round of Library Generation (Round C):

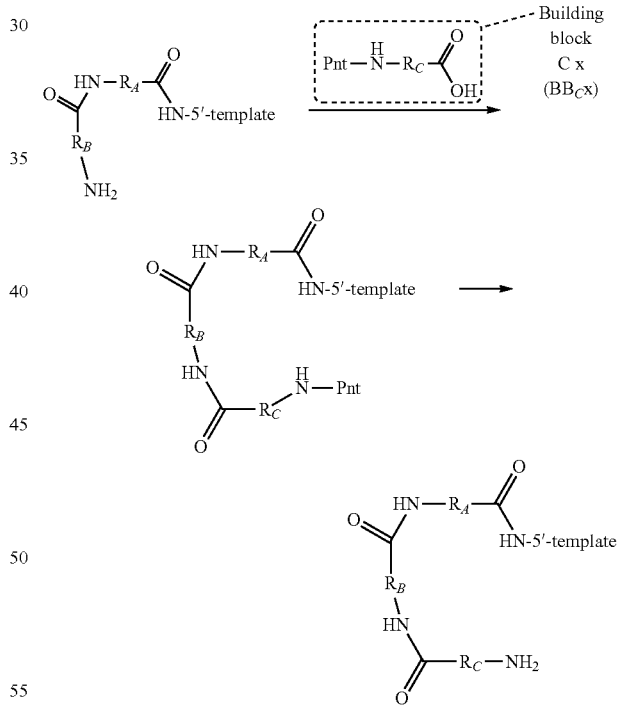

General Procedure: Library Generation, Selection and Mismatch Subsequent Selection First Round of Library Generation (Round A):
First oligonucleotides of the A series are each modified by adding to each type of oligo a small molecule building block ($BB_Ax$) to the 5' amine forming an amide bond. After this step the identifier is comprised of oligo Ax.

Second Round of Library Generation (Round B):
4 nmol of a mixture of different modified A oligos are then split into a number tubes corresponding to the number of different building blocks to be used in round B. 190 µmol Oligo a and 2 µl heering DNA is added to each tube and the DNA material in each tube is lyophilized. The lyophilized DNA is then redissolved in 50 µl water and purified by spining through Biospin P-6 columns (Biorad) equilibrated with water.

Addition of Building Block

The DNA material in each tube is again lyophilized and redissolved in 2 µl 100 mM Na-borate pH 8.0/100 mM sulfo N-hydroxy succinimide (sNHS). For each tube 10 µl building block $BB_Bx$ (100 mM in dimethyl sulfoxide [DMSO]) is preactivated by mixing with 10 µl 1-Ethyl-3-(3-dimethylaminopropyl)-carbodiimide (EDC) (90 mM in dimethylformamide [DMF]) and incubating at 30° C. for 30 min. 3 µl of this preactivated mixture is then mixed with the 2 µl in each tube and allowed to react 45 min at 30° C. Then an additional 3 µl freshly preactivated BB is added and the reaction is allowed to proceed for 45 min at 30° C. The resulting mixture is then purified by spinning through Bio-Rad P6 DG (Desalting gel).

Addition of Codon Oligonucleotide

The DNA material is then lyophilized and redissolved in 10 µl water containing 200 µmol oligo Bx (eg. B1) and the corresponding oligo bx (eg. b1). This is done so that the codon in oligo Bx identifies the $BB_Bx$ added to the DNA identifier. 10 units of T4 DNA ligase (Promega) and 1.2 µl T4 DNA ligase buffer is then added to each tube and the mixture is incubated at 20° C. for 1 hour. The DNAn identifier linked to the small molecules now comprises an Ax oligo with a Bx oligo ligated to its 3' end. The reactions are then pooled, an appropriate volume of water is allowed to evaporate and the remaining sample is purified by spinning through Biospin P-6 columns (Biorad) equilibrated with water.

Removal of Building Block Protecting Group

The pooled sample (~50 µl) is adjusted to 10 mM Na-acetate (pH 5). 0.25 volumes of 25 mM Iodine in tetrahydrofuran/water (1:1) is added and the sample is incubate at 37° C. for 2 h. The reaction is then quenched by addition of 2 µl of 1M $Na_2S_2O_3$ and incubation at room temperature for 5 min. The complexes are then purified by spining through Biospin P-6 columns (Biorad) equilibrated with water To remove sulphonamide protecting groups, the sample is adjusted to 50 µl 100 mM sodium borate pH 8.5 and 20 µl 500 mM 4-methoxy thiophenol (in acetonitrile) is added and the reaction is incubated at 25° C. overnight. Then the complexes are purified by spinning through Biospin P-6 columns (Biorad) equilibrated with water and then lyophilized.

Third Round of Library Generation (Round C):

The samples are dissolved in 175 µl 100 mM Na-borate pH 8.0 and distributed into 25 wells (7 µl/well). 2 µl 100 mM $BB_cx$ in water/DMSO and 1 µl of 250 mM DMT-MM is added to each reaction and incubated at 30° C. overnight. Water is added to 50 µl and the reactions are then spin purified using Bio-Rad P6 DG (Desalting gel) and subsequently water is allowed to evaporate so that the final volume is 10 µl.

Addition of Building Block

The DNA material is then lyophilized and redissolved in 10 µl water containing 200 µmol oligo Cx (eg. C1) and the corresponding oligo cx (eg. c1). This is done so that the codon in oligo Cx corresponds to the $BB_cx$ added to the DNA identifier. 10 units of T4 DNA ligase (Promega) and 1.2 µl T4 DNA ligase buffer is then added to each tube and incubated at 20° C. for 1 hour. The DNAn identifier linked to the small molecules now comprises and Ax oligo with a Bx ligated to its 3' end and a Cx oligo ligated to the 3' end of the Bx oligo. The reactions are then pooled, the pooled sample volume is reduced by evaporation and the sample is purified by spining through Biospin P-6 columns (Biorad) equilibrated with water. The pooled sample (~50 µl) is adjusted to 10 mM Na-acetate (pH 5). 0.25 volumes of 25 mM Iodine in tetrahydrofuran/water (1:1) is added and the sample is incubate at 37° C. for 2 h. The reaction is then quenched by addition of 2 µl of 1M $Na_2S_2O_3$ and incubation at RT for 5 min. Then the DNA identifiers (carrying small molecules) are purified by spinning through Biospin P-6 columns (Biorad) equilibrated with water and then lyophilized.

Final Deprotection Step

Some building blocks contain methyl esters that are deprotected to acids by dissolving the pooled sample in 5 µl 20 mM NaOH, heating to 80° C. for 10 minutes and adding 5 µl of 20 mM HCl.

Final Extension Step

To ensure that the DNA identifiers are double stranded prior to selection oligo d is extended along the identifier by adding to the sample 10 µl of 5× sequenase EX-buffer [100 mM Hepes, pH 7.5, 50 mM $MgCl_2$, 750 mM NaCl] and 4000 µmol oligo d. Anneal ing is performed by heating to 80° C. and cooling to 20° C. To the sample is then added 500 µL dNTP, water to 50 µl and 39 units of Sequenase version 2.0 (USB). The reaction is incubated at 37° C. for 1 hour.

Selection

This library is subjected to selection, whereby binders to the selection target are enriched.

Maxisorp ELISA wells (NUNC A/S, Denmark) were coated with each 100 µL 2 µg/mL integrin aVβ3 in PBS buffer [2.8 mM $NaH_2PO_4$, 7.2 mM $Na_2HPO_4$, 0.15 M NaCl, pH 7.2] overnight at 4° C. Then the integrin solution was substituted for 200 µl blocking buffer [TBS, 0.05% Tween 20 (Sigma P-9416), 1% bovine serum alnumin (Sigma A-7030), 1 mM $MnCl_2$] which was left on for 3 hours at room temperature. Then the wells were washed 10 times with blocking buffer and the encoded library was added to the wells after diluting it 100 times with blocking buffer. Following 2 hours incubation at room temperature the wells were washed 10 times with blocking buffer. After the final wash the wells were cleared of wash buffer and subsequently inverted and exposed to UV light at 300-350 nm for 30 seconds using a trans-illuminator set at 70% power. Then 100 µl blocking buffer without Tween-20 was immediately added to each well, the wells were shaken for 30 seconds, and the solutions containing eluted identifiers were removed for PCR amplification.

Cloning

A TOPO-TA (Invitrogen) ligation reaction is assembled with 4 µl PCR product, 1 µl salt solution (Invitrogen) and 1 µl vector. Water is added to 6 µl. The reaction is then incubated at RT for 30 min. Heat-shock competent TOP10 *E. coli* cells are then thawed on ice and 5 µl of the ligation reaction is added to the thawed cells. The cells are then incubated 30 min on ice, heatshocked in 42° C. water for 30 sec, and then put on ice again. 250 µl of growth medium is added to the cells and they are incubated 1 h at 37° C. The medium containing cells is then spread on a growth plate containing 100 µg/ml ampicillin and incubated at 37° C. for 16 hours.

Sequencing

Individual *E. coli* clones are then picked and transferred to PCR wells containing 50 µl water. These 50 µl were incubated at 94° C. for 5 minutes and used in a 20 µl in a 25 µl PCR reaction with 5 µmol of each TOPO primer M13 forward & M13 reverse and Ready-To-Go PCR beads (Amersham Biosciences). The following PCR profile is used: 94° C. 2 min, then 30×(94° C. 4 sec, 50° C. 30 sec, 72° C. 1, min) then 72° C. 10 min. Primers and nucleotides are then degraded by adding 1 µl 1:1 EXO/SAP mixture (USB corp.) to 2 µl PCR product and incubating at 37° C. for 15 min and then 80° C. for 15 min to heat-inactivate the enzymes. 5 µmol T7 primer is added and water is added to 12 μl. Then 8 μl DYEnamic ET cycle sequencing Terminator Mix (Applied biosystems) is added to each well. A thermocycling profile of 30×(95° C. 20 sec, 50° C. 15 sec, 60° C. 1 min) is then run. Then 10 μl water is added to each well and sequencing reactions are purified using seq96 spinplates (Amersham Biosciences). Reactions are then run on a MegaBace capillary electrophoresis instrument (Molecular Dynamics) using injection parameters 2 kV, 50 sec and run parameters: 9 kV 45 min and analyzed using Contig Express software (Informax).

The chemical entities used in each position are shown below.

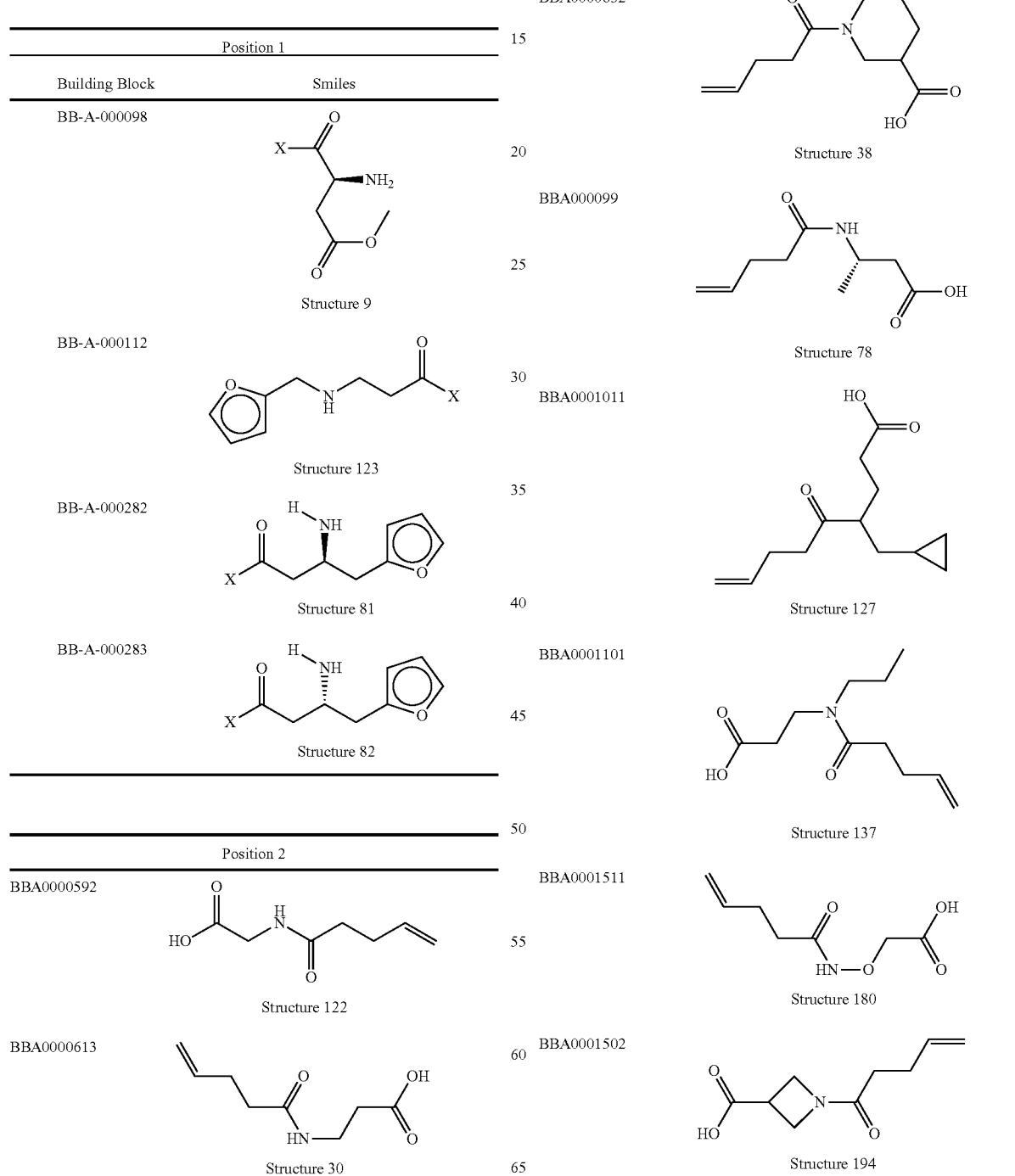

-continued
Position 2
BBA0001592
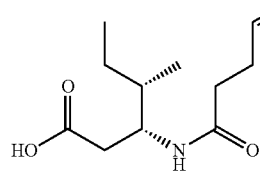
Structure 196
BBA0001614
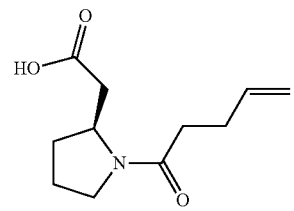
Structure 200
BBA0001642
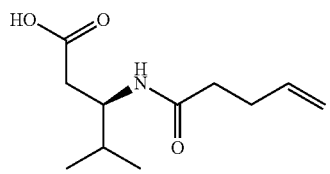
Structure 208
BBA0003132
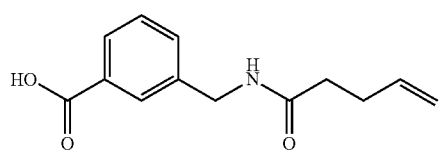
Structure 444
BBA0003142
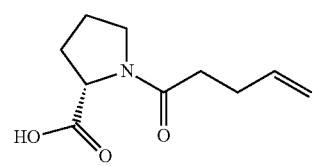
Structure 446
BBA0003152
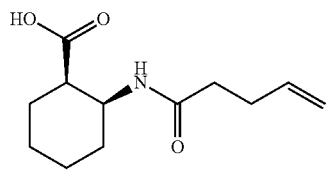
Structure 449
BBA0003162
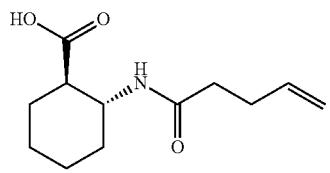
Structure 451
-continued
Position 2
BBA0003172
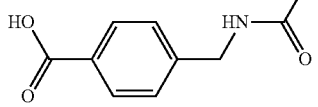
Structure 453
BBA0003182
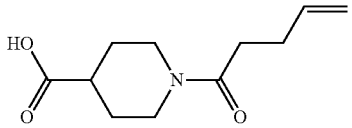
Structure 454
BBA0004182
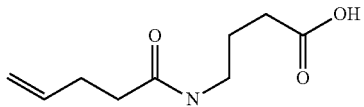
Structure 669
BBA0004193
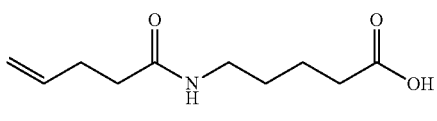
Structure 672
BBA0004202
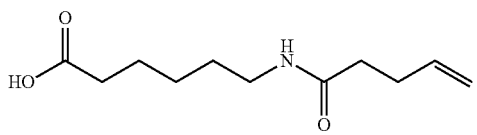
Structure 675
BBA0004212
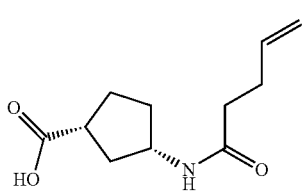
Structure 678
BBA0004222
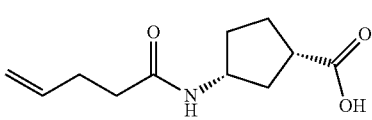
Structure 680
BBA0004232
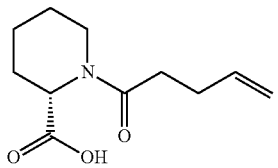
Structure 681

Position 2

BBA0004242

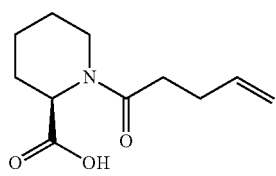

Structure 683

Position 3

BBA0000531

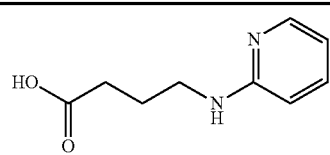

Structure 1

BBA0001006

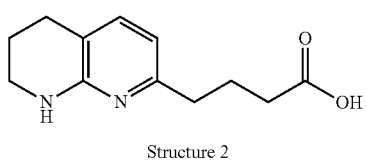 [SMILES: O=C(O)CCCc1ccc2c(n1)NCCC2]

Structure 2

BBA0001391

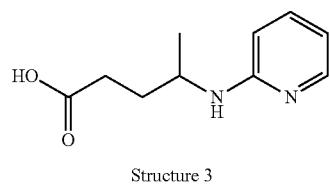

Structure 3

BBA0001401

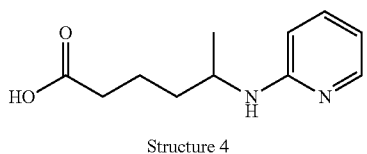

Structure 4

BBA0008312

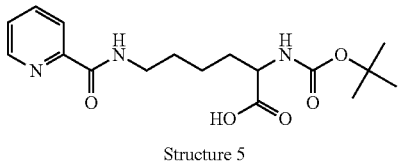 [SMILES: CC(C)(C)OC(=O)NC(CCCCNC(=O)c1ccccn1)C(=O)O]

Structure 5

BBA0008512

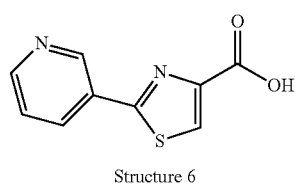 [SMILES: O=C(O)c1csc(-c2cccnc2)n1]

Structure 6

BBA0008612

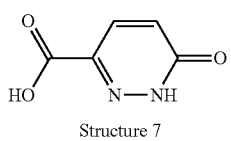

Structure 7

After the selection as described above, the codons in the identifier oligonucleotides were analysed. Before the analysis, the identifier oligonucleotides were amplified using the constant flanking regions and the amplified material was used in the identifier sequence analysis.

A sequence codon analysis of the selected codons showed a bias for specific chemical entities. They are listed in the table below. For instance, in position 1 chemical entity 98 was seem 47 times (out of 51 sequences, 92%, compare to 25% before the selection) and chemical entity 99 was seen 14 times (out 51 sequences, 27%, compare to 4% before selection) and chemical entity 53 was seen 35 times (out of 51 sequences, 68%, compare to 14% before selection).

The chemical entities listed in the table below can then be used to generate a new and more focused library.

| Oligo(-s) | Count | pos 1 | pos 2 | pos 3 |
| --- | --- | --- | --- | --- |
| BB-A-000098 | 47 | 98 | | |
| BB-A-000282 | 4 | 282 | | |
| BBA000099 | 14 | | | 99 |
| BBA0001582 | 13 | | | 158 |
| BBA0004242 | 6 | | | 424 |
| BBA0004182 | 5 | | | 418 |
| BBA0001101 | 2 | | | |
| BBA0003172 | 2 | | | |
| BBA0004212 | 2 | | | |
| BBA0004232 | 2 | | | |
| BBA000064 | 1 | | | |
| BBA0001011 | 1 | | | |
| BBA0003132 | 1 | | | |
| BBA0003142 | 1 | | | |
| BBA0003152 | 1 | | | |
| BBA0000531 | 35 | | | 53 |
| BBA0001391 | 9 | | | 139 |
| BBA0001006 | 4 | | | 100 |
| BBA0008512 | 2 | | | |
| BBA0008312 | 1 | | | |

The new focused library with the selected chemical entities can be selected against the target and the outcome from the selection can be analysed. The most abundant binders will be the combination between the chemical entities 98-99-53 and the second most abundant binder is 98-158-53 as shown below.

| Oligo(-s) | Count | pos 1 | pos 2 | pos 3 |
| --- | --- | --- | --- | --- |
| BB-A-000098 BBA000099 BBA0000531 | 11 | 98 | 99 | 53 |
| BB-A-000098 BBA0001582 BBA0000531 | 7 | 98 | 158 | 53 |
| BB-A-000098 BBA0004242 BBA0000531 | 4 | 98 | 424 | 53 |
| BB-A-000098 BBA0001582 BBA0001391 | 3 | 98 | 158 | 139 |
| BB-A-000098 BBA0004182 BBA0000531 | 3 | 98 | 418 | 53 |
| BB-A-000098 BBA000099 BBA0001391 | 2 | 98 | 99 | 139 |
| BB-A-000098 BBA0001582 BBA0001006 | 2 | 98 | 158 | 100 |

This example exemplifies the possibility to reduce the library diversity by using the enriched chemical entities in a new library and perform another round of selection on the chosen chemical entities.

Example 7

The following experiment illustrates the principle of chemical entity (also termed building block herein) evolution through multiple rounds of library generation and selection. The experiment is not intended to limit the scope of the current invention.

Libraries were assembled by the combination of building blocks (BB) each of which was encoded by an oligonucleotide (oligo). Some of the building blocks carried an amine functional group and a carboxylic acid functional group. The building block amine was protected by N-pentenoylation and deprotected by iodine treatment prior to the reaction of the following building block. Oligonucleotide 1 (Oligo1) carried an amine functional group to allow reaction with the building block1's carboxylic acid and oligonucleotides are optionally derivatized by phosphorylation to allow ligation. Oligonucleotide3 (oligo3) also comprised a primer region for PCR amplification. EDC/NHS, EDC/sulfoNHS or DMTMM was used as coupling reagents.

The following scheme describes the split and mix assembly of the libraries:
i.) n times [BB1+Oligo1→BB1–Oligo1] in separate wells
Optionally purify product
ii.) mix all n wells into one tube
iii.) split product of ii.) into m separate wells
iv.) m times [BB2+BB1–Oligo1+Oligo2→BB2–BB1–Oligo1–Oligo2] in separate wells
Optionally purify product
v.) mix all m wells into one tube
vi.) split product of v.) into p separate wells
vii.) p times [BB3+BB2–BB1–Oligo1–Oligo2+Oligo3→BB3–BB2–BB1–Oligo1–Oligo2–Oligo3] in separate wells
Optionally purify product
viii.) mix all p wells into one tube
ix.) Selection was performed and binders isolated
x.) PCR of DNA and sequencing
xi.) Analyse for building block abundancy and full sequence information Building block abundances analysis may be done by QPCR or by sequencing full sequences and then analyzing for the abundance of individual building blocks.

The following types of building blocks were used, wherein R describes a group which is varied for different building blocks:

Building Block Types Used in Position 1, 2 and 3

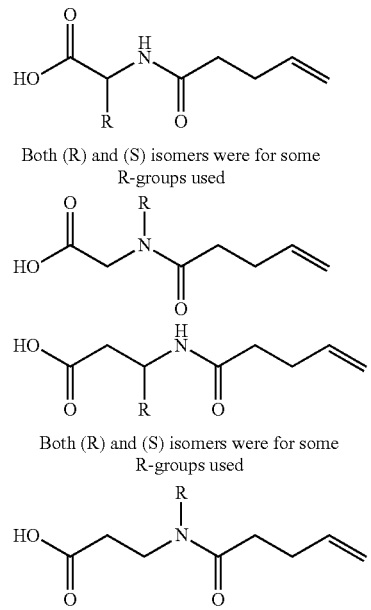

Both (R) and (S) isomers were for some R-groups used

Both (R) and (S) isomers were for some R-groups used

Building Block Types which were Only Used in Position 3

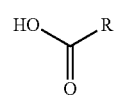

The overall process leads to molecules of the following structure, where the oligonucleotide was double stranded.

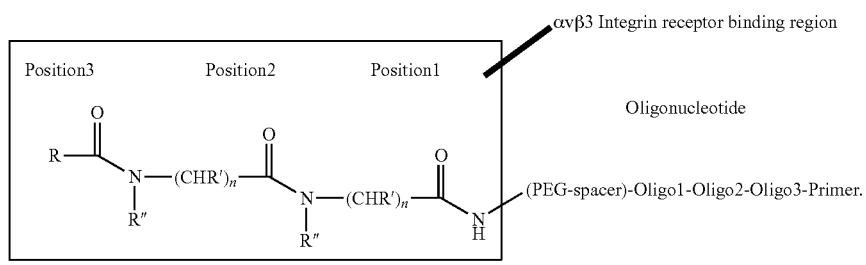

R' = H or (as indicated for building blocks)
R" = H or R (as indicated for building blocks)
R = H or R (as indicated for building blocks)
n = 1-2

The oligonucleotide was made double stranded by the use of double stranded Oligo's 1, 2 and 3 with an overhang to allow ligation of both strands.

Summary of the experimental outcome:

Two libraries of 61,875 members (Library 1 and 2) were generated as described in example 6 above and selected for binders of the Integrin αvβ3 receptor separately. The libraries were generated with 99 different building blocks in position 1, 25 different building blocks in position 2 and 25 different building blocks in position 3.

The identified sequences were then analyzed for the abundances of building blocks at each position in the sequence. The most abundant building blocks at each position from the two libraries 1 and 2 were then used again to generate a new and smaller library of 1,365 members, which was selected for binders of the Integrin αvβ3 receptor. The library was generated with 7 different building blocks in position 1, 13 different building blocks in position 2 and 15 different building blocks in position 3.

In the tables below, each of the building block numbers identify one specific building block or in two instances (library 1) a mixture of three different building blocks. The same numbers are used for each building block in all libraries, however the oligonucleotide used to identify each building block may not necessarily be the same between libraries to avoid potential problems of cross contamination.

The following tables describes the codon sequences and corresponding building blocks used. The codon is only indicated for one of the strands.

Library 1, Position 1

| Codon no. | Codon sequence ID | Building Block ID |
|---|---|---|
| 1 | TGTTC (SEQ ID NO: 92) | BBA000092 |
| 2 | CGAGC (SEQ ID NO: 93) | BBA000354 |
| 3 | GGATA (SEQ ID NO: 94) | BBA000085 |
| 4 | CGCTG (SEQ ID NO: 95) | BBA000086 |
| 5 | GTTAT (SEQ ID NO: 96) | BBA000098 |
| 6 | AGTGC (SEQ ID NO: 97) | BBA000099 |
| 7 | ACCTG (SEQ ID NO: 98) | BBA000089 |
| 8 | CTGGT (SEQ ID NO: 99) | BBA000090 |
| 9 | TAGGA (SEQ ID NO: 100) | BBA000087 |
| 10 | ACTCA (SEQ ID NO: 101) | BBA000088 |
| 11 | CTTAC (SEQ ID NO: 102) | BBA000153 |
| 12 | CGCAC (SEQ ID NO: 103) | BBA000154 |
| 13 | TCGCG (SEQ ID NO: 104) | BBA000059 |
| 14 | CGGAT (SEQ ID NO: 105) | BBA000152 |
| 15 | GAGAT (SEQ ID NO: 106) | BBA000101 |
| 16 | TGTAG (SEQ ID NO: 107) | BBA000110 |
| 17 | GTGTT (SEQ ID NO: 108) | BBA000112 |
| 18 | AGATG (SEQ ID NO: 109) | BBA000113 |
| 19 | ATCCT (SEQ ID NO: 110) | BBA000114 |
| 20 | TTGCT (SEQ ID NO: 111) | BBA000286 |

-continued

| Codon no. | Codon sequence ID | Building Block ID |
|---|---|---|
| 21 | ACGTA (SEQ ID NO: 112) | BBA000123 |
| 22 | ATCAC (SEQ ID NO: 113) | BBA000124 |
| 23 | TATCC (SEQ ID NO: 114) | BBA000155 |
| 24 | GGAAG (SEQ ID NO: 115) | BBA000156 |
| 25 | CGGTC (SEQ ID NO: 116) | BBA000158 |
| 26 | TGCTT (SEQ ID NO: 117) | BBA000159 |
| 27 | TTAGC (SEQ ID NO: 118) | BBA000160 |
| 28 | GCTGA (SEQ ID NO: 119) | BBA000161 |
| 29 | GAACG (SEQ ID NO: 120) | BBA000162 |
| 30 | CATGG (SEQ ID NO: 121) | BBA000163 |
| 31 | TGGTA (SEQ ID NO: 122) | BBA000165 |
| 32 | TCAAG (SEQ ID NO: 123) | BBA000166 |
| 33 | ATCGA (SEQ ID NO: 124) | BBA000167 |
| 34 | ATGCA (SEQ ID NO: 125) | BBA000168 |
| 35 | ACTAG (SEQ ID NO: 126) | BBA000169 |
| 36 | TACCT (SEQ ID NO: 127) | BBA000170 |
| 37 | TACGA (SEQ ID NO: 128) | BBA000171 |
| 38 | CTTCA (SEQ ID NO: 129) | BBA000172 |
| 39 | CTCTT (SEQ ID NO: 130) | BBA000173 |
| 40 | TCATC (SEQ ID NO: 131) | BBA000174 |
| 41 | ATTCC (SEQ ID NO: 132) | BBA000175 |
| 42 | CGACG (SEQ ID NO: 133) | BBA000176 |
| 43 | CCTGT (SEQ ID NO: 134) | BBA000177 |
| 44 | CCTTC (SEQ ID NO: 135) | BBA000178 |
| 45 | ACACC (SEQ ID NO: 136) | BBA000179 |
| 46 | TAACA (SEQ ID NO: 137) | BBA000180 |
| 47 | TAACA (SEQ ID NO: 138) | BBA000098 |
| 48 | CCAGG (SEQ ID NO: 139) | BBA000181 |
| 49 | ATGTC (SEQ ID NO: 140) | BBA000182 |
| 50 | GAGGA (SEQ ID NO: 141) | BBA000183 |
| 51 | GGTCA (SEQ ID NO: 142) | BBA000184 |
| 52 | GACTT (SEQ ID NO: 143) | BBA000185 |
| 53 | GGTGG (SEQ ID NO: 144) | BBA000186 |
| 54 | CAACT (SEQ ID NO: 145) | BBA000190 |
| 55 | ATGAG (SEQ ID NO: 146) | BBA000195 |
| 56 | TCTGC (SEQ ID NO: 147) | BBA000196 |
| 57 | ATAGG (SEQ ID NO: 148) | BBA000197 |
| 58 | CTACC (SEQ ID NO: 149) | BBA000198 |

| Codon no. | Codon sequence ID | | Building Block ID |
|---|---|---|---|
| 59 | AAGTG | (SEQ ID NO: 150) | BBA000201 |
| 60 | TCCAA | (SEQ ID NO: 151) | BBA000202 |
| 61 | GCTCT | (SEQ ID NO: 152) | BBA000203 |
| 62 | GGAGT | (SEQ ID NO: 153) | BBA000204 |
| 63 | AATCG | (SEQ ID NO: 154) | BBA000205 |
| 64 | AAGCT | (SEQ ID NO: 155) | BBA000206 |
| 65 | CCGAA | (SEQ ID NO: 156) | BBA000207 |
| 66 | TTTGT | (SEQ ID NO: 157) | BBA000208 |
| 67 | CCGTG | (SEQ ID NO: 158) | BBA000209 |
| 68 | TTTCG | (SEQ ID NO: 159) | BBA000210 |
| 69 | TGAGG | (SEQ ID NO: 160) | BBA000211 |
| 70 | GTTGC | (SEQ ID NO: 161) | BBA000212 |
| 71 | AACTA | (SEQ ID NO: 162) | BBA000112 |
| 72 | AACTA | (SEQ ID NO: 163) | BBA000280 |
| 73 | CCTCG | (SEQ ID NO: 164) | BBA000281 |
| 74 | AGCAA | (SEQ ID NO: 165) | BBA000282 |
| 75 | TTCCA | (SEQ ID NO: 166) | BBA000313 |
| 76 | AGACT | (SEQ ID NO: 167) | BBA000314 |
| 77 | AGGTT | (SEQ ID NO: 168) | BBA000315 |
| 78 | GCGTC | (SEQ ID NO: 169) | BBA000316 |
| 79 | AACGT | (SEQ ID NO: 170) | BBA000317 |
| 80 | CAAGA | (SEQ ID NO: 171) | BBA000287 |
| 81 | AGAGA | (SEQ ID NO: 172) | BBA000419 |
| 82 | GTACT | (SEQ ID NO: 173) | BBA000420 |
| 83 | TAGAG | (SEQ ID NO: 174) | BBA000421 |
| 84 | ACGAT | (SEQ ID NO: 175) | BBA000422 |
| 85 | GACCA | (SEQ ID NO: 176) | BBA000200 |
| 86 | TCGTT | (SEQ ID NO: 177) | BBA000194 |
| 87 | GTCTC | (SEQ ID NO: 178) | BBA000427 |
| 88 | CAGCA | (SEQ ID NO: 179) | BBA000428 |
| 89 | TAGTC | (SEQ ID NO: 180) | BBA000199 |
| 90 | GGGTG | (SEQ ID NO: 181) | BBA000187 |
| 91 | CTCAG | (SEQ ID NO: 182) | BBA000191 |
| 92 | AGAAC | (SEQ ID NO: 183) | BBA000284 |
| 93 | GCGAG | (SEQ ID NO: 184) | BBA000458 |
| 94 | GATGT | (SEQ ID NO: 185) | BBA000459 |
| 95 | TCACT | (SEQ ID NO: 186) | BBA000461 |
| 96 | CGTCT | (SEQ ID NO: 187) | OBA000610 |
| 97 | AGCTC | (SEQ ID NO: 188) | OBA000611 |
| 98 | CACTC | (SEQ ID NO: 189) | OBA000609 |
| 99 | CAGTT | (SEQ ID NO: 190) | OBA000615 |

Library 1, Position 2

| Codon no. | Codon sequence ID | | Building Block ID |
|---|---|---|---|
| 1 | AGTACGAACGTGCATCAGAG | (SEQ ID NO: 191) | BBA000098 |
| 2 | TAGTCTCCTCCACTTCCATG | (SEQ ID NO: 192) | BBA000099 |
| 3 | TACATCGTTCCAGACTACCG | (SEQ ID NO: 193) | BBA000085 |
| 4 | TCCAGTGCAAGACTGAACAG | (SEQ ID NO: 194) | BBA000153 |
| 5 | AGCATCACTACTCTGTCTGG | (SEQ ID NO: 195) | BBA000206 |
| 6 | TCTTGTCAACCTTCCATGCG | (SEQ ID NO: 196) | BBA000200 |
| 7 | AAGGACGTTCCTAGTAGGTG | (SEQ ID NO: 197) | BBA000208 |
| 8 | GGAACCATCAAGATCCTGAG | (SEQ ID NO: 198) | BBA000091 |
| 9 | ATCTCTGACGAGATCCAAGG | (SEQ ID NO: 199) | BBA000090 |
| 10 | TCAAGGTTGGTGGTGTACTG | (SEQ ID NO: 200) | BBA000092 |
| 11 | TCGAACTTGTTGCTTCCTCG | (SEQ ID NO: 201) | BBA000123 |
| 12 | CTGAGTGTGTAGTACCAACG | (SEQ ID NO: 202) | BBA000156 |
| 13 | ATCTTGGTTGTTCTCCTGCG | (SEQ ID NO: 203) | BBA000163 |
| 14 | TAGTAGCTTGGAGTAGACCG | (SEQ ID NO: 204) | BBA000197 |

-continued

| Codon no. | Codon sequence ID | | Building Block ID |
|---|---|---|---|
| 15 | TTCACTCCATGCAGCATGTG | (SEQ ID NO: 205) | BBA000083 |
| 16 | ACGATGGTGATCGATCAACG | (SEQ ID NO: 206) | BBA000181 |
| 17 | TTCAGTGCTTGAGCTACCTG | (SEQ ID NO: 207) | BBA000152 |
| 18 | TTGGACTCTTCTTGCACCAG | (SEQ ID NO: 208) | BBA000088 |
| 19 | TCAACCAACTGGTTCTTGGG | (SEQ ID NO: 209) | BBA000100 |
| 20 | TAGTACTCTACACTGCTGCG | (SEQ ID NO: 210) | BBA00087/101/196 |
| 21 | TACACCATGACTTGCAGACG | (SEQ ID NO: 211) | BBA00087/101/196 |
| 22 | GCATCTTGAGTCGTTGAACG | (SEQ ID NO: 212) | BBA000059 |
| 23 | GACTCATCTCACTGGAGTTG | (SEQ ID NO: 213) | BBA000124 |
| 24 | TCCAGCTTCTAGGAAGACAG | (SEQ ID NO: 214) | BBA000160 |
| 25 | CTTCTTGAGTGCACTAGCAG | (SEQ ID NO: 215) | BBA000201 |

Library 1, Position 3

| Codon no. | Codon sequence ID | | Building Block ID |
|---|---|---|---|
| 1 | CGAGCAGGACCTGGAACCTGGTGC | (SEQ ID NO: 216) | BBA000098 |
| 2 | CTCGACCACTGCAGGTGGAGCTCC | (SEQ ID NO: 217) | BBA000099 |
| 3 | CGTGCTTCCTCTGCTGCACCACCG | (SEQ ID NO: 218) | BBA000085 |
| 4 | CCTGGTGTCGAGGTGAGCAGCAGC | (SEQ ID NO: 219) | BBA000153 |
| 5 | CTCGACGAGGTCCATCCTGGTCGC | (SEQ ID NO: 220) | BBA000206 |
| 6 | CGTGAGGAGCAGGTCCTCCTGTCG | (SEQ ID NO: 221) | BBA000200 |
| 7 | CCTGACACTGGTCGTGGTCGAGGC | (SEQ ID NO: 222) | BBA000208 |
| 8 | CCATCTCGACGACCTGCTCCTGGG | (SEQ ID NO: 223) | BBA000091 |
| 9 | CCACGAGGTCTCCACTGGTCCAGG | (SEQ ID NO: 224) | BBA000090 |
| 10 | CCACTGAGCTGCTCCTCCAGGTGG | (SEQ ID NO: 225) | BBA000092 |
| 11 | CCTCCTGTCCTGCACGTCCATCCG | (SEQ ID NO: 226) | BBA000123 |
| 12 | CAGCACCTGGAGGTAGGACCACGG | (SEQ ID NO: 227) | BBA000156 |
| 13 | CGACCAGACGAGGACCAGGTAGGC | (SEQ ID NO: 228) | BBA000163 |
| 14 | CCAGGTTCGAGGACCTCGTCAGCC | (SEQ ID NO: 229) | BBA000197 |
| 15 | CGAGCACGAGGAGCACGTGTCCAG | (SEQ ID NO: 230) | BBA000100 |
| 16 | CCACGTCCACAGGTGCACCAGGTG | (SEQ ID NO: 231) | BBA000181 |
| 17 | CCTGGTGCTCCACGACGTGCTTCG | (SEQ ID NO: 232) | BBA000152 |
| 18 | CACGTGACGACCTGGTCAGGTGGG | (SEQ ID NO: 233) | BBA000088 |
| 19 | CGTAGCTCGTGCTGGTCCTCCTGG | (SEQ ID NO: 234) | BBA000101 |
| 20 | CGACGACCACCACCTTGGACACCC | (SEQ ID NO: 235) | BBA000196 |
| 21 | CCTACGTCGTGCTCACGTCCTGCC | (SEQ ID NO: 236) | BBA00087 |
| 22 | CGACGACAGCTAGGAGGAGGTGGG | (SEQ ID NO: 237) | BBA000083 |
| 23 | CTGGTGGAGCTGCACGAGCACAGC | (SEQ ID NO: 238) | BBA000059 |

-continued

| Codon no. | Codon sequence ID | | Building Block ID |
|---|---|---|---|
| 24 | CAGGACTGGACGACGACCAGGTCG | (SEQ ID NO: 239) | BBA000124 |
| 25 | CGATGCTGCAGACGACCAGCACCC | (SEQ ID NO: 240) | BBA000160 |

Library 2, Position 1

| Codon no. | Codon sequence ID | | Building Block ID |
|---|---|---|---|
| 1 | TGTTC | (SEQ ID NO: 241) | BBA000092 |
| 2 | CGAGC | (SEQ ID NO: 242) | BBA000354 |
| 3 | GGATA | (SEQ ID NO: 243) | BBA000085 |
| 4 | CGCTG | (SEQ ID NO: 244) | BBA000086 |
| 5 | GTTAT | (SEQ ID NO: 245) | BBA000098 |
| 6 | AGTGC | (SEQ ID NO: 246) | BBA000099 |
| 7 | ACCTG | (SEQ ID NO: 247) | BBA000089 |
| 8 | CTGGT | (SEQ ID NO: 248) | BBA000090 |
| 9 | TAGGA | (SEQ ID NO: 249) | BBA000087 |
| 10 | ACTCA | (SEQ ID NO: 250) | BBA000088 |
| 11 | CTTAC | (SEQ ID NO: 251) | BBA000153 |
| 12 | CGCAC | (SEQ ID NO: 252) | BBA000154 |
| 13 | TCGCG | (SEQ ID NO: 253) | BBA000059 |
| 14 | CGGAT | (SEQ ID NO: 254) | BBA000152 |
| 15 | GAGAT | (SEQ ID NO: 255) | BBA000101 |
| 16 | TGTAG | (SEQ ID NO: 256) | BBA000110 |
| 17 | GTGTT | (SEQ ID NO: 257) | BBA000112 |
| 18 | AGATG | (SEQ ID NO: 258) | BBA000113 |
| 19 | ATCCT | (SEQ ID NO: 259) | BBA000114 |
| 20 | TTGCT | (SEQ ID NO: 260) | BBA000286 |
| 21 | ACGTA | (SEQ ID NO: 261) | BBA000123 |
| 22 | ATCAC | (SEQ ID NO: 262) | BBA000124 |
| 23 | TATCC | (SEQ ID NO: 263) | BBA000155 |
| 24 | GGAAG | (SEQ ID NO: 264) | BBA000156 |
| 25 | CGGTC | (SEQ ID NO: 265) | BBA000158 |
| 26 | TGCTT | (SEQ ID NO: 266) | BBA000159 |
| 27 | TTAGC | (SEQ ID NO: 267) | BBA000160 |
| 28 | GCTGA | (SEQ ID NO: 268) | BBA000161 |
| 29 | GAACG | (SEQ ID NO: 269) | BBA000162 |
| 30 | CATGG | (SEQ ID NO: 270) | BBA000163 |
| 31 | TGGTA | (SEQ ID NO: 271) | BBA000165 |
| 32 | TCAAG | (SEQ ID NO: 272) | BBA000166 |
| 33 | ATCGA | (SEQ ID NO: 273) | BBA000167 |
| 34 | ATGCA | (SEQ ID NO: 274) | BBA000168 |
| 35 | ACTAG | (SEQ ID NO: 275) | BBA000169 |
| 36 | TACCT | (SEQ ID NO: 276) | BBA000170 |
| 37 | TACGA | (SEQ ID NO: 277) | BBA000171 |
| 38 | CTTCA | (SEQ ID NO: 278) | BBA000172 |
| 39 | CTCTT | (SEQ ID NO: 279) | BBA000173 |
| 40 | TCATC | (SEQ ID NO: 280) | BBA000174 |
| 41 | ATTCC | (SEQ ID NO: 281) | BBA000175 |
| 42 | CGACG | (SEQ ID NO: 282) | BBA000176 |
| 43 | CCTGT | (SEQ ID NO: 283) | BBA000177 |
| 44 | CCTTC | (SEQ ID NO: 284) | BBA000178 |
| 45 | ACACC | (SEQ ID NO: 285) | BBA000179 |
| 46 | TAACA | (SEQ ID NO: 286) | BBA000180 |
| 47 | TAACA | (SEQ ID NO: 287) | BBA000098 |
| 48 | CCAGG | (SEQ ID NO: 288) | BBA000181 |
| 49 | ATGTC | (SEQ ID NO: 289) | BBA000182 |
| 50 | GAGGA | (SEQ ID NO: 290) | BBA000183 |
| 51 | GGTCA | (SEQ ID NO: 291) | BBA000184 |
| 52 | GACTT | (SEQ ID NO: 292) | BBA000185 |
| 53 | GGTGG | (SEQ ID NO: 293) | BBA000186 |
| 54 | CAACT | (SEQ ID NO: 294) | BBA000190 |
| 55 | ATGAG | (SEQ ID NO: 295) | BBA000195 |
| 56 | TCTGC | (SEQ ID NO: 296) | BBA000196 |
| 57 | ATAGG | (SEQ ID NO: 297) | BBA000197 |
| 58 | CTACC | (SEQ ID NO: 298) | BBA000198 |
| 59 | AAGTG | (SEQ ID NO: 299) | BBA000201 |
| 60 | TCCAA | (SEQ ID NO: 300) | BBA000202 |
| 61 | GCTCT | (SEQ ID NO: 301) | BBA000203 |
| 62 | GGAGT | (SEQ ID NO: 302) | BBA000204 |
| 63 | AATCG | (SEQ ID NO: 303) | BBA000205 |
| 64 | AAGCT | (SEQ ID NO: 304) | BBA000206 |
| 65 | CCGAA | (SEQ ID NO: 305) | BBA000207 |

| Codon no. | Codon sequence | ID | Building Block ID |
|---|---|---|---|
| 66 | TTTGT | (SEQ ID NO: 306) | BBA000208 |
| 67 | CCGTG | (SEQ ID NO: 307) | BBA000209 |
| 68 | TTTCG | (SEQ ID NO: 308) | BBA000210 |
| 69 | TGAGG | (SEQ ID NO: 309) | BBA000211 |
| 70 | GTTGC | (SEQ ID NO: 310) | BBA000212 |
| 71 | AACTA | (SEQ ID NO: 311) | BBA000112 |
| 72 | AACTA | (SEQ ID NO: 312) | BBA000280 |
| 73 | CCTCG | (SEQ ID NO: 313) | BBA000281 |
| 74 | AGCAA | (SEQ ID NO: 314) | BBA000282 |
| 75 | TTCCA | (SEQ ID NO: 315) | BBA000313 |
| 76 | AGACT | (SEQ ID NO: 316) | BBA000314 |
| 77 | AGGTT | (SEQ ID NO: 317) | BBA000315 |
| 78 | GCGTC | (SEQ ID NO: 318) | BBA000316 |
| 79 | AACGT | (SEQ ID NO: 319) | BBA000317 |
| 80 | CAAGA | (SEQ ID NO: 320) | BBA000287 |
| 81 | AGAGA | (SEQ ID NO: 321) | BBA000419 |
| 82 | GTACT | (SEQ ID NO: 322) | BBA000420 |
| 83 | TAGAG | (SEQ ID NO: 323) | BBA000421 |
| 84 | ACGAT | (SEQ ID NO: 324) | BBA000422 |
| 85 | GACCA | (SEQ ID NO: 325) | BBA000200 |
| 86 | TCGTT | (SEQ ID NO: 326) | BBA000194 |
| 87 | GTCTC | (SEQ ID NO: 327) | BBA000427 |
| 88 | CAGCA | (SEQ ID NO: 328) | BBA000428 |
| 89 | TAGTC | (SEQ ID NO: 329) | BBA000199 |
| 90 | GGGTG | (SEQ ID NO: 330) | BBA000187 |
| 91 | CTCAG | (SEQ ID NO: 331) | BBA000191 |
| 92 | AGAAC | (SEQ ID NO: 332) | BBA000284 |
| 93 | GCGAG | (SEQ ID NO: 333) | BBA000458 |
| 94 | GATGT | (SEQ ID NO: 334) | BBA000459 |
| 95 | TCACT | (SEQ ID NO: 335) | BBA000461 |
| 96 | CGTCT | (SEQ ID NO: 336) | OBA000610 |
| 97 | AGCTC | (SEQ ID NO: 337) | OBA000611 |
| 98 | CACTC | (SEQ ID NO: 338) | OBA000609 |
| 99 | CAGTT | (SEQ ID NO: 339) | OBA000615 |

Library 2, Position 2

| Codon no. | Codon sequence | ID | Building Block ID |
|---|---|---|---|
| 1 | AGTACGAACGTGCATCAGAG | (SEQ ID NO: 340) | BBA000059 |
| 2 | TAGTCTCCTCCACTTCCATG | (SEQ ID NO: 341) | BBA000085 |
| 3 | TACATCGTTCCAGACTACCG | (SEQ ID NO: 342) | BBA000098 |
| 4 | TCCAGTGCAAGACTGAACAG | (SEQ ID NO: 343) | BBA000099 |
| 5 | AGCATCACTACTCTGTCTGG | (SEQ ID NO: 344) | BBA000101 |
| 6 | TCTTGTCAACCTTCCATGCG | (SEQ ID NO: 345) | BBA000110 |
| 7 | AAGGACGTTCCTAGTAGGTG | (SEQ ID NO: 346) | BBA000113 |
| 8 | GGAACCATCAAGATCCTGAG | (SEQ ID NO: 347) | BBA000114 |
| 9 | ATCTCTGACGAGATCCAAGG | (SEQ ID NO: 348) | BBA000123 |
| 10 | TCAAGGTTGGTGGTGTACTG | (SEQ ID NO: 349) | BBA000124 |
| 11 | TCGAACTTGTTGCTTCCTCG | (SEQ ID NO: 350) | BBA000152 |
| 12 | CTGAGTGTGTAGTACCAACG | (SEQ ID NO: 351) | BBA000158 |
| 13 | ATCTTGGTTGTTCTCCTGCG | (SEQ ID NO: 352) | BBA000160 |
| 14 | TAGTAGCTTGGAGTAGACCG | (SEQ ID NO: 353) | BBA000161 |
| 15 | TTCACTCCATGCAGCATGTG | (SEQ ID NO: 354) | BBA000167 |
| 16 | ACGATGGTGATCGATCAACG | (SEQ ID NO: 355) | BBA000176 |
| 17 | TTCAGTGCTTGAGCTACCTG | (SEQ ID NO: 356) | BBA000181 |
| 18 | TTGGACTCTTCTTGCACCAG | (SEQ ID NO: 357) | BBA000313 |

-continued

| Codon no. | Codon sequence ID | | Building Block ID |
|---|---|---|---|
| 19 | TCAACCAACTGGTTCTTGGG | (SEQ ID NO: 358) | BBA000314 |
| 20 | TAGTACTCTACACTGCTGCG | (SEQ ID NO: 359) | BBA000315 |
| 21 | TACACCATGACTTGCAGACG | (SEQ ID NO: 360) | BBA000316 |
| 22 | GCATCTTGAGTCGTTGAACG | (SEQ ID NO: 361) | BBA000317 |
| 23 | GACTCATCTCACTGGAGTTG | (SEQ ID NO: 362) | BBA000420 |
| 24 | TCCAGCTTCTAGGAAGACAG | (SEQ ID NO: 363) | BBA000421 |
| 25 | CTTCTTGAGTGCACTAGCAG | (SEQ ID NO: 364) | BBA000422 |

Library 2, Position 3

| Codon no. | Codon sequence ID | | Building Block ID |
|---|---|---|---|
| 1 | CGAGCAGGACCTGGAACCTGGTGC | (SEQ ID NO: 365) | BBA000052 |
| 2 | CTCGACCACTGCAGGTGGAGCTCC | (SEQ ID NO: 366) | BBA000053 |
| 3 | CGTGCTTCCTCTGCTGCACCACCG | (SEQ ID NO: 367) | BBA000054 |
| 4 | CCTGGTGTCGAGGTGAGCAGCAGC | (SEQ ID NO: 368) | BBA000056 |
| 5 | CTCGACGAGGTCCATCCTGGTCGC | (SEQ ID NO: 369) | BBA000057 |
| 6 | CGTGAGGAGCAGGTCCTCCTGTCG | (SEQ ID NO: 370) | BBA000058 |
| 7 | CCTGACACTGGTCGTGGTCGAGGC | (SEQ ID NO: 371) | BBA000062 |
| 8 | CCATCTCGACGACCTGCTCCTGGG | (SEQ ID NO: 372) | BBA000139 |
| 9 | CCACGAGGTCTCCACTGGTCCAGG | (SEQ ID NO: 373) | BBA000140 |
| 10 | CCACTGAGCTGCTCCTCCAGGTGG | (SEQ ID NO: 374) | BBA000100 |
| 11 | CCTCCTGTCCTGCACGTCCATCCG | (SEQ ID NO: 375) | BBA000059 |
| 12 | CAGCACCTGGAGGTAGGACCACGG | (SEQ ID NO: 376) | BBA000085 |
| 13 | CGACCAGACGAGGACCAGGTAGGC | (SEQ ID NO: 377) | BBA000098 |
| 14 | CCAGGTTCGAGGACCTCGTCAGCC | (SEQ ID NO: 378) | BBA000099 |
| 15 | CGAGCACGAGGAGCACGTGTCCAG | (SEQ ID NO: 379) | BBA000101 |
| 16 | CCACGTCCACAGGTGCACCAGGTG | (SEQ ID NO: 380) | BBA000110 |
| 17 | CCTGGTGCTCCACGACGTGCTTCG | (SEQ ID NO: 381) | BBA000113 |
| 18 | CACGTGACGACCTGGTCAGGTGGG | (SEQ ID NO: 382) | BBA000114 |
| 19 | CGTAGCTCGTGCTGGTCCTCCTGG | (SEQ ID NO: 383) | BBA000123 |
| 20 | CGACGACCACCACCTTGGACACCC | (SEQ ID NO: 384) | BBA000124 |
| 21 | CCTACGTCGTGCTCACGTCCTGCC | (SEQ ID NO: 385) | BBA000152 |
| 22 | CGACGACAGCTAGGAGGAGGTGGG | (SEQ ID NO: 386) | BBA000158 |
| 23 | CTGGTGGAGCTGCACGAGCACAGC | (SEQ ID NO: 387) | BBA000160 |
| 24 | CAGGACTGGACGACGACCAGGTCG | (SEQ ID NO: 388) | BBA000161 |
| 25 | CGATGCTGCAGACGACCAGCACCC | (SEQ ID NO: 389) | BBA000167 |

Library 3, Position 1

| Codon no | Codon sequence ID | Building Block ID | More abundant in no. position 1 in library |
|---|---|---|---|
| 1 | TGTTC (SEQ ID NO: 390) | BBA000092 | 1 |
| 2 | ACTCA (SEQ ID NO: 391) | BBA000088 | 1 |
| 3 | CTTAC (SEQ ID NO: 392) | BBA000153 | 1 and 2 |
| 4 | CGGAT (SEQ ID NO: 393) | BBA000152 | 1 |
| 5 | ATTCC (SEQ ID NO: 394) | BBA000175 | 1 and 2 |
| 6 | GTCTC (SEQ ID NO: 395) | BBA000427 | |
| 7 | ACAGT (SEQ ID NO: 396) | BBA000098 | 1 and 2 |

Library 3, Position 2

| Codon no. | Codon sequence ID | Building Block ID | More abundant in in position 2 in library no. |
|---|---|---|---|
| 1 | 6CACAAGTACGAACGTGCATCAGAG (SEQ ID NO: 397) | BBA000059 | 1 |
| 2 | 6CACATAGTCTCCTCCACTTCCATG (SEQ ID NO: 398) | BBA000083 | 1 |
| 3 | 6CACATACATCGTTCCAGACTACCG (SEQ ID NO: 399) | BBA000085 | 2 |
| 4 | 6CACATCCAGTGCAAGACTGAACAG (SEQ ID NO: 400) | BBA000088 | 1 |
| 5 | 6CACAAGCATCACTACTCTGTCTGG (SEQ ID NO: 401) | BBA000090 | 1 |
| 6 | 6CACATCTTGTCAACCTTCCATGCG (SEQ ID NO: 402) | BBA000099 | 1 and 2 |
| 7 | 6CACAAAGGACGTTCCTAGTAGGTG (SEQ ID NO: 403) | BBA000110 | |
| 8 | 6CACAGGAACCATCAAGATCCTGAG (SEQ ID NO: 404) | BBA000114 | 2 |
| 9 | 6CACAATCTCTGACGAGATCCAAGG (SEQ ID NO: 405) | BBA000152 | 2 |
| 10 | 6CACATCAAGGTTGGTGGTGTACTG (SEQ ID NO: 406) | BBA000160 | 2 |
| 11 | 6CACATCGAACTTGTTGCTTCCTCG (SEQ ID NO: 407) | BBA000200 | 1 |
| 12 | 6CACACTGAGTGTGTAGTACCAACG (SEQ ID NO: 408) | BBA000201 | 1 |
| 13 | 6CACAATCTTGGTTGTTCTCCTGCG (SEQ ID NO: 409) | BBA000422 | 2 |

Library 3, Position 3

| Codon no. | Codon sequence ID | Building Block ID | More abundant in in position 3 in library no. |
|---|---|---|---|
| 1 | 6AGGACGAGCAGGACCTGGAACCTGGTGCGTTCCTCCACCACGTCTCCG (SEQ ID NO: 410) | BBA000053 | 2 |

| Codon no. | Codon sequence ID | Building Block ID | More abundant in position 3 in library no. |
|---|---|---|---|
| 2 | 6AGGACTCGACCACTGCAGGTGGAGCTCCGTTCCTCCACCAC GTCTCCG (SEQ ID NO: 411) | BBA000085 | 1 |
| 3 | 6AGGACGTGCTTCCTCTGCTGCACCACCGGTTCCTCCACCAC GTCTCCG (SEQ ID NO: 412) | BBA000087 | 1 |
| 4 | 6AGGACCTGGTGTCGAGGTGAGCAGCAGCGTTCCTCCACCAC GTCTCCG (SEQ ID NO: 413) | BBA000090 | 1 |
| 5 | 6AGGACTCGACGAGGTCCATCCTGGTCGCGTTCCTCCACCAC GTCTCCG (SEQ ID NO: 414) | BBA000091 | 1 |
| 6 | 6AGGACGTGAGGAGCAGGTCCTCCTGTCGGTTCCTCCACCAC GTCTCCG (SEQ ID NO: 415) | BBA000098 | 1 |
| 7 | 6AGGACCTGACACTGGTCGTGGTCGAGGCGTTCCTCCACCAC GTCTCCG (SEQ ID NO: 416) | BBA000100 | 1 and 2 |
| 8 | 6AGGACCATCTCGACGACCTGCTCCTGGGGTTCCTCCACCAC GTCTCCG (SEQ ID NO: 417) | BBA000139 | 2 |
| 9 | 6AGGACCACGAGGTCTCCACTGGTCCAGGGTTCCTCCACCAC GTCTCCG (SEQ ID NO: 418) | BBA000140 | 2 |
| 10 | 6AGGACCACTGAGCTGCTCCTCCAGGTGGGTTCCTCCACCAC GTCTCCG (SEQ ID NO: 419) | BBA000152 | |
| 11 | 6AGGACCTCCTGTCCTGCACGTCCATCCGGTTCCTCCACCAC GTCTCCG (SEQ ID NO: 420) | BBA000153 | 1 |
| 12 | 6AGGACAGCACCTGGAGGTAGGACCACGGGTTCCTCCACCAC GTCTCCG (SEQ ID NO: 421) | BBA000161 | |
| 13 | 6AGGACGACCAGACGA GGACCAGGTAGGCGTTCCTCCAC-C ACGTCTCCG (SEQ ID NO: 422) | BBA000167 | 2 |
| 14 | 6AGGACCAGGTTCGAGGACCTCGTCAGCCGTTCCTCCACCAC GTCTCCG (SEQ ID NO: 423) | BBA000197 | 1 |
| 15 | 6AGGACGAGCACGAGGAGCACGTGTCCAGGTTCCTCCACCAC GTCTCCG (SEQ ID NO: 424) | BBA000200 | 1 |

A subset of the isolated sequences from the library post selection was analysed:

(1)
(SEQ ID NO: 425)
GGCAGCACAGTCGTCGCACATACATCGTTCCAGACTACCGAGGACCTGA

CAC-TGGTCGTGGTCGAGGCGTTCCT (2)
(SEQ ID NO: 426)
GGCAGCACAGT CGTCGCTACATGCTTGTCAACCTTCCATGCGAGTACC

TTACAC-TGGTTCGTGGTCGAGGCGTTCCT (3)
(SEQ ID NO: 427)
GGCAGCCG-GAT423CGTCGCACATCTTGTCAACCTTCCATGCGAGGAC

CTGACACTGGTCGTGGTCGAGGCGTTCCT (4)
(SEQ ID NO: 428)
GGCAGCCTTACGTCGCACAATTCTCTGACAGAAATCCAACGGAGGACCT

GACAC-GTGCGTCGTGGCTCGATGCGTTCCTC (5)
(SEQ ID NO: 429)
GGCAGCACAGTCGTCGCACATCATTGTACAAACCTTCCATGCGAGGACC

ATCTCGACGAC-CTGCTCCTGGGGTNCCTC (6)
(SEQ ID NO: 430)
GGCAGCACAGTCGTCGCACATCTTGTCAACCTTCCATGCGAGGACCATC

TCGACGAC-CTGCTCCTGGGGTTCCTC (7)
(SEQ ID NO: 431)
GGCAGCACAGTCGTCGCACATCTTGTCAACCITCCATGCGAGGACCATC

TCGACGAC-CTGCTCCTGGGGTTCCTC (8)
(SEQ ID NO: 432)
GGCAGCACAGTCGTCGCACATCTTGTCAACCTTCCATGCGAGGACCATC

TCGACGAC-CTGCTCCTGGGGTTCCTC (9)
(SEQ ID NO: 433)
GGCAGCACAGTCGTCGCACATCTTGTCAACCTTCCATGCGAGGACCATC

TCGACGAC-CTGCTCCTGGGGTTCCTC

(10)
(SEQ ID NO: 434)
GGCAGCACAGTCGTCGCACATCTTGICAACCTTCCATGCGAGGACCATC

TCGAC-GAGCTGCTCCTGGGGTTCCTC

(11)
(SEQ ID NO: 435)
GGCAGCACTAGATCGTCGCACATCTTGTCAACCTTCCATGCGAGGAC-

CATCTTCGACTGANCTGCCTCCTGTGGGCTTCCTC

(12)
(SEQ ID NO: 436)
GGCAGCACAGAT CGTCGCACATCTTGTCAACCTTCCATGCGAGGACCA

TCTCGAC-GANCTGCTCCTGGGGTTCCTC

(13)
(SEQ ID NO: 437)
GGCAGCACAGTCGTCGCACATCTTGTCAACCTTCCATGCGAGGACCATC

ACGACTACCTT-GGCTCCCTGGGGTTCCTC

(14)
(SEQ ID NO: 438)
GGCAGCACAGTCGTCGCACATCTTGTCACCTTCCATGCGAGGACCATCT

CGACGAC-CTGCTCCTGGGGTTCCTC

(15)
(SEQ ID NO: 439)
GGCAGCACAGTCGTCGCACATCTTGTCAACCTTCCATGCGAGGACCATC

TCGACGAC-CTGCTCCTGGGGTTCCTC

(16)
(SEQ ID NO: 440)
GGCAGCCGGATCGTCGCACATCTTGTCAACCTTCCATGCGAGGACCATC

TCGACGAC-CTGCTCCTGGGGTTCCTC

(17)
(SEQ ID NO: 441)
GGCAGCCGGATCGTCGCACATCTTGTCACCTTCCATGCGAGGACCATCT

CGACGAC-CTGCTCCTGGGGTTCCTC

(18)
(SEQ ID NO: 442)
GGCAGCCGGATCGTCGCACATCTTGTCAACCTTCCATGCGAGGACCATC

TCGACGAC-CTGCTCCTGGGGTTCCTC

(19)
(SEQ ID NO: 443)
GGCAGCACAGTCGTCGCAATCCAGTCAAGACTGAACAGAGGACCATCTC

GACGACCTGCTCCTGGGTT

(20)
(SEQ ID NO: 444)
GGCAGCACAGTCGTCGCACATCTTGTCAACCTTTTCCATGCGAGGACGA

GCAGGACCTG-GAACCTGGTGCGTTCCTC

(21)
(SEQ ID NO: 445)
GGCAGCACAGTCGTCGCACATCTTGTCACCTTCCATGCGAGGACGAGCA

GGACCTGGAAC-CTGGTGCGTTCCTC

(22)
(SEQ ID NO: 446)
GGCAGCACAGTCGTCGCACATCTTGTCAACCTTCCATGCGAGGACGATG

CAGGACCTGGAAC-CTGGTGCGTTCCTC

(23)
(SEQ ID NO: 447)
GGCAGCCGGATCGTCGCACATCTTGGTNAANCTTCCATGCGAGGACGAG

CATGAACTGGAAC-CTGGTGCGTTCCTC

(24)
(SEQ ID NO: 448)
GGCGGATCGTCGCACATCTTGTCAACCTTCCATGCGAGGACCACGAGGT

CTCCACTGGTCCAGGGGTTCCTC

(25)
(SEQ ID NO: 449)
GGCAGCACAGTCGTCGGCAATCTTTGGTCAACCTTCCATGCGAGGACCA

CGAGGTCTCCAC-TGGTCCAGGGTTCCTC

(26)
(SEQ ID NO: 450)
GGCAGCCGGATCGTCGCACATCTTGTCAACCTTCCATGCGAGGACGACC

AAGACGAGGAC-CAGGTAGGCGTTCCT

(27)
(SEQ ID NO: 451)
GGCAGCCG-GAT423CGTCGCACATCTTGTCAACCTTCCATGCGAGGAC

GTGATGGAGCAAGTCCTCCTGTCGGTTCCTC

(28)
(SEQ ID NO: 452)
GGCAGCACAGTCGTCGCACATCTTGTCAACCTTCCATGCGAGGACACGA

GGTCTCCAC-TGGTCCAGGTTCCTC

(29)
(SEQ ID NO: 453)
GCCCAAACAAGTCGTCGCACATCTTGTCAACCTTCCATGCGAGGACCGA

GNNNGTAGCTG-GANNCTCGGATGCGTTCCT

(30)
(SEQ ID NO: 454)
GCAGCACAGATCGTCGCACATGCTTGTCAAGCCTTTCCATCGCGAGGAC

CATCCTAC-GGAGCGAGCACTTGCTGCCTGGGGTTC

(31)
(SEQ ID NO: 455)
GGCAGCCGGATCGTCGCACATCAATGGTTTGGCTGGTGATACTGAGGAC

CACGACGTC-TACACTTGGTTCCAGGGTTCCTC

These sequences could be translated into the following building block compositions:

| Sequence no. | Position 1 | Position 2 | Position 3 |
|---|---|---|---|
| 1 | BBA000098 | BBA000085 | BBA000100 |
| 2 | BBA000098 | BBA000099 | BBA000100 |
| 3 | BBA000152 | BBA000099 | BBA000100 |
| 4 | BBA000153 | BBA000152 | BBA000100 |
| 5 | BBA000098 | BBA000099 | BBA000139 |
| 6 | BBA000098 | BBA000099 | BBA000139 |
| 7 | BBA000098 | BBA000099 | BBA000139 |
| 8 | BBA000098 | BBA000099 | BBA000139 |
| 9 | BBA000098 | BBA000099 | BBA000139 |
| 10 | BBA000098 | BBA000099 | BBA000139 |
| 11 | BBA000098 | BBA000099 | BBA000139 |
| 12 | BBA000098 | BBA000099 | BBA000139 |
| 13 | BBA000098 | BBA000099 | BBA000139 |
| 14 | BBA000098 | BBA000099 | BBA000139 |
| 15 | BBA000098 | BBA000099 | BBA000139 |
| 16 | BBA000152 | BBA000099 | BBA000139 |
| 17 | BBA000152 | BBA000099 | BBA000139 |
| 18 | BBA000152 | BBA000099 | BBA000139 |
| 19 | BBA000098 | BBA000088 | BBA000139 |
| 20 | BBA000098 | BBA000099 | BBA000053 |
| 21 | BBA000098 | BBA000099 | BBA000053 |
| 22 | BBA000098 | BBA000099 | BBA000053 |
| 23 | BBA000152 | BBA000099 | BBA000053 |
| 24 | BBA000152 | BBA000099 | BBA000140 |
| 25 | BBA000098 | BBA000099 | BBA000140 |
| 26 | BBA000152 | BBA000099 | BBA000167 |
| 27 | BBA000152 | BBA000099 | BBA000098 |
| 28 | BBA000098 | BBA000099 | BBA000200 |

-continued

| Sequence no. | Position 1 | Position 2 | Position 3 |
|---|---|---|---|
| 29 | BBA000098 | BBA000099 | — |
| 30 | BBA000098 | BBA000099 | — |
| 31 | BBA000152 | BBA000160 | — |

In position 1 L-Asp (BBA00098) dominated. D-Asp was also found (BBA000152)

In position 2 Gly (BBA00099) dominated.

In position 3 building blocks carrying an amidine and no amine functionality was found to dominate:

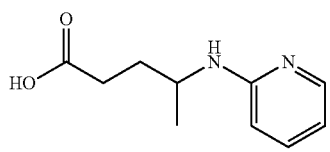

BBA000139

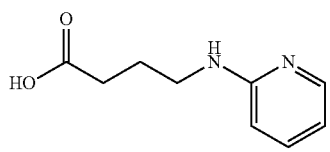

BBA000053

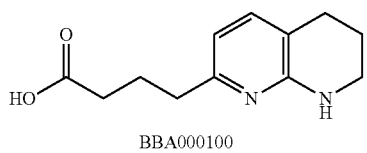

BBA000100

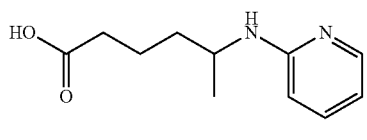

BBA000140

The most abundant sequence was thereby found to correspond to the following structure:

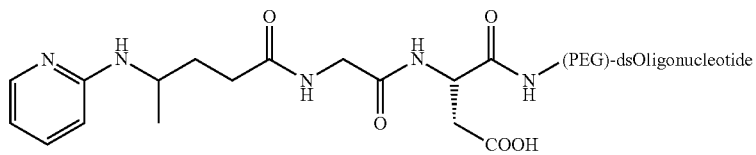

BBA000139-BBA000099-BBA000098

The following 3 sequences

BBA000098-BBA000099-BBA000139
BBA000098-BBA000099-BBA000100
BBA000098-BBA000099-BBA000053 out of the 31 identified sequences were selected for further analysis using an standard ELISA assay and thereby verified as binders of the αvβ3 Integrin receptor.

While the invention has been described with references to specific methods and embodiments, it will be appreciated that various modifications and changes may be made without departing from the invention. All patent and literature references cited herein are hereby incorporated by reference in their entirety.

The invention claimed is:

1. A method for producing a focused library comprising a plurality of different molecules, wherein each molecule is linked to an identifier oligonucleotide comprising tags identifying a plurality of reactants that participated in formation of the molecule, the method comprising the steps of:
   i) producing an initial library comprising a plurality of different initial molecules, wherein each initial molecule is linked to an identifier oligonucleotide comprising tags identifying a plurality of reactants that participated in formation of the initial molecule, the initial library having a higher diversity than the focused library, and wherein said initial library is produced by a split-and-mix method comprising the steps of:
   a. providing, in separate compartments, a plurality of nascent bifunctional complexes each comprising a chemical reaction site and a priming site, and reacting the nascent bifunctional complexes at their chemical reaction sites with one or more reactants;
   b. reacting the priming sites of the plurality of nascent bifunctional complexes with one or more tags, wherein the reaction between the priming site and the one or more tags is catalyzed by an enzyme;
   wherein steps (a) and (b) provide a plurality of intermediate bifunctional complexes having a modified chemical reaction site containing a structural entity formed from the chemical reaction site and the one or more reactants and a modified priming site containing the one or more tags;
   c. pooling the intermediate bifunctional complexes into a single compartment to provide a mixture, and splitting the mixture into separate compartments
   d. reacting each compartment containing a mixture of intermediate bifunctional complexes with one or more additional reactants at the modified reactant sites and one or more additional tags identifying the one or more additional reactants at the modified priming sites using the methods of steps (a) and (b); and
   e. optionally repeating steps (c) and (d) as many times as desired
   ii) subjecting said initial library to a partitioning step, wherein said partitioning step provides a partitioned library synthesized from some, but not all, of the plurality of reactants used in the synthesis of the initial library, and
   iii) identifying the reactants used in the synthesis of at least some of the molecules of the partitioned library,
   iv) producing a focused library having a lower diversity than the initial library, wherein said focused library is produced by a split-and-mix method comprising the steps of:
   a. providing at least some of the reactants used in the synthesis of the molecules of the partitioned library,
   b. providing either i) at least some, but not all, of the reactants used in the synthesis of the initial library but not used in the synthesis of the partitioned library, and/or ii) further reactants not used in the synthesis of the initial library, c. reacting the reactants provided in steps (iv)(a) and (iv)(b) in a split-and-mix method comprising the steps cited in (i)(a)-(i)(e); and
d. producing the focused library comprising a plurality of different molecules.

2. The method of claim 1 comprising the further step of partitioning the focused library.

3. The method of claim 1, wherein the molecules are covalently associated with the identifier oligonucleotides.

4. The method of claim 1, wherein identifier oligonucleotide tags identifying individual chemical entities each have 4 or more nucleotides.

5. The method of claim 1, wherein identifier oligonucleotide tags are separated by a framing sequence.

6. The method of claim 1, wherein the identifier oligonucleotide has at least three tags.

7. The method of claim 1, wherein the focused library is prepared using reactants used to synthesize the molecules appearing in the initial library and reactants that are different than those used in the synthesis of the initial library.

8. The method of claim 1, wherein a reactant is allowed in every position of a reaction sequence used to generate the focused library.

9. The method of claim 1, wherein a reactant is allowed in one position of a reaction sequence used to generate the focused library.

10. The method of claim 1, wherein the identifier comprises 3 or more codons.

11. The method of claim 1, wherein identifier oligonucleotide tags are separated by a framing sequence and wherein the identifier oligonucleotide tags and the framing sequence has a total length of 15 or more nucleotides.

12. The method of claim 1, wherein the initial library contains from $10^4$ to $10^{20}$ different molecules.

* * * * *

SEQUENCE LISTING

<160> NUMBER OF SEQ ID NOS: 455

<210> SEQ ID NO 1
<211> LENGTH: 27
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: biotin

<400> SEQUENCE: 1
aattccggaa catactagtc aacatga                                               27

<210> SEQ ID NO 2
<211> LENGTH: 37
<212> TYPE: DNA
<213> ORGANISM: Artificial Sequence
<220> FEATURE:
<223> OTHER INFORMATION: synthetic construct

<400> SEQUENCE: 2
tcatgttgac tagtatggtg tgctcaagct agtgtgc                                    37

<210> SEQ ID NO 3
<211> LENGTH: 37
<212> TYPE: DNA
<213> ORGANISM: Artificial Sequence
<220> FEATURE:
<223> OTHER INFORMATION: synthetic construct

<400> SEQUENCE: 3
tcattggctg atctatggtg tgctcaagct agtgtgc                                    37

<210> SEQ ID NO 4
<211> LENGTH: 37
<212> TYPE: DNA
<213> ORGANISM: Artificial Sequence
<220> FEATURE:
<223> OTHER INFORMATION: synthetic construct

<400> SEQUENCE: 4
tcatttgtga gcttatggtg tgctcaagct agtgtgc                                    37

<210> SEQ ID NO 5
<211> LENGTH: 37
<212> TYPE: DNA
<213> ORGANISM: Artificial Sequence
<220> FEATURE:
<223> OTHER INFORMATION: synthetic construct

<400> SEQUENCE: 5
tcatggtact cgatatggtg tgctcaagct agtgtgc                                    37

<210> SEQ ID NO 6
<211> LENGTH: 89
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: displayed molecule

<400> SEQUENCE: 6

```
gcacactagc ttgagcacac tgacacatgg agatcacatg cttcgacaat gcaggactcc    60
cgcagcttta cgatcccgca ggtaaccgt                                      89
```

<210> SEQ ID NO 7
<211> LENGTH: 25
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: biotin

<400> SEQUENCE: 7

```
gcacactagc ttgagcacac tgaca                                          25
```

<210> SEQ ID NO 8
<211> LENGTH: 25
<212> TYPE: DNA
<213> ORGANISM: Artificial Sequence
<220> FEATURE:
<223> OTHER INFORMATION: synthetic construct

<400> SEQUENCE: 8

```
acggttacct gcgggatcgt aaagc                                          25
```

<210> SEQ ID NO 9
<211> LENGTH: 89
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: biotin

<400> SEQUENCE: 9

```
gcacactagc ttgagcacac tgacacatgg agatcacatg cttcgacaat gcaggactcc    60
cgcagcttta cgatcccgca ggtaaccgt                                      89
```

<210> SEQ ID NO 10
<211> LENGTH: 25
<212> TYPE: DNA
<213> ORGANISM: Artificial Sequence
<220> FEATURE:
<223> OTHER INFORMATION: synthetic construct

<400> SEQUENCE: 10

```
tgtcagtgtg ctcaagctag tgtgc                                          25
```

<210> SEQ ID NO 11
<211> LENGTH: 25
<212> TYPE: DNA
<213> ORGANISM: Artificial Sequence
<220> FEATURE:
<223> OTHER INFORMATION: synthetic construct

<400> SEQUENCE: 11

```
acggttacct gcgggatcgt aaagc                                          25
```

<210> SEQ ID NO 12
<211> LENGTH: 40
<212> TYPE: DNA

```
<213> ORGANISM: Artificial Sequence
<220> FEATURE:
<223> OTHER INFORMATION: synthetic construct
<220> FEATURE:
<221> NAME/KEY: misc_feature
<222> LOCATION: (40)..(40)
<223> OTHER INFORMATION: chemical entity

<400> SEQUENCE: 12
catgtgatct ccatgtgtca gtgtgctcaa gctagtgtgc                            40

<210> SEQ ID NO 13
<211> LENGTH: 37
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(9)
<223> OTHER INFORMATION: N represents inosine (I)

<400> SEQUENCE: 13
nnnnnnnnna tgtgtcagtg tgctcaagct agtgtgc                              37

<210> SEQ ID NO 14
<211> LENGTH: 25
<212> TYPE: DNA
<213> ORGANISM: Artificial Sequence
<220> FEATURE:
<223> OTHER INFORMATION: synthetic construct

<400> SEQUENCE: 14
acggttacct gcgggatcgt aaagc                                           25

<210> SEQ ID NO 15
<211> LENGTH: 52
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (52)..(52)
<223> OTHER INFORMATION: chemical entity
<220> FEATURE:
<221> NAME/KEY: misc_feature
<222> LOCATION: (16)..(24)
<223> OTHER INFORMATION: N represents inosine (I)

<400> SEQUENCE: 15
gcattgtcga agcatnnnnn nnnnatgtgt cagtgtgctc aagctagtgt gc              52

<210> SEQ ID NO 16
<211> LENGTH: 49
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(9)
<223> OTHER INFORMATION: N represents inosine (I)
<220> FEATURE:
<221> NAME/KEY: misc_feature
<222> LOCATION: (13)..(21)
<223> OTHER INFORMATION: N represents inosine (I)

<400> SEQUENCE: 16
nnnnnnnnnc atnnnnnnnn natgtgtcag tgtgctcaag ctagtgtgc                 49
```

```
<210> SEQ ID NO 17
<211> LENGTH: 25
<212> TYPE: DNA
<213> ORGANISM: Artificial Sequence
<220> FEATURE:
<223> OTHER INFORMATION: synthetic construct

<400> SEQUENCE: 17
acggttacct gcgggatcgt aaagc                                              25

<210> SEQ ID NO 18
<211> LENGTH: 64
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (16)..(24)
<223> OTHER INFORMATION: N represents inosine (I)
<220> FEATURE:
<221> NAME/KEY: misc_feature
<222> LOCATION: (64)..(64)
<223> OTHER INFORMATION: chemical entity
<220> FEATURE:
<221> NAME/KEY: misc_feature
<222> LOCATION: (28)..(36)
<223> OTHER INFORMATION: N represents inosine (I)

<400> SEQUENCE: 18
tgcgggagtc ctgcannnnn nnnncatnnn nnnnnnatgt gtcagtgtgc tcaagctagt        60
gtgc                                                                    64

<210> SEQ ID NO 19
<211> LENGTH: 139
<212> TYPE: DNA
<213> ORGANISM: Artificial Sequence
<220> FEATURE:
<223> OTHER INFORMATION: synthetic construct

<400> SEQUENCE: 19
cagcttggac accacgtcat actagctgct agagatgtgg tgatattagt gtgtgacgat        60
ggtacgcaca agtacgaacg tgcatcagag aggacgagca ggacctggaa cctggtgctt       120
cctccaccac gtctctgac                                                   139

<210> SEQ ID NO 20
<211> LENGTH: 20
<212> TYPE: DNA
<213> ORGANISM: Artificial Sequence
<220> FEATURE:
<223> OTHER INFORMATION: synthetic construct

<400> SEQUENCE: 20
ggaagaagac agaagacctg                                                   20

<210> SEQ ID NO 21
<211> LENGTH: 24
<212> TYPE: DNA
<213> ORGANISM: Artificial Sequence
<220> FEATURE:
<223> OTHER INFORMATION: synthetic construct

<400> SEQUENCE: 21
ctcgaccact gcaggtggag ctcc                                              24
```

<210> SEQ ID NO 22
<211> LENGTH: 20
<212> TYPE: DNA
<213> ORGANISM: Artificial Sequence
<220> FEATURE:
<223> OTHER INFORMATION: synthetic construct

<400> SEQUENCE: 22
tcaggagtcg agaactgaag                                                   20

<210> SEQ ID NO 23
<211> LENGTH: 24
<212> TYPE: DNA
<213> ORGANISM: Artificial Sequence
<220> FEATURE:
<223> OTHER INFORMATION: synthetic construct

<400> SEQUENCE: 23
cgtgcttcct ctgctgcacc accg                                              24

<210> SEQ ID NO 24
<211> LENGTH: 20
<212> TYPE: DNA
<213> ORGANISM: Artificial Sequence
<220> FEATURE:
<223> OTHER INFORMATION: synthetic construct

<400> SEQUENCE: 24
tgtgtacgtc aacacgtcag                                                   20

<210> SEQ ID NO 25
<211> LENGTH: 24
<212> TYPE: DNA
<213> ORGANISM: Artificial Sequence
<220> FEATURE:
<223> OTHER INFORMATION: synthetic construct

<400> SEQUENCE: 25
cctggtgtcg aggtgagcag cagc                                              24

<210> SEQ ID NO 26
<211> LENGTH: 20
<212> TYPE: DNA
<213> ORGANISM: Artificial Sequence
<220> FEATURE:
<223> OTHER INFORMATION: synthetic construct

<400> SEQUENCE: 26
tgtggaacta ccatccaagg                                                   20

<210> SEQ ID NO 27
<211> LENGTH: 24
<212> TYPE: DNA
<213> ORGANISM: Artificial Sequence
<220> FEATURE:
<223> OTHER INFORMATION: synthetic construct

<400> SEQUENCE: 27
ctcgacgagg tccatcctgg tcgc                                              24

<210> SEQ ID NO 28
<211> LENGTH: 20
<212> TYPE: DNA
<213> ORGANISM: Artificial Sequence
<220> FEATURE:
<223> OTHER INFORMATION: synthetic construct

```
<400> SEQUENCE: 28
ccatccaaca tcgttggaag                                                   20

<210> SEQ ID NO 29
<211> LENGTH: 24
<212> TYPE: DNA
<213> ORGANISM: Artificial Sequence
<220> FEATURE:
<223> OTHER INFORMATION: synthetic construct

<400> SEQUENCE: 29
cgtgaggagc aggtcctcct gtcg                                              24

<210> SEQ ID NO 30
<211> LENGTH: 20
<212> TYPE: DNA
<213> ORGANISM: Artificial Sequence
<220> FEATURE:
<223> OTHER INFORMATION: synthetic construct

<400> SEQUENCE: 30
aacctgtcct gtgagatctg                                                   20

<210> SEQ ID NO 31
<211> LENGTH: 24
<212> TYPE: DNA
<213> ORGANISM: Artificial Sequence
<220> FEATURE:
<223> OTHER INFORMATION: synthetic construct

<400> SEQUENCE: 31
cctgacactg gtcgtggtcg aggc                                              24

<210> SEQ ID NO 32
<211> LENGTH: 20
<212> TYPE: DNA
<213> ORGANISM: Artificial Sequence
<220> FEATURE:
<223> OTHER INFORMATION: synthetic construct

<400> SEQUENCE: 32
tcacgaagct ggatgatgag                                                   20

<210> SEQ ID NO 33
<211> LENGTH: 24
<212> TYPE: DNA
<213> ORGANISM: Artificial Sequence
<220> FEATURE:
<223> OTHER INFORMATION: synthetic construct

<400> SEQUENCE: 33
ccatctcgac gacctgctcc tggg                                              24

<210> SEQ ID NO 34
<211> LENGTH: 20
<212> TYPE: DNA
<213> ORGANISM: Artificial Sequence
<220> FEATURE:
<223> OTHER INFORMATION: synthetic construct

<400> SEQUENCE: 34
tagcatcgat cgaacgtagg                                                   20

<210> SEQ ID NO 35
```

```
<211> LENGTH: 24
<212> TYPE: DNA
<213> ORGANISM: Artificial Sequence
<220> FEATURE:
<223> OTHER INFORMATION: synthetic construct

<400> SEQUENCE: 35
ccacgaggtc tccactggtc cagg                                            24

<210> SEQ ID NO 36
<211> LENGTH: 20
<212> TYPE: DNA
<213> ORGANISM: Artificial Sequence
<220> FEATURE:
<223> OTHER INFORMATION: synthetic construct

<400> SEQUENCE: 36
tcgaagctac tgtcgagatg                                                 20

<210> SEQ ID NO 37
<211> LENGTH: 24
<212> TYPE: DNA
<213> ORGANISM: Artificial Sequence
<220> FEATURE:
<223> OTHER INFORMATION: synthetic construct

<400> SEQUENCE: 37
ccactgagct gctcctccag gtgg                                            24

<210> SEQ ID NO 38
<211> LENGTH: 22
<212> TYPE: DNA
<213> ORGANISM: Artificial Sequence
<220> FEATURE:
<223> OTHER INFORMATION: synthetic construct

<400> SEQUENCE: 38
cagcttggac accacgtcat ac                                              22

<210> SEQ ID NO 39
<211> LENGTH: 21
<212> TYPE: DNA
<213> ORGANISM: Artificial Sequence
<220> FEATURE:
<223> OTHER INFORMATION: synthetic construct

<400> SEQUENCE: 39
gtcagagacg tggtggagga a                                               21

<210> SEQ ID NO 40
<211> LENGTH: 60
<212> TYPE: DNA
<213> ORGANISM: Artificial Sequence
<220> FEATURE:
<223> OTHER INFORMATION: synthetic construct

<400> SEQUENCE: 40
cagcttggac accacgtcat actagctgct agagatgtgg tgatattagt gtgtgacgat     60

<210> SEQ ID NO 41
<211> LENGTH: 60
<212> TYPE: DNA
<213> ORGANISM: Artificial Sequence
<220> FEATURE:
<223> OTHER INFORMATION: synthetic construct

<400> SEQUENCE: 41
```
cagcttggac accacgtcat acggaagaag acagaagacc tgatattagt gtgtgacgat    60

<210> SEQ ID NO 42
<211> LENGTH: 60
<212> TYPE: DNA
<213> ORGANISM: Artificial Sequence
<220> FEATURE:
<223> OTHER INFORMATION: synthetic construct

<400> SEQUENCE: 42
cagcttggac accacgtcat actcaggagt cgagaactga agatattagt gtgtgacgat    60

<210> SEQ ID NO 43
<211> LENGTH: 60
<212> TYPE: DNA
<213> ORGANISM: Artificial Sequence
<220> FEATURE:
<223> OTHER INFORMATION: synthetic construct

<400> SEQUENCE: 43
cagcttggac accacgtcat actgtgtacg tcaacacgtc agatattagt gtgtgacgat    60

<210> SEQ ID NO 44
<211> LENGTH: 60
<212> TYPE: DNA
<213> ORGANISM: Artificial Sequence
<220> FEATURE:
<223> OTHER INFORMATION: synthetic construct

<400> SEQUENCE: 44
cagcttggac accacgtcat actgtggaac taccatccaa ggatattagt gtgtgacgat    60

<210> SEQ ID NO 45
<211> LENGTH: 60
<212> TYPE: DNA
<213> ORGANISM: Artificial Sequence
<220> FEATURE:
<223> OTHER INFORMATION: synthetic construct

<400> SEQUENCE: 45
cagcttggac accacgtcat acccatccaa catcgttgga agatattagt gtgtgacgat    60

<210> SEQ ID NO 46
<211> LENGTH: 60
<212> TYPE: DNA
<213> ORGANISM: Artificial Sequence
<220> FEATURE:
<223> OTHER INFORMATION: synthetic construct

<400> SEQUENCE: 46
cagcttggac accacgtcat acaacctgtc ctgtgagatc tgatattagt gtgtgacgat    60

<210> SEQ ID NO 47
<211> LENGTH: 60
<212> TYPE: DNA
<213> ORGANISM: Artificial Sequence
<220> FEATURE:
<223> OTHER INFORMATION: synthetic construct

<400> SEQUENCE: 47
cagcttggac accacgtcat actcacgaag ctggatgatg agatattagt gtgtgacgat    60

<210> SEQ ID NO 48
<211> LENGTH: 60
<212> TYPE: DNA

<213> ORGANISM: Artificial Sequence
<220> FEATURE:
<223> OTHER INFORMATION: synthetic construct

<400> SEQUENCE: 48
cagcttggac accacgtcat actagcatcg atcgaacgta ggatattagt gtgtgacgat    60

<210> SEQ ID NO 49
<211> LENGTH: 60
<212> TYPE: DNA
<213> ORGANISM: Artificial Sequence
<220> FEATURE:
<223> OTHER INFORMATION: synthetic construct

<400> SEQUENCE: 49
cagcttggac accacgtcat actcgaagct actgtcgaga tgatattagt gtgtgacgat    60

<210> SEQ ID NO 50
<211> LENGTH: 54
<212> TYPE: DNA
<213> ORGANISM: Artificial Sequence
<220> FEATURE:
<223> OTHER INFORMATION: synthetic construct

<400> SEQUENCE: 50
gtcctctctg atgcacgttc gtacttgtgc gtaccatcgt cacacactaa tatc    54

<210> SEQ ID NO 51
<211> LENGTH: 65
<212> TYPE: DNA
<213> ORGANISM: Artificial Sequence
<220> FEATURE:
<223> OTHER INFORMATION: synthetic construct

<400> SEQUENCE: 51
gaacgtgcat cagagaggac gagcaggacc tggaacctgg tgcaattcca gcttctagga    60
agact    65

<210> SEQ ID NO 52
<211> LENGTH: 65
<212> TYPE: DNA
<213> ORGANISM: Artificial Sequence
<220> FEATURE:
<223> OTHER INFORMATION: synthetic construct

<400> SEQUENCE: 52
gaacgtgcat cagagaggac tcgaccactg caggtggagc tccaattcca gcttctagga    60
agact    65

<210> SEQ ID NO 53
<211> LENGTH: 65
<212> TYPE: DNA
<213> ORGANISM: Artificial Sequence
<220> FEATURE:
<223> OTHER INFORMATION: synthetic construct

<400> SEQUENCE: 53
gaacgtgcat cagagaggac gtgcttcctc tgctgcacca ccgaattcca gcttctagga    60
agact    65

<210> SEQ ID NO 54
<211> LENGTH: 65
<212> TYPE: DNA
<213> ORGANISM: Artificial Sequence

```
<220> FEATURE:
<223> OTHER INFORMATION: synthetic construct

<400> SEQUENCE: 54
gaacgtgcat cagagaggac ctggtgtcga ggtgagcagc agcaattcca gcttctagga    60
agact                                                                65

<210> SEQ ID NO 55
<211> LENGTH: 65
<212> TYPE: DNA
<213> ORGANISM: Artificial Sequence
<220> FEATURE:
<223> OTHER INFORMATION: synthetic construct

<400> SEQUENCE: 55
gaacgtgcat cagagaggac tcgacgaggt ccatcctggt cgcaattcca gcttctagga    60
agact                                                                65

<210> SEQ ID NO 56
<211> LENGTH: 65
<212> TYPE: DNA
<213> ORGANISM: Artificial Sequence
<220> FEATURE:
<223> OTHER INFORMATION: synthetic construct

<400> SEQUENCE: 56
gaacgtgcat cagagaggac gtgaggagca ggtcctcctg tcgaattcca gcttctagga    60
agact                                                                65

<210> SEQ ID NO 57
<211> LENGTH: 65
<212> TYPE: DNA
<213> ORGANISM: Artificial Sequence
<220> FEATURE:
<223> OTHER INFORMATION: synthetic construct

<400> SEQUENCE: 57
gaacgtgcat cagagaggac ctgacactgg tcgtggtcga ggcaattcca gcttctagga    60
agact                                                                65

<210> SEQ ID NO 58
<211> LENGTH: 65
<212> TYPE: DNA
<213> ORGANISM: Artificial Sequence
<220> FEATURE:
<223> OTHER INFORMATION: synthetic construct

<400> SEQUENCE: 58
gaacgtgcat cagagaggac catctcgacg acctgctcct gggaattcca gcttctagga    60
agact                                                                65

<210> SEQ ID NO 59
<211> LENGTH: 65
<212> TYPE: DNA
<213> ORGANISM: Artificial Sequence
<220> FEATURE:
<223> OTHER INFORMATION: synthetic construct

<400> SEQUENCE: 59
gaacgtgcat cagagaggac cacgaggtct ccactggtcc aggaattcca gcttctagga    60
agact                                                                65
```

```
<210> SEQ ID NO 60
<211> LENGTH: 65
<212> TYPE: DNA
<213> ORGANISM: Artificial Sequence
<220> FEATURE:
<223> OTHER INFORMATION: synthetic construct

<400> SEQUENCE: 60
gaacgtgcat cagagaggac cactgagctg ctcctccagg tggaattcca gcttctagga     60
agact                                                                 65

<210> SEQ ID NO 61
<211> LENGTH: 42
<212> TYPE: DNA
<213> ORGANISM: Artificial Sequence
<220> FEATURE:
<223> OTHER INFORMATION: synthetic construct

<400> SEQUENCE: 61
gtcagagacg tggtggagga agtcttccta gaagctggaa tt                        42

<210> SEQ ID NO 62
<211> LENGTH: 18
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (1)..(1)
<223> OTHER INFORMATION: 6-FAM
<220> FEATURE:
<221> NAME/KEY: misc_feature
<222> LOCATION: (18)..(18)
<223> OTHER INFORMATION: MGBNFQ

<400> SEQUENCE: 62
tccagcttct aggaagac                                                   18

<210> SEQ ID NO 63
<211> LENGTH: 30
<212> TYPE: DNA
<213> ORGANISM: Artificial Sequence
<220> FEATURE:
<223> OTHER INFORMATION: synthetic construct

<400> SEQUENCE: 63
gtcatactag ctgctagaga tgtggtgata                                      30

<210> SEQ ID NO 64
<211> LENGTH: 28
<212> TYPE: DNA
<213> ORGANISM: Artificial Sequence
<220> FEATURE:
<223> OTHER INFORMATION: synthetic construct

<400> SEQUENCE: 64
catacggaag aagacagaag acctgata                                        28

<210> SEQ ID NO 65
<211> LENGTH: 29
<212> TYPE: DNA
<213> ORGANISM: Artificial Sequence
<220> FEATURE:
<223> OTHER INFORMATION: synthetic construct

<400> SEQUENCE: 65
```

```
tcatactcag gagtcgagaa ctgaagata                                              29

<210> SEQ ID NO 66
<211> LENGTH: 28
<212> TYPE: DNA
<213> ORGANISM: Artificial Sequence
<220> FEATURE:
<223> OTHER INFORMATION: synthetic construct

<400> SEQUENCE: 66
catactgtgt acgtcaacac gtcagata                                               28

<210> SEQ ID NO 67
<211> LENGTH: 28
<212> TYPE: DNA
<213> ORGANISM: Artificial Sequence
<220> FEATURE:
<223> OTHER INFORMATION: synthetic construct

<400> SEQUENCE: 67
catactgtgg aactaccatc caaggata                                               28

<210> SEQ ID NO 68
<211> LENGTH: 22
<212> TYPE: DNA
<213> ORGANISM: Artificial Sequence
<220> FEATURE:
<223> OTHER INFORMATION: synthetic construct

<400> SEQUENCE: 68
ccatccaaca tcgttggaag at                                                     22

<210> SEQ ID NO 69
<211> LENGTH: 28
<212> TYPE: DNA
<213> ORGANISM: Artificial Sequence
<220> FEATURE:
<223> OTHER INFORMATION: synthetic construct

<400> SEQUENCE: 69
catacaacct gtcctgtgag atctgata                                               28

<210> SEQ ID NO 70
<211> LENGTH: 27
<212> TYPE: DNA
<213> ORGANISM: Artificial Sequence
<220> FEATURE:
<223> OTHER INFORMATION: synthetic construct

<400> SEQUENCE: 70
atactcacga agctggatga tgagata                                                27

<210> SEQ ID NO 71
<211> LENGTH: 28
<212> TYPE: DNA
<213> ORGANISM: Artificial Sequence
<220> FEATURE:
<223> OTHER INFORMATION: synthetic construct

<400> SEQUENCE: 71
catactagca tcgatcgaac gtaggata                                               28

<210> SEQ ID NO 72
<211> LENGTH: 29
<212> TYPE: DNA
```

```
<213> ORGANISM: Artificial Sequence
<220> FEATURE:
<223> OTHER INFORMATION: synthetic construct

<400> SEQUENCE: 72
tcatactcga agctactgtc gagatgata                                          29

<210> SEQ ID NO 73
<211> LENGTH: 26
<212> TYPE: DNA
<213> ORGANISM: Artificial Sequence
<220> FEATURE:
<223> OTHER INFORMATION: synthetic construct

<400> SEQUENCE: 73
atattagtgt gtgacgatgg tacgca                                             26

<210> SEQ ID NO 74
<211> LENGTH: 24
<212> TYPE: DNA
<213> ORGANISM: Artificial Sequence
<220> FEATURE:
<223> OTHER INFORMATION: synthetic construct

<400> SEQUENCE: 74
acaagtacga acgtgcatca gaga                                               24

<210> SEQ ID NO 75
<211> LENGTH: 19
<212> TYPE: DNA
<213> ORGANISM: Artificial Sequence
<220> FEATURE:
<223> OTHER INFORMATION: synthetic construct

<400> SEQUENCE: 75
cgagcaggac ctggaacct                                                     19

<210> SEQ ID NO 76
<211> LENGTH: 18
<212> TYPE: DNA
<213> ORGANISM: Artificial Sequence
<220> FEATURE:
<223> OTHER INFORMATION: synthetic construct

<400> SEQUENCE: 76
tcgaccactg caggtgga                                                      18

<210> SEQ ID NO 77
<211> LENGTH: 18
<212> TYPE: DNA
<213> ORGANISM: Artificial Sequence
<220> FEATURE:
<223> OTHER INFORMATION: synthetic construct

<400> SEQUENCE: 77
gcttcctctg ctgcacca                                                      18

<210> SEQ ID NO 78
<211> LENGTH: 19
<212> TYPE: DNA
<213> ORGANISM: Artificial Sequence
<220> FEATURE:
<223> OTHER INFORMATION: synthetic construct

<400> SEQUENCE: 78
ggtgtcgagg tgagcagca                                                     19
```

<210> SEQ ID NO 79
<211> LENGTH: 19
<212> TYPE: DNA
<213> ORGANISM: Artificial Sequence
<220> FEATURE:
<223> OTHER INFORMATION: synthetic construct

<400> SEQUENCE: 79
cgacgaggtc catcctggt                                                  19

<210> SEQ ID NO 80
<211> LENGTH: 21
<212> TYPE: DNA
<213> ORGANISM: Artificial Sequence
<220> FEATURE:
<223> OTHER INFORMATION: synthetic construct

<400> SEQUENCE: 80
gtgaggagca ggtcctcctg t                                               21

<210> SEQ ID NO 81
<211> LENGTH: 20
<212> TYPE: DNA
<213> ORGANISM: Artificial Sequence
<220> FEATURE:
<223> OTHER INFORMATION: synthetic construct

<400> SEQUENCE: 81
ctgacactgg tcgtggtcga                                                 20

<210> SEQ ID NO 82
<211> LENGTH: 20
<212> TYPE: DNA
<213> ORGANISM: Artificial Sequence
<220> FEATURE:
<223> OTHER INFORMATION: synthetic construct

<400> SEQUENCE: 82
catctcgacg acctgctcct                                                 20

<210> SEQ ID NO 83
<211> LENGTH: 20
<212> TYPE: DNA
<213> ORGANISM: Artificial Sequence
<220> FEATURE:
<223> OTHER INFORMATION: synthetic construct

<400> SEQUENCE: 83
acgaggtctc cactggtcca                                                 20

<210> SEQ ID NO 84
<211> LENGTH: 20
<212> TYPE: DNA
<213> ORGANISM: Artificial Sequence
<220> FEATURE:
<223> OTHER INFORMATION: synthetic construct

<400> SEQUENCE: 84
actgagctgc tcctccaggt                                                 20

<210> SEQ ID NO 85
<211> LENGTH: 62
<212> TYPE: DNA
<213> ORGANISM: Artificial Sequence
<220> FEATURE:

<223> OTHER INFORMATION: synthetic construct

<400> SEQUENCE: 85
ggcgggtttg ggtgcggggt ttgggtcggg ggtttgggtg gcaatgctcg ggaaggctac    60
tc                                                                   62

<210> SEQ ID NO 86
<211> LENGTH: 62
<212> TYPE: DNA
<213> ORGANISM: Artificial Sequence
<220> FEATURE:
<223> OTHER INFORMATION: synthetic construct

<400> SEQUENCE: 86
gcggggtttg ggtcggggt ttgggtggcg ggtttgggtc ggatcccgtg agtcgatggt    60
tt                                                                   62

<210> SEQ ID NO 87
<211> LENGTH: 62
<212> TYPE: DNA
<213> ORGANISM: Artificial Sequence
<220> FEATURE:
<223> OTHER INFORMATION: synthetic construct

<400> SEQUENCE: 87
cgggggtttg ggtggcgggt ttgggtgcgg ggtttgggtg cgcgcaccgc agtttggtca    60
at                                                                   62

<210> SEQ ID NO 88
<211> LENGTH: 60
<212> TYPE: DNA
<213> ORGANISM: Artificial Sequence
<220> FEATURE:
<223> OTHER INFORMATION: synthetic construct

<400> SEQUENCE: 88
gcggggtttg ggtcggggtt tgggtgcggg tttgggtcgg cacgcggcag tcgagttaat    60

<210> SEQ ID NO 89
<211> LENGTH: 57
<212> TYPE: DNA
<213> ORGANISM: Artificial Sequence
<220> FEATURE:
<223> OTHER INFORMATION: synthetic construct

<400> SEQUENCE: 89
gcggggtttg ggtcgggttt gggtcgggtt tgggtcggag cccggtctca tcgttgt       57

<210> SEQ ID NO 90
<211> LENGTH: 56
<212> TYPE: DNA
<213> ORGANISM: Artificial Sequence
<220> FEATURE:
<223> OTHER INFORMATION: synthetic construct

<400> SEQUENCE: 90
gcggggtttg ggtgggtttg ggtgggtttg ggtcggtccg acgcaacaat agggca         56

<210> SEQ ID NO 91
<211> LENGTH: 16
<212> TYPE: DNA
<213> ORGANISM: Artificial Sequence
<220> FEATURE:
<223> OTHER INFORMATION: synthetic construct

```
<220> FEATURE:
<221> NAME/KEY: misc_feature
<222> LOCATION: (1)..(1)
<223> OTHER INFORMATION: biotin

<400> SEQUENCE: 91
gccacccaaa cccccg                                                      16

<210> SEQ ID NO 92
<211> LENGTH: 5
<212> TYPE: DNA
<213> ORGANISM: Artificial Sequence
<220> FEATURE:
<223> OTHER INFORMATION: synthetic construct

<400> SEQUENCE: 92 tgttc                                                                   5

<210> SEQ ID NO 93
<211> LENGTH: 5
<212> TYPE: DNA
<213> ORGANISM: Artificial Sequence
<220> FEATURE:
<223> OTHER INFORMATION: synthetic construct

<400> SEQUENCE: 93 cgagc                                                                   5

<210> SEQ ID NO 94
<211> LENGTH: 5
<212> TYPE: DNA
<213> ORGANISM: Artificial Sequence
<220> FEATURE:
<223> OTHER INFORMATION: synthetic construct

<400> SEQUENCE: 94 ggata                                                                   5

<210> SEQ ID NO 95
<211> LENGTH: 5
<212> TYPE: DNA
<213> ORGANISM: Artificial Sequence
<220> FEATURE:
<223> OTHER INFORMATION: synthetic construct

<400> SEQUENCE: 95 cgctg                                                                   5

<210> SEQ ID NO 96
<211> LENGTH: 5
<212> TYPE: DNA
<213> ORGANISM: Artificial Sequence
<220> FEATURE:
<223> OTHER INFORMATION: synthetic construct

<400> SEQUENCE: 96 gttat                                                                   5

<210> SEQ ID NO 97
<211> LENGTH: 5
<212> TYPE: DNA
<213> ORGANISM: Artificial Sequence
<220> FEATURE:
<223> OTHER INFORMATION: synthetic construct

<400> SEQUENCE: 97
``` agtgc                                                         5

<210> SEQ ID NO 98
<211> LENGTH: 5
<212> TYPE: DNA
<213> ORGANISM: Artificial Sequence
<220> FEATURE:
<223> OTHER INFORMATION: synthetic construct

<400> SEQUENCE: 98 acctg                                                         5

<210> SEQ ID NO 99
<211> LENGTH: 5
<212> TYPE: DNA
<213> ORGANISM: Artificial Sequence
<220> FEATURE:
<223> OTHER INFORMATION: synthetic construct

<400> SEQUENCE: 99 ctggt                                                         5

<210> SEQ ID NO 100
<211> LENGTH: 5
<212> TYPE: DNA
<213> ORGANISM: Artificial Sequence
<220> FEATURE:
<223> OTHER INFORMATION: synthetic construct

<400> SEQUENCE: 100 tagga                                                         5

<210> SEQ ID NO 101
<211> LENGTH: 5
<212> TYPE: DNA
<213> ORGANISM: Artificial Sequence
<220> FEATURE:
<223> OTHER INFORMATION: synthetic construct

<400> SEQUENCE: 101 actca                                                         5

<210> SEQ ID NO 102
<211> LENGTH: 5
<212> TYPE: DNA
<213> ORGANISM: Artificial Sequence
<220> FEATURE:
<223> OTHER INFORMATION: synthetic construct

<400> SEQUENCE: 102 cttac                                                         5

<210> SEQ ID NO 103
<211> LENGTH: 5
<212> TYPE: DNA
<213> ORGANISM: Artificial Sequence
<220> FEATURE:
<223> OTHER INFORMATION: synthetic construct

<400> SEQUENCE: 103 cgcac                                                         5

<210> SEQ ID NO 104
<211> LENGTH: 5
<212> TYPE: DNA
<213> ORGANISM: Artificial Sequence

```
<220> FEATURE:
<223> OTHER INFORMATION: synthetic construct

<400> SEQUENCE: 104 tcgcg                                                                        5

<210> SEQ ID NO 105
<211> LENGTH: 5
<212> TYPE: DNA
<213> ORGANISM: Artificial Sequence
<220> FEATURE:
<223> OTHER INFORMATION: synthetic construct

<400> SEQUENCE: 105 cggat                                                                        5

<210> SEQ ID NO 106
<211> LENGTH: 5
<212> TYPE: DNA
<213> ORGANISM: Artificial Sequence
<220> FEATURE:
<223> OTHER INFORMATION: synthetic construct

<400> SEQUENCE: 106 gagat                                                                        5

<210> SEQ ID NO 107
<211> LENGTH: 5
<212> TYPE: DNA
<213> ORGANISM: Artificial Sequence
<220> FEATURE:
<223> OTHER INFORMATION: synthetic construct

<400> SEQUENCE: 107 tgtag                                                                        5

<210> SEQ ID NO 108
<211> LENGTH: 5
<212> TYPE: DNA
<213> ORGANISM: Artificial Sequence
<220> FEATURE:
<223> OTHER INFORMATION: synthetic construct

<400> SEQUENCE: 108 gtgtt                                                                        5

<210> SEQ ID NO 109
<211> LENGTH: 5
<212> TYPE: DNA
<213> ORGANISM: Artificial Sequence
<220> FEATURE:
<223> OTHER INFORMATION: synthetic construct

<400> SEQUENCE: 109 agatg                                                                        5

<210> SEQ ID NO 110
<211> LENGTH: 5
<212> TYPE: DNA
<213> ORGANISM: Artificial Sequence
<220> FEATURE:
<223> OTHER INFORMATION: synthetic construct

<400> SEQUENCE: 110 atcct                                                                        5
```

```
<210> SEQ ID NO 111
<211> LENGTH: 5
<212> TYPE: DNA
<213> ORGANISM: Artificial Sequence
<220> FEATURE:
<223> OTHER INFORMATION: synthetic construct

<400> SEQUENCE: 111 ttgct                                                                      5

<210> SEQ ID NO 112
<211> LENGTH: 5
<212> TYPE: DNA
<213> ORGANISM: Artificial Sequence
<220> FEATURE:
<223> OTHER INFORMATION: synthetic construct

<400> SEQUENCE: 112 acgta                                                                      5

<210> SEQ ID NO 113
<211> LENGTH: 5
<212> TYPE: DNA
<213> ORGANISM: Artificial Sequence
<220> FEATURE:
<223> OTHER INFORMATION: synthetic construct

<400> SEQUENCE: 113 atcac                                                                      5

<210> SEQ ID NO 114
<211> LENGTH: 5
<212> TYPE: DNA
<213> ORGANISM: Artificial Sequence
<220> FEATURE:
<223> OTHER INFORMATION: synthetic construct

<400> SEQUENCE: 114 tatcc                                                                      5

<210> SEQ ID NO 115
<211> LENGTH: 5
<212> TYPE: DNA
<213> ORGANISM: Artificial Sequence
<220> FEATURE:
<223> OTHER INFORMATION: synthetic construct

<400> SEQUENCE: 115 ggaag                                                                      5

<210> SEQ ID NO 116
<211> LENGTH: 5
<212> TYPE: DNA
<213> ORGANISM: Artificial Sequence
<220> FEATURE:
<223> OTHER INFORMATION: synthetic construct

<400> SEQUENCE: 116 cggtc                                                                      5

<210> SEQ ID NO 117
<211> LENGTH: 5
<212> TYPE: DNA
<213> ORGANISM: Artificial Sequence
<220> FEATURE:
<223> OTHER INFORMATION: synthetic construct
```

```
<400> SEQUENCE: 117 tgctt                                                               5

<210> SEQ ID NO 118
<211> LENGTH: 5
<212> TYPE: DNA
<213> ORGANISM: Artificial Sequence
<220> FEATURE:
<223> OTHER INFORMATION: synthetic construct

<400> SEQUENCE: 118 ttagc                                                               5

<210> SEQ ID NO 119
<211> LENGTH: 5
<212> TYPE: DNA
<213> ORGANISM: Artificial Sequence
<220> FEATURE:
<223> OTHER INFORMATION: synthetic construct

<400> SEQUENCE: 119 gctga                                                               5

<210> SEQ ID NO 120
<211> LENGTH: 5
<212> TYPE: DNA
<213> ORGANISM: Artificial Sequence
<220> FEATURE:
<223> OTHER INFORMATION: synthetic construct

<400> SEQUENCE: 120 gaacg                                                               5

<210> SEQ ID NO 121
<211> LENGTH: 5
<212> TYPE: DNA
<213> ORGANISM: Artificial Sequence
<220> FEATURE:
<223> OTHER INFORMATION: synthetic construct

<400> SEQUENCE: 121 catgg                                                               5

<210> SEQ ID NO 122
<211> LENGTH: 5
<212> TYPE: DNA
<213> ORGANISM: Artificial Sequence
<220> FEATURE:
<223> OTHER INFORMATION: synthetic construct

<400> SEQUENCE: 122 tggta                                                               5

<210> SEQ ID NO 123
<211> LENGTH: 5
<212> TYPE: DNA
<213> ORGANISM: Artificial Sequence
<220> FEATURE:
<223> OTHER INFORMATION: synthetic construct

<400> SEQUENCE: 123 tcaag                                                               5

<210> SEQ ID NO 124
```

```
<211> LENGTH: 5
<212> TYPE: DNA
<213> ORGANISM: Artificial Sequence
<220> FEATURE:
<223> OTHER INFORMATION: synthetic construct

<400> SEQUENCE: 124 atcga                                                                   5

<210> SEQ ID NO 125
<211> LENGTH: 5
<212> TYPE: DNA
<213> ORGANISM: Artificial Sequence
<220> FEATURE:
<223> OTHER INFORMATION: synthetic construct

<400> SEQUENCE: 125 atgca                                                                   5

<210> SEQ ID NO 126
<211> LENGTH: 5
<212> TYPE: DNA
<213> ORGANISM: Artificial Sequence
<220> FEATURE:
<223> OTHER INFORMATION: synthetic construct

<400> SEQUENCE: 126 actag                                                                   5

<210> SEQ ID NO 127
<211> LENGTH: 5
<212> TYPE: DNA
<213> ORGANISM: Artificial Sequence
<220> FEATURE:
<223> OTHER INFORMATION: synthetic construct

<400> SEQUENCE: 127 tacct                                                                   5

<210> SEQ ID NO 128
<211> LENGTH: 5
<212> TYPE: DNA
<213> ORGANISM: Artificial Sequence
<220> FEATURE:
<223> OTHER INFORMATION: synthetic construct

<400> SEQUENCE: 128 tacga                                                                   5

<210> SEQ ID NO 129
<211> LENGTH: 5
<212> TYPE: DNA
<213> ORGANISM: Artificial Sequence
<220> FEATURE:
<223> OTHER INFORMATION: synthetic construct

<400> SEQUENCE: 129 cttca                                                                   5

<210> SEQ ID NO 130
<211> LENGTH: 5
<212> TYPE: DNA
<213> ORGANISM: Artificial Sequence
<220> FEATURE:
<223> OTHER INFORMATION: synthetic construct

<400> SEQUENCE: 130
``` ctctt                                                                       5

<210> SEQ ID NO 131
<211> LENGTH: 5
<212> TYPE: DNA
<213> ORGANISM: Artificial Sequence
<220> FEATURE:
<223> OTHER INFORMATION: synthetic construct

<400> SEQUENCE: 131 tcatc                                                                       5

<210> SEQ ID NO 132
<211> LENGTH: 5
<212> TYPE: DNA
<213> ORGANISM: Artificial Sequence
<220> FEATURE:
<223> OTHER INFORMATION: synthetic construct

<400> SEQUENCE: 132 attcc                                                                       5

<210> SEQ ID NO 133
<211> LENGTH: 5
<212> TYPE: DNA
<213> ORGANISM: Artificial Sequence
<220> FEATURE:
<223> OTHER INFORMATION: synthetic construct

<400> SEQUENCE: 133 cgacg                                                                       5

<210> SEQ ID NO 134
<211> LENGTH: 5
<212> TYPE: DNA
<213> ORGANISM: Artificial Sequence
<220> FEATURE:
<223> OTHER INFORMATION: synthetic construct

<400> SEQUENCE: 134 cctgt                                                                       5

<210> SEQ ID NO 135
<211> LENGTH: 5
<212> TYPE: DNA
<213> ORGANISM: Artificial Sequence
<220> FEATURE:
<223> OTHER INFORMATION: synthetic construct

<400> SEQUENCE: 135 ccttc                                                                       5

<210> SEQ ID NO 136
<211> LENGTH: 5
<212> TYPE: DNA
<213> ORGANISM: Artificial Sequence
<220> FEATURE:
<223> OTHER INFORMATION: synthetic construct

<400> SEQUENCE: 136 acacc                                                                       5

<210> SEQ ID NO 137
<211> LENGTH: 5
<212> TYPE: DNA

```
<213> ORGANISM: Artificial Sequence
<220> FEATURE:
<223> OTHER INFORMATION: synthetic construct

<400> SEQUENCE: 137 taaca                                                              5

<210> SEQ ID NO 138
<211> LENGTH: 5
<212> TYPE: DNA
<213> ORGANISM: Artificial Sequence
<220> FEATURE:
<223> OTHER INFORMATION: synthetic construct

<400> SEQUENCE: 138 taaca                                                              5

<210> SEQ ID NO 139
<211> LENGTH: 5
<212> TYPE: DNA
<213> ORGANISM: Artificial Sequence
<220> FEATURE:
<223> OTHER INFORMATION: synthetic construct

<400> SEQUENCE: 139 ccagg                                                              5

<210> SEQ ID NO 140
<211> LENGTH: 5
<212> TYPE: DNA
<213> ORGANISM: Artificial Sequence
<220> FEATURE:
<223> OTHER INFORMATION: synthetic construct

<400> SEQUENCE: 140 atgtc                                                              5

<210> SEQ ID NO 141
<211> LENGTH: 5
<212> TYPE: DNA
<213> ORGANISM: Artificial Sequence
<220> FEATURE:
<223> OTHER INFORMATION: synthetic construct

<400> SEQUENCE: 141 gagga                                                              5

<210> SEQ ID NO 142
<211> LENGTH: 5
<212> TYPE: DNA
<213> ORGANISM: Artificial Sequence
<220> FEATURE:
<223> OTHER INFORMATION: synthetic construct

<400> SEQUENCE: 142 ggtca                                                              5

<210> SEQ ID NO 143
<211> LENGTH: 5
<212> TYPE: DNA
<213> ORGANISM: Artificial Sequence
<220> FEATURE:
<223> OTHER INFORMATION: synthetic construct

<400> SEQUENCE: 143 gactt                                                              5
```

```
<210> SEQ ID NO 144
<211> LENGTH: 5
<212> TYPE: DNA
<213> ORGANISM: Artificial Sequence
<220> FEATURE:
<223> OTHER INFORMATION: synthetic construct

<400> SEQUENCE: 144 ggtgg                                                                    5

<210> SEQ ID NO 145
<211> LENGTH: 5
<212> TYPE: DNA
<213> ORGANISM: Artificial Sequence
<220> FEATURE:
<223> OTHER INFORMATION: synthetic construct

<400> SEQUENCE: 145 caact                                                                    5

<210> SEQ ID NO 146
<211> LENGTH: 5
<212> TYPE: DNA
<213> ORGANISM: Artificial Sequence
<220> FEATURE:
<223> OTHER INFORMATION: synthetic construct

<400> SEQUENCE: 146 atgag                                                                    5

<210> SEQ ID NO 147
<211> LENGTH: 5
<212> TYPE: DNA
<213> ORGANISM: Artificial Sequence
<220> FEATURE:
<223> OTHER INFORMATION: synthetic construct

<400> SEQUENCE: 147 tctgc                                                                    5

<210> SEQ ID NO 148
<211> LENGTH: 5
<212> TYPE: DNA
<213> ORGANISM: Artificial Sequence
<220> FEATURE:
<223> OTHER INFORMATION: synthetic construct

<400> SEQUENCE: 148 atagg                                                                    5

<210> SEQ ID NO 149
<211> LENGTH: 5
<212> TYPE: DNA
<213> ORGANISM: Artificial Sequence
<220> FEATURE:
<223> OTHER INFORMATION: synthetic construct

<400> SEQUENCE: 149 ctacc                                                                    5

<210> SEQ ID NO 150
<211> LENGTH: 5
<212> TYPE: DNA
<213> ORGANISM: Artificial Sequence
<220> FEATURE:
```

<223> OTHER INFORMATION: synthetic construct

<400> SEQUENCE: 150 aagtg                                                                    5

<210> SEQ ID NO 151
<211> LENGTH: 5
<212> TYPE: DNA
<213> ORGANISM: Artificial Sequence
<220> FEATURE:
<223> OTHER INFORMATION: synthetic construct

<400> SEQUENCE: 151 tccaa                                                                    5

<210> SEQ ID NO 152
<211> LENGTH: 5
<212> TYPE: DNA
<213> ORGANISM: Artificial Sequence
<220> FEATURE:
<223> OTHER INFORMATION: synthetic construct

<400> SEQUENCE: 152 gctct                                                                    5

<210> SEQ ID NO 153
<211> LENGTH: 5
<212> TYPE: DNA
<213> ORGANISM: Artificial Sequence
<220> FEATURE:
<223> OTHER INFORMATION: synthetic construct

<400> SEQUENCE: 153 ggagt                                                                    5

<210> SEQ ID NO 154
<211> LENGTH: 5
<212> TYPE: DNA
<213> ORGANISM: Artificial Sequence
<220> FEATURE:
<223> OTHER INFORMATION: synthetic construct

<400> SEQUENCE: 154 aatcg                                                                    5

<210> SEQ ID NO 155
<211> LENGTH: 5
<212> TYPE: DNA
<213> ORGANISM: Artificial Sequence
<220> FEATURE:
<223> OTHER INFORMATION: synthetic construct

<400> SEQUENCE: 155 aagct                                                                    5

<210> SEQ ID NO 156
<211> LENGTH: 5
<212> TYPE: DNA
<213> ORGANISM: Artificial Sequence
<220> FEATURE:
<223> OTHER INFORMATION: synthetic construct

<400> SEQUENCE: 156 ccgaa                                                                    5

```
<210> SEQ ID NO 157
<211> LENGTH: 5
<212> TYPE: DNA
<213> ORGANISM: Artificial Sequence
<220> FEATURE:
<223> OTHER INFORMATION: synthetic construct

<400> SEQUENCE: 157 tttgt                                                                    5

<210> SEQ ID NO 158
<211> LENGTH: 5
<212> TYPE: DNA
<213> ORGANISM: Artificial Sequence
<220> FEATURE:
<223> OTHER INFORMATION: synthetic construct

<400> SEQUENCE: 158 ccgtg                                                                    5

<210> SEQ ID NO 159
<211> LENGTH: 5
<212> TYPE: DNA
<213> ORGANISM: Artificial Sequence
<220> FEATURE:
<223> OTHER INFORMATION: synthetic construct

<400> SEQUENCE: 159 tttcg                                                                    5

<210> SEQ ID NO 160
<211> LENGTH: 5
<212> TYPE: DNA
<213> ORGANISM: Artificial Sequence
<220> FEATURE:
<223> OTHER INFORMATION: synthetic construct

<400> SEQUENCE: 160 tgagg                                                                    5

<210> SEQ ID NO 161
<211> LENGTH: 5
<212> TYPE: DNA
<213> ORGANISM: Artificial Sequence
<220> FEATURE:
<223> OTHER INFORMATION: synthetic construct

<400> SEQUENCE: 161 gttgc                                                                    5

<210> SEQ ID NO 162
<211> LENGTH: 5
<212> TYPE: DNA
<213> ORGANISM: Artificial Sequence
<220> FEATURE:
<223> OTHER INFORMATION: synthetic construct

<400> SEQUENCE: 162 aacta                                                                    5

<210> SEQ ID NO 163
<211> LENGTH: 5
<212> TYPE: DNA
<213> ORGANISM: Artificial Sequence
<220> FEATURE:
<223> OTHER INFORMATION: synthetic construct
```

```
<400> SEQUENCE: 163 aacta                                                              5

<210> SEQ ID NO 164
<211> LENGTH: 5
<212> TYPE: DNA
<213> ORGANISM: Artificial Sequence
<220> FEATURE:
<223> OTHER INFORMATION: synthetic construct

<400> SEQUENCE: 164 cctcg                                                              5

<210> SEQ ID NO 165
<211> LENGTH: 5
<212> TYPE: DNA
<213> ORGANISM: Artificial Sequence
<220> FEATURE:
<223> OTHER INFORMATION: synthetic construct

<400> SEQUENCE: 165 agcaa                                                              5

<210> SEQ ID NO 166
<211> LENGTH: 5
<212> TYPE: DNA
<213> ORGANISM: Artificial Sequence
<220> FEATURE:
<223> OTHER INFORMATION: synthetic construct

<400> SEQUENCE: 166 ttcca                                                              5

<210> SEQ ID NO 167
<211> LENGTH: 5
<212> TYPE: DNA
<213> ORGANISM: Artificial Sequence
<220> FEATURE:
<223> OTHER INFORMATION: synthetic construct

<400> SEQUENCE: 167 agact                                                              5

<210> SEQ ID NO 168
<211> LENGTH: 5
<212> TYPE: DNA
<213> ORGANISM: Artificial Sequence
<220> FEATURE:
<223> OTHER INFORMATION: synthetic construct

<400> SEQUENCE: 168 aggtt                                                              5

<210> SEQ ID NO 169
<211> LENGTH: 5
<212> TYPE: DNA
<213> ORGANISM: Artificial Sequence
<220> FEATURE:
<223> OTHER INFORMATION: synthetic construct

<400> SEQUENCE: 169 gcgtc                                                              5

<210> SEQ ID NO 170
<211> LENGTH: 5
```

```
<212> TYPE: DNA
<213> ORGANISM: Artificial Sequence
<220> FEATURE:
<223> OTHER INFORMATION: synthetic construct

<400> SEQUENCE: 170 aacgt                                                                     5

<210> SEQ ID NO 171
<211> LENGTH: 5
<212> TYPE: DNA
<213> ORGANISM: Artificial Sequence
<220> FEATURE:
<223> OTHER INFORMATION: synthetic construct

<400> SEQUENCE: 171 caaga                                                                     5

<210> SEQ ID NO 172
<211> LENGTH: 5
<212> TYPE: DNA
<213> ORGANISM: Artificial Sequence
<220> FEATURE:
<223> OTHER INFORMATION: synthetic construct

<400> SEQUENCE: 172 agaga                                                                     5

<210> SEQ ID NO 173
<211> LENGTH: 5
<212> TYPE: DNA
<213> ORGANISM: Artificial Sequence
<220> FEATURE:
<223> OTHER INFORMATION: synthetic construct

<400> SEQUENCE: 173 gtact                                                                     5

<210> SEQ ID NO 174
<211> LENGTH: 5
<212> TYPE: DNA
<213> ORGANISM: Artificial Sequence
<220> FEATURE:
<223> OTHER INFORMATION: synthetic construct

<400> SEQUENCE: 174 tagag                                                                     5

<210> SEQ ID NO 175
<211> LENGTH: 5
<212> TYPE: DNA
<213> ORGANISM: Artificial Sequence
<220> FEATURE:
<223> OTHER INFORMATION: synthetic construct

<400> SEQUENCE: 175 acgat                                                                     5

<210> SEQ ID NO 176
<211> LENGTH: 5
<212> TYPE: DNA
<213> ORGANISM: Artificial Sequence
<220> FEATURE:
<223> OTHER INFORMATION: synthetic construct

<400> SEQUENCE: 176
``` gacca                                                              5

<210> SEQ ID NO 177
<211> LENGTH: 5
<212> TYPE: DNA
<213> ORGANISM: Artificial Sequence
<220> FEATURE:
<223> OTHER INFORMATION: synthetic construct

<400> SEQUENCE: 177 tcgtt                                                              5

<210> SEQ ID NO 178
<211> LENGTH: 5
<212> TYPE: DNA
<213> ORGANISM: Artificial Sequence
<220> FEATURE:
<223> OTHER INFORMATION: synthetic construct

<400> SEQUENCE: 178 gtctc                                                              5

<210> SEQ ID NO 179
<211> LENGTH: 5
<212> TYPE: DNA
<213> ORGANISM: Artificial Sequence
<220> FEATURE:
<223> OTHER INFORMATION: synthetic construct

<400> SEQUENCE: 179 cagca                                                              5

<210> SEQ ID NO 180
<211> LENGTH: 5
<212> TYPE: DNA
<213> ORGANISM: Artificial Sequence
<220> FEATURE:
<223> OTHER INFORMATION: synthetic construct

<400> SEQUENCE: 180 tagtc                                                              5

<210> SEQ ID NO 181
<211> LENGTH: 5
<212> TYPE: DNA
<213> ORGANISM: Artificial Sequence
<220> FEATURE:
<223> OTHER INFORMATION: synthetic construct

<400> SEQUENCE: 181 gggtg                                                              5

<210> SEQ ID NO 182
<211> LENGTH: 5
<212> TYPE: DNA
<213> ORGANISM: Artificial Sequence
<220> FEATURE:
<223> OTHER INFORMATION: synthetic construct

<400> SEQUENCE: 182 ctcag                                                              5

<210> SEQ ID NO 183
<211> LENGTH: 5
<212> TYPE: DNA
<213> ORGANISM: Artificial Sequence

```
<220> FEATURE:
<223> OTHER INFORMATION: synthetic construct

<400> SEQUENCE: 183 agaac                                                                   5

<210> SEQ ID NO 184
<211> LENGTH: 5
<212> TYPE: DNA
<213> ORGANISM: Artificial Sequence
<220> FEATURE:
<223> OTHER INFORMATION: synthetic construct

<400> SEQUENCE: 184 gcgag                                                                   5

<210> SEQ ID NO 185
<211> LENGTH: 5
<212> TYPE: DNA
<213> ORGANISM: Artificial Sequence
<220> FEATURE:
<223> OTHER INFORMATION: synthetic construct

<400> SEQUENCE: 185 gatgt                                                                   5

<210> SEQ ID NO 186
<211> LENGTH: 5
<212> TYPE: DNA
<213> ORGANISM: Artificial Sequence
<220> FEATURE:
<223> OTHER INFORMATION: synthetic construct

<400> SEQUENCE: 186 tcact                                                                   5

<210> SEQ ID NO 187
<211> LENGTH: 5
<212> TYPE: DNA
<213> ORGANISM: Artificial Sequence
<220> FEATURE:
<223> OTHER INFORMATION: synthetic construct

<400> SEQUENCE: 187 cgtct                                                                   5

<210> SEQ ID NO 188
<211> LENGTH: 5
<212> TYPE: DNA
<213> ORGANISM: Artificial Sequence
<220> FEATURE:
<223> OTHER INFORMATION: synthetic construct

<400> SEQUENCE: 188 agctc                                                                   5

<210> SEQ ID NO 189
<211> LENGTH: 5
<212> TYPE: DNA
<213> ORGANISM: Artificial Sequence
<220> FEATURE:
<223> OTHER INFORMATION: synthetic construct

<400> SEQUENCE: 189 cactc                                                                   5
```

```
<210> SEQ ID NO 190
<211> LENGTH: 5
<212> TYPE: DNA
<213> ORGANISM: Artificial Sequence
<220> FEATURE:
<223> OTHER INFORMATION: synthetic construct

<400> SEQUENCE: 190 cagtt                                                                    5

<210> SEQ ID NO 191
<211> LENGTH: 20
<212> TYPE: DNA
<213> ORGANISM: Artificial Sequence
<220> FEATURE:
<223> OTHER INFORMATION: synthetic construct

<400> SEQUENCE: 191
agtacgaacg tgcatcagag                                                   20

<210> SEQ ID NO 192
<211> LENGTH: 20
<212> TYPE: DNA
<213> ORGANISM: Artificial Sequence
<220> FEATURE:
<223> OTHER INFORMATION: synthetic construct

<400> SEQUENCE: 192
tagtctcctc cacttccatg                                                   20

<210> SEQ ID NO 193
<211> LENGTH: 20
<212> TYPE: DNA
<213> ORGANISM: Artificial Sequence
<220> FEATURE:
<223> OTHER INFORMATION: synthetic construct

<400> SEQUENCE: 193
tacatcgttc cagactaccg                                                   20

<210> SEQ ID NO 194
<211> LENGTH: 20
<212> TYPE: DNA
<213> ORGANISM: Artificial Sequence
<220> FEATURE:
<223> OTHER INFORMATION: synthetic construct

<400> SEQUENCE: 194
tccagtgcaa gactgaacag                                                   20

<210> SEQ ID NO 195
<211> LENGTH: 20
<212> TYPE: DNA
<213> ORGANISM: Artificial Sequence
<220> FEATURE:
<223> OTHER INFORMATION: synthetic construct

<400> SEQUENCE: 195
agcatcacta ctctgtctgg                                                   20

<210> SEQ ID NO 196
<211> LENGTH: 20
<212> TYPE: DNA
<213> ORGANISM: Artificial Sequence
<220> FEATURE:
<223> OTHER INFORMATION: synthetic construct
```

```
<400> SEQUENCE: 196
tcttgtcaac cttccatgcg                                               20

<210> SEQ ID NO 197
<211> LENGTH: 20
<212> TYPE: DNA
<213> ORGANISM: Artificial Sequence
<220> FEATURE:
<223> OTHER INFORMATION: synthetic construct

<400> SEQUENCE: 197
aaggacgttc ctagtaggtg                                               20

<210> SEQ ID NO 198
<211> LENGTH: 20
<212> TYPE: DNA
<213> ORGANISM: Artificial Sequence
<220> FEATURE:
<223> OTHER INFORMATION: synthetic construct

<400> SEQUENCE: 198
ggaaccatca agatcctgag                                               20

<210> SEQ ID NO 199
<211> LENGTH: 20
<212> TYPE: DNA
<213> ORGANISM: Artificial Sequence
<220> FEATURE:
<223> OTHER INFORMATION: synthetic construct

<400> SEQUENCE: 199
atctctgacg agatccaagg                                               20

<210> SEQ ID NO 200
<211> LENGTH: 20
<212> TYPE: DNA
<213> ORGANISM: Artificial Sequence
<220> FEATURE:
<223> OTHER INFORMATION: synthetic construct

<400> SEQUENCE: 200
tcaaggttgg tggtgtactg                                               20

<210> SEQ ID NO 201
<211> LENGTH: 20
<212> TYPE: DNA
<213> ORGANISM: Artificial Sequence
<220> FEATURE:
<223> OTHER INFORMATION: synthetic construct

<400> SEQUENCE: 201
tcgaacttgt tgcttcctcg                                               20

<210> SEQ ID NO 202
<211> LENGTH: 20
<212> TYPE: DNA
<213> ORGANISM: Artificial Sequence
<220> FEATURE:
<223> OTHER INFORMATION: synthetic construct

<400> SEQUENCE: 202
ctgagtgtgt agtaccaacg                                               20

<210> SEQ ID NO 203
```

```
<211> LENGTH: 20
<212> TYPE: DNA
<213> ORGANISM: Artificial Sequence
<220> FEATURE:
<223> OTHER INFORMATION: synthetic construct

<400> SEQUENCE: 203
atcttggttg ttctcctgcg                                              20

<210> SEQ ID NO 204
<211> LENGTH: 20
<212> TYPE: DNA
<213> ORGANISM: Artificial Sequence
<220> FEATURE:
<223> OTHER INFORMATION: synthetic construct

<400> SEQUENCE: 204
tagtagcttg gagtagaccg                                              20

<210> SEQ ID NO 205
<211> LENGTH: 20
<212> TYPE: DNA
<213> ORGANISM: Artificial Sequence
<220> FEATURE:
<223> OTHER INFORMATION: synthetic construct

<400> SEQUENCE: 205
ttcactccat gcagcatgtg                                              20

<210> SEQ ID NO 206
<211> LENGTH: 20
<212> TYPE: DNA
<213> ORGANISM: Artificial Sequence
<220> FEATURE:
<223> OTHER INFORMATION: synthetic construct

<400> SEQUENCE: 206
acgatggtga tcgatcaacg                                              20

<210> SEQ ID NO 207
<211> LENGTH: 20
<212> TYPE: DNA
<213> ORGANISM: Artificial Sequence
<220> FEATURE:
<223> OTHER INFORMATION: synthetic construct

<400> SEQUENCE: 207
ttcagtgctt gagctacctg                                              20

<210> SEQ ID NO 208
<211> LENGTH: 20
<212> TYPE: DNA
<213> ORGANISM: Artificial Sequence
<220> FEATURE:
<223> OTHER INFORMATION: synthetic construct

<400> SEQUENCE: 208
ttggactctt cttgcaccag                                              20

<210> SEQ ID NO 209
<211> LENGTH: 20
<212> TYPE: DNA
<213> ORGANISM: Artificial Sequence
<220> FEATURE:
<223> OTHER INFORMATION: synthetic construct

<400> SEQUENCE: 209
```
tcaaccaact ggttcttggg                                              20

<210> SEQ ID NO 210
<211> LENGTH: 20
<212> TYPE: DNA
<213> ORGANISM: Artificial Sequence
<220> FEATURE:
<223> OTHER INFORMATION: synthetic construct

<400> SEQUENCE: 210
tagtactcta cactgctgcg                                              20

<210> SEQ ID NO 211
<211> LENGTH: 20
<212> TYPE: DNA
<213> ORGANISM: Artificial Sequence
<220> FEATURE:
<223> OTHER INFORMATION: synthetic construct

<400> SEQUENCE: 211
tacaccatga cttgcagacg                                              20

<210> SEQ ID NO 212
<211> LENGTH: 20
<212> TYPE: DNA
<213> ORGANISM: Artificial Sequence
<220> FEATURE:
<223> OTHER INFORMATION: synthetic construct

<400> SEQUENCE: 212
gcatcttgag tcgttgaacg                                              20

<210> SEQ ID NO 213
<211> LENGTH: 20
<212> TYPE: DNA
<213> ORGANISM: Artificial Sequence
<220> FEATURE:
<223> OTHER INFORMATION: synthetic construct

<400> SEQUENCE: 213
gactcatctc actggagttg                                              20

<210> SEQ ID NO 214
<211> LENGTH: 20
<212> TYPE: DNA
<213> ORGANISM: Artificial Sequence
<220> FEATURE:
<223> OTHER INFORMATION: synthetic construct

<400> SEQUENCE: 214
tccagcttct aggaagacag                                              20

<210> SEQ ID NO 215
<211> LENGTH: 20
<212> TYPE: DNA
<213> ORGANISM: Artificial Sequence
<220> FEATURE:
<223> OTHER INFORMATION: synthetic construct

<400> SEQUENCE: 215
cttcttgagt gcactagcag                                              20

<210> SEQ ID NO 216
<211> LENGTH: 24
<212> TYPE: DNA

```
<213> ORGANISM: Artificial Sequence
<220> FEATURE:
<223> OTHER INFORMATION: synthetic construct

<400> SEQUENCE: 216
cgagcaggac ctggaacctg gtgc                                              24

<210> SEQ ID NO 217
<211> LENGTH: 24
<212> TYPE: DNA
<213> ORGANISM: Artificial Sequence
<220> FEATURE:
<223> OTHER INFORMATION: synthetic construct

<400> SEQUENCE: 217
ctcgaccact gcaggtggag ctcc                                              24

<210> SEQ ID NO 218
<211> LENGTH: 24
<212> TYPE: DNA
<213> ORGANISM: Artificial Sequence
<220> FEATURE:
<223> OTHER INFORMATION: synthetic construct

<400> SEQUENCE: 218
cgtgcttcct ctgctgcacc accg                                              24

<210> SEQ ID NO 219
<211> LENGTH: 24
<212> TYPE: DNA
<213> ORGANISM: Artificial Sequence
<220> FEATURE:
<223> OTHER INFORMATION: synthetic construct

<400> SEQUENCE: 219
cctggtgtcg aggtgagcag cagc                                              24

<210> SEQ ID NO 220
<211> LENGTH: 24
<212> TYPE: DNA
<213> ORGANISM: Artificial Sequence
<220> FEATURE:
<223> OTHER INFORMATION: synthetic construct

<400> SEQUENCE: 220
ctcgacgagg tccatcctgg tcgc                                              24

<210> SEQ ID NO 221
<211> LENGTH: 24
<212> TYPE: DNA
<213> ORGANISM: Artificial Sequence
<220> FEATURE:
<223> OTHER INFORMATION: synthetic construct

<400> SEQUENCE: 221
cgtgaggagc aggtcctcct gtcg                                              24

<210> SEQ ID NO 222
<211> LENGTH: 24
<212> TYPE: DNA
<213> ORGANISM: Artificial Sequence
<220> FEATURE:
<223> OTHER INFORMATION: synthetic construct

<400> SEQUENCE: 222
cctgacactg gtcgtggtcg aggc                                              24
```

<210> SEQ ID NO 223
<211> LENGTH: 24
<212> TYPE: DNA
<213> ORGANISM: Artificial Sequence
<220> FEATURE:
<223> OTHER INFORMATION: synthetic construct

<400> SEQUENCE: 223
ccatctcgac gacctgctcc tggg                                          24

<210> SEQ ID NO 224
<211> LENGTH: 24
<212> TYPE: DNA
<213> ORGANISM: Artificial Sequence
<220> FEATURE:
<223> OTHER INFORMATION: synthetic construct

<400> SEQUENCE: 224
ccacgaggtc tccactggtc cagg                                          24

<210> SEQ ID NO 225
<211> LENGTH: 24
<212> TYPE: DNA
<213> ORGANISM: Artificial Sequence
<220> FEATURE:
<223> OTHER INFORMATION: synthetic construct

<400> SEQUENCE: 225
ccactgagct gctcctccag gtgg                                          24

<210> SEQ ID NO 226
<211> LENGTH: 24
<212> TYPE: DNA
<213> ORGANISM: Artificial Sequence
<220> FEATURE:
<223> OTHER INFORMATION: synthetic construct

<400> SEQUENCE: 226
cctcctgtcc tgcacgtcca tccg                                          24

<210> SEQ ID NO 227
<211> LENGTH: 24
<212> TYPE: DNA
<213> ORGANISM: Artificial Sequence
<220> FEATURE:
<223> OTHER INFORMATION: synthetic construct

<400> SEQUENCE: 227
cagcacctgg aggtaggacc acgg                                          24

<210> SEQ ID NO 228
<211> LENGTH: 24
<212> TYPE: DNA
<213> ORGANISM: Artificial Sequence
<220> FEATURE:
<223> OTHER INFORMATION: synthetic construct

<400> SEQUENCE: 228
cgaccagacg aggaccaggt aggc                                          24

<210> SEQ ID NO 229
<211> LENGTH: 24
<212> TYPE: DNA
<213> ORGANISM: Artificial Sequence
<220> FEATURE:

```
<223> OTHER INFORMATION: synthetic construct

<400> SEQUENCE: 229
ccaggttcga ggacctcgtc agcc                                              24

<210> SEQ ID NO 230
<211> LENGTH: 24
<212> TYPE: DNA
<213> ORGANISM: Artificial Sequence
<220> FEATURE:
<223> OTHER INFORMATION: synthetic construct

<400> SEQUENCE: 230
cgagcacgag gagcacgtgt ccag                                              24

<210> SEQ ID NO 231
<211> LENGTH: 24
<212> TYPE: DNA
<213> ORGANISM: Artificial Sequence
<220> FEATURE:
<223> OTHER INFORMATION: synthetic construct

<400> SEQUENCE: 231
ccacgtccac aggtgcacca ggtg                                              24

<210> SEQ ID NO 232
<211> LENGTH: 24
<212> TYPE: DNA
<213> ORGANISM: Artificial Sequence
<220> FEATURE:
<223> OTHER INFORMATION: synthetic construct

<400> SEQUENCE: 232
cctggtgctc cacgacgtgc ttcg                                              24

<210> SEQ ID NO 233
<211> LENGTH: 24
<212> TYPE: DNA
<213> ORGANISM: Artificial Sequence
<220> FEATURE:
<223> OTHER INFORMATION: synthetic construct

<400> SEQUENCE: 233
cacgtgacga cctggtcagg tggg                                              24

<210> SEQ ID NO 234
<211> LENGTH: 24
<212> TYPE: DNA
<213> ORGANISM: Artificial Sequence
<220> FEATURE:
<223> OTHER INFORMATION: synthetic construct

<400> SEQUENCE: 234
cgtagctcgt gctggtcctc ctgg                                              24

<210> SEQ ID NO 235
<211> LENGTH: 24
<212> TYPE: DNA
<213> ORGANISM: Artificial Sequence
<220> FEATURE:
<223> OTHER INFORMATION: synthetic construct

<400> SEQUENCE: 235
cgacgaccac caccttggac accc                                              24
```

```
<210> SEQ ID NO 236
<211> LENGTH: 24
<212> TYPE: DNA
<213> ORGANISM: Artificial Sequence
<220> FEATURE:
<223> OTHER INFORMATION: synthetic construct

<400> SEQUENCE: 236
cctacgtcgt gctcacgtcc tgcc                                              24

<210> SEQ ID NO 237
<211> LENGTH: 24
<212> TYPE: DNA
<213> ORGANISM: Artificial Sequence
<220> FEATURE:
<223> OTHER INFORMATION: synthetic construct

<400> SEQUENCE: 237
cgacgacagc taggaggagg tggg                                              24

<210> SEQ ID NO 238
<211> LENGTH: 24
<212> TYPE: DNA
<213> ORGANISM: Artificial Sequence
<220> FEATURE:
<223> OTHER INFORMATION: synthetic construct

<400> SEQUENCE: 238
ctggtggagc tgcacgagca cagc                                              24

<210> SEQ ID NO 239
<211> LENGTH: 24
<212> TYPE: DNA
<213> ORGANISM: Artificial Sequence
<220> FEATURE:
<223> OTHER INFORMATION: synthetic construct

<400> SEQUENCE: 239
caggactgga cgacgaccag gtcg                                              24

<210> SEQ ID NO 240
<211> LENGTH: 24
<212> TYPE: DNA
<213> ORGANISM: Artificial Sequence
<220> FEATURE:
<223> OTHER INFORMATION: synthetic construct

<400> SEQUENCE: 240
cgatgctgca gacgaccagc accc                                              24

<210> SEQ ID NO 241
<211> LENGTH: 5
<212> TYPE: DNA
<213> ORGANISM: Artificial Sequence
<220> FEATURE:
<223> OTHER INFORMATION: synthetic construct

<400> SEQUENCE: 241 tgttc                                                                    5

<210> SEQ ID NO 242
<211> LENGTH: 5
<212> TYPE: DNA
<213> ORGANISM: Artificial Sequence
<220> FEATURE:
<223> OTHER INFORMATION: synthetic construct
```

```
<400> SEQUENCE: 242 cgagc                                                               5

<210> SEQ ID NO 243
<211> LENGTH: 5
<212> TYPE: DNA
<213> ORGANISM: Artificial Sequence
<220> FEATURE:
<223> OTHER INFORMATION: synthetic construct

<400> SEQUENCE: 243 ggata                                                               5

<210> SEQ ID NO 244
<211> LENGTH: 5
<212> TYPE: DNA
<213> ORGANISM: Artificial Sequence
<220> FEATURE:
<223> OTHER INFORMATION: synthetic construct

<400> SEQUENCE: 244 cgctg                                                               5

<210> SEQ ID NO 245
<211> LENGTH: 5
<212> TYPE: DNA
<213> ORGANISM: Artificial Sequence
<220> FEATURE:
<223> OTHER INFORMATION: synthetic construct

<400> SEQUENCE: 245 gttat                                                               5

<210> SEQ ID NO 246
<211> LENGTH: 5
<212> TYPE: DNA
<213> ORGANISM: Artificial Sequence
<220> FEATURE:
<223> OTHER INFORMATION: synthetic construct

<400> SEQUENCE: 246 agtgc                                                               5

<210> SEQ ID NO 247
<211> LENGTH: 5
<212> TYPE: DNA
<213> ORGANISM: Artificial Sequence
<220> FEATURE:
<223> OTHER INFORMATION: synthetic construct

<400> SEQUENCE: 247 acctg                                                               5

<210> SEQ ID NO 248
<211> LENGTH: 5
<212> TYPE: DNA
<213> ORGANISM: Artificial Sequence
<220> FEATURE:
<223> OTHER INFORMATION: synthetic construct

<400> SEQUENCE: 248 ctggt                                                               5

<210> SEQ ID NO 249
<211> LENGTH: 5
```

```
<212> TYPE: DNA
<213> ORGANISM: Artificial Sequence
<220> FEATURE:
<223> OTHER INFORMATION: synthetic construct

<400> SEQUENCE: 249 tagga                                                                     5

<210> SEQ ID NO 250
<211> LENGTH: 5
<212> TYPE: DNA
<213> ORGANISM: Artificial Sequence
<220> FEATURE:
<223> OTHER INFORMATION: synthetic construct

<400> SEQUENCE: 250 actca                                                                     5

<210> SEQ ID NO 251
<211> LENGTH: 5
<212> TYPE: DNA
<213> ORGANISM: Artificial Sequence
<220> FEATURE:
<223> OTHER INFORMATION: synthetic construct

<400> SEQUENCE: 251 cttac                                                                     5

<210> SEQ ID NO 252
<211> LENGTH: 5
<212> TYPE: DNA
<213> ORGANISM: Artificial Sequence
<220> FEATURE:
<223> OTHER INFORMATION: synthetic construct

<400> SEQUENCE: 252 cgcac                                                                     5

<210> SEQ ID NO 253
<211> LENGTH: 5
<212> TYPE: DNA
<213> ORGANISM: Artificial Sequence
<220> FEATURE:
<223> OTHER INFORMATION: synthetic construct

<400> SEQUENCE: 253 tcgcg                                                                     5

<210> SEQ ID NO 254
<211> LENGTH: 5
<212> TYPE: DNA
<213> ORGANISM: Artificial Sequence
<220> FEATURE:
<223> OTHER INFORMATION: synthetic construct

<400> SEQUENCE: 254 cggat                                                                     5

<210> SEQ ID NO 255
<211> LENGTH: 5
<212> TYPE: DNA
<213> ORGANISM: Artificial Sequence
<220> FEATURE:
<223> OTHER INFORMATION: synthetic construct

<400> SEQUENCE: 255
```

-continued

```
gagat                                                           5

<210> SEQ ID NO 256
<211> LENGTH: 5
<212> TYPE: DNA
<213> ORGANISM: Artificial Sequence
<220> FEATURE:
<223> OTHER INFORMATION: synthetic construct

<400> SEQUENCE: 256 tgtag                                                           5

<210> SEQ ID NO 257
<211> LENGTH: 5
<212> TYPE: DNA
<213> ORGANISM: Artificial Sequence
<220> FEATURE:
<223> OTHER INFORMATION: synthetic construct

<400> SEQUENCE: 257 gtgtt                                                           5

<210> SEQ ID NO 258
<211> LENGTH: 5
<212> TYPE: DNA
<213> ORGANISM: Artificial Sequence
<220> FEATURE:
<223> OTHER INFORMATION: synthetic construct

<400> SEQUENCE: 258 agatg                                                           5

<210> SEQ ID NO 259
<211> LENGTH: 5
<212> TYPE: DNA
<213> ORGANISM: Artificial Sequence
<220> FEATURE:
<223> OTHER INFORMATION: synthetic construct

<400> SEQUENCE: 259 atcct                                                           5

<210> SEQ ID NO 260
<211> LENGTH: 5
<212> TYPE: DNA
<213> ORGANISM: Artificial Sequence
<220> FEATURE:
<223> OTHER INFORMATION: synthetic construct

<400> SEQUENCE: 260 ttgct                                                           5

<210> SEQ ID NO 261
<211> LENGTH: 5
<212> TYPE: DNA
<213> ORGANISM: Artificial Sequence
<220> FEATURE:
<223> OTHER INFORMATION: synthetic construct

<400> SEQUENCE: 261 acgta                                                           5

<210> SEQ ID NO 262
<211> LENGTH: 5
<212> TYPE: DNA
<213> ORGANISM: Artificial Sequence
```

```
<220> FEATURE:
<223> OTHER INFORMATION: synthetic construct

<400> SEQUENCE: 262 atcac                                                                    5

<210> SEQ ID NO 263
<211> LENGTH: 5
<212> TYPE: DNA
<213> ORGANISM: Artificial Sequence
<220> FEATURE:
<223> OTHER INFORMATION: synthetic construct

<400> SEQUENCE: 263 tatcc                                                                    5

<210> SEQ ID NO 264
<211> LENGTH: 5
<212> TYPE: DNA
<213> ORGANISM: Artificial Sequence
<220> FEATURE:
<223> OTHER INFORMATION: synthetic construct

<400> SEQUENCE: 264 ggaag                                                                    5

<210> SEQ ID NO 265
<211> LENGTH: 5
<212> TYPE: DNA
<213> ORGANISM: Artificial Sequence
<220> FEATURE:
<223> OTHER INFORMATION: synthetic construct

<400> SEQUENCE: 265 cggtc                                                                    5

<210> SEQ ID NO 266
<211> LENGTH: 5
<212> TYPE: DNA
<213> ORGANISM: Artificial Sequence
<220> FEATURE:
<223> OTHER INFORMATION: synthetic construct

<400> SEQUENCE: 266 tgctt                                                                    5

<210> SEQ ID NO 267
<211> LENGTH: 5
<212> TYPE: DNA
<213> ORGANISM: Artificial Sequence
<220> FEATURE:
<223> OTHER INFORMATION: synthetic construct

<400> SEQUENCE: 267 ttagc                                                                    5

<210> SEQ ID NO 268
<211> LENGTH: 5
<212> TYPE: DNA
<213> ORGANISM: Artificial Sequence
<220> FEATURE:
<223> OTHER INFORMATION: synthetic construct

<400> SEQUENCE: 268 gctga                                                                    5
```

```
<210> SEQ ID NO 269
<211> LENGTH: 5
<212> TYPE: DNA
<213> ORGANISM: Artificial Sequence
<220> FEATURE:
<223> OTHER INFORMATION: synthetic construct

<400> SEQUENCE: 269 gaacg                                                                      5

<210> SEQ ID NO 270
<211> LENGTH: 5
<212> TYPE: DNA
<213> ORGANISM: Artificial Sequence
<220> FEATURE:
<223> OTHER INFORMATION: synthetic construct

<400> SEQUENCE: 270 catgg                                                                      5

<210> SEQ ID NO 271
<211> LENGTH: 5
<212> TYPE: DNA
<213> ORGANISM: Artificial Sequence
<220> FEATURE:
<223> OTHER INFORMATION: synthetic construct

<400> SEQUENCE: 271 tggta                                                                      5

<210> SEQ ID NO 272
<211> LENGTH: 5
<212> TYPE: DNA
<213> ORGANISM: Artificial Sequence
<220> FEATURE:
<223> OTHER INFORMATION: synthetic construct

<400> SEQUENCE: 272 tcaag                                                                      5

<210> SEQ ID NO 273
<211> LENGTH: 5
<212> TYPE: DNA
<213> ORGANISM: Artificial Sequence
<220> FEATURE:
<223> OTHER INFORMATION: synthetic construct

<400> SEQUENCE: 273 atcga                                                                      5

<210> SEQ ID NO 274
<211> LENGTH: 5
<212> TYPE: DNA
<213> ORGANISM: Artificial Sequence
<220> FEATURE:
<223> OTHER INFORMATION: synthetic construct

<400> SEQUENCE: 274 atgca                                                                      5

<210> SEQ ID NO 275
<211> LENGTH: 5
<212> TYPE: DNA
<213> ORGANISM: Artificial Sequence
<220> FEATURE:
<223> OTHER INFORMATION: synthetic construct
```

```
<400> SEQUENCE: 275 actag                                                                5

<210> SEQ ID NO 276
<211> LENGTH: 5
<212> TYPE: DNA
<213> ORGANISM: Artificial Sequence
<220> FEATURE:
<223> OTHER INFORMATION: synthetic construct

<400> SEQUENCE: 276 tacct                                                                5

<210> SEQ ID NO 277
<211> LENGTH: 5
<212> TYPE: DNA
<213> ORGANISM: Artificial Sequence
<220> FEATURE:
<223> OTHER INFORMATION: synthetic construct

<400> SEQUENCE: 277 tacga                                                                5

<210> SEQ ID NO 278
<211> LENGTH: 5
<212> TYPE: DNA
<213> ORGANISM: Artificial Sequence
<220> FEATURE:
<223> OTHER INFORMATION: synthetic construct

<400> SEQUENCE: 278 cttca                                                                5

<210> SEQ ID NO 279
<211> LENGTH: 5
<212> TYPE: DNA
<213> ORGANISM: Artificial Sequence
<220> FEATURE:
<223> OTHER INFORMATION: synthetic construct

<400> SEQUENCE: 279 ctctt                                                                5

<210> SEQ ID NO 280
<211> LENGTH: 5
<212> TYPE: DNA
<213> ORGANISM: Artificial Sequence
<220> FEATURE:
<223> OTHER INFORMATION: synthetic construct

<400> SEQUENCE: 280 tcatc                                                                5

<210> SEQ ID NO 281
<211> LENGTH: 5
<212> TYPE: DNA
<213> ORGANISM: Artificial Sequence
<220> FEATURE:
<223> OTHER INFORMATION: synthetic construct

<400> SEQUENCE: 281 attcc                                                                5

<210> SEQ ID NO 282
```

<211> LENGTH: 5
<212> TYPE: DNA
<213> ORGANISM: Artificial Sequence
<220> FEATURE:
<223> OTHER INFORMATION: synthetic construct

<400> SEQUENCE: 282 cgacg    5

<210> SEQ ID NO 283
<211> LENGTH: 5
<212> TYPE: DNA
<213> ORGANISM: Artificial Sequence
<220> FEATURE:
<223> OTHER INFORMATION: synthetic construct

<400> SEQUENCE: 283 cctgt    5

<210> SEQ ID NO 284
<211> LENGTH: 5
<212> TYPE: DNA
<213> ORGANISM: Artificial Sequence
<220> FEATURE:
<223> OTHER INFORMATION: synthetic construct

<400> SEQUENCE: 284 ccttc    5

<210> SEQ ID NO 285
<211> LENGTH: 5
<212> TYPE: DNA
<213> ORGANISM: Artificial Sequence
<220> FEATURE:
<223> OTHER INFORMATION: synthetic construct

<400> SEQUENCE: 285 acacc    5

<210> SEQ ID NO 286
<211> LENGTH: 5
<212> TYPE: DNA
<213> ORGANISM: Artificial Sequence
<220> FEATURE:
<223> OTHER INFORMATION: synthetic construct

<400> SEQUENCE: 286 taaca    5

<210> SEQ ID NO 287
<211> LENGTH: 5
<212> TYPE: DNA
<213> ORGANISM: Artificial Sequence
<220> FEATURE:
<223> OTHER INFORMATION: synthetic construct

<400> SEQUENCE: 287 taaca    5

<210> SEQ ID NO 288
<211> LENGTH: 5
<212> TYPE: DNA
<213> ORGANISM: Artificial Sequence
<220> FEATURE:
<223> OTHER INFORMATION: synthetic construct

<400> SEQUENCE: 288

```
ccagg                                                               5

<210> SEQ ID NO 289
<211> LENGTH: 5
<212> TYPE: DNA
<213> ORGANISM: Artificial Sequence
<220> FEATURE:
<223> OTHER INFORMATION: synthetic construct

<400> SEQUENCE: 289 atgtc                                                               5

<210> SEQ ID NO 290
<211> LENGTH: 5
<212> TYPE: DNA
<213> ORGANISM: Artificial Sequence
<220> FEATURE:
<223> OTHER INFORMATION: synthetic construct

<400> SEQUENCE: 290 gagga                                                               5

<210> SEQ ID NO 291
<211> LENGTH: 5
<212> TYPE: DNA
<213> ORGANISM: Artificial Sequence
<220> FEATURE:
<223> OTHER INFORMATION: synthetic construct

<400> SEQUENCE: 291 ggtca                                                               5

<210> SEQ ID NO 292
<211> LENGTH: 5
<212> TYPE: DNA
<213> ORGANISM: Artificial Sequence
<220> FEATURE:
<223> OTHER INFORMATION: synthetic construct

<400> SEQUENCE: 292 gactt                                                               5

<210> SEQ ID NO 293
<211> LENGTH: 5
<212> TYPE: DNA
<213> ORGANISM: Artificial Sequence
<220> FEATURE:
<223> OTHER INFORMATION: synthetic construct

<400> SEQUENCE: 293 ggtgg                                                               5

<210> SEQ ID NO 294
<211> LENGTH: 5
<212> TYPE: DNA
<213> ORGANISM: Artificial Sequence
<220> FEATURE:
<223> OTHER INFORMATION: synthetic construct

<400> SEQUENCE: 294 caact                                                               5

<210> SEQ ID NO 295
<211> LENGTH: 5
<212> TYPE: DNA
```

```
<213> ORGANISM: Artificial Sequence
<220> FEATURE:
<223> OTHER INFORMATION: synthetic construct

<400> SEQUENCE: 295 atgag                                                                    5

<210> SEQ ID NO 296
<211> LENGTH: 5
<212> TYPE: DNA
<213> ORGANISM: Artificial Sequence
<220> FEATURE:
<223> OTHER INFORMATION: synthetic construct

<400> SEQUENCE: 296 tctgc                                                                    5

<210> SEQ ID NO 297
<211> LENGTH: 5
<212> TYPE: DNA
<213> ORGANISM: Artificial Sequence
<220> FEATURE:
<223> OTHER INFORMATION: synthetic construct

<400> SEQUENCE: 297 atagg                                                                    5

<210> SEQ ID NO 298
<211> LENGTH: 5
<212> TYPE: DNA
<213> ORGANISM: Artificial Sequence
<220> FEATURE:
<223> OTHER INFORMATION: synthetic construct

<400> SEQUENCE: 298 ctacc                                                                    5

<210> SEQ ID NO 299
<211> LENGTH: 5
<212> TYPE: DNA
<213> ORGANISM: Artificial Sequence
<220> FEATURE:
<223> OTHER INFORMATION: synthetic construct

<400> SEQUENCE: 299 aagtg                                                                    5

<210> SEQ ID NO 300
<211> LENGTH: 5
<212> TYPE: DNA
<213> ORGANISM: Artificial Sequence
<220> FEATURE:
<223> OTHER INFORMATION: synthetic construct

<400> SEQUENCE: 300 tccaa                                                                    5

<210> SEQ ID NO 301
<211> LENGTH: 5
<212> TYPE: DNA
<213> ORGANISM: Artificial Sequence
<220> FEATURE:
<223> OTHER INFORMATION: synthetic construct

<400> SEQUENCE: 301 gctct                                                                    5
```

```
<210> SEQ ID NO 302
<211> LENGTH: 5
<212> TYPE: DNA
<213> ORGANISM: Artificial Sequence
<220> FEATURE:
<223> OTHER INFORMATION: synthetic construct

<400> SEQUENCE: 302 ggagt                                                                    5

<210> SEQ ID NO 303
<211> LENGTH: 5
<212> TYPE: DNA
<213> ORGANISM: Artificial Sequence
<220> FEATURE:
<223> OTHER INFORMATION: synthetic construct

<400> SEQUENCE: 303 aatcg                                                                    5

<210> SEQ ID NO 304
<211> LENGTH: 5
<212> TYPE: DNA
<213> ORGANISM: Artificial Sequence
<220> FEATURE:
<223> OTHER INFORMATION: synthetic construct

<400> SEQUENCE: 304 aagct                                                                    5

<210> SEQ ID NO 305
<211> LENGTH: 5
<212> TYPE: DNA
<213> ORGANISM: Artificial Sequence
<220> FEATURE:
<223> OTHER INFORMATION: synthetic construct

<400> SEQUENCE: 305 ccgaa                                                                    5

<210> SEQ ID NO 306
<211> LENGTH: 5
<212> TYPE: DNA
<213> ORGANISM: Artificial Sequence
<220> FEATURE:
<223> OTHER INFORMATION: synthetic construct

<400> SEQUENCE: 306 tttgt                                                                    5

<210> SEQ ID NO 307
<211> LENGTH: 5
<212> TYPE: DNA
<213> ORGANISM: Artificial Sequence
<220> FEATURE:
<223> OTHER INFORMATION: synthetic construct

<400> SEQUENCE: 307 ccgtg                                                                    5

<210> SEQ ID NO 308
<211> LENGTH: 5
<212> TYPE: DNA
<213> ORGANISM: Artificial Sequence
<220> FEATURE:
```

```
<223> OTHER INFORMATION: synthetic construct

<400> SEQUENCE: 308 tttcg                                                              5

<210> SEQ ID NO 309
<211> LENGTH: 5
<212> TYPE: DNA
<213> ORGANISM: Artificial Sequence
<220> FEATURE:
<223> OTHER INFORMATION: synthetic construct

<400> SEQUENCE: 309 tgagg                                                              5

<210> SEQ ID NO 310
<211> LENGTH: 5
<212> TYPE: DNA
<213> ORGANISM: Artificial Sequence
<220> FEATURE:
<223> OTHER INFORMATION: synthetic construct

<400> SEQUENCE: 310 gttgc                                                              5

<210> SEQ ID NO 311
<211> LENGTH: 5
<212> TYPE: DNA
<213> ORGANISM: Artificial Sequence
<220> FEATURE:
<223> OTHER INFORMATION: synthetic construct

<400> SEQUENCE: 311 aacta                                                              5

<210> SEQ ID NO 312
<211> LENGTH: 5
<212> TYPE: DNA
<213> ORGANISM: Artificial Sequence
<220> FEATURE:
<223> OTHER INFORMATION: synthetic construct

<400> SEQUENCE: 312 aacta                                                              5

<210> SEQ ID NO 313
<211> LENGTH: 5
<212> TYPE: DNA
<213> ORGANISM: Artificial Sequence
<220> FEATURE:
<223> OTHER INFORMATION: synthetic construct

<400> SEQUENCE: 313 cctcg                                                              5

<210> SEQ ID NO 314
<211> LENGTH: 5
<212> TYPE: DNA
<213> ORGANISM: Artificial Sequence
<220> FEATURE:
<223> OTHER INFORMATION: synthetic construct

<400> SEQUENCE: 314 agcaa                                                              5
```

```
<210> SEQ ID NO 315
<211> LENGTH: 5
<212> TYPE: DNA
<213> ORGANISM: Artificial Sequence
<220> FEATURE:
<223> OTHER INFORMATION: synthetic construct

<400> SEQUENCE: 315 ttcca                                                                      5

<210> SEQ ID NO 316
<211> LENGTH: 5
<212> TYPE: DNA
<213> ORGANISM: Artificial Sequence
<220> FEATURE:
<223> OTHER INFORMATION: synthetic construct

<400> SEQUENCE: 316 agact                                                                      5

<210> SEQ ID NO 317
<211> LENGTH: 5
<212> TYPE: DNA
<213> ORGANISM: Artificial Sequence
<220> FEATURE:
<223> OTHER INFORMATION: synthetic construct

<400> SEQUENCE: 317 aggtt                                                                      5

<210> SEQ ID NO 318
<211> LENGTH: 5
<212> TYPE: DNA
<213> ORGANISM: Artificial Sequence
<220> FEATURE:
<223> OTHER INFORMATION: synthetic construct

<400> SEQUENCE: 318 gcgtc                                                                      5

<210> SEQ ID NO 319
<211> LENGTH: 5
<212> TYPE: DNA
<213> ORGANISM: Artificial Sequence
<220> FEATURE:
<223> OTHER INFORMATION: synthetic construct

<400> SEQUENCE: 319 aacgt                                                                      5

<210> SEQ ID NO 320
<211> LENGTH: 5
<212> TYPE: DNA
<213> ORGANISM: Artificial Sequence
<220> FEATURE:
<223> OTHER INFORMATION: synthetic construct

<400> SEQUENCE: 320 caaga                                                                      5

<210> SEQ ID NO 321
<211> LENGTH: 5
<212> TYPE: DNA
<213> ORGANISM: Artificial Sequence
<220> FEATURE:
<223> OTHER INFORMATION: synthetic construct
```

```
<400> SEQUENCE: 321 agaga                                                                    5

<210> SEQ ID NO 322
<211> LENGTH: 5
<212> TYPE: DNA
<213> ORGANISM: Artificial Sequence
<220> FEATURE:
<223> OTHER INFORMATION: synthetic construct

<400> SEQUENCE: 322 gtact                                                                    5

<210> SEQ ID NO 323
<211> LENGTH: 5
<212> TYPE: DNA
<213> ORGANISM: Artificial Sequence
<220> FEATURE:
<223> OTHER INFORMATION: synthetic construct

<400> SEQUENCE: 323 tagag                                                                    5

<210> SEQ ID NO 324
<211> LENGTH: 5
<212> TYPE: DNA
<213> ORGANISM: Artificial Sequence
<220> FEATURE:
<223> OTHER INFORMATION: synthetic construct

<400> SEQUENCE: 324 acgat                                                                    5

<210> SEQ ID NO 325
<211> LENGTH: 5
<212> TYPE: DNA
<213> ORGANISM: Artificial Sequence
<220> FEATURE:
<223> OTHER INFORMATION: synthetic construct

<400> SEQUENCE: 325 gacca                                                                    5

<210> SEQ ID NO 326
<211> LENGTH: 5
<212> TYPE: DNA
<213> ORGANISM: Artificial Sequence
<220> FEATURE:
<223> OTHER INFORMATION: synthetic construct

<400> SEQUENCE: 326 tcgtt                                                                    5

<210> SEQ ID NO 327
<211> LENGTH: 5
<212> TYPE: DNA
<213> ORGANISM: Artificial Sequence
<220> FEATURE:
<223> OTHER INFORMATION: synthetic construct

<400> SEQUENCE: 327 gtctc                                                                    5

<210> SEQ ID NO 328
<211> LENGTH: 5
```

```
<212> TYPE: DNA
<213> ORGANISM: Artificial Sequence
<220> FEATURE:
<223> OTHER INFORMATION: synthetic construct

<400> SEQUENCE: 328 cagca                                                                    5

<210> SEQ ID NO 329
<211> LENGTH: 5
<212> TYPE: DNA
<213> ORGANISM: Artificial Sequence
<220> FEATURE:
<223> OTHER INFORMATION: synthetic construct

<400> SEQUENCE: 329 tagtc                                                                    5

<210> SEQ ID NO 330
<211> LENGTH: 5
<212> TYPE: DNA
<213> ORGANISM: Artificial Sequence
<220> FEATURE:
<223> OTHER INFORMATION: synthetic construct

<400> SEQUENCE: 330 gggtg                                                                    5

<210> SEQ ID NO 331
<211> LENGTH: 5
<212> TYPE: DNA
<213> ORGANISM: Artificial Sequence
<220> FEATURE:
<223> OTHER INFORMATION: synthetic construct

<400> SEQUENCE: 331 ctcag                                                                    5

<210> SEQ ID NO 332
<211> LENGTH: 5
<212> TYPE: DNA
<213> ORGANISM: Artificial Sequence
<220> FEATURE:
<223> OTHER INFORMATION: synthetic construct

<400> SEQUENCE: 332 agaac                                                                    5

<210> SEQ ID NO 333
<211> LENGTH: 5
<212> TYPE: DNA
<213> ORGANISM: Artificial Sequence
<220> FEATURE:
<223> OTHER INFORMATION: synthetic construct

<400> SEQUENCE: 333 gcgag                                                                    5

<210> SEQ ID NO 334
<211> LENGTH: 5
<212> TYPE: DNA
<213> ORGANISM: Artificial Sequence
<220> FEATURE:
<223> OTHER INFORMATION: synthetic construct

<400> SEQUENCE: 334
``` gatgt 5

<210> SEQ ID NO 335
<211> LENGTH: 5
<212> TYPE: DNA
<213> ORGANISM: Artificial Sequence
<220> FEATURE:
<223> OTHER INFORMATION: synthetic construct

<400> SEQUENCE: 335 tcact 5

<210> SEQ ID NO 336
<211> LENGTH: 5
<212> TYPE: DNA
<213> ORGANISM: Artificial Sequence
<220> FEATURE:
<223> OTHER INFORMATION: synthetic construct

<400> SEQUENCE: 336 cgtct 5

<210> SEQ ID NO 337
<211> LENGTH: 5
<212> TYPE: DNA
<213> ORGANISM: Artificial Sequence
<220> FEATURE:
<223> OTHER INFORMATION: synthetic construct

<400> SEQUENCE: 337 agctc 5

<210> SEQ ID NO 338
<211> LENGTH: 5
<212> TYPE: DNA
<213> ORGANISM: Artificial Sequence
<220> FEATURE:
<223> OTHER INFORMATION: synthetic construct

<400> SEQUENCE: 338 cactc 5

<210> SEQ ID NO 339
<211> LENGTH: 5
<212> TYPE: DNA
<213> ORGANISM: Artificial Sequence
<220> FEATURE:
<223> OTHER INFORMATION: synthetic construct

<400> SEQUENCE: 339 cagtt 5

<210> SEQ ID NO 340
<211> LENGTH: 20
<212> TYPE: DNA
<213> ORGANISM: Artificial Sequence
<220> FEATURE:
<223> OTHER INFORMATION: synthetic construct

<400> SEQUENCE: 340
agtacgaacg tgcatcagag 20

<210> SEQ ID NO 341
<211> LENGTH: 20
<212> TYPE: DNA
<213> ORGANISM: Artificial Sequence

```
<220> FEATURE:
<223> OTHER INFORMATION: synthetic construct

<400> SEQUENCE: 341
tagtctcctc cacttccatg                                               20

<210> SEQ ID NO 342
<211> LENGTH: 20
<212> TYPE: DNA
<213> ORGANISM: Artificial Sequence
<220> FEATURE:
<223> OTHER INFORMATION: synthetic construct

<400> SEQUENCE: 342
tacatcgttc cagactaccg                                               20

<210> SEQ ID NO 343
<211> LENGTH: 20
<212> TYPE: DNA
<213> ORGANISM: Artificial Sequence
<220> FEATURE:
<223> OTHER INFORMATION: synthetic construct

<400> SEQUENCE: 343
tccagtgcaa gactgaacag                                               20

<210> SEQ ID NO 344
<211> LENGTH: 20
<212> TYPE: DNA
<213> ORGANISM: Artificial Sequence
<220> FEATURE:
<223> OTHER INFORMATION: synthetic construct

<400> SEQUENCE: 344
agcatcacta ctctgtctgg                                               20

<210> SEQ ID NO 345
<211> LENGTH: 20
<212> TYPE: DNA
<213> ORGANISM: Artificial Sequence
<220> FEATURE:
<223> OTHER INFORMATION: synthetic construct

<400> SEQUENCE: 345
tcttgtcaac cttccatgcg                                               20

<210> SEQ ID NO 346
<211> LENGTH: 20
<212> TYPE: DNA
<213> ORGANISM: Artificial Sequence
<220> FEATURE:
<223> OTHER INFORMATION: synthetic construct

<400> SEQUENCE: 346
aaggacgttc ctagtaggtg                                               20

<210> SEQ ID NO 347
<211> LENGTH: 20
<212> TYPE: DNA
<213> ORGANISM: Artificial Sequence
<220> FEATURE:
<223> OTHER INFORMATION: synthetic construct

<400> SEQUENCE: 347
ggaaccatca agatcctgag                                               20
```

```
<210> SEQ ID NO 348
<211> LENGTH: 20
<212> TYPE: DNA
<213> ORGANISM: Artificial Sequence
<220> FEATURE:
<223> OTHER INFORMATION: synthetic construct

<400> SEQUENCE: 348
atctctgacg agatccaagg                                               20

<210> SEQ ID NO 349
<211> LENGTH: 20
<212> TYPE: DNA
<213> ORGANISM: Artificial Sequence
<220> FEATURE:
<223> OTHER INFORMATION: synthetic construct

<400> SEQUENCE: 349
tcaaggttgg tggtgtactg                                               20

<210> SEQ ID NO 350
<211> LENGTH: 20
<212> TYPE: DNA
<213> ORGANISM: Artificial Sequence
<220> FEATURE:
<223> OTHER INFORMATION: synthetic construct

<400> SEQUENCE: 350
tcgaacttgt tgcttcctcg                                               20

<210> SEQ ID NO 351
<211> LENGTH: 20
<212> TYPE: DNA
<213> ORGANISM: Artificial Sequence
<220> FEATURE:
<223> OTHER INFORMATION: synthetic construct

<400> SEQUENCE: 351
ctgagtgtgt agtaccaacg                                               20

<210> SEQ ID NO 352
<211> LENGTH: 20
<212> TYPE: DNA
<213> ORGANISM: Artificial Sequence
<220> FEATURE:
<223> OTHER INFORMATION: synthetic construct

<400> SEQUENCE: 352
atcttggttg ttctcctgcg                                               20

<210> SEQ ID NO 353
<211> LENGTH: 20
<212> TYPE: DNA
<213> ORGANISM: Artificial Sequence
<220> FEATURE:
<223> OTHER INFORMATION: synthetic construct

<400> SEQUENCE: 353
tagtagcttg gagtagaccg                                               20

<210> SEQ ID NO 354
<211> LENGTH: 20
<212> TYPE: DNA
<213> ORGANISM: Artificial Sequence
<220> FEATURE:
<223> OTHER INFORMATION: synthetic construct
```

<400> SEQUENCE: 354
ttcactccat gcagcatgtg                                          20

<210> SEQ ID NO 355
<211> LENGTH: 20
<212> TYPE: DNA
<213> ORGANISM: Artificial Sequence
<220> FEATURE:
<223> OTHER INFORMATION: synthetic construct

<400> SEQUENCE: 355
acgatggtga tcgatcaacg                                          20

<210> SEQ ID NO 356
<211> LENGTH: 20
<212> TYPE: DNA
<213> ORGANISM: Artificial Sequence
<220> FEATURE:
<223> OTHER INFORMATION: synthetic construct

<400> SEQUENCE: 356
ttcagtgctt gagctacctg                                          20

<210> SEQ ID NO 357
<211> LENGTH: 20
<212> TYPE: DNA
<213> ORGANISM: Artificial Sequence
<220> FEATURE:
<223> OTHER INFORMATION: synthetic construct

<400> SEQUENCE: 357
ttggactctt cttgcaccag                                          20

<210> SEQ ID NO 358
<211> LENGTH: 20
<212> TYPE: DNA
<213> ORGANISM: Artificial Sequence
<220> FEATURE:
<223> OTHER INFORMATION: synthetic construct

<400> SEQUENCE: 358
tcaaccaact ggttcttggg                                          20

<210> SEQ ID NO 359
<211> LENGTH: 20
<212> TYPE: DNA
<213> ORGANISM: Artificial Sequence
<220> FEATURE:
<223> OTHER INFORMATION: synthetic construct

<400> SEQUENCE: 359
tagtactcta cactgctgcg                                          20

<210> SEQ ID NO 360
<211> LENGTH: 20
<212> TYPE: DNA
<213> ORGANISM: Artificial Sequence
<220> FEATURE:
<223> OTHER INFORMATION: synthetic construct

<400> SEQUENCE: 360
tacaccatga cttgcagacg                                          20

<210> SEQ ID NO 361

```
<210> SEQ ID NO 361
<211> LENGTH: 20
<212> TYPE: DNA
<213> ORGANISM: Artificial Sequence
<220> FEATURE:
<223> OTHER INFORMATION: synthetic construct

<400> SEQUENCE: 361
gcatcttgag tcgttgaacg                                           20

<210> SEQ ID NO 362
<211> LENGTH: 20
<212> TYPE: DNA
<213> ORGANISM: Artificial Sequence
<220> FEATURE:
<223> OTHER INFORMATION: synthetic construct

<400> SEQUENCE: 362
gactcatctc actggagttg                                           20

<210> SEQ ID NO 363
<211> LENGTH: 20
<212> TYPE: DNA
<213> ORGANISM: Artificial Sequence
<220> FEATURE:
<223> OTHER INFORMATION: synthetic construct

<400> SEQUENCE: 363
tccagcttct aggaagacag                                           20

<210> SEQ ID NO 364
<211> LENGTH: 20
<212> TYPE: DNA
<213> ORGANISM: Artificial Sequence
<220> FEATURE:
<223> OTHER INFORMATION: synthetic construct

<400> SEQUENCE: 364
cttcttgagt gcactagcag                                           20

<210> SEQ ID NO 365
<211> LENGTH: 24
<212> TYPE: DNA
<213> ORGANISM: Artificial Sequence
<220> FEATURE:
<223> OTHER INFORMATION: synthetic construct

<400> SEQUENCE: 365
cgagcaggac ctggaacctg gtgc                                      24

<210> SEQ ID NO 366
<211> LENGTH: 24
<212> TYPE: DNA
<213> ORGANISM: Artificial Sequence
<220> FEATURE:
<223> OTHER INFORMATION: synthetic construct

<400> SEQUENCE: 366
ctcgaccact gcaggtggag ctcc                                      24

<210> SEQ ID NO 367
<211> LENGTH: 24
<212> TYPE: DNA
<213> ORGANISM: Artificial Sequence
<220> FEATURE:
<223> OTHER INFORMATION: synthetic construct

<400> SEQUENCE: 367
```
cgtgcttcct ctgctgcacc accg                                          24

<210> SEQ ID NO 368
<211> LENGTH: 24
<212> TYPE: DNA
<213> ORGANISM: Artificial Sequence
<220> FEATURE:
<223> OTHER INFORMATION: synthetic construct

<400> SEQUENCE: 368
cctggtgtcg aggtgagcag cagc                                          24

<210> SEQ ID NO 369
<211> LENGTH: 24
<212> TYPE: DNA
<213> ORGANISM: Artificial Sequence
<220> FEATURE:
<223> OTHER INFORMATION: synthetic construct

<400> SEQUENCE: 369
ctcgacgagg tccatcctgg tcgc                                          24

<210> SEQ ID NO 370
<211> LENGTH: 24
<212> TYPE: DNA
<213> ORGANISM: Artificial Sequence
<220> FEATURE:
<223> OTHER INFORMATION: synthetic construct

<400> SEQUENCE: 370
cgtgaggagc aggtcctcct gtcg                                          24

<210> SEQ ID NO 371
<211> LENGTH: 24
<212> TYPE: DNA
<213> ORGANISM: Artificial Sequence
<220> FEATURE:
<223> OTHER INFORMATION: synthetic construct

<400> SEQUENCE: 371
cctgacactg gtcgtggtcg aggc                                          24

<210> SEQ ID NO 372
<211> LENGTH: 24
<212> TYPE: DNA
<213> ORGANISM: Artificial Sequence
<220> FEATURE:
<223> OTHER INFORMATION: synthetic construct

<400> SEQUENCE: 372
ccatctcgac gacctgctcc tggg                                          24

<210> SEQ ID NO 373
<211> LENGTH: 24
<212> TYPE: DNA
<213> ORGANISM: Artificial Sequence
<220> FEATURE:
<223> OTHER INFORMATION: synthetic construct

<400> SEQUENCE: 373
ccacgaggtc tccactggtc cagg                                          24

<210> SEQ ID NO 374
<211> LENGTH: 24
<212> TYPE: DNA

```
<213> ORGANISM: Artificial Sequence
<220> FEATURE:
<223> OTHER INFORMATION: synthetic construct

<400> SEQUENCE: 374
ccactgagct gctcctccag gtgg                                              24

<210> SEQ ID NO 375
<211> LENGTH: 24
<212> TYPE: DNA
<213> ORGANISM: Artificial Sequence
<220> FEATURE:
<223> OTHER INFORMATION: synthetic construct

<400> SEQUENCE: 375
cctcctgtcc tgcacgtcca tccg                                              24

<210> SEQ ID NO 376
<211> LENGTH: 24
<212> TYPE: DNA
<213> ORGANISM: Artificial Sequence
<220> FEATURE:
<223> OTHER INFORMATION: synthetic construct

<400> SEQUENCE: 376
cagcacctgg aggtaggacc acgg                                              24

<210> SEQ ID NO 377
<211> LENGTH: 24
<212> TYPE: DNA
<213> ORGANISM: Artificial Sequence
<220> FEATURE:
<223> OTHER INFORMATION: synthetic construct

<400> SEQUENCE: 377
cgaccagacg aggaccaggt aggc                                              24

<210> SEQ ID NO 378
<211> LENGTH: 24
<212> TYPE: DNA
<213> ORGANISM: Artificial Sequence
<220> FEATURE:
<223> OTHER INFORMATION: synthetic construct

<400> SEQUENCE: 378
ccaggttcga ggacctcgtc agcc                                              24

<210> SEQ ID NO 379
<211> LENGTH: 24
<212> TYPE: DNA
<213> ORGANISM: Artificial Sequence
<220> FEATURE:
<223> OTHER INFORMATION: synthetic construct

<400> SEQUENCE: 379
cgagcacgag gagcacgtgt ccag                                              24

<210> SEQ ID NO 380
<211> LENGTH: 24
<212> TYPE: DNA
<213> ORGANISM: Artificial Sequence
<220> FEATURE:
<223> OTHER INFORMATION: synthetic construct

<400> SEQUENCE: 380
ccacgtccac aggtgcacca ggtg                                              24
```

```
<210> SEQ ID NO 381
<211> LENGTH: 24
<212> TYPE: DNA
<213> ORGANISM: Artificial Sequence
<220> FEATURE:
<223> OTHER INFORMATION: synthetic construct

<400> SEQUENCE: 381
cctggtgctc cacgacgtgc ttcg                                           24

<210> SEQ ID NO 382
<211> LENGTH: 24
<212> TYPE: DNA
<213> ORGANISM: Artificial Sequence
<220> FEATURE:
<223> OTHER INFORMATION: synthetic construct

<400> SEQUENCE: 382
cacgtgacga cctggtcagg tggg                                           24

<210> SEQ ID NO 383
<211> LENGTH: 24
<212> TYPE: DNA
<213> ORGANISM: Artificial Sequence
<220> FEATURE:
<223> OTHER INFORMATION: synthetic construct

<400> SEQUENCE: 383
cgtagctcgt gctggtcctc ctgg                                           24

<210> SEQ ID NO 384
<211> LENGTH: 24
<212> TYPE: DNA
<213> ORGANISM: Artificial Sequence
<220> FEATURE:
<223> OTHER INFORMATION: synthetic construct

<400> SEQUENCE: 384
cgacgaccac caccttggac accc                                           24

<210> SEQ ID NO 385
<211> LENGTH: 24
<212> TYPE: DNA
<213> ORGANISM: Artificial Sequence
<220> FEATURE:
<223> OTHER INFORMATION: synthetic construct

<400> SEQUENCE: 385
cctacgtcgt gctcacgtcc tgcc                                           24

<210> SEQ ID NO 386
<211> LENGTH: 24
<212> TYPE: DNA
<213> ORGANISM: Artificial Sequence
<220> FEATURE:
<223> OTHER INFORMATION: synthetic construct

<400> SEQUENCE: 386
cgacgacagc taggaggagg tggg                                           24

<210> SEQ ID NO 387
<211> LENGTH: 24
<212> TYPE: DNA
<213> ORGANISM: Artificial Sequence
<220> FEATURE:
```

```
<223> OTHER INFORMATION: synthetic construct

<400> SEQUENCE: 387
ctggtggagc tgcacgagca cagc                                              24

<210> SEQ ID NO 388
<211> LENGTH: 25
<212> TYPE: DNA
<213> ORGANISM: Artificial Sequence
<220> FEATURE:
<223> OTHER INFORMATION: synthetic construct

<400> SEQUENCE: 388
caggactgga cgacgaccag gtcgs                                             25

<210> SEQ ID NO 389
<211> LENGTH: 24
<212> TYPE: DNA
<213> ORGANISM: Artificial Sequence
<220> FEATURE:
<223> OTHER INFORMATION: synthetic construct

<400> SEQUENCE: 389
cgatgctgca gacgaccagc accc                                              24

<210> SEQ ID NO 390
<211> LENGTH: 5
<212> TYPE: DNA
<213> ORGANISM: Artificial Sequence
<220> FEATURE:
<223> OTHER INFORMATION: synthetic construct

<400> SEQUENCE: 390 tgttc                                                                    5

<210> SEQ ID NO 391
<211> LENGTH: 5
<212> TYPE: DNA
<213> ORGANISM: Artificial Sequence
<220> FEATURE:
<223> OTHER INFORMATION: synthetic construct

<400> SEQUENCE: 391 actca                                                                    5

<210> SEQ ID NO 392
<211> LENGTH: 5
<212> TYPE: DNA
<213> ORGANISM: Artificial Sequence
<220> FEATURE:
<223> OTHER INFORMATION: synthetic construct

<400> SEQUENCE: 392 cttac                                                                    5

<210> SEQ ID NO 393
<211> LENGTH: 5
<212> TYPE: DNA
<213> ORGANISM: Artificial Sequence
<220> FEATURE:
<223> OTHER INFORMATION: synthetic construct

<400> SEQUENCE: 393 cggat                                                                    5
```

```
<210> SEQ ID NO 394
<211> LENGTH: 5
<212> TYPE: DNA
<213> ORGANISM: Artificial Sequence
<220> FEATURE:
<223> OTHER INFORMATION: synthetic construct

<400> SEQUENCE: 394 attcc                                                                      5

<210> SEQ ID NO 395
<211> LENGTH: 5
<212> TYPE: DNA
<213> ORGANISM: Artificial Sequence
<220> FEATURE:
<223> OTHER INFORMATION: synthetic construct

<400> SEQUENCE: 395 gtctc                                                                      5

<210> SEQ ID NO 396
<211> LENGTH: 5
<212> TYPE: DNA
<213> ORGANISM: Artificial Sequence
<220> FEATURE:
<223> OTHER INFORMATION: synthetic construct

<400> SEQUENCE: 396 acagt                                                                      5

<210> SEQ ID NO 397
<211> LENGTH: 24
<212> TYPE: DNA
<213> ORGANISM: Artificial Sequence
<220> FEATURE:
<223> OTHER INFORMATION: synthetic construct

<400> SEQUENCE: 397
cacaagtacg aacgtgcatc agag                                                24

<210> SEQ ID NO 398
<211> LENGTH: 24
<212> TYPE: DNA
<213> ORGANISM: Artificial Sequence
<220> FEATURE:
<223> OTHER INFORMATION: synthetic construct

<400> SEQUENCE: 398
cacatagtct cctccacttc catg                                                24

<210> SEQ ID NO 399
<211> LENGTH: 24
<212> TYPE: DNA
<213> ORGANISM: Artificial Sequence
<220> FEATURE:
<223> OTHER INFORMATION: synthetic construct

<400> SEQUENCE: 399
cacatacatc gttccagact accg                                                24

<210> SEQ ID NO 400
<211> LENGTH: 24
<212> TYPE: DNA
<213> ORGANISM: Artificial Sequence
<220> FEATURE:
<223> OTHER INFORMATION: synthetic construct
```

```
<400> SEQUENCE: 400
cacatccagt gcaagactga acag                                          24

<210> SEQ ID NO 401
<211> LENGTH: 24
<212> TYPE: DNA
<213> ORGANISM: Artificial Sequence
<220> FEATURE:
<223> OTHER INFORMATION: synthetic construct

<400> SEQUENCE: 401
cacaagcatc actactctgt ctgg                                          24

<210> SEQ ID NO 402
<211> LENGTH: 24
<212> TYPE: DNA
<213> ORGANISM: Artificial Sequence
<220> FEATURE:
<223> OTHER INFORMATION: synthetic construct

<400> SEQUENCE: 402
cacatcttgt caaccttcca tgcg                                          24

<210> SEQ ID NO 403
<211> LENGTH: 24
<212> TYPE: DNA
<213> ORGANISM: Artificial Sequence
<220> FEATURE:
<223> OTHER INFORMATION: synthetic construct

<400> SEQUENCE: 403
cacaaaggac gttcctagta ggtg                                          24

<210> SEQ ID NO 404
<211> LENGTH: 24
<212> TYPE: DNA
<213> ORGANISM: Artificial Sequence
<220> FEATURE:
<223> OTHER INFORMATION: synthetic construct

<400> SEQUENCE: 404
cacaggaacc atcaagatcc tgag                                          24

<210> SEQ ID NO 405
<211> LENGTH: 24
<212> TYPE: DNA
<213> ORGANISM: Artificial Sequence
<220> FEATURE:
<223> OTHER INFORMATION: synthetic construct

<400> SEQUENCE: 405
cacaatctct gacgagatcc aagg                                          24

<210> SEQ ID NO 406
<211> LENGTH: 24
<212> TYPE: DNA
<213> ORGANISM: Artificial Sequence
<220> FEATURE:
<223> OTHER INFORMATION: synthetic construct

<400> SEQUENCE: 406
cacatcaagg ttggtggtgt actg                                          24

<210> SEQ ID NO 407
<211> LENGTH: 24
```

```
<212> TYPE: DNA
<213> ORGANISM: Artificial Sequence
<220> FEATURE:
<223> OTHER INFORMATION: synthetic construct

<400> SEQUENCE: 407
cacatcgaac ttgttgcttc ctcg                                          24

<210> SEQ ID NO 408
<211> LENGTH: 24
<212> TYPE: DNA
<213> ORGANISM: Artificial Sequence
<220> FEATURE:
<223> OTHER INFORMATION: synthetic construct

<400> SEQUENCE: 408
cacactgagt gtgtagtacc aacg                                          24

<210> SEQ ID NO 409
<211> LENGTH: 24
<212> TYPE: DNA
<213> ORGANISM: Artificial Sequence
<220> FEATURE:
<223> OTHER INFORMATION: synthetic construct

<400> SEQUENCE: 409
cacaatcttg gttgttctcc tgcg                                          24

<210> SEQ ID NO 410
<211> LENGTH: 48
<212> TYPE: DNA
<213> ORGANISM: Artificial Sequence
<220> FEATURE:
<223> OTHER INFORMATION: synthetic construct

<400> SEQUENCE: 410
aggacgagca ggacctggaa cctggtgcgt tcctccacca cgtctccg                48

<210> SEQ ID NO 411
<211> LENGTH: 48
<212> TYPE: DNA
<213> ORGANISM: Artificial Sequence
<220> FEATURE:
<223> OTHER INFORMATION: synthetic construct

<400> SEQUENCE: 411
aggactcgac cactgcaggt ggagctccgt tcctccacca cgtctccg                48

<210> SEQ ID NO 412
<211> LENGTH: 48
<212> TYPE: DNA
<213> ORGANISM: Artificial Sequence
<220> FEATURE:
<223> OTHER INFORMATION: synthetic construct

<400> SEQUENCE: 412
aggacgtgct tcctctgctg caccaccggt tcctccacca cgtctccg                48

<210> SEQ ID NO 413
<211> LENGTH: 48
<212> TYPE: DNA
<213> ORGANISM: Artificial Sequence
<220> FEATURE:
<223> OTHER INFORMATION: synthetic construct

<400> SEQUENCE: 413
```

-continued

```
aggacctggt gtcgaggtga gcagcagcgt tcctccacca cgtctccg            48

<210> SEQ ID NO 414
<211> LENGTH: 48
<212> TYPE: DNA
<213> ORGANISM: Artificial Sequence
<220> FEATURE:
<223> OTHER INFORMATION: synthetic construct

<400> SEQUENCE: 414
aggactcgac gaggtccatc ctggtcgcgt tcctccacca cgtctccg            48

<210> SEQ ID NO 415
<211> LENGTH: 48
<212> TYPE: DNA
<213> ORGANISM: Artificial Sequence
<220> FEATURE:
<223> OTHER INFORMATION: synthetic construct

<400> SEQUENCE: 415
aggacgtgag gagcaggtcc tcctgtcggt tcctccacca cgtctccg            48

<210> SEQ ID NO 416
<211> LENGTH: 48
<212> TYPE: DNA
<213> ORGANISM: Artificial Sequence
<220> FEATURE:
<223> OTHER INFORMATION: synthetic construct

<400> SEQUENCE: 416
aggacctgac actggtcgtg gtcgaggcgt tcctccacca cgtctccg            48

<210> SEQ ID NO 417
<211> LENGTH: 48
<212> TYPE: DNA
<213> ORGANISM: Artificial Sequence
<220> FEATURE:
<223> OTHER INFORMATION: synthetic construct

<400> SEQUENCE: 417
aggaccatct cgacgacctg ctcctggggt tcctccacca cgtctccg            48

<210> SEQ ID NO 418
<211> LENGTH: 48
<212> TYPE: DNA
<213> ORGANISM: Artificial Sequence
<220> FEATURE:
<223> OTHER INFORMATION: synthetic construct

<400> SEQUENCE: 418
aggaccacga ggtctccact ggtccagggt tcctccacca cgtctccg            48

<210> SEQ ID NO 419
<211> LENGTH: 48
<212> TYPE: DNA
<213> ORGANISM: Artificial Sequence
<220> FEATURE:
<223> OTHER INFORMATION: synthetic construct

<400> SEQUENCE: 419
aggaccactg agctgctcct ccaggtgggt tcctccacca cgtctccg            48

<210> SEQ ID NO 420
<211> LENGTH: 48
<212> TYPE: DNA
<213> ORGANISM: Artificial Sequence
```

```
<220> FEATURE:
<223> OTHER INFORMATION: synthetic construct

<400> SEQUENCE: 420
aggacctcct gtcctgcacg tccatccggt tcctccacca cgtctccg          48

<210> SEQ ID NO 421
<211> LENGTH: 48
<212> TYPE: DNA
<213> ORGANISM: Artificial Sequence
<220> FEATURE:
<223> OTHER INFORMATION: synthetic construct

<400> SEQUENCE: 421
aggacagcac ctggaggtag gaccacgggt tcctccacca cgtctccg          48

<210> SEQ ID NO 422
<211> LENGTH: 48
<212> TYPE: DNA
<213> ORGANISM: Artificial Sequence
<220> FEATURE:
<223> OTHER INFORMATION: synthetic construct

<400> SEQUENCE: 422
aggacgacca gacgaggacc aggtaggcgt tcctccacca cgtctccg          48

<210> SEQ ID NO 423
<211> LENGTH: 48
<212> TYPE: DNA
<213> ORGANISM: Artificial Sequence
<220> FEATURE:
<223> OTHER INFORMATION: synthetic construct

<400> SEQUENCE: 423
aggaccaggt tcgaggacct cgtcagccgt tcctccacca cgtctccg          48

<210> SEQ ID NO 424
<211> LENGTH: 48
<212> TYPE: DNA
<213> ORGANISM: Artificial Sequence
<220> FEATURE:
<223> OTHER INFORMATION: synthetic construct

<400> SEQUENCE: 424
aggacgagca cgaggagcac gtgtccaggt tcctccacca cgtctccg          48

<210> SEQ ID NO 425
<211> LENGTH: 74
<212> TYPE: DNA
<213> ORGANISM: Artificial Sequence
<220> FEATURE:
<223> OTHER INFORMATION: synthetic construct

<400> SEQUENCE: 425
ggcagcacag tcgtcgcaca tacatcgttc cagactaccg aggacctgac actggtcgtg   60
gtcgaggcgt tcct                                                     74

<210> SEQ ID NO 426
<211> LENGTH: 77
<212> TYPE: DNA
<213> ORGANISM: Artificial Sequence
<220> FEATURE:
<223> OTHER INFORMATION: synthetic construct

<400> SEQUENCE: 426
```

```
ggcagcacag tcgtcgctac atgcttgtca accttccatg cgagtacctt acactggttc    60
gtggtcgagg cgttcct                                                    77

<210> SEQ ID NO 427
<211> LENGTH: 74
<212> TYPE: DNA
<213> ORGANISM: Artificial Sequence
<220> FEATURE:
<223> OTHER INFORMATION: synthetic construct

<400> SEQUENCE: 427
ggcagccgga tcgtcgcaca tcttgtcaac cttccatgcg aggacctgac actggtcgtg    60
gtcgaggcgt tcct                                                       74

<210> SEQ ID NO 428
<211> LENGTH: 80
<212> TYPE: DNA
<213> ORGANISM: Artificial Sequence
<220> FEATURE:
<223> OTHER INFORMATION: synthetic construct

<400> SEQUENCE: 428
ggcagcctta cgtcgcacaa ttctctgaca gaaatccaac ggaggacctg acacgtgcgt    60
cgtggctcga tgcgttcctc                                                 80

<210> SEQ ID NO 429
<211> LENGTH: 78
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (74)..(74)
<223> OTHER INFORMATION: N

<400> SEQUENCE: 429
ggcagcacag tcgtcgcaca tcattgtaca aaccttccat gcgaggacca tctcgacgac    60
ctgctcctgg ggtncctc                                                   78

<210> SEQ ID NO 430
<211> LENGTH: 75
<212> TYPE: DNA
<213> ORGANISM: Artificial Sequence
<220> FEATURE:
<223> OTHER INFORMATION: synthetic construct

<400> SEQUENCE: 430
ggcagcacag tcgtcgcaca tcttgtcaac cttccatgcg aggaccatct cgacgacctg    60
ctcctggggt tcctc                                                      75

<210> SEQ ID NO 431
<211> LENGTH: 75
<212> TYPE: DNA
<213> ORGANISM: Artificial Sequence
<220> FEATURE:
<223> OTHER INFORMATION: synthetic construct

<400> SEQUENCE: 431
ggcagcacag tcgtcgcaca tcttgtcaac cttccatgcg aggaccatct cgacgacctg    60
ctcctggggt tcctc                                                      75
```

```
<210> SEQ ID NO 432
<211> LENGTH: 75
<212> TYPE: DNA
<213> ORGANISM: Artificial Sequence
<220> FEATURE:
<223> OTHER INFORMATION: synthetic construct

<400> SEQUENCE: 432
ggcagcacag tcgtcgcaca tcttgtcaac cttccatgcg aggaccatct cgacgacctg    60
ctcctggggt tcctc                                                    75

<210> SEQ ID NO 433
<211> LENGTH: 75
<212> TYPE: DNA
<213> ORGANISM: Artificial Sequence
<220> FEATURE:
<223> OTHER INFORMATION: synthetic construct

<400> SEQUENCE: 433
ggcagcacag tcgtcgcaca tcttgtcaac cttccatgcg aggaccatct cgacgacctg    60
ctcctggggt tcctc                                                    75

<210> SEQ ID NO 434
<211> LENGTH: 75
<212> TYPE: DNA
<213> ORGANISM: Artificial Sequence
<220> FEATURE:
<223> OTHER INFORMATION: synthetic construct

<400> SEQUENCE: 434
ggcagcacag tcgtcgcaca tcttgtcaac cttccatgcg aggaccatct cgacgagctg    60
ctcctggggt tcctc                                                    75

<210> SEQ ID NO 435
<211> LENGTH: 82
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (61)..(61)
<223> OTHER INFORMATION: N

<400> SEQUENCE: 435
ggcagcacta gatcgtcgca catcttgtca accttccatg cgaggaccat cttcgactga    60
nctgcctcct gtgggcttcc tc                                            82

<210> SEQ ID NO 436
<211> LENGTH: 76
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (58)..(58)
<223> OTHER INFORMATION: N

<400> SEQUENCE: 436
ggcagcacag atcgtcgcac atcttgtcaa ccttccatgc gaggaccatc tcgacganct    60
gctcctgggg ttcctc                                                   76

<210> SEQ ID NO 437
```

```
<211> LENGTH: 78
<212> TYPE: DNA
<213> ORGANISM: Artificial Sequence
<220> FEATURE:
<223> OTHER INFORMATION: synthetic construct

<400> SEQUENCE: 437
ggcagcacag tcgtcgcaca tcttgtcaac cttccatgcg aggaccatca cgactacctt    60
ggctccctgg ggttcctc                                                  78

<210> SEQ ID NO 438
<211> LENGTH: 74
<212> TYPE: DNA
<213> ORGANISM: Artificial Sequence
<220> FEATURE:
<223> OTHER INFORMATION: synthetic construct

<400> SEQUENCE: 438
ggcagcacag tcgtcgcaca tcttgtcacc ttccatgcga ggaccatctc gacgacctgc    60
tcctggggtt cctc                                                      74

<210> SEQ ID NO 439
<211> LENGTH: 75
<212> TYPE: DNA
<213> ORGANISM: Artificial Sequence
<220> FEATURE:
<223> OTHER INFORMATION: synthetic construct

<400> SEQUENCE: 439
ggcagcacag tcgtcgcaca tcttgtcaac cttccatgcg aggaccatct cgacgacctg    60
ctcctggggt cctc                                                      75

<210> SEQ ID NO 440
<211> LENGTH: 75
<212> TYPE: DNA
<213> ORGANISM: Artificial Sequence
<220> FEATURE:
<223> OTHER INFORMATION: synthetic construct

<400> SEQUENCE: 440
ggcagccgga tcgtcgcaca tcttgtcaac cttccatgcg aggaccatct cgacgacctg    60
ctcctggggt cctc                                                      75

<210> SEQ ID NO 441
<211> LENGTH: 74
<212> TYPE: DNA
<213> ORGANISM: Artificial Sequence
<220> FEATURE:
<223> OTHER INFORMATION: synthetic construct

<400> SEQUENCE: 441
ggcagccgga tcgtcgcaca tcttgtcacc ttccatgcga ggaccatctc gacgacctgc    60
tcctggggtt cctc                                                      74

<210> SEQ ID NO 442
<211> LENGTH: 75
<212> TYPE: DNA
<213> ORGANISM: Artificial Sequence
<220> FEATURE:
<223> OTHER INFORMATION: synthetic construct

<400> SEQUENCE: 442
ggcagccgga tcgtcgcaca tcttgtcaac cttccatgcg aggaccatct cgacgacctg    60
```

```
ctcctggggt tcctc                                                    75

<210> SEQ ID NO 443
<211> LENGTH: 68
<212> TYPE: DNA
<213> ORGANISM: Artificial Sequence
<220> FEATURE:
<223> OTHER INFORMATION: synthetic construct

<400> SEQUENCE: 443
ggcagcacag tcgtcgcaat ccagtcaaga ctgaacagag gaccatctcg acgacctgct   60
cctgggtt                                                           68

<210> SEQ ID NO 444
<211> LENGTH: 77
<212> TYPE: DNA
<213> ORGANISM: Artificial Sequence
<220> FEATURE:
<223> OTHER INFORMATION: synthetic construct

<400> SEQUENCE: 444
ggcagcacag tcgtcgcaca tcttgtcaac cttttccatg cgaggacgag caggacctgg   60
aacctggtgc gttcctc                                                 77

<210> SEQ ID NO 445
<211> LENGTH: 74
<212> TYPE: DNA
<213> ORGANISM: Artificial Sequence
<220> FEATURE:
<223> OTHER INFORMATION: synthetic construct

<400> SEQUENCE: 445
ggcagcacag tcgtcgcaca tcttgtcacc ttccatgcga ggacgagcag gacctggaac   60
ctggtgcgtt cctc                                                    74

<210> SEQ ID NO 446
<211> LENGTH: 76
<212> TYPE: DNA
<213> ORGANISM: Artificial Sequence
<220> FEATURE:
<223> OTHER INFORMATION: synthetic construct

<400> SEQUENCE: 446
ggcagcacag tcgtcgcaca tcttgtcaac cttccatgcg aggacgatgc aggacctgga   60
acctggtgcg ttcctc                                                  76

<210> SEQ ID NO 447
<211> LENGTH: 76
<212> TYPE: DNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (28)..(28)
<223> OTHER INFORMATION: N
<220> FEATURE:
<221> NAME/KEY: misc_feature
<222> LOCATION: (31)..(31)
<223> OTHER INFORMATION: N

<400> SEQUENCE: 447
ggcagccgga tcgtcgcaca tcttggtnaa ncttccatgc gaggacgagc atgaactgga   60
```

```
acctggtgcg ttcctc                                                    76

<210> SEQ ID NO 448
<211> LENGTH: 72
<212> TYPE: DNA
<213> ORGANISM: Artificial Sequence
<220> FEATURE:
<223> OTHER INFORMATION: synthetic construct

<400> SEQUENCE: 448
ggcggatcgt cgcacatctt gtcaaccttc catgcgagga ccacgaggtc tccactggtc    60
caggggttcc tc                                                        72

<210> SEQ ID NO 449
<211> LENGTH: 77
<212> TYPE: DNA
<213> ORGANISM: Artificial Sequence
<220> FEATURE:
<223> OTHER INFORMATION: synthetic construct

<400> SEQUENCE: 449
ggcagcacag tcgtcggcaa tctttggtca accttccatg cgaggaccac gaggtctcca    60
ctggtccagg gttcctc                                                   77

<210> SEQ ID NO 450
<211> LENGTH: 75
<212> TYPE: DNA
<213> ORGANISM: Artificial Sequence
<220> FEATURE:
<223> OTHER INFORMATION: synthetic construct

<400> SEQUENCE: 450
ggcagccgga tcgtcgcaca tcttgtcaac cttccatgcg aggacgacca agacgaggac    60
caggtaggcg ttcct                                                     75

<210> SEQ ID NO 451
<211> LENGTH: 76
<212> TYPE: DNA
<213> ORGANISM: Artificial Sequence
<220> FEATURE:
<223> OTHER INFORMATION: synthetic construct

<400> SEQUENCE: 451
ggcagccgga tcgtcgcaca tcttgtcaac cttccatgcg aggacgtgat ggagcaagtc    60
ctcctgtcgg ttcctc                                                    76

<210> SEQ ID NO 452
<211> LENGTH: 73
<212> TYPE: DNA
<213> ORGANISM: Artificial Sequence
<220> FEATURE:
<223> OTHER INFORMATION: synthetic construct

<400> SEQUENCE: 452
ggcagcacag tcgtcgcaca tcttgtcaac cttccatgcg aggacacgag gtctccactg    60
gtccaggttc ctc                                                       73

<210> SEQ ID NO 453
<211> LENGTH: 79
<212> TYPE: DNA
<213> ORGANISM: Artificial Sequence
<220> FEATURE:
<223> OTHER INFORMATION: synthetic construct
```

```
<220> FEATURE:
<221> NAME/KEY: misc_feature
<222> LOCATION: (51)..(53)
<223> OTHER INFORMATION: N
<220> FEATURE:
<221> NAME/KEY: misc_feature
<222> LOCATION: (63)..(64)
<223> OTHER INFORMATION: N

<400> SEQUENCE: 453
gcccaaacaa gtcgtcgcac atcttgtcaa ccttccatgc gaggaccgag nnngtagctg     60
gannctcgga tgcgttcct                                                  79

<210> SEQ ID NO 454
<211> LENGTH: 84
<212> TYPE: DNA
<213> ORGANISM: Artificial Sequence
<220> FEATURE:
<223> OTHER INFORMATION: synthetic construct

<400> SEQUENCE: 454
gcagcacaga tcgtcgcaca tgcttgtcaa gcctttccat cgcgaggacc atcctacgga     60
gcgagcactt gctgcctggg gttc                                            84

<210> SEQ ID NO 455
<211> LENGTH: 81
<212> TYPE: DNA
<213> ORGANISM: Artificial Sequence
<220> FEATURE:
<223> OTHER INFORMATION: synthetic construct

<400> SEQUENCE: 455
ggcagccgga tcgtcgcaca tcaatggttt ggctggtgat actgaggacc acgacgtcta     60
cacttggttc cagggttcct c                                               81
```